US008211653B2

(12) United States Patent
Klass et al.

(10) Patent No.: US 8,211,653 B2
(45) **Date of Patent: *Jul. 3, 2012**

(54) METHODS AND SYSTEMS OF USING EXOSOMES FOR DETERMINING PHENOTYPES

(75) Inventors: Michael Klass, Oro Valley, AZ (US); Christine Kuslich, Gilbert, AZ (US); George Poste, Cave Creek, AZ (US)

(73) Assignee: Caris Life Sciences Luxembourg Holdings, S.A.R.L., Luxembourg (LU)

( * ) Notice: Subject to any disclaimer, the term of this patent is extended or adjusted under 35 U.S.C. 154(b) by 0 days.

This patent is subject to a terminal disclaimer.

(21) Appl. No.: 13/009,285

(22) Filed: Jan. 19, 2011

(65) Prior Publication Data

US 2011/0151460 A1 Jun. 23, 2011

Related U.S. Application Data

(63) Continuation of application No. 12/658,452, filed on Feb. 5, 2010, now abandoned, which is a continuation of application No. 12/591,226, filed on Nov. 12, 2009, now Pat. No. 7,897,356.

(60) Provisional application No. 61/114,045, filed on Nov. 12, 2008, provisional application No. 61/114,058, filed on Nov. 12, 2008, provisional application No. 61/114,065, filed on Nov. 13, 2008, provisional application No. 61/151,183, filed on Feb. 9, 2009, provisional application No. 61/278,049, filed on Oct. 2, 2009, provisional application No. 61/250,454, filed on Oct. 9, 2009, provisional application No. 61/253,027, filed on Oct. 19, 2009.

(51) Int. Cl.
*G01N 33/53* (2006.01)

(52) U.S. Cl. ........................................................ 435/7.1

(58) Field of Classification Search ........................ None
See application file for complete search history.

(56) References Cited

U.S. PATENT DOCUMENTS

| | | | |
|---|---|---|---|
| 5,089,181 | A | 2/1992 | Hauser |
| 6,812,023 | B1 | 11/2004 | Lamparski et al. |
| 8,021,847 | B2 | 9/2011 | Pietrzkowski |
| 8,048,418 | B2 | 11/2011 | Noguera-Troise |
| 2003/0036077 | A1 | 2/2003 | Chenchik et al. |
| 2003/0068642 | A1 | 4/2003 | Urnovitz |
| 2005/0158708 | A1 | 7/2005 | Alroy et al. |
| 2007/0059765 | A1 | 3/2007 | Wang et al. |
| 2008/0268429 | A1 | 10/2008 | Pietrzkowski |
| 2009/0011428 | A1 | 1/2009 | Nam et al. |
| 2009/0226887 | A1 | 9/2009 | Brisson |

OTHER PUBLICATIONS

Tockman et al (Cancer Res., 1992, 52:2711s-2718s).*

Clayton et al., "Exosomes in tumour immunity." Curr Oncol, 2009;16(3):46-9.

International search report and written opinion dated Jan. 24, 2011 for PCT application No. US10/58461.

Andre, et al. Exosomes for cancer immunotherapy, Annals of Oncology, 2004, 15 (Supplement 4): iv141-iv144; available at http://annonc.oxfordjournals.org, accessed Dec. 22, 2011.

Andre, et al. Tumor-derived exosomes: a new source of tumor rejection antigens, Vaccine 20, 2002: A28-A31; available at www.elsevier.com/locate/vaccine.

Bard, et al. Proteomic analysis of exosomes isolated from human malignant pleural effusions, Am. J. Respir. Cell Mol. Biol., 2004, vol. 31: 114-21.

Caby, et al. Exosomal-like vesicles are present in human blood plasma, International Immunology, 2005, vol. 17, No. 7: 879-87.

Ceccarini, et al. Biochemical and NMR studies on structure and release conditions of RNA-containing vesicles shed by human colon adenocarcinoma cells, Int. J. Cancer: 44, 1989: 714-21.

Clayton, et al. Analysis of antigen presenting cell derived exosomes, based on immune-magnetic isolation and flow cytometry, Journal of Immunological Methods 247, 2001: 163-74.

Dolo, et al. Membrane vesicles shed into the extracellular medium by human breast carcinoma cells carry tumor-associated surface antigens, Clin. Exp. Metastasis, 1995, 13: 277-86.

Fevrier, et al. Exosomes: endosomal-derived vesicles shipping extracellular messages, Current Opinion in Cell Biology 2004, 16: 415-21.

Gassart, et al. Lipid raft-associated protein sorting in exosomes, Blood, Dec. 15, 2003, vol. 102, No. 13: 4336-44; available at bloodjournal.hematologylibrary.org, accessed Dec. 17, 2011.

Geuze et al. Sorting of mannose 6-phosphate receptors and lysomal membrane proteins in endocytic vesicles, J. Cell Biol, 1988, 107(6pt2): Abstract.

Hemler. Tetraspanin proteins mediate cellular penetration, invasion, and fusion events and define a novel type of membrane microdomain. Annu. Rev. Cell Dev. Biol. 2003. 19:397-422.

Lamparski, et al. Production and characterization of clinical grade exosomes derived from dendritic cells, Journal of Immunological Methods, 270, 2002: 211-26.

Monleon, et al. Differential secretion of fas ligand- or APO2 ligand/TNF-related apoptosis-inducing ligand-carrying microvesicles during activation-induced death of human t cells, The Journal of Immunology, 2001, 167: 6736-44.

Pang, et al. MicroRNAs and prostate cancer, Acta Biochim Biophys Sin, 2010, 42(6): 363-69.

(Continued)

*Primary Examiner* — Sean Aeder

(74) *Attorney, Agent, or Firm* — Wilson Sonsini Goodrich & Rosati

(57) ABSTRACT

Exosomes can be used for detecting biomarkers for diagnostic, therapy-related or prognostic methods to identify phenotypes, such as a condition or disease, for example, the stage or progression of a disease. Cell-of-origin exosomes can be used in profiling of physiological states or determining phenotypes. Biomarkers or markers from cell-of-origin specific exosomes can be used to determine treatment regimens for diseases, conditions, disease stages, and stages of a condition, and can also be used to determine treatment efficacy. Markers from cell-of-origin specific exosomes can also be used to identify conditions of diseases of unknown origin.

34 Claims, 149 Drawing Sheets

OTHER PUBLICATIONS

Office Action dated Nov. 25, 2011 for U.S. Appl. No. 13/009,393.

Thery, et al. Exosomes: composition, biogenesis and function, Nature Reviews, Immunology,vol. 2, Aug. 2002: 569-79.

Tockman, et al. Considerations in bringing a cancer biomarker to clinical application, Cancer Res., 1992, 52: 2711s-2718s.

Trubey, et al. Quantitation of HLA class II protein incorporated into human immunodeficiency type 1 virions purified by anti-CD45 immunoaffinity depletion of microvesicles, Journal of Virology, Dec. 2003: 12699-709; available at http://jvi.asm.org, accessed Dec. 17, 2011.

Wang, et al. Down-regulation of CD9 expression during prostate carcinoma progression is associated with CD9 mRNA modifications, Clinical Cancer Research, 2007, 13(8): 2354-2361.

Office Action dated Jan. 16, 2012 for United Kingdom Patent Application No. 0921348.9.

* cited by examiner

FIG. 1a

| Cancer Lineage, Group Comparison, Disease State | Antigens | References |
|---|---|---|
| **Breast** | BCA-225 | Cerani et al., 1985 |
| **Breast** | BCA-225 | Mesa-Tejada et al., 1988 |
| **Breast** | BCA-225 | Loy et al., 1991 |
| **Breast** | BCA-225 | Ma et al., 1993 |
| **Breast** | hsp70 | Wolfers et al. 2001 Nat Med 793: 297 |
| **Breast** | MART-1 | Wolfers et al. 2001 Nat Med 793: 297 |
| **Breast** | ER | Oldenhuis CN et al., Eur J Cancer. 2008 May;44(7):946-53. Epub 2008 Apr 7; Payne SJ et al., Histopathology. 2008 Jan;52(1):82-90 |
| **Breast** | Class III b-tubulin | Galmarini CM et al., Clin Cancer Res. 2008 Jul 15;14(14):4511-6 |
| **Breast** | VEGFA | Linderholm BK et al., Cancer Res. 2001 Mar 1;61(5):2256-60 |
| **Breast** | HER2/neu (for Her2+BC) | De Laurentiis M et al., Ann Oncol. 2005 May;16 Suppl 4:iv7-13. |
| **Breast** | GPR30 | Filardo EJ et al., Steroids. 2008 Oct;73(9-10):870-3. |
| **Breast** | ErbB4(JM) isoform | Määttä JA et al., Mol Biol Cell. 2006 Jan;17(1):67-79. |
| **Breast** | MPR8 | Bera TK et al., Molecular Medicine 7(8): 509-516, 2001 |
| **Breast** | MISIIR | Jamie N Bakkum-Gamez et al., Gynecologic oncology (Gynecol Oncol) Vol. 108 Issue 1 Pg. 141-8 |
| **Ovarian** | CA125 (0C125)# | Bast et al., 1981 |
| **Ovarian** | CA125 | Dabawat S, et al., 1983 |
| **Ovarian** | CA125 | Davis H et al., 1986 |
| **Ovarian** | CA125 | Nouwen E, et al., 1986 |
| **Ovarian** | CA125 | Quirk J, et al., 1988 |
| **Ovarian** | CA-125 | Fukazawa I et al., 1988 |
| **Ovarian** | VEGFA | Osada R et al., Hum Pathol. 2006 Nov;37(11):1414-25. |
| **Ovarian** | VEGFR2 | Chen BY et al., Zhonghua Zhong Liu Za Zhi. 2005 Jan;27(1):33-7 |
| **Ovarian** | HER2 | Steffensen KD et al., Int J Oncol. 2008 Jul;33(1):195-204 |
| **Ovarian** | MISIIR | Jamie N Bakkum-Gamez et al., Gynecologic oncology (Gynecol Oncol) Vol. 108 Issue 1 Pq. 141-8 |
| **Lung** | CYFRA 21-1 | Kulpa J, et al., C Clin Chem 48: 1931-1937 (2002) |
| **Lung** | TPA-M | Kulpa J, et al., *supra.* |
| **Lung** | TPS | Kulpa J, et al., *supra.* |
| **Lung** | CEA | Kulpa J, et al., *supra.* |
| **Lung** | SCC-Ag | Kulpa J, et al., *supra.* |
| **Lung** | XAGE-1b | Kikuchi et al., Cancer Immunity, 8:13 (2008) |
| **Lung** | HLA class I | Kikuchi et al., *supra.* |
| **Lung** | TA-MUC1 | Kuemmel et al., Lung Cancer Jun 6, 2008 |
| **Lung** | KRAS | Zhang Z et al., Cancer Biol Ther. 2006 Nov;5(11):1481-6 |
| **Lung** | hENT1 | Oguri T et al., Cancer Lett. 2007 Oct 18;256(1):112-9. |
| **Lung** | kinin B1 receptor | Chee J et al., Biol Chem. 2008 Sep;389(9):1225-33. |

FIG. 1b

| Cancer Lineage, Group Comparison, Disease State | Antigens | References |
|---|---|---|
| **Lung** | kinin B2 receptor | Chee J et al., Biol Chem. 2008 Sep;389(9):1225-33. |
| **Lung** | TSC403 | Ozaki K et al., CANCER RESEARCH 58, 3499-3503, August 15, 1998 |
| **Lung** | HTI56 | Dobbs LG et al., JHC Volume 47(2): 129-137, 1999 |
| **Lung** | DC-LAMP | Salaun B et al., American Journal of Pathology. 2004;164:861-871 |
| **Colon** | CEA | Park et al., 2002 |
| **Colon** | MUC2 | Park et al., 2002 |
| **Colon** | GPA33 | Huber et al., 2005 |
| **Colon** | CEACAM5 | Huber et al., 2005 |
| **Colon** | ENFB1 | Huber et al., 2006 |
| **Colon** | CCSA-3 | Leman et al., 2007 |
| **Colon** | CCSA-4 | Leman et al., 2008 |
| **Colon** | ADAM 10 | Choi et al., 2007, J Ethnopharmacol 110(1): 49-55. |
| **Colon** | CD44 | Choi et al., 2007, J Ethnopharmacol 110(1): 49-55. |
| **Colon** | NG2 | Choi et al., 2007, J Ethnopharmacol 110(1): 49-55. |
| **Colon** | ephrin-B1 | Choi et al., 2007, J Ethnopharmacol 110(1): 49-55. |
| **Colon** | plakoglobin | Choi et al., 2007, J Ethnopharmacol 110(1): 49-55. |
| **Colon** | galectin-4 | Choi et al., 2007, J Ethnopharmacol 110(1): 49-55. |
| **Colon** | RACK1 | Choi et al., 2007, J Ethnopharmacol 110(1): 49-55 |
| **Colon** | tetraspanin-8 | Choi et al., 2007, J Ethnopharmacol 110(1): 49-55 |
| **Colon** | FasL | Choi et al., 2007, J Ethnopharmacol 110(1): 49-55 |
| **Colon** | A33 | Choi et al., 2007, J Ethnopharmacol 110(1): 49-55 |
| **Colon** | CEA | Choi et al., 2007, J Ethnopharmacol 110(1): 49-55 |
| **Colon** | EGFR | Choi et al., 2007, J Ethnopharmacol 110(1): 49-55 |
| **Colon** | dipeptidase 1 | Choi et al., 2007, J Ethnopharmacol 110(1): 49-55 |
| **Colon** | PTEN | Frattini et al., 2007 |
| **Colon** | Na(+)-dependent glucose transporter | Wang Y et al., Pediatr Res. 1994 Oct;36(4):514-21. |
| **Colon** | UDP-glucuronosyltransferase 1A | Gong QH et al., Pharmacogenetics 11:357-368(2001). |
| **Benign Prostatic Hyperplasia** | KIA1 | Ueda T, et al., 1996 |
| **Benign Prostatic Hyperplasia** | Intact Fibronectin | Janković MM, Kosanović MM, Dis Markers. 2008;25(1):49-58. |
| **Prostate** | PSA | Nurmikko P et al., 2000 |
| **Prostate** | TMPRSS2 | Wilson S et al., Biochem J. 2005 Jun 15;388(Pt 3):967-72. |
| **Prostate** | FASLG | Huber et al., 2005, Gastroenterol Nurs 28(6): 510-1. |
| **Prostate** | TNFSF10 | Huber et al., 2005, Gastroenterol Nurs 28(6): 510-1 |
| **Prostate** | PSMA | Pinto JT et al., Clin Cancer Res. 1996 Sep;2(9):1445-51. |
| **Prostate** | NGEP | Das S et al., Cancer Res. 2007 Feb 15;67 (4):1594-1601 |
| **Prostate** | IL-7R1 | Haudenschild DR et al., Prostate. 2006 Sep 1;66(12):1268-74. |

FIG. 1c

| Cancer Lineage, Group Comparison, Disease State | Antigens | References |
|---|---|---|
| **Prostate** | CSCR4 | Chinni SR et al., Mol Cancer Res. 2008 Mar;6(3):446-57. |
| **Prostate** | CysLT1R | Matsuyama M et al., Oncol Rep. 2007 Jul;18(1):99-104. |
| **Prostate** | TRPM8 | Bidaux G et al., J Clin Invest. 2007 Jun;117(6):1647-57. |
| **Prostate** | Kv1.3 | Prevarskaya N et al., Cell Death Differ. 2007 Jul;14(7):1295-304. |
| **Prostate** | TRPV6 | Prevarskaya N et al., Cell Death Differ. 2007 Jul;14(7):1295-304. |
| **Prostate** | TRPM8 | Prevarskaya N et al., Cell Death Differ. 2007 Jul;14(7):1295-304. |
| **Prostate** | PSGR | Xu LL et al., Cancer Res. 2000 Dec 1;60(23):6568-72. |
| **Prostate** | MISIIR | Bakkum-Gamez J.N. et al., Gynecol Oncol Vol. 108 Issue 1 Pg. 141-8 |
| **Melanoma** | TYRP1 | Mears et al., 2004 |
| **Melanoma** | SILV | Mears et al., 2004 |
| **Melanoma** | MLANA | Mears et al., 2004 |
| **Melanoma** | MCAM | Mears et al., 2004 |
| **Melanoma** | CD63 | Azorsa et al. 1991 |
| **Melanoma** | CD63 | Barrio et al. 1998 |
| **Melanoma** | CD63 | Demetrick et al., 1992 |
| **Melanoma** | CD63 | Mete et al., 2005 |
| **Melanoma** | CD63 | Kwon et al., 2007 |
| **Melanoma** | Alix | Mears et al., 2004, Proteomics 4(12): 4019-31. |
| **Melanoma** | hsp70 | Mears et al., 2004, Proteomics 4(12): 4019-31 |
| **Melanoma** | moesin | Mears et al., 2004, Proteomics 4(12): 4019-31. |
| **Melanoma** | p120 catenin | Mears et al., 2004, Proteomics 4(12): 4019-31 |
| **Melanoma** | PGRL | Mears et al., 2004, Proteomics 4(12): 4019-31 |
| **Melanoma** | syntaxin-binding protein 1 & 2 | Mears et al., 2004, Proteomics 4(12): 4019-31 |
| **Melanoma** | DUSP1 | |
| **Brain** | PRMT8 | Lee et al., 2005 |
| **Brain** | BDNF | Binder and Scharfman, 2004 |
| **Brain** | EGFR | Hicke et al., J. Biol. Chem. 276, 48644-48654, 2001; Daniels et al., PNAS 100, 15416-15421, 2003 |
| **Brain** | DPPX | Kim et al., J. Biochem, 2001, Vol. 129, No. 2 289-295 |
| **Brain** | Elk | Lhotak V et al., MOLECULAR AND CELLULAR BIOLOGY, May 1991, p. 2496-2502 |
| **Brain** | Densin-180 | Apperson ML et al., Journal of Neuroscience Volume 16, Number 21, Issue of November 1, 1996 pp. 6839-6852 |
| **Brain** | BAI2 | Shiratsuchi T et al., Cytogenet Cell Genet. 1997;79(1-2):103-8. |
| **Brain** | BAI3 | Shiratsuchi T et al., Cytogenet Cell Genet. 1997;79(1-2):103-8. |
| **Psoriasis** | flt-1 | Detmar M, et al., 1994 |
| **Psoriasis** | VPF receptors | Detmar M, et al., 1994 |
| **Psoriasis** | kdr | Detmar M, et al., 1994 |
| **CVD** | FATP6 | Gimeno RE et al., J Biol Chem. 2003 May 2;278(18):16039-44. |
| **Hematological malignancies** | CD44 | Liu J and Jiang G, Il Mol Immunol. 2006 Oct;3(5):359-65. |

FIG. 1d

| Cancer Lineage, Group Comparison, Disease State | Antigens | References |
|---|---|---|
| Hematological malignancies | CD58 | Kroger N, et al., 1997 |
| Hematological malignancies | CD31 | Kroger N, et al., 1998 |
| Hematological malignancies | CD11a | Kroger N, et al., 1999 |
| Hematological malignancies | CD49d | Kroger N, et al., 2000 |
| Hematological malignancies | GARP | Wang R et al., PLoS ONE. 2008 Jul 16;3(7):e2705. |
| Hematological malignancies | BTS | Suenaga T et al., Eur J Immunol. 2007 Nov;37(11):3197-207. |
| Hematological malignancies | Raftlin | Saeki K et al., The EMBO Journal (2003) 22, 3015-3026 |
| Hepatocellular Carcinoma | HBxAg | Wang W, et al., 1991 |
| Hepatocellular Carcinoma | HBsAg | Wang W, et al., 1991 |
| Hepatocellular Carcinoma | NLT | Simonson GD et al., Journal of Cell Science 107, 1065-1072 (1994) |
| Cervical Cancer | MCT-1 | Pinheiro C, et al., 2008 |
| Cervical Cancer | MCT-2 | Pinheiro C, et al., 2008 |
| Cervical Cancer | MCT-4 | Pinheiro C, et al., 2008 |
| Head and Neck Cancer | EGFR | Sheikh Ali MA et al., Cancer Sci. 2008 Aug;99(8):1589-94 |
| Head and Neck Cancer | EphB4 | Yavrouian EJ et al., Arch Otolaryngol Head Neck Surg. 2008 Sep;134(9):985-91. |
| Head and Neck Cancer | EphrinB2 | Yavrouian EJ et al., Arch Otolaryngol Head Neck Surg. 2008 Sep;134(9):985-91. |
| Endometrial Cancer | AlphaV Beta6 integrin | Hecht JL et al., Appl Immunohistochem Mol Morphol. 2008 Aug 11. |
| Autoimmune Disease | Tim-2 | Chakravarti S, et al., 2005 |
| Irritable Bowel Disease | Il-16 | Seegert D, et al., 2001 |
| Irritable Bowel Disease | 5-HT | Kerckhoffs AP et al., Neurogastroenterol Motil. 2008 Aug;20(8):900-7. |
| Irritable Bowel Disease | Il-1beta | Seegert D, et al., 2001 |
| Irritable Bowel Disease | Il-12 | Seegert D, et al., 2001 |
| Irritable Bowel Disease | TNF-alpha | Seegert D, et al., 2001 |
| Irritable Bowel Disease | interferon gamma | Seegert D, et al., 2001 |

FIG. 1e

| Cancer Lineage, Group Comparison, Disease State | Antigens | References |
|---|---|---|
| **Irritable Bowel Disease** | Il-6 | Seegert D, et al., 2001 |
| **Irritable Bowel Disease** | Rantes | Seegert D, et al., 2001 |
| **Irritable Bowel Disease** | MCP-1 | Seegert D, et al., 2001 |
| **Diabetes** | IL-6 | Pradhan A, et al., 2001 |
| **Diabetes** | CRP | Pradhan A, et al., 2001 |
| **Diabetes** | RBP4 | Lee SJ et al., Anal Chem. 2008 Apr 15;80(8):2867-73. |
| **Barrett's Esophagus** | p53 | Hamelin R, et al., 1994 |
| **Barrett's Esophagus** | MUC1 | Burjonrappa SC et al., Indian J Cancer. 2007 Jan-Mar;44(1):1-5. |
| **Barrett's Esophagus** | MUC6 | Glickman JN et al., Am J Surg Pathol. 2003 Oct;27(10):1357-65 |
| **Fibromyalgia** | neopterin | Bonaccorso S, et al., 1997 |
| **Fibromyalgia** | gp130 | Maes M et al., 1999 |
| **Stroke** | S-100 | Missler U, et al., 1997 |
| **Stroke** | Neuron specific enolase | Missler U, et al., 1997 |
| **Stroke** | PARK7 | Allard L, et al., 2005 |
| **Stroke** | NDKA | Allard L, et al., 2005 |
| **Stroke** | ApoC-I | Allard L, et al., 2005 |
| **Stroke** | ApoC-III | Allard L, et al., 2003 |
| **Stroke** | SAA | Allard L, et al., 2003 |
| **Stroke** | AT-III fragment | Allard L, et al., 2003 |
| **Stroke** | Lp-PLA2 | http://www.doctorslounge.com/neurology/news/stroke_lp-pla2_crp.shtml; Gorelick PB, Am J Cardiol. 2008 Jun 16;101(12A):34F-40F |
| **Stroke** | hs-CRP | http://www.doctorslounge.com/neurology/news/stroke_lp-pla2_crp.shtml |
| **Multiple Sclerosis** | B7 | Ferrante P, et al., 1998 |
| **Multiple Sclerosis** | B7-2 | Ferrante P, et al., 1998 |
| **Multiple Sclerosis** | CD-95(fas) | Ferrante P, et al., 1998 |
| **Multiple Sclerosis** | Apo-1/Fas | Ferrante P, et al., 1998 |
| **Parkinsons Disease** | PARK2 | Shimura H, eat al., 2000 |
| **Parkinsons Disease** | Ceruloplasmin | Shi M et al., Neurobiol Dis. 2008 Sep 26. |
| **Parkinsons Disease** | VDBP | Zhang et al., 2008 Am. J. Clin. Pathol. 129, 526-9., |
| **Parkinsons Disease** | tau | Zhang et al., 2008 Am. J. Clin. Pathol. 129, 526-9; Mollenhauer B et al., Dement Geriatr Cogn Disord; 2006;22(3):200-8; Davidsson P and Sjögren M, Dis Markers. 2005;21(2):81-92. |
| **Parkinsons Disease** | DJ-1 | Waragai et al., 2007 Neurosci. Lett. 425, 18-22 & Waragai et at 2006 Biochem. Biophys. Res. Commun. 345, 967-72 |
| **Rheumatic Disease** | Citrulinated fibrin a-chain | Skriner et al., 2006 |
| **Rheumatic Disease** | CD5 antigen-like fibrinogen fragment D | Skriner et al., 2006 |

FIG. 1f

| Cancer Lineage, Group Comparison, Disease State | Antigens | References |
|---|---|---|
| **Rheumatic Disease** | CD5 antigen-like fibrinogen fragment B | Skriner et al., 2006 |
| **Rheumatic Disease** | TNFalpha | Anderson AK et al., Arthritis Res Ther. 2008;10(2):204. Epub 2008 Mar 14. |
| **Alzheimers Disease** | APP695 | Rebeck G, et al., 2001 |
| **Alzheimers Disease** | APP751 | Rebeck G, et al., 2001 |
| **Alzheimers Disease** | APP770 | Rebeck G, et al., 2001 |
| **Alzheimers Disease** | BACE1 | Hebert SS et al., 2008. Proc Natl Acad Sci U.S.A., 105(17): 6415-20 |
| **Alzheimers Disease** | Cystatin C | Simonsen et al., 2008 Neurobiol. Aging. 29, 961-8 |
| **Alzheimers Disease** | Amyloid Beta | Simonsen et al., 2008 Neurobiol. Aging. 29, 961-8 |
| **Alzheimers Disease** | t-Tau | Simonsen et al., 2008 Neurobiol. Aging. 29, 961-8 |
| **Alzheimers Disease** | Complement factor H | Hye et al., 2006 Brain. 129, 3042-50 |
| **Alzheimers Disease** | alpha-2-macroglobulin | Hye et al., 2006 Brain. 129, 3042-50 |
| **Alzheimers Disease** | APOE4 | Albert MS, Proc Natl Acad Sci U S A. 1996 Nov 26;93(24):13547-51. |
| **Prion Diseases** | PrPSc | Takemura K et al., Exp Biol Med (Maywood) Feb;231(2)204-14, 2006 |
| **Prion Diseases** | 14-3-3 zeta | Kubler E et at , British Medical Bulletin 66:267-279, 2003 |
| **Prion Diseases** | S-100 | Kubler E et al , British Medical Bulletin 66:267-279, 2003 |
| **Prion Diseases** | AQP-4 | Kubler E et al , British Medical Bulletin 66:267-279, 2003 |
| **Chronic Neuropathic Pain** | Chemokine receptor (CCR2/4) | White FA et al., Proc Natl Acad Sci U S A. 2007 Dec 18;104(51):20151-8 |
| **Peripheral Neuropathic Pain** | OX42 (rodent) | Blackbeard J et al., J Neurosci Methods. 2007 Aug 30;164(2):207-17 |
| **Peripheral Neuropathic Pain** | ED9 (rodent) | Blackbeard J et al., J Neurosci Methods. 2007 Aug 30;164(2):207-17 |
| **Schizophrenia** | ATP5B | Altar CA, Neuropsychopharmacology. 2008 Oct 15. |
| **Schizophrenia** | ATP5H | Altar CA, Neuropsychopharmacology. 2008 Oct 15. |
| **Schizophrenia** | ATP6V1B | Altar CA, Neuropsychopharmacology. 2008 Oct 15. |
| **Schizophrenia** | DNM1 | Altar CA, Neuropsychopharmacology. 2008 Oct 15. |
| **GIST** | PDGFRA | Yang J et al., ncer. 2008 Oct 1;113(7):1532-43 |
| **GIST** | c-kit | Yang J et al., ncer. 2008 Oct 1;113(7):1532-43 |
| **GIST** | NHE-3 | Kulaksiz H et al., Cell Tissue Res. 2001 Mar;303(3):337-43. |
| **Renal Cell Carcinoma** | HIF1alpha | Rathmell WK, Chen S, Expert Rev Anticancer Ther. 2008 Jan;8(1):63-73. |
| **Renal Cell Carcinoma** | VEGF | Rathmell WK, Chen S, Expert Rev Anticancer Ther. 2008 Jan;8(1):63-74. |
| **Renal Cell Carcinoma** | PDGFRA | Rathmell WK, Chen S, Expert Rev Anticancer Ther. 2008 Jan;8(1):63-74. |
| **Cirrhosis** | NLT | Simonson GD et al., Journal of Cell Science 107,1065-1072 (1994) |
| **Cirrhosis** | HBsAg | Wang, W. et al., 1991 |
| **Esophageal cancer** | CaSR | Justinich CJ et al., Am J Physiol Gastrointest Liver Physiol. 2008 Jan;294(1):G120-9. |

FIG. 1g

| Cancer Lineage, Group Comparison, Disease State | Antigens | References |
|---|---|---|
| **Influenza** | Hemmaglutanin | Verma RK and Jain Amita, FEMS Immunol Med Microbiol 51 (2007) 453-461 |
| **Influenza** | Neurominidase | Verma RK and Jain Amita, *supra.* |
| **TB** | Antigen 60 | Verma RK and Jain Amita, *supra.* |
| **TB** | HSP antigen | Verma RK and Jain Amita, *supra.* |
| **TB** | Lipoarabinomannan antigen | Verma RK and Jain Amita, *supra.* |
| **TB** | Antigen of acylated trehalose family | Verma RK and Jain Amita, *supra.* |
| **TB** | DAT antigen | Verma RK and Jain Amita, *supra.* |
| **TB** | Sulfolipid antigen | Verma RK and Jain Amita, *supra.* |
| **TB** | TAT antigen | Verma RK and Jain Amita, *supra.* |
| **TB** | Trehalose 6,6-dimycolate (cord-factor) antigen | Verma RK and Jain Amita, *supra.* |
| **HIV** | Gp41 | Phogat S et al., J Intern Med. 2007 July ; 262(1): 26-43. |
| **HIV** | gp120 | Phogat S et al., J Intern Med. 2007 July ; 262(1): 26-43. |
| **Autism** | VIP | Nelson KB et al Annals of Neurology 2001, 49:597-606.. |
| **Autism** | PACAP | Nelson KB et al Annals of Neurology 2001, 49:597-606. |
| **Autism** | CGRP | Nelson KB et al Annals of Neurology 2001, 49:597-606. |
| **Autism** | NT3 | Nelson KB et al Annals of Neurology 2001, 49:597-606. |
| **Asthma** | YKL-40 | Scot, I., Thorax 2008;63:365, A New Biomarker in Asthma |
| **Asthma** | S-nitrosothiols | Holgate, ST., Lancet. 1998 May 2;351(9112):1317-9. |
| **Asthma** | SCCA2 | Izuhara, K., Allergol Int. 2006 Dec ;55 (4):361-7. |
| **Asthma** | PAI | Izuhara, K., Allergol Int. 2006 Dec ;55 (4):361-7. |
| **Asthma** | amphiregulin | Izuhara, K., Allergol Int. 2006 Dec ;55 (4):361-7. |
| **Asthma** | Periostin | Izuhara, K., Allergol Int. 2006 Dec ;55 (4):361-7. |
| **Lupus** | TNFR | Suh CH and Kim HA, Expert Rev Mol Diagn. 2008 Mar;8(2):189-98 |
| **Vulnerable plaque** | Alpha v Beta 3 integrin | Burtea C et al., Cardiovasc Res. 2008 Apr 1;78(1):148-57. |
| **Vulnerable plaque** | MMP9 | Blankenberg S et al., 2003 Circulation 107:1579-1585. |

FIG. 2a

| Cancer Lineage, Group Comparison, Other Significant Disease State | Binding Agents | Select Reference(s) |
|---|---|---|
| **Breast** | Herceptin (Trastuzumab) | Adams GP, Weiner LM, Nat Biotechnol. 2005 Sep;23(9):1147-57. |
| **Breast** | CCND1 PNA | Tian et al , NAR 24(5-7):1085-91, 2005; Tian et al., Ann NY Acad Sci 1059, 106-44, 2005 |
| **Breast** | MYC PNA | Tian et at , NAR 24(5-7):1085-91, 2005; Tian et al., Ann NY Acad Sci 1059, 106-44, 2005 |
| **Breast** | IGF-1 PNA | Tian et al , J. of Nucl Med 48(10), 1699-707, 20007 |
| **Breast** | MYC PNA | Tian et al., Bioconjug Chem 16)1)70-9, 2005 |
| **Breast** | SC4 aptamer (Ku) | Zhang et al. 2004 |
| **Breast** | All-7 aptamer (ERB2) | Kunz et al., MolecularCancer Research(4) 983998, 2006 |
| **Breast** | Galectin -3 binding agent | Cancer Invest 26(6)615-23, 2008 |
| **Breast** | mucin-type O-glycans binding agent | Cancer Invest 26(6)615-23, 2008 |
| **Breast** | L-PHA binding agent | Abbott et al., J Proteome Res 7(4)1470-80, 2008 |
| **Breast** | Galectin-9 binding agent | Yamaguchi et al., Breast J 5(2), 2006 |
| **Breast** | ER | Payne SJ et al., Histopathology. 2008 Jan;52(1):82-90. |
| **Breast** | PR | Payne SJ et al., Histopathology. 2008 Jan;52(1):82-90. |
| **Ovarian** | (90)Y-muHMFG1 binding agent | Oei et al 2008 |
| **Ovarian** | OC125 (anti-CA125 antibody) | Matsuoka et al 1987 |
| **Ovarian** | monoclonal antibodies (HMFG1, HMFG2, H317, and H17E2), Hu2PLAP | Kosmas et al , Oncology 55 (5),435-446, 1998 |
| **Lung** | SCLC specific aptamer HCA 12 | Chen et at , Chem Med Chem (3)991-1001, 2008 |
| **Lung** | SCLC specific aptamer HCC03 | Chen et al , Chem Med Chem (3)991-1001, 2008 |
| **Lung** | SCLC specific aptamer HCH07 | Chen et al , Chem Med Chem (3)991-1001, 2008 |
| **Lung** | SCLC specific aptamer HCH01 | Chen et at , Chem Med Chem (3)991-1001, 2008 |
| **Lung** | A-p50 aptamer (NF-KB) | Mi et al., Mol Ther 16(1)66-73, 2008 |
| **Lung** | Cetuximab | Rossi A et al., Rev Recent Clin Trials. 2008 Sep;3(3):217-27 |
| **Lung** | Panitumumab | Rossi A et al., Rev Recent Clin Trials. 2008 Sep;3(3):217-27 |
| **Lung** | Bevacizumab | Gettinger S et al., Semin Respir Crit Care Med. 2008 Jun;29(3):291-301 |
| **Lung** | L19 antibody | Pedretti et al., Lung Cancer Sep 15, 2008 |
| **Lung** | F16 antibody | Pedretti et al., Lung Cancer Sep 15, 2008 |
| **Lung** | anti-CD45 (anti-ICAM-1 antibody, aka UV3) | Brooks et al., Int J Cancer 2438(10)2438-45, 2008 |
| **Lung** | L2G7 Ab (anti-HGF antibody) | Stabile et al., Mol Cancer Ther 7(7)1913-22, 2008 |
| **Colon** | angiopoietin 2 specific aptamer | Sarraf-Yazdi et al., J SURG Res 146(1)16-23, 2008. |

FIG. 2b

| Cancer Lineage, Group Comparison, Other Significant Disease State | Binding Agents | Select Reference(s) |
|---|---|---|
| **Colon** | beta-catenin aptamer | Lee et al., Cancer Research 66(21)10560-6, 2006. |
| **Colon** | TCF1 aptamer | Choi et al., Mol Caner Therapy (9)2428-34, 2006. |
| **Colon** | anti-Derlin1 antibody | Ran et al., Clin Cancer Res 14(206538-45, 2008 |
| **Colon** | anti-RAGE antibody | Turovskaya et al., Carcinogenesis 29(10)2035-2043, 2008. |
| **Colon** | monoclonal antibody gb3.1 | Turovskaya et al., Carcinogenesis 29(10)2035-2043, 2008. |
| **Colon** | Galectin-3 binding agent | Greco et al., Glycobiology 14(9)783-92, 2004. |
| **Colon** | Cetuximab | Giuliani F, Colucci G et al., Int J Biol Markers. 2007 Jan-Mar;22(1 Suppl 4):S62-70 |
| **Colon** | Panitumumab | Chua YJ, Cunningham D, Clin Colorectal Cancer. 2005 Nov;5 Suppl 2:S81-8. |
| **Colon** | Matuzumab | Chua YJ, Cunningham D, Clin Colorectal Cancer. 2005 Nov;5 Suppl 2:S81-8. |
| **Colon** | Bevacizumab | Majer M et al., Anticancer Agents Med Chem. 2007 Sep;7(5):492-503 |
| **Colon** | Mac-2 binding agent | Lotz MM et al., Proc Natl Acad Sci U S A. 1993 90(18): 8319-23, "Mitogen-activated protein kinases p42mapk and p44mapk are required for fibroblast proliferation." |
| **Adenoma versus CRC** | Complement C3 | Qui et al , J of Proteome Res 7(4)1693-1703, 2008 |
| **Adenoma versus CRC** | histidine-rich glycoprotein binding agent | Qui et al , J of Proteome Res 7(4)1693-1703, 2008 |
| **Adenoma versus CRC** | kininogen-1 binding agent | Qui et al , J of Proteome Res 7(4)1693-1703, 2008 |
| **Adenoma versus CRC** | Galectin-3 binding agent | Schoeppner HL et al., Cancer. 1995 Jun 15;75(12):2818-26. |
| **Adenoma with low grade versus high grade dysplasia** | Galectin-3 binding agent | Schoeppner HL et al., Cancer. 1995 Jun 15;75(12):2818-26. |
| **CRC versus normal** | anti-ODC monoclonal antibody | Hu HY et al., World J Gastroenterol. 2005 Apr 21;11(15):2244-8. |
| **CRC versus normal** | anti-CEA monoclonal antibody | Zhang HZ et al., Cancer Res. 1989 Oct 15;49(20):5766-73. |
| **CRC versus normal** | Mac-2 binding agent | Lotz MM et al., Proc Natl Acad Sci U S A. 1993 Apr 15;90(8):3466-70. |
| **Prostate** | PSA binding agent | Nurmikko P et al., 2000, Clin Chem 46(10): 1610-8. |
| **Prostate** | PSMA binding agent | Aggarwal S et al., Cancer Res. 2006 Sep 15;66(18):9171-7. |
| **Prostate** | TMPRSS2 binding agent | Wilson S et al., Biochem J. 2005 Jun 15;388(Pt 3):967-72. |
| **Prostate** | monoclonal antibody 5D4 | Sawant et al., J Drug Target 16(7)601-4, 2008. |
| **Prostate** | XPSM-A9 | Lupold et al., Cancer Research 62(14): 4029-4033, 2002. |
| **Prostate** | XPSM-A10 | Lupold et al., Cancer Research 62(14): 4029-4033, 2002. |
| **Prostate** | Galectin-3 binding agent | Califice et al., Int J Oncol 25(4)983-92, 2004 |
| **Prostate** | E-selectin binding agent | Bhaskar et al., Cancer Research 63(19(6387-94, 2003. |

FIG. 2c

| Cancer Lineage, Group Comparison, Other Significant Disease State | Binding Agents | Select Reference(s) |
|---|---|---|
| **Prostate** | Galectin-1 binding agent | van den Brule et al., J Pathology 193(1)80-7, 2001 |
| **Prostate** | E4 (IgG2a kappa) | Nilsson S et al., Cancer Biother Radiopharm. 1997 Dec;12(6):395-403. |
| **Melanoma** | Tremelimumab (anti-CTLA4 antibody) | Camacho LH, Expert Opin Investig Drugs 17(3)371-85, 2008. |
| **Melanoma** | 1pilimumumab (anti-CTLA4 antibody) | Lens M et al., Recent Patents Anticancer Drug Discovery Jun3(2)105-13, 2008. |
| **Melanoma** | CTLA-4 aptamers | Santulli-Marotto et al., Cancer Research 63(21)7483-9, 2003. |
| **Melanoma** | STAT-3 peptide aptamers | Nagel Wolfrum et al., Molecular Cancer Research 2:170-182, 2004 |
| **Melanoma** | Galectin-1 binding agent | Mathieu et al., J Invest Dermatol 127(10)2399-410, 2007, Le Mercier et al., J Neuropathol Exp Neurol. 67(5)456-69, 2008. |
| **Melanoma** | Galectin-3 binding agent | Prieto et al., Clin Cancer Res 12(22)6709-15, 2006; Vereecken et al., Arch Dermatol Res 296(8)353-8, 2005 |
| **Melanoma** | PNA | Dore et al., Pigment Cell Res 7(6)461-4, 1994. |
| **Pancreatic** | H38-15 (HGF aptamer) | Saito T and Tomida M, DNA Cell Biol. 2005 Oct;24(10):624-33. |
| **Pancreatic** | H38-21(HGF aptamer) | Saito T and Tomida M, DNA Cell Biol. 2005 Oct;24(10):624-33. |
| **Pancreatic** | Matuzumab | Kleepspeies A et al., Clin Cancer Res. 2008 Sep 1;14(17):5426-36 |
| **Pancreatic** | Cetuximanb | Burris H 3rd et al., Oncologist. 2008 Mar;13(3):289-98. |
| **Pancreatic** | Bevacizumab | Burris H 3rd et al., Oncologist. 2008 Mar;13(3):289-98. |
| **Brain** | aptamer 111.1 (pigpen) | Blank Met al., JBC May 11; 276(19)16464-8, 2001 |
| **Brain** | TTA1 (Tenascin-C ) aptamer | Hicke et al., J. Biol. Chem. 276, 48644-48654, 2001; Daniels et al., PNAS 100, 15416-15421, 2003 |
| **Psoriasis** | E-selectin binding agent | Rottman JB et al., Lab Invest. 2001 Mar;81(3):335-47. |
| **Psoriasis** | ICAM-1 binding agent | Rottman JB et al., Lab Invest. 2001 Mar;81(3):335-47. |
| **Psoriasis** | VLA-4 binding agent | Rottman JB et al., Lab Invest. 2001 Mar;81(3):335-47. |
| **Psoriasis** | VCAM-1 binding agent | Rottman JB et al., Lab Invest. 2001 Mar;81(3):335-47. |
| **Psoriasis** | alphaEbeta7 binding agent | Rottman JB et al., Lab Invest. 2001 Mar;81(3):335-47. |
| **Cardiovascular Disease** | RB007 (factor IXA aptamer) | Chan MY et al., Circulation. 2008 Jun 3;117(22):2865-74. Epub 2008 May 27 |
| **Cardiovascular Disease** | ARC1779 (anti VWF) aptamer | Gilbert JC et al., Circulation. 2007 Dec 4;116(23):2678-86. Epub 2007 Nov 19 |
| **Cardiovascular Disease** | LOX1 binding agent | Dunn S et al., Biochem J. 2008 Jan 15;409(2):349-55. |
| **Hematological malignancies** | anti-CD20 | Ravandi F et al., Clin Cancer Res. 2003 Feb;9(2):535. |
| **Hematological malignancies** | anti-CD52 | Ravandi F et al., Clin Cancer Res. 2003 Feb;9(2):535. |
| **B-Cell Chronic Lymphocytic Leukemias** | Rituximab | Robak T, Leuk Lymphoma. 2004 Feb;45(2):205-19. |

FIG. 2d

| Cancer Lineage, Group Comparison, Other Significant Disease State | Binding Agents | Select Reference(s) |
|---|---|---|
| **B-Cell Chronic Lymphocytic Leukemias** | Alemtuzumab | Robak T, Leuk Lymphoma. 2004 Feb;45(2):205-19. |
| **B-Cell Chronic Lymphocytic Leukemias** | Apt48 (BCL6) | Chattopadhyay et al 2006, J Assoc Physicians India 54: 547. |
| **B-Cell Chronic Lymphocytic Leukemias** | R0-60 aptamer | Wu CC et al., Hum Gene Ther. 2003 Jun 10;14(9):849-60. |
| **B-Cell Chronic Lymphocytic Leukemias** | D-R15-8 aptamer | Wu CC et al., Hum Gene Ther. 2003 Jun 10;14(9):849-60. |
| **B-cell lymphoma** | Ibritumomab | Cheson BD, Leonard JP, N Engl J Med. 2008 Aug 7;359(6):613-26. |
| **B-cell lymphoma** | Tositumomab | Cheson BD, Leonard JP, *supra.* |
| **B-cell lymphoma** | Anti-CD20 Antibodies | Cheson BD, Leonard JP, *supra.* |
| **B-cell lymphoma** | Alemtuzumab | Cheson BD, Leonard JP, *supra.* |
| **B-cell lymphoma** | Galiximab | Cheson BD, Leonard JP, *supra.* |
| **B-cell lymphoma** | Anti-CD40 Antibodies | Cheson BD, Leonard JP, *supra.* |
| **B-cell lymphoma** | Epratuzumab | Cheson BD, Leonard JP, *supra..* |
| **B-cell lymphoma** | Lumiliximab | Cheson BD, Leonard JP, *supra.* |
| **B-cell lymphoma** | Monoclonal antibody Hu1D10 | Cheson BD, Leonard JP, *supra.* |
| **B-cell lymphoma-DLBCL** | Galectin-3 binding agent | D'Haene N et al., Int J Immunopathol Pharmacol. 2005 Jul-Sep;18(3):431-43. |
| **B-cell lymphoma** | Apt48 | Chattopadhyay A et al., Oncogene. 2006 Apr 6;25(15):2223-33. |
| **Burkitt's lymphoma** | TD05 aptamer | Mallikaratchy P et al., Mol Cell Proteomics Dec; 6(12)2230-8, 2007. |
| **Burkitt's lymphoma** | IgM monoclonal antibody (38-13) | Wiels J et al., Cancer Res. 1984 Jan;44(1):129- 33. |
| **Cervical Cancer** | Galectin-9 binding agent | Liang et al., Clin Oncol 134(8)899-907, 2008. |
| **Cervical Cancer** | HPVE7 aptamer | Nauenburg S et al., FASEB J. 2001 Mar;15(3):592-4. Epub 2001 Jan 19. |
| **Endometrial Cancer** | Galectin-1 binding agent | Mylonas I et al., Anticancer Res. 2007 JulAug;27(4A):1975-80. |
| **Head and Neck Cancer** | (111)In-cMAb U36 | Sandstrom K et al., Tumour Biol. 2008;29(3):137-44. |
| **Head and Neck Cancer** | anti-LOXL4 antibody | Weise JB et al., Eur J Cancer. 2008 Jun;44(9):1323-31. |
| **Head and Neck Cancer** | U36 monoclonal antibody | Verel I et al., Int J Cancer. 2002 May 20;99(3):396-402. |
| **Head and Neck Cancer** | BIWA-1 monoclonal antibody | Verel I et al., Int J Cancer. 2002 May 20;99(3):396-402. |

FIG. 2e

| Cancer Lineage, Group Comparison, Other Significant Disease State | Binding Agents | Select Reference(s) |
|---|---|---|
| Head and Neck Cancer | BIWA-2 monoclonal antibody | Verel I et al., Int J Cancer. 2002 May 20;99(3):396-402. |
| Head and Neck Cancer | BIWA-4 monoclonal antibody | Verel I et al., Int J Cancer. 2002 May 20;99(3):396-402. |
| Head and Neck Cancer | BIWA-8 monoclonal antibody | Verel I et al., Int J Cancer. 2002 May 20;99(3):396-402. |
| Irritable Bowel Disease | ACCA (anti-glycan antibody) | Li X et al., World J Gastroenterol. 2008 Sep 7;14(33):5115-24. |
| Irritable Bowel Disease | ALCA(anti-glycan antibody) | Li X et al., World J Gastroenterol. 2008 Sep 7;14(33):5115-24. |
| Irritable Bowel Disease | AMCA (anti-glycan antibody) | Li X et al., World J Gastroenterol. 2008 Sep 7;14(33):5115-24. |
| Diabetes | RBP4 aptamer | Lee SJ et al., Anal Chem. 2008 Apr 15;80(8):2867-73. |
| Fibromyalgia | L-selectin binding agent | Macedo JA et al., J Neuroimmunol. 2007 Aug;188(1-2):159-66,. |
| Multiple Sclerosis | Natalizumab (Tysabri) | Goodin DS et al., Neurology. 2008 Sep 2;71(10):766-73. |
| Rheumatic Disease | Rituximab (anti-CD20 antibody) | Anderson AK et al., Arthritis Res Ther. 2008;10(2):204. Epub 2008 Mar 14. |
| Rheumatic Disease | Keliximab (anti-CD4 antibody) | Anderson AK et al., Arthritis Res Ther. 2008;10(2):204. Epub 2008 Mar 14. |
| Alzheimers Disease | TH14-BACE1 aptamers | Rentmeister A et al., RNA. 2006 Sep;12(9):1650-60. Epub 2006 Aug 3 |
| Alzheimers Disease | S10-BACE1 aptamers | Rentmeister A et al., RNA. 2006 Sep;12(9):1650-60. Epub 2006 Aug 3 |
| Alzheimers Disease | anti-Abeta monoclonal antibody | Geylis V et al., Autoimmun Rev. 2006 Jan;5(1):33-9. Epub 2005 Aug 1. Review. |
| Alzheimers Disease | Bapineuzumab (AAB-001) - Elan | Hock C et al., Neuron. 2003 May 22;38(4):54754 |
| Alzheimers Disease | LY2062430 (anti-amyloid beta Ab)-Eli Lilly | Irena Melnikova, Nature Reviews Drug Discovery 6, 341-342 (May 2007) |
| Alzheimers Disease | BACE1-Anti sense | Faghihi MA et al., Nat Med. 2008 Jul;14(7):723- 30. Epub 2008 Jun 29 |
| Prion Diseases | rhuPrP© aptamer | Takemura K et al., Exp Biol Med (Maywood) Feb;231(2)204-14, 2006 |
| Prion Diseases | DP7 aptamer | Proske D et al., Chembiochem. 2002 Aug 2;3(8):717-25. |
| Prion Diseases | Thioaptamer 97 | King DJ et al., J Mol Biol. 2007 Jun 15;369(4):1001-14. Epub 2007 Feb 9 |
| Prion Diseases | SAF-93 aptamer | Rhie A et al., J Biol Chem. 2003 Oct 10;278(41):39697-705. Epub 2003 Aug 5 |
| Prion Diseases | 15B3 (anti-PrPSc antibody) | Korth C et al., Nature 390:74-77, 1997 |
| Prion Diseases | monoclonal anti PrPSc antibody P1:1 | Jones M et al., Brain Pathol. 2008 May 26. |
| Prion Diseases | 1.5D7, 1.6F4 antibodies | Cordes H, J Immunol Methods Sep 15;337(2)106-20, 2008 |

FIG. 2f

| Cancer Lineage, Group Comparison, Other Significant Disease State | Binding Agents | Select Reference(s) |
|---|---|---|
| **Prion Diseases** | monoclonal antibody 14D3 | Krasemann S et al., Mol Med. 1996 Nov;2(6):725-34 |
| **Prion Diseases** | monoclonal antibody 4F2 | Krasemann S et al., Mol Med. 1996 Nov;2(6):725-34 |
| **Prion Diseases** | monoclonal antibody 8G8 | Krasemann S et al., Mol Med. 1996 Nov;2(6):725-34 |
| **Prion Diseases** | monoclonal antibody 12F10 | Krasemann S et al., Mol Med. 1996 Nov;2(6):725-34 |
| **Sepsis** | HA-1A monoclonal antibody | Cross AS and Opal S Journal of Endotoxin Research, Vol. 1, No. 1, 57-69 (1994) |
| **Sepsis** | E-5 monoclonal antibody | Cross AS and Opal S Journal of Endotoxin Research, Vol. 1, No. 1, 57-69 (1994) |
| **Sepsis** | TNF-alpha monoclonal antibody | Abraham E et al., JAMA Vol. 273 No. 12, March 22, 1995 |
| **Sepsis** | Afelimomab | Vincent JL Int J Clin Pract. 2000 Apr;54(3):190- 3 |
| **Sepsis** | E-selectin binding agent | Tsokos M et al., Int Journal of Legal Medicine, Volume 113, Number 6:338-342, 2000 |
| **Schizophrenia** | L-selectin binding agent | Iwata Y et al., Schizophr Res. 2007 Jan;89(1- 3):154-60. Epub 2006 Oct 17 |
| **Schizophrenia** | N-CAM binding agent | Vawter MP et al., Exp Neurol. 1998 Feb;149(2):424-32 |
| **Depression** | GPIb binding agent | Walsh MT et al., Life Sci. 2002 May 17;70(26):3155-65 |
| **GIST** | anti-DOG1 antibody | Espinosa F et al., Am J Surg Pathol Feb;32(2)210-8, 2008 |
| **Esophageal cancer** | CaSR binding agent | Justinich CJ et al., Am J Physiol Gastrointest Liver Physiol. 2008 Jan;294(1):G120-9. |
| **Gastric cancer** | Calpain nCL-2 binding agent | Hata et al., J. Biol. Chem., Vol. 281, Issue 16, 11214-11224, April 21, 2006 |
| **Gastric cancer** | drebrin binding agent | Keon BH et al., Journal of Cell Science, Vol 113, Issue 2 325-336 |
| **Osteoarthritis** | DDR-2 binding agent | Xu et al., Arthritis Rheum. 2007 Aug;56(8):2663-73. |
| **COPD** | CXCR3 binding agent | Freeman CM et al., Am J Pathol. 2007 Sep;171(3):767-76. |
| **COPD** | CCR5 binding agent | Freeman CM et al., Am J Pathol. 2007 Sep;171(3):767-76. |
| **COPD** | CXCR6 binding agent | Freeman CM et al., Am J Pathol. 2007 Sep;171(3):767-76. |
| **Asthma** | VIP binding agent | Nelson KB et alAnnals of Neurology 2001, 49:597-606. |
| **Asthma** | PACAP binding agent | Nelson KB et alAnnals of Neurology 2001, 49:597-606.. |
| **Asthma** | CGRP binding agent | Nelson KB et alAnnals of Neurology 2001, 49:597-606.. |
| **Asthma** | NT3 binding agent | Nelson KB et alAnnals of Neurology 2001, 49:597-606.. |
| **Asthma** | YKL-40 binding agent | Scot, I., Thorax 2008;63:365, A New Biomarker in Asthma |
| **Asthma** | S-nitrosothiols | Holgate, ST., Lancet. 1998 May 2;351(9112):1317-9. |
| **Asthma** | SCCA2 binding agent | Izuhara, K., Allergol Int. 2006 Dec ;55 (4):3617. |
| **Asthma** | PAI binding agent | Izuhara, K., Allergol Int. 2006 Dec ;55 (4):3617. |
| **Asthma** | amphiregulin binding agent | Izuhara, K., Allergol Int. 2006 Dec ;55 (4):3617. |
| **Asthma** | Periostin binding agent | Izuhara, K., Allergol Int. 2006 Dec ;55 (4):3617. |
| **Vulnerable plaque** | Gd-DTPA-g-mimRGD (Alpha v Beta 3 integrin binding peptide) | Burtea C et al., Cardiovasc Res. 2008 Apr 1;78(1):148-57. |
| **Vulnerable plaque** | MMP-9 binding agent | Blankenberg S et al., 2003 Circulation 107:1579-1585. |

FIG. 3a

| Cancer Lineage, Group Comparison, Other Significant Disease State | Up-regulated miRs | Down-regulated miRs | mRNAs | Mutational Analysis | Proteins Ligands Peptides | snoRNA | Select Reference(s) |
|---|---|---|---|---|---|---|---|
| **Breast** | miR-21 | let-7 | | | | | Iorio et al., Cancer Research 65, 7065-7070, August 15, 2005. |
| **Breast** | miR-155 | miR-10b | | | | | Iorio et al., *supra.* |
| **Breast** | miR-206 | miR-125a | | | | | Iorio et al., *supra.* |
| **Breast** | miR-122a | miR-125b | | | | | Iorio et al., *supra.* |
| **Breast** | miR-210 | miR-145 | | | | | Iorio et al., *supra.* |
| **Breast** | | miR-143 | | | | | Michael et al.Mol Cancer Res 1: 882-891, 2003. |
| **Breast** | | miR-145 | | | | | Michael et al.*supra* |
| **Breast** | | miR-16 | | | | | Michael et al.*supra* |
| **Breast** | | let-7 | | | | | Michael et al.*supra.* |
| **Breast** | miR-21 | let-7 | | | | | Lu et al. Nature 435: 834-838, 2005. |
| **Breast** | miR-21 | let-7 | | | | | Volinia et al. Proc Natl Acad Sci USA 103: 2257-2261, 2006. |
| **Breast** | miR-155 | miR-10b | | | | | Volinia et al. *supra.* |
| **Breast** | miR-206 | miR-125a | | | | | Volinia et al. *supra.* |
| **Breast** | miR-122a | miR-125b | | | | | Volinia et al. *supra.* |
| **Breast** | miR-210 | miR-145 | | | | | Volinia et al. *supra.* |
| **Breast** | miR-21 | | | | | | Si et al. Oncogene 26: 2799-2803, 2006. |
| **Breast** | | | | | hsp70 | | Wolfers et al. 2001 Nat Med 793): 297-302. |
| **Breast** | | | | | MART-1 | | Wolfers et al. 2001 Nat Med 793): 297-302. |
| **Breast** | | | | | TRP | | Wolfers et al. 2001 Nat Med 793): 297-302. |
| **Breast** | | | | | HER2 | | Wolfers et al. 2001 Nat Med 793): 297-302. |
| **Breast** | | | | | hsp70 | | Koga et al., 2005, Antican, Res 25(6A):3703-5 |
| **Breast** | | | | | MART-1 | | Koga et al., *supra.* |
| **Breast** | | | | | TRP | | Koga et al., *supra.* |
| **Breast** | | | | | HER2 | | Koga et al., *supra.* |
| **Breast** | | | | | GASS | | Mourtada-Maarabouni et at 2008 |
| **Breast** | | | ER | | ER | | Oldenhuls CN et al., Eur J Cancer. 2008 May;44(7):946- 53. Epub 2008 Apr 7; Payne SJ et al., Histopathology. 2008 Jan;52(1):82-90 |
| **Breast** | | | PR | | PR | | Oldenhuis et al., *supra.*; Payne et al., *supra.* |
| **Breast** | | | HER2 | | | | Oldenhuis et al., *supra.*; Payne et al., *supra* |

FIG. 3b

| Cancer Lineage, Group Comparison, Other Significant Disease State | Up-regulated miRs | Down-regulated miRs | mRNAs | Mutational Analysis | Proteins Ligands Peptides | snoRNA | Select Reference(s) |
|---|---|---|---|---|---|---|---|
| **Breast** | | | MUC1 | | | | Singh R, Bandyopadhyay D, Cancer Biol Ther. 2007 Apr;6(4):481-6 |
| **Breast** | | | | | Class III b-tubulin | | Galmarini CM et al., Clin Cancer Res. 2008 Jul 15;14(14):4511-6 |
| **Breast** | | | EGFR | | | | Rajkumar T, Gullick WJ, Breast Cancer Res Treat. 1994 Jan;29(1):3-9 |
| **Breast** | | | | KRAS | | | Hollestelle A et al., Mol Cancer Res. 2007 Feb;5(2):195-201 |
| **Breast** | | | | | VEGFA | | Linderholm BK et al., Cancer Res. 2001 Mar 1:61(5):2256-60 |
| **Breast** | | | | B-Raf | | | Hollestelle A et al., Mol Cancer Res. 2007 Feb;5(2):195-201 |
| **Breast** | | | | CYP2D6 | | | Punglia RS et al., J Natl Cancer Inst. 2008 May 7;100(9):642-8 |

FIG. 4a

| Cancer Lineage, Group Comparison, Other Significant Disease State | Up-regulated miRs | Down-regulated miRs | mRNAs | Mutational Analysis | Proteins Ligands Peptides | snoRNA | Select Reference(s) |
|---|---|---|---|---|---|---|---|
| **Ovarian** | | | ERCC1 | | | | Rosell R "et al., Drugs Today (Barc). 2003 Oct;39(10):775-86 |
| **Ovarian** | | | ER | | | | Geisler JP et al., Eur J Gynaecol Oncol. 2008;29(2):126-8; Fujimoto J et al., J Steroid Biochem Mol Biol. 2007 May;104(3-5):301-4 |
| **Ovarian** | | | TOP01 | | | | Naniwa, J et al., . Int J Gynecol Cancer, 2007. 17(1): p. 76-82 |
| **Ovarian** | | | TOP2A | | | | Chekerov R et al., Neoplasia. 2006 Jan;8(1):38-45. |
| **Ovarian** | | | AR | | | | Ito K et al., Int J Cancer. 2002 Jun 10;99(5):652-7; Akahira JI et al., Jpn J Cancer Res. 2001 Sep;92(9):926-32 |
| **Ovarian** | | | PTEN | | | | Chen Y et al., Chin Med Sci J. 2004 Mar;19(1):25-30 |
| **Ovarian** | | | HER2/ neu | | | | Mileo AM et al., Int J Biol Markers. 1992 Jan-Mar;7(1):47-51 |
| **Ovarian** | | | EGFR | | | | Vermeij J et al., BMC Cancer. 2008 Jan 8;8:3; Lassus H et al., J Mol Med. 2006 Auq;84(8):671-81 |
| **Ovarian** | | | | KRAS | | | Mayr D et al., Gynecol Oncol. 2006 Dec;103(3):883-7 |
| **Ovarian** | | | | | VEGFA | | Osada R et al., Hum Pathol. 2006 Nov;37(11):1414-25. |
| **Ovarian** | | | | | VEGFR2 | | Chen BY et al., Zhonghua Zhong Liu Za Zhi. 2005 Jan;27(1):33-7 |
| **Ovarian** | | | | B-Raf | | | Sieben NL et al., J Pathol. 2004 Mar;202(3):336-40 |
| **Ovarian** | miR-200a | miR-199a | | | | | Iorio el al. Cancer Res. 2007; 67: (18). September 15, 2007 |
| **Ovarian** | miR-141 | miR-140 | | | | | Iorio el al. *Supra.* |
| **Ovarian** | miR-200c | miR-145 | | | | | Iorio el al. *Supra.* |
| **Ovarian** | miR-200b | miR-125b-1 | | | | | Iorio el al. *Supra.* |
| **Ovarian** | | | | | HER2 | | Steffensen KD et al., Int J Oncol. 2008 Jul;33(1):195-204 |

FIG. 4b

| Cancer Lineage, Group Comparison, Other Significant Disease State | Up-regulated miRs | Down-regulated miRs | mRNAs | Mutational Analysis | Proteins Ligands Peptides | snoRNA | Select Reference(s) |
|---|---|---|---|---|---|---|---|
| **Ovarian** | miR-21 | | | | | | Taylor et al., Gynecologic Oncology 110 (2008) 13-21. |
| **Ovarian** | miR-141 | | | | | | Taylor et al., *supra.* |
| **Ovarian** | miR-200a | | | | | | Taylor et al., *supra.* |
| **Ovarian** | miR-200b | | | | | | Taylor et al., *supra.* |
| **Ovarian** | mIR-200c | | | | | | Taylor et al., *supra.* |
| **Ovarian** | miR-203 | | | | | | Taylor et al., *supra..* |
| **Ovarian** | miR-205 | | | | | | Taylor et al., *supra..* |
| **Ovarian** | miR-214 | | | | | | Taylor et al., *supra.* |
| **Ovarian** | miR-215 | | | | | | Taylor et al., *supra..* |

FIG. 5

| Cancer Lineage, Group Comparison, Other Significant Disease State | Up-regulated miRs | Down-regulated miRs | mRNAs | Mutational Analysis | Proteins Ligands Peptides | snoRNA | Select Reference(s) |
|---|---|---|---|---|---|---|---|
| **Lung** | miR-21 | | | | | | Markou A et al., Clin Chem. 2008 Oct;54(10):1696-704 |
| **Lung** | miR-205 | | | | | | Markou A et al., *supra.* |
| **Lung** | miR-221 | | | | | | Garofalo M et al., Oncogene. 2008 Jun 19;27(27):3845-55 |
| **Lung** | miR-221 (protective) | | | | | | Yu SL et al., Cancer Cell. 2008 Jan;13(1):48-57 |
| **Lung** | Let-7a(protective) | | | | | | Yu SL et al., *supra.* |
| **Lung** | miR-137 (risky) | | | | | | Yu SL et al., *supra.* |
| **Lung** | miR-372(risky) | | | | | | Yu SL et al., *supra.* |
| **Lung** | miR-122a(risky) | | | | | | Yu SL et al., *supra.* |
| **Lung** | | | EGFR | | | | Rosell R et al., Clin Cancer Res. 2006 12(24):7222-31 |
| **Lung** | | | | | KRAS | | Zhang Z et al., Cancer Biol Ther. 2006 Nov;5(11):1481-6 |
| **Lung** | | | PTEN | | | | Sos ML et al., J Thorac Oncol. 2008 Feb;3(2):170-3 |
| **Lung** | | | RRM1 | | | | Souglakos et al., 2008; Rosell et al., 2004 |
| **Lung** | | | RRM2 | | | | Souglakos et al., 2008 |
| **Lung** | | | | | hENT1 | | Oguri T et al., Cancer Lett. 2007 Oct 18;256(1):112-9. |
| **Lung** | | | ABCB1 | | | | Sekine I et al., J Thorac Oncol. 2006 Jan;1(1):31-7; Ushijima R et al., Anticancer Res. 2007 Nov-Dec;27(6C):4351-8 |
| **Lung** | | | ABCG2 | | | | Nakano H et al., Cancer. 2008 Mar 1;112(5):1122-30 |
| **Lung** | | | LRP | | | | Paredes Lario A et al., Arch Bronconeumol. 2007 Sep;43(9):479-84 |
| **Lung** | | | class III b- tubulin | | | | Sève P et al., Clin Cancer Res. 2005 Aug 1;11(15):5481-6; Sève P, Clin Cancer Res. 2007 Feb 1;13(3):994-9 |
| **Lung** | | | | EGFR | | | Rosell R et al., Clin Cancer Res. 2006 Dec 15;12(24):7222-31 |
| **Lung** | | | | KRAS | | | Massarelli E et al., Clin Cancer Res, 2007. 13(10): p. 2890-6 |
| **Lung** | | | | B-Raf | | | Yousem SA et al., Am J Surg Pathol. 2008 Sep;32(9):1317-21. |
| **Lung** | | | | UGT1A1 | | | Han JY et al., J Clin Oncol. 2006 May 20;24(15):2237-44 |
| **Lung** | | | VEGFR 2/3 | | | | PCT Publication No. WO/2009/105223 |

FIG. 6a

| Cancer Lineage, Group Comparison, Other Significant Disease State | Up-regulated miRs | Down-regulated miRs | mRNAs | Mutational Analysis | Proteins Ligands Peptides | snoRNA | Select Reference(s) |
|---|---|---|---|---|---|---|---|
| **Colon** | | miR-143 | | | | | Michael et al., 2003, Mol Cancer Res 1(12): 882-91 |
| **Colon** | | miR-145 | | | | | Michael et al., 2003, *supra.* |
| **Colon** | | miR-143 | | | | | Akao et al., 2006, Oncol Rep 16(4): 845-50 |
| **Colon** | | miR-126 | | | | | Guo et al., 2008, Plant Physiol 165(16): 1745-55 |
| **Colon** | | miR-34b | | | | | Toyota et al., 2008, Cancer Res 68(11): 4123-31 |
| **Colon** | | miR-34c | | | | | Toyota et al., 2008, *supra.* |
| **Colon** | | let-7 | | | | | Akao et al., 2006, Oncol Rep, 16(4): 845-50 |
| **Colon** | miR-24-1 | | | | | | Volinia et al. Proc Natl Acad Sci USA 103: 2257-2261, 2006. |
| **Colon** | miR-29b-2 | | | | | | Volinia et al. *supra.* |
| **Colon** | miR-20a | | | | | | Volinia et al. *supra.* |
| **Colon** | miR-10a | | | | | | Volinia et al. *supra.*" |
| **Colon** | miR-32 | | | | | | Volinia et al. *supra.* |
| **Colon** | miR-203 | | | | | | Volinia et al. *supra.* |
| **Colon** | miR-106a | | | | | | Volinia et al. *supra.* |
| **Colon** | miR-17-5p | | | | | | Volinia et al. *supra.* |
| **Colon** | miR-30c | | | | | | Volinia et al. *supra.* |
| **Colon** | miR-223 | | | | | | Volinia et al. *supra.* |
| **Colon** | miR-126 | | | | | | Volinia et al. *supra.*" |
| **Colon** | miR-128b | | | | | | Volinia et al. *supra.* |
| **Colon** | miR-21 | | | | | | Volinia et al. *supra.* |
| **Colon** | miR-24-2 | | | | | | Volinia et al. *supra.* |
| **Colon** | miR-99b | | | | | | Volinia et al. *supra.* |
| **Colon** | miR-155 | | | | | | Volinia et al. *supra.* |
| **Colon** | miR-213 | | | | | | Volinia et al. *supra.* |
| **Colon** | miR-150 | | | | | | Volinia et al. *supra.* |
| **Colon** | miR-107 | | | | | | Volinia et al. *supra.* |
| **Colon** | miR-191 | | | | | | Volinia et al. *supra.*" |
| **Colon** | mIR-221 | | | | | | Volinia et al. *supra.* |
| **Colon** | | miR-9-3 | | | | | Volinia et al. *supra.* |
| **Colon** | | miR-34a | | | | | Tazawa et al., 2007, J Urol, 156(3): 967-71 |
| **Colon** | | miR-145 | | | | | Schepeler et al., 2008, Cancer Res, 68(15): 6416-23 |
| **Colon** | | miR-455 | | | | | Schepeler et al., *supra.* |
| **Colon** | | miR-484 | | | | | Schepeler et al., *supra.* |
| **Colon** | | miR-101 | | | | | Schepeler et al., *supra.* |
| **Colon** | miR-20a | | | | | | Schepeler et al., *supra.* |
| **Colon** | MiR-510 | | | | | | Schepeler et al., *supra.* |
| **Colon** | miR-92 | | | | | | Schepeler et al., *supra.* |
| **Colon** | miR-513 | | | | | | Schepeler et al., *supra.* |

FIG. 6b

| Cancer Lineage, Group Comparison, Other Significant Disease State | Up-regulated miRs | Down-regulated miRs | mRNAs | Mutational Analysis | Proteins Ligands Peptides | snoRNA | Select Reference(s) |
|---|---|---|---|---|---|---|---|
| **Colon** | miR-19a | | | | | | Bandres et al., 2006, Mol Cancer, 5:29 |
| **Colon** | miR-21 | | | | | | Bandres et al., *supra.* |
| **Colon** | miR-20 | | | | | | Bandres et al., *supra.* |
| **Colon** | miR-183 | | | | | | Bandres et al., *supra.* |
| **Colon** | miR-96 | | | | | | Bandres et al., *supra.* |
| **Colon** | miR-135b | | | | | | Bandres et al., *supra.* |
| **Colon** | miR-31 | | | | | | Bandres et al., *supra.* |
| **Colon** | | miR-145 | | | | | Bandres et al., *supra.*36 |
| **Colon** | | miR-133b | | | | | Bandres et al., *supra.* |
| **Colon** | | miR-129 | | | | | Bandres et al., *supra.* |
| **Colon** | | miR-124a | | | | | Bandres et al., *supra.* |
| **Colon** | | miR-30-3p | | | | | Bandres et al., *supra.* |
| **Colon** | | miR-328 | | | | | Bandres et al., *supra.* |
| **Colon** | | miR-106a | | | | | Diaz et al., 2008, Br J Anaesth, 101(2): 161-4 |
| **Colon** | | miR-17-5p | | | | | Diaz et al., *supra.* |
| **Colon** | mIR-21 | | | | | | Schetter et al. 2008, JAMA, 299(4): 425 |
| **Colon** | miR-92 | | | | | | Schetter et al. *supra.* |
| **Colon** | miR-222 | | | | | | Schetter et al. *supra.* |
| **Colon** | miR-181b | | | | | | Schetter et al. *supra.* |
| **Colon** | miR-210 | | | | | | Schetter et al. *supra.* |
| **Colon** | miR-20a | | | | | | Schetter et al. *supra.* |
| **Colon** | miR-106a | | | | | | Schetter et al. *supra.* |
| **Colon** | miR-93 | | | | | | Schetter et al. *supra.* |
| **Colon** | miR-335 | | | | | | Schetter et al. *supra.* |
| **Colon** | miR-338 | | | | | | Schetter et al. *supra.* |
| **Colon** | miR-133b | | | | | | Schetter et al. *supra.* |
| **Colon** | miR-346 | | | | | | Schetter et al. *supra.* |
| **Colon** | miR-106b | | | | | | Schetter et al. *supra.* |
| **Colon** | miR-153a | | | | | | Schetter et al. *supra.* |
| **Colon** | miR-219 | | | | | | Schetter et al. *supra.* |
| **Colon** | miR-34a | | | | | | Schetter et al. *supra.* |
| **Colon** | miR-99b | | | | | | Schetter et al. *supra.* |
| **Colon** | miR-185 | | | | | | Schetter et al. *supra.* |
| **Colon** | miR-223 | | | | | | Schetter et al. *supra.* |
| **Colon** | miR-211 | | | | | | Schetter et al. *supra.* |
| **Colon** | miR-135a | | | | | | Schetter et al. *supra.* |
| **Colon** | miR-127 | | | | | | Schetter et al. *supra.* |
| **Colon** | miR-203 | | | | | | Schetter et al. *supra.* |
| **Colon** | miR-212 | | | | | | Schetter et al. *supra.* |
| **Colon** | miR-95 | | | | | | Schetter et al. *supra.* |
| **Colon** | miR-17-5p | | | | | | Schetter et al. *supra.* |
| **Colon** | | miR-342 | | | | | Schetter et al. *supra.* |
| **Colon** | | miR-192 | | | | | Schetter et al. *supra.* |
| **Colon** | | miR-1 | | | | | Schetter et al. *supra.* |
| **Colon** | | miR-34b | | | | | Schetter et al. *supra.* |

FIG. 6c

| Cancer Lineage, Group Comparison, Other Significant Disease State | Up-regulated miRs | Down-regulated miRs | mRNAs | Mutational Analysis | Proteins Ligands Peptides | snoRNA | Select Reference(s) |
|---|---|---|---|---|---|---|---|
| Colon | | miR-215 | | | | | Schetter et al. *supra.* |
| Colon | | miR-192 | | | | | Schetter et al. *supra.* |
| Colon | | miR-301 | | | | | Schetter et al. *supra.* |
| Colon | | miR-324-5p | | | | | Schetter et al. *supra.* |
| Colon | | miR-30a-3p | | | | | Schetter et al. *supra.* |
| Colon | | miR-34c | | | | | Schetter et al. *supra.* |
| Colon | | miR-331 | | | | | Schetter et al. *supra.* |
| Colon | | miR-148b | | | | | Schetter et al. *supra.* |
| Colon | | | | | AFRs | | Choi et al., 2007, J Ethnopharmacol 110(1): 49-55. |
| Colon | | | | | Rabs | | Choi et al., *supra.* |
| Colon | | | | | ADAM10 | | Choi et al., *supra.* |
| Colon | | | | | CD44 | | Choi et al., *supra.* |
| Colon | | | | | NG2 | | Choi et al., *supra..* |
| Colon | | | | | ephrin-B1 | | Choi et al., *supra.* |
| Colon | | | | | MIF | | Choi et al., *supra.* |
| Colon | | | | | b-catenin | | Choi et al., *supra.* |
| Colon | | | | | Junction | | Choi et al., *supra.* |
| Colon | | | | | plakoglobin | | Choi et al., *supra.* |
| Colon | | | | | glalectin-4 | | Choi et al., *supra.* |
| Colon | | | | | RACK1 | | Choi et al., *supra.* |
| Colon | | | | | tetrspanin-8 | | Choi et al., *supra.* |
| Colon | | | | | FastL | | Choi et al., *supra.* |
| Colon | | | | | TRAIL | | Choi et al., *supra.* |
| Colon | | | | | A33 | | Choi et al., *supra.* |
| Colon | | | | | CEA | | Choi et al., *supra.* |
| Colon | | | | | EGFR | | Choi et al., *supra.* |
| Colon | | | | | dipeptidase 1 | | Choi et al., *supra.* |
| Colon | | | | | hsc-70 | | Choi et al., *supra.* |
| Colon | | | | | tetraspanins | | Choi et al., *supra.* |
| Colon | | | | | ESCRT | | Choi et al., *supra.* |
| Colon | | | EFNB1 | | | | Huber et al., 2005, Gastroenterol Nurs 28(6): 510-1. |
| Colon | | | ERCC1 | | | | Shirota Y et al., J Clin Oncol, 2001. 19(23): p. 4298-304 |
| Colon | | | | | TS | | Cascinu S et al., Ann Oncol, 2001. 12(2): p. 239-44; Ciaparrone M et al., Oncology, 2006. 70(5): p. 366-77 |
| Colon | | | | | PTEN | | Frattini et al., 2007 |

FIG. 6d

| Cancer Lineage, Group Comparison, Other Significant Disease State | Up-regulated miRs | Down-regulated miRs | mRNAs | Mutational Analysis | Proteins Ligands Peptides | snoRNA | Select Reference(s) |
|---|---|---|---|---|---|---|---|
| **Colon** | | | | | TOPO1 | | Braun MS et al., J Clin Oncol, 2008. 26(16): p. 2690-8 |
| **Colon** | | | HER2 | | | | Ochs AM et al., Clin Colorectal Cancer. 2004 Nov;4(4):262-7 |
| **Colon** | | | VEGF | | | | Ochs AM et al., *supra.* |
| **Colon** | | | EGFR | | | | Cappuzo et al 2008, Sartore-Bianche et al 2007 |
| **Colon** | | | | EGFR | | | Zhang X et al., Oncol Rep. 2008 Jun;19(6):1541-4; Riese DJ 2nd et al., Bioessays. 2007 Jun;29(6):558-65 |
| **Colon** | | | | KRAS | | | Amado RG et al., J Clin Oncol, 2008. 26(10): p. 1626-34; De Roock W et al., Ann Oncol, 2008. 19(3): p. 508-15. |
| **Colon** | | | | VEGFA | | | Uthoff SM et al., Int J Cancer. 2002 Sep 1;101(1):32-6. |
| **Colon** | | | | B-Raf | | | Ogino S et al., Gut. 2008 Oct 2; Matos P et al., Gastroenterology. 2008 Sep;135(3):899-906 |
| **Colon** | | | | APC | | | Conlin A et al., Gut, 2005. 54(9): p. 1283-6 |
| **Colon** | | | | p53 | | | Conlin A et al., *supra.* |

FIG. 7

| Cancer Lineage, Group Comparison, Other Significant Disease State | Up-regulated miRs | Down-regulated miRs | mRNAs | Mutational Analysis | Proteins Ligands Peptides | snoRNA | Select Reference(s) |
|---|---|---|---|---|---|---|---|
| **Adenoma versus Hyperplastic Polyp** | | | ABCA8 | | | did not find any | Galamb et al., 2008,Cancer Epidemiol Biomarkers Prev 17(10): 2835-45 |
| **Adenoma versus Hyperplastic Polyp** | | | KIAA1199 | | | | Galamb et al., *supra.* |
| **Adenoma versus Hyperplastic Polyp** | | | GCG | | | | Galamb et al., *supra.* |
| **Adenoma versus Hyperplastic Polyp** | | | MAMDC2 | | | | Galamb et al., *supra.* |
| **Adenoma versus Hyperplastic Polyp** | | | C2orf32 | | | | Galamb et al., *supra.* |
| **Adenoma versus Hyperplastic Polyp** | | | 229670_at | | | | Galamb et al., *supra.* |
| **Adenoma versus Hyperplastic Polyp** | | | IGF1 | | | | Galamb et al., *supra.* |
| **Adenoma versus Hyperplastic Polyp** | | | PCDH7 | | | | Galamb et al., *supra.* |
| **Adenoma versus Hyperplastic Polyp** | | | PRDX6 | | | | Galamb et al., *supra.* |
| **Adenoma versus Hyperplastic Polyp** | | | | BRAF | | | Kim YH et al., Int J Cancer. 2008 Dec 1;123(11):2587-93 |
| **Adenoma versus Hyperplastic Polyp** | | | | KRAS | | | Rashid A et al., Gastroenterology. 2000 Aug;119(2)•323-32 |
| **Adenoma versus Hyperplastic Polyp** | | | PCNA | | | | Barletta A et al., Anticancer Res. 1998 May-Jun;18(3A):1677-82 |
| **Adenoma versus Hyperplastic Polyp** | | | COX2 | | | | McLean MH et al., Histopathology. 2008 Jun;52(7):806-15. Epub 2008 May 6. |
| **Adenoma versus Hyperplastic Polyp** | | | MUC6 | | | | Owens SR et al., Mod Pathol. 2008 Jun;21(6):660-9. |
| **Adenoma versus Hyperplastic Polyp** | | | | | hTERT | | Oka S et al., Scand J Gastroenterol. 2002 Oct;37(10):1194-200 |

FIG. 8

| Cancer Lineage, Group Comparison, Other Significant Disease State | Up-regulated miRs | Down-regulated miRs | mRNAs | Mutational Analysis | Proteins Ligands Peptides | snoRNA | Select Reference(s) |
|---|---|---|---|---|---|---|---|
| **IBD versus normal** | | | REG1A | | | | Galamb et al., 2008, "Inflammation, Adenoma and Cancer Objective Classification of Colon Biopsy Specimens with Gene Expression Signature", Dis Markers, 25(1): 1-16 |
| **IBD versus normal** | | | MMP3 | | | | Galamb et al., *supra.* |

FIG. 9a

| Cancer Lineage, Group Comparison, Other Significant Disease State | Up-regulated miRs | Down-regulated miRs | mRNAs | Mutational Analysis | Proteins Ligands Peptides | snoRNA | Select Reference(s) |
|---|---|---|---|---|---|---|---|
| **Adenoma versus CRC** | | | GREM1 | | | | Galamb et al., 2008, Dis Markers, 25(1): 1-16. |
| **Adenoma versus CRC** | | | DDR2 | | | | Galamb et al., *supra.* |
| **Adenoma versus CRC** | | | GUCY1A3 | | | | Galamb et al., *supra.* |
| **Adenoma versus CRC** | | | TNS1 | | | | Galamb et al., *supra.* |
| **Adenoma versus CRC** | | | ADAMTS1 | | | | Galamb et al., *supra.* |
| **Adenoma versus CRC** | | | FBLN1 | | | | Galamb et al., *supra.* |
| **Adenoma versus CRC** | | | FLJ38028 | | | | Galamb et al., *supra.* |
| **Adenoma versus CRC** | | | RDX | | | | Galamb et al., *supra.* |
| **Adenoma versus CRC** | | | FAM129A | | | | Galamb et al., *supra.* |
| **Adenoma versus CRC** | | | ASPN | | | | Galamb et al., *supra.* |
| **Adenoma versus CRC** | | | FRMD6 | | | | Galamb et al., *supra.* |
| **Adenoma versus CRC** | | | MCC | | | | Galamb et al., *supra.* |
| **Adenoma versus CRC** | | | RBMS1 | | | | Galamb et al., *supra.* |
| **Adenoma versus CRC** | | | SNAI2 | | | | Galamb et al., *supra.* |
| **Adenoma versus CRC** | | | MEIS1 | | | | Galamb et al., *supra.* |
| **Adenoma versus CRC** | | | DOCK10 | | | | Galamb et al., *supra.* |
| **Adenoma versus CRC** | | | PLEKHC1 | | | | Galamb et al., *supra.* |
| **Adenoma versus CRC** | | | FAM126A | | | | Galamb et al., *supra.* |
| **Adenoma versus CRC** | | | TBC1D9 | | | | Galamb et al., *supra.* |
| **Adenoma versus CRC** | | | VWF | | | | Galamb et al., *supra.* |
| **Adenoma versus CRC** | | | DCN | | | | Galamb et al., *supra.* |
| **Adenoma versus CRC** | | | ROBO1 | | | | Galamb et al., *supra.* |
| **Adenoma versus CRC** | | | MSRB3 | | | | Galamb et al., *supra.* |
| **Adenoma versus CRC** | | | LATS2 | | | | Galamb et al., *supra.* |

FIG. 9b

| Cancer Lineage, Group Comparison, Other Significant Disease State | Up-regulated miRs | Down-regulated miRs | mRNAs | Mutational Analysis | Proteins Ligands Peptides | snoRNA | Select Reference(s) |
|---|---|---|---|---|---|---|---|
| Adenoma versus CRC | | | MEF2C | | | | Galamb et al., *supra.* |
| Adenoma versus CRC | | | IGFBP3 | | | | Galamb et al., *supra.* |
| Adenoma versus CRC | | | GNB4 | | | | Galamb et al., *supra.* |
| Adenoma versus CRC | | | RCN3 | | | | Galamb et al., *supra.* |
| Adenoma versus CRC | | | AKAP12 | | | | Galamb et al., *supra.* |
| Adenoma versus CRC | | | RFTN1 | | | | Galamb et al., *supra.* |
| Adenoma versus CRC | | | 226834_at | | | | Galamb et al., *supra.* |
| Adenoma versus CRC | | | COL5A1 | | | | Galamb et al., *supra.* |
| Adenoma versus CRC | | | GNG2 | | | | Galamb et al., *supra.* |
| Adenoma versus CRC | | | NR3C1 | | | | Galamb et al., *supra.* |
| Adenoma versus CRC | | | SPARCL1 | | | | Galamb et al., *supra.* |
| Adenoma versus CRC | | | MAB21L2 | | | | Galamb et al., *supra.* |
| Adenoma versus CRC | | | AXIN2 | | | | Galamb et al., *supra.* |
| Adenoma versus CRC | | | 236894_at | | | | Galamb et al., *supra.* |
| Adenoma versus CRC | | | AEBP1 | | | | Galamb et al., *supra.* |
| Adenoma versus CRC | | | AP1S2 | | | | Galamb et al., *supra.* |
| Adenoma versus CRC | | | C10orf56 | | | | Galamb et al., *supra.* |
| Adenoma versus CRC | | | LPHN2 | | | | Galamb et al., *supra.* |
| Adenoma versus CRC | | | AKT3 | | | | Galamb et al., *supra.* |
| Adenoma versus CRC | | | FRMD6 | | | | Galamb et al., *supra.* |
| Adenoma versus CRC | | | COL15A1 | | | | Galamb et al., *supra.* |
| Adenoma versus CRC | | | CRYAB | | | | Galamb et al., *supra.* |
| Adenoma versus CRC | | | COL14A1 | | | | Galamb et al., *supra.* |
| Adenoma versus CRC | | | LOC286167 | | | | Galamb et al., *supra.* |

FIG. 9c

| Cancer Lineage, Group Comparison, Other Significant Disease State | Up-regulated miRs | Down-regulated miRs | mRNAs | Mutational Analysis | Proteins Ligands Peptides | snoRNA | Select Reference(s) |
|---|---|---|---|---|---|---|---|
| **Adenoma versus CRC** | | | QKI | | | | Galamb et al., *supra.* |
| **Adenoma versus CRC** | | | WWTR1 | | | | Galamb et al., *supra.* |
| **Adenoma versus CRC** | | | GNG11 | | | | Galamb et al., *supra.* |
| **Adenoma versus CRC** | | | PAPPA | | | | Galamb et al., *supra.* |
| **Adenoma versus CRC** | | | ELDT1 | | | | Galamb et al., *supra.* |

FIG. 10

| Cancer Lineage, Group Comparison, Other Significant Disease State | Up-regulated miRs | Down-regulated miRs | mRNAs | Mutational Analysis | Proteins Ligands Peptides | snoRNA | Select Reference(s) |
|---|---|---|---|---|---|---|---|
| **IBD versus CRC** | | | 227458_at | | | | Galamb et al., 2008, Helicobacter, 13(2); 112-26. |
| **IBD versus CRC** | | | INDO | | | | Galamb et al., *supra.* |
| **IBD versus CRC** | | | CXCL9 | | | | Galamb et al., *supra.* |
| **IBD versus CRC** | | | CCR2 | | | | Galamb et al., *supra.* |
| **IBD versus CRC** | | | CD38 | | | | Galamb et al., *supra.* |
| **IBD versus CRC** | | | RARRES3 | | | | Galamb et al., *supra.* |
| **IBD versus CRC** | | | CXCL10 | | | | Galamb et al., *supra.* |
| **IBD versus CRC** | | | FAM26F | | | | Galamb et al., *supra.* |
| **IBD versus CRC** | | | TNIP3 | | | | Galamb et al., *supra.* |
| **IBD versus CRC** | | | NOS2A | | | | Galamb et al., *supra.* |
| **IBD versus CRC** | | | CCRL1 | | | | Galamb et al., *supra.* |
| **IBD versus CRC** | | | TLR8 | | | | Galamb et al., *supra.* |
| **IBD versus CRC** | | | IL18BP | | | | Galamb et al., *supra.* |
| **IBD versus CRC** | | | FCRL5 | | | | Galamb et al., *supra.* |
| **IBD versus CRC** | | | SAMD9L | | | | Galamb et al., *supra.* |
| **IBD versus CRC** | | | ECGF1 | | | | Galamb et al., *supra.* |
| **IBD versus CRC** | | | TNFSF13B | | | | Galamb et al., *supra.* |
| **IBD versus CRC** | | | GBP5 | | | | Galamb et al., *supra.* |
| **IBD versus CRC** | | | GBP1 | | | | Galamb et al., *supra.* |

FIG. 11a

| Cancer Lineage, Group Comparison, Other Significant Disease State | Up-regulated miRs | Down-regulated miRs | mRNAs | Mutational Analysis | Proteins Ligands Peptides | snoRNA | Select Reference(s) |
|---|---|---|---|---|---|---|---|
| CRC Dukes B versus Dukes C-D | | | TMEM37* | | | | Galamb et al., 2008, Helicobacter, 13(2); 112-26. |
| CRC Dukes B versus Dukes C-D | | | IL33 | | | | Galamb et al., *supra.* |
| CRC Dukes B versus Dukes C-D | | | CA4 | | | | Galamb et al., *supra.* |
| CRC Dukes B versus Dukes C-D | | | CCDC58 | | | | Galamb et al., *supra.* |
| CRC Dukes B versus Dukes C-D | | | CLIC6 | | | | Galamb et al., *supra.* |
| CRC Dukes B versus Dukes C-D | | | VSNL1 | | | | Galamb et al., *supra.* |
| CRC Dukes B versus Dukes C-D | | | ESPN | | | | Galamb et al., *supra.* |
| CRC Dukes B versus Dukes C-D | | | APCDDI | | | | Galamb et al., *supra.* |
| CRC Dukes B versus Dukes C-D | | | C13orf18 | | | | Galamb et al., *supra.* |
| CRC Dukes B versus Dukes C-D | | | CYP4X1 | | | | Galamb et al., *supra.* |
| CRC Dukes B versus Dukes C-D | | | ATP2A3 | | | | Galamb et al., *supra.* |
| CRC Dukes B versus Dukes C-D | | | LOC646627 | | | | Galamb et al., *supra.* |
| CRC Dukes B versus Dukes C-D | | | MUPCDH | | | | Galamb et al., *supra.* |
| CRC Dukes B versus Dukes C-D | | | ANPEP | | | | Galamb et al., *supra.* |
| CRC Dukes B versus Dukes C-D | | | C1orf115 | | | | Galamb et al., *supra.* |
| CRC Dukes B versus Dukes C-D | | | HSD3B2 | | | | Galamb et al., *supra.* |
| CRC Dukes B versus Dukes C-I) | | | GBA3 | | | | Galamb et al., *supra.* |
| CRC Dukes B versus Dukes C-D | | | GABRB2 | | | | Galamb et al., *supra.* |
| CRC Dukes B versus Dukes C-13 | | | GYLTL1 B | | | | Galamb et al., *supra.* |
| CRC Dukes B versus Dukes C-D | | | LYZ | | | | Galamb et al., *supra.* |
| CRC Dukes B versus Dukes C-D | | | SPC25 | | | | Galamb et al., *supra.* |
| CRC Dukes B versus Dukes C-D | | | CDKN2B | | | | Galamb et al., *supra.* |
| CRC Dukes B versus Dukes C-D | | | FAM89A | | | | Galamb et al., *supra.* |

FIG. 11b

| Cancer Lineage, Group Comparison, Other Significant Disease State | Up-regulated miRs | Down-regulated miRs | mRNAs | Mutational Analysis | Proteins Ligands Peptides | snoRNA | Select Reference(s) |
|---|---|---|---|---|---|---|---|
| **CRC Dukes B versus Dukes C-D** | | | MOGAT2 | | | | Galamb et al., *supra.* |
| **CRC Dukes B versus Dukes C-D** | | | SEMA6D | | | | Galamb et al., *supra.* |
| **CRC Dukes B versus Dukes C-D** | | | 229376_at | | | | Galamb et al., *supra.* |
| **CRC Dukes B versus Dukes C-D** | | | TSPAN5 | | | | Galamb et al., *supra.* |
| **CRC Dukes B versus Dukes C-D** | | | IL6R | | | | Galamb et al., *supra.* |
| **CRC Dukes B versus Dukes C-D** | | | SLC26A2 | | | | Galamb et al., *supra.* |
| **CRC Dukes B versus Dukes C-D** | | | | | PAR4 | | Madoz-Gúrpide et al., Mol. Cell. Prot. 6:2150-64, 2007 |
| **CRC Dukes B versus Dukes C-D** | | | | | DIABLO | | Madoz-Gúrpide J et al., *supra.* |
| **CRC Dukes B versus Dukes C-D** | | | | | caspase-3 | | Madoz-Gúrpide J et al., *supra* |
| **CRC Dukes B versus Dukes C-D** | | | | | p53 | | Madoz-Gúrpide J et al., *supra* |
| **CRC Dukes B versus Dukes C-D** | | | | | TRF1 | | Madoz-Gúrpide J et al., *supra* |
| **CRC Dukes B versus Dukes C-D** | | | | | c-myc | | Madoz-Gúrpide J et al., *supra* |

FIG. 12a

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Adenoma with low grade versus high grade dysplasia** | | | SI | | | | Galamb et al., 2008, Dis Markers, 25(1): 1-16 |
| **Adenoma with low grade versus high grade dysplasia** | | | DMBT1 | | | | Galamb et al. *supra.* |
| **Adenoma with low grade versus high grade dysplasia** | | | CFI* | | | | Galamb et al. *supra.* |
| **Adenoma with low grade versus high grade dysplasia** | | | AQP1 | | | | Galamb et al. *supra.* |
| **Adenoma with low grade versus high grade dysplasia** | | | APOD | | | | Galamb et al. *supra..* |
| **Adenoma with low grade versus high grade dysplasia** | | | TNFRSF17 | | | | Galamb et al. *supra.* |
| **Adenoma with low grade versus high grade dysplasia** | | | CXCL10 | | | | Galamb et al. *supra.* |
| **Adenoma with low grade versus high grade dysplasia** | | | CTSE | | | | Galamb et al. *supra..* |
| **Adenoma with low grade versus high grade dysplasia** | | | IGHA1 | | | | Galamb et al. *supra.* |
| **Adenoma with low grade versus high grade dysplasia** | | | SLC9A3 | | | | Galamb et al. *supra..* |
| **Adenoma with low grade versus high grade dysplasia** | | | SLC7A1 | | | | Galamb et al. *supra..* |
| **Adenoma with low grade versus high grade dysplasia** | | | BATF2 | | | | Galamb et al. *supra.* |
| **Adenoma with low grade versus high grade dysplasia** | | | SOCS1 | | | | Galamb et al. *supra.* |
| **Adenoma with low grade versus high grade dysplasia** | | | DOCK2 | | | | Galamb et al. *supra.* |
| **Adenoma with low grade versus high grade dysplasia** | | | NOS2A | | | | Galamb et al. *supra.* |
| **Adenoma with low grade versus high grade dysplasia** | | | HK2 | | | | Galamb et al. *supra.* |

FIG. 12b

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| Adenoma with low grade versus high grade dysplasia | | | CXCL2 | | | | Galamb et al. *supra.* |
| Adenoma with low grade versus high grade dysplasia | | | IL15RA | | | | Galamb et al. *supra..* |
| Adenoma with low grade versus high grade dysplasia | | | POU2AF1 | | | | Galamb et al. *supra.* |
| Adenoma with low grade versus high grade dysplasia | | | CLEC3B | | | | Galamb et al. *supra.* |
| Adenoma with low grade versus high grade dysplasia | | | ANI3BP | | | | Galamb et al. *supra.* |
| Adenoma with low grade versus high grade dysplasia | | | MGC13057 | | | | Galamb et al. *supra.* |
| Adenoma with low grade versus high grade dysplasia | | | LCK* | | | | Galamb et al. *supra.* |
| Adenoma with low grade versus high grade dysplasia | | | C4BPA | | | | Galamb et al. *supra.* |
| Adenoma with low grade versus high grade dysplasia | | | HOXC6 | | | | Galamb et al. *supra.* |
| Adenoma with low grade versus high grade dysplasia | | | GOLT1A | | | | Galamb et al. *supra.* |
| Adenoma with low grade versus high grade dysplasia | | | C2orf32 | | | | Galamb et al. *supra.* |
| Adenoma with low grade versus high grade dysplasia | | | IL10RA | | | | Galamb et al. *supra.* |
| Adenoma with low grade versus high grade dysplasia | | | 240856_at | | | | Galamb et al. *supra.* |
| Adenoma with low grade versus high grade dysplasia | | | SOCS3 | | | | Galamb et al. *supra.* |
| Adenoma with low grade versus high grade dysplasia | | | MEIS3P1 | | | | Galamb et al. *supra.* |
| Adenoma with low grade versus high grade dysplasia | | | HIPK1 | | | | Galamb et al. *supra.* |

FIG. 12c

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| Adenoma with low grade versus high grade dysplasia | | | GLS | | | | Galamb et al. *supra.* |
| Adenoma with low grade versus high grade dysplasia | | | CPLX1 | | | | Galamb et al. *supra.* |
| Adenoma with low grade versus high grade dysplasia | | | 236045_x_at | | | | Galamb et al. *supra.* |
| Adenoma with low grade versus high grade dysplasia | | | GALC | | | | Galamb et al. *supra.* |
| Adenoma with low grade versus high grade dysplasia | | | AMN | | | | Galamb et al. *supra.* |
| Adenoma with low grade versus high grade dysplasia | | | CCDC69 | | | | Galamb et al. *supra.* |
| Adenoma with low grade versus high grade dysplasia | | | CCL28 | | | | Galamb et al. *supra.* |
| Adenoma with low grade versus high grade dysplasia | | | CPA3 | | | | Galamb et al. *supra.* |
| Adenoma with low grade versus high grade dysplasia | | | TRIB2 | | | | Galamb et al. *supra.* |
| Adenoma with low grade versus high grade dysplasia | | | HMGA2 | | | | Galamb et al. *supra.* |
| Adenoma with low grade versus high grade dysplasia | | | PLCL2 | | | | Galamb et al. *supra.* |
| Adenoma with low grade versus high grade dysplasia | | | NR3C1 | | | | Galamb et al. *supra.* |
| Adenoma with low grade versus high grade dysplasia | | | EIF5A | | | | Galamb et al. *supra.* |
| Adenoma with low grade versus high grade dysplasia | | | LARP4 | | | | Galamb et al. *supra.* |
| Adenoma with low grade versus high grade dysplasia | | | RP5-1022P6.2 | | | | Galamb et al. *supra.* |
| Adenoma with low grade versus high grade dysplasia | | | PHLDB2 | | | | Galamb et al. *supra.* |

FIG. 12d

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| Adenoma with low grade versus high grade dysplasia | | | FKBP1B | | | | Galamb et al. *supra.* |
| Adenoma with low grade versus high grade dysplasia | | | INDO | | | | Galamb et al. *supra.* |
| Adenoma with low grade versus high grade dysplasia | | | CLDN8 | | | | Galamb et al. *supra.* |
| Adenoma with low grade versus high grade dysplasia | | | CNTN3 | | | | Galamb et al. *supra.* |
| Adenoma with low grade versus high grade dysplasia | | | PBEF1 | | | | Galamb et al. *supra.* |
| Adenoma with low grade versus high grade dysplasia | | | SLC16A9 | | | | Galamb et al. *supra.* |
| Adenoma with low grade versus high grade dysplasia | | | CDC25B | | | | Galamb et al. *supra.* |
| Adenoma with low grade versus high grade dysplasia | | | TPSB2 | | | | Galamb et al. *supra.* |
| Adenoma with low grade versus high grade dysplasia | | | PBEF1 | | | | Galamb et al. *supra.* |
| Adenoma with low grade versus high grade dysplasia | | | ID4 | | | | Galamb et al. *supra.* |
| Adenoma with low grade versus high grade dysplasia | | | GJB5 | | | | Galamb et al. *supra.* |
| Adenoma with low grade versus high grade dysplasia | | | CHN2 | | | | Galamb et al. *supra.* |
| Adenoma with low grade versus high grade dysplasia | | | LIMCH1 | | | | Galamb et al. *supra.* |
| Adenoma with low grade versus high grade dysplasia | | | CXCL9 | | | | Galamb et al. *supra.* |

FIG. 13a

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **UC vs CD** | | | IFITM1 | | | | Wu F., et al., 2007, Inflamm Bowel Dis, 13(7): 807-21. |
| **UC vs CD** | | | IFITM3 | | | | Wu F., et al., 2007 *supra.* |
| **UC vs CD** | | | STAT1 | | | | Wu F., et al., 2007 *supra* |
| **UC vs CD** | | | STAT3 | | | | Wu F., et al., 2007 *supra* |
| **UC vs CD** | | | TAP1 | | | | Wu F., et al., 2007 *supra* |
| **UC vs CD** | | | PSME2 | | | | Wu F., et al., 2007 *supra* |
| **UC vs CD** | | | PSMB8 | | | | Wu F., et al., 2007 *supra* |
| **UC vs CD** | | | HNF4G | | | | Wu F., et al., 2007 *supra* |
| **UC vs CD** | | | KLF5 | | | | Wu F., et al., 2007 *supra* |
| **UC vs CD** | | | AQP8 | | | | Wu F., et al., 2007 *supra* |
| **UC vs CD** | | | APT2B1 | | | | Wu F., et al., 2007 *supra* |
| **UC vs CD** | | | SLC16A | | | | Wu F., et al., 2007 *supra* |
| **UC vs CD** | | | MFAP4 | | | | Galamb et al., 2008, Helicobacter, 13(2); 112-26. |
| **UC vs CD** | | | CCNG2 | | | | Galamb et al., *supra.* |
| **UC vs CD** | | | SLC44A4 | | | | Galamb et al., *supra.* |
| **UC vs CD** | | | DDAH1 | | | | Galamb et al., *supra.* |
| **UC vs CD** | | | TOB1 | | | | Galamb et al., *supra.* |
| **UC vs CD** | | | 231152_at | | | | Galamb et al., *supra.* |
| **UC vs CD** | | | MKNK1 | | | | Galamb et al., *supra.* |
| **UC vs CD** | | | CEACAM7* | | | | Galamb et al., *supra.* |
| **UC vs CD** | | | 1562836_at | | | | Galamb et al., *supra.* |
| **UC vs CD** | | | CDC42SE2 | | | | Galamb et al., *supra.* |
| **UC vs CD** | | | PSD3 | | | | Galamb et al., *supra.* |
| **UC vs CD** | | | 231169_at | | | | Galamb et al., *supra.* |
| **UC vs CD** | | | IGL@* | | | | Galamb et al., *supra.* |
| **UC vs CD** | | | GSN | | | | Galamb et al., *supra.* |
| **UC vs CD** | | | GPM6B | | | | Galamb et al., *supra.* |
| **UC vs CD** | | | CDV3* | | | | Galamb et al., *supra.* |
| **UC vs CD** | | | PDPK1 | | | | Galamb et al., *supra.* |
| **UC vs CD** | | | ANP32E | | | | Galamb et al., *supra.* |
| **UC vs CD** | | | ADAM9 | | | | Galamb et al., *supra.* |
| **UC vs CD** | | | CDH1 | | | | Galamb et al., *supra.* |
| **UC vs CD** | | | NLRP2 | | | | Galamb et al., *supra.* |
| **UC vs CD** | | | 215777_at | | | | Galamb et al., *supra.* |
| **UC vs CD** | | | OSBPL1 | | | | Galamb et al., *supra.* |
| **UC vs CD** | | | VNN1 | | | | Galamb et al., *supra.* |
| **UC vs CD** | | | RABGAP1L | | | | Galamb et al., *supra.* |
| **UC vs CD** | | | PHACTR2 | | | | Galamb et al., *supra.* |
| **UC vs CD** | | | ASH1L | | | | Galamb et al., *supra.* |
| **UC vs CD** | | | 213710_s_at | | | | Galamb et al., *supra.* |
| **UC vs CD** | | | CDH1 | | | | Galamb et al., *supra.* |
| **UC vs CD** | | | NLRP2 | | | | Galamb et al., *supra.* |
| **UC vs CD** | | | 215777_at | | | | Galamb et al., *supra.* |
| **UC vs CD** | | | OSBPLI | | | | Galamb et al., *supra.* |

FIG. 13b

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **UC vs CD** | | | VNN1 | | | | Galamb et al., *supra.* |
| **UC vs CD** | | | RABGAP1L | | | | Galamb et al., *supra.* |
| **UC vs CD** | | | PHACTR2 | | | | Galamb et al., *supra.* |
| **UC vs CD** | | | ASH1 | | | | Galamb et al., *supra.* |
| **UC vs CD** | | | 213710_s_at | | | | Galamb et al., *supra.* |
| **UC vs CD** | | | ZNF3 | | | | Galamb et al., *supra.* |
| **UC vs CD** | | | FUT2 | | | | Galamb et al., *supra.* |
| **UC vs CD** | | | IGHA1 | | | | Galamb et al., *supra.* |
| **UC vs CD** | | | EDEM1 | | | | Galamb et al., *supra.* |
| **UC vs CD** | | | GPR171 | | | | Galamb et al., *supra.* |
| **UC vs CD** | | | 229713_at | | | | Galamb et al., *supra.* |
| **UC vs CD** | | | LOC643187 | | | | Galamb et al., *supra.* |
| **UC vs CD** | | | FLVCRI | | | | Galamb et al., *supra.* |
| **UC vs CD** | | | SNAP23* | | | | Galamb et al., *supra.* |
| **UC vs CD** | | | ETNK1 | | | | Galamb et al., *supra.* |
| **UC vs CD** | | | LOC728411 | | | | Galamb et al., *supra.* |
| **UC vs CD** | | | POSTN | | | | Galamb et al., *supra.* |
| **UC vs CD** | | | MUC12 | | | | Galamb et al., *supra.* |
| **UC vs CD** | | | HOXA5 | | | | Galamb et al., *supra.* |
| **UC vs CD** | | | SIGLEC1 | | | | Galamb et al., *supra.* |
| **UC vs CD** | | | LARP5 | | | | Galamb et al., *supra.* |
| **UC vs CD** | | | PIGR | | | | Galamb et al., *supra.* |
| **UC vs CD** | | | SPTBN1 | | | | Galamb et al., *supra.* |
| **UC vs CD** | | | UFM1 | | | | Galamb et al., *supra.* |
| **UC vs CD** | | | C6orf62 | | | | Galamb et al., *supra.* |
| **UC vs CD** | | | WDR90 | | | | Galamb et al., *supra.* |
| **UC vs CD** | | | ALDH1A3 | | | | Galamb et al., *supra.* |
| **UC vs CD** | | | F2RL1 | | | | Galamb et al., *supra.* |
| **UC vs CD** | | | IGHV1-69 | | | | Galamb et al., *supra.* |
| **UC vs CD** | | | DUOX2 | | | | Galamb et al., *supra.* |
| **UC vs CD** | | | RAB5A | | | | Galamb et al., *supra.* |
| **UC vs CD** | | | CP | | | | Galamb et al., *supra.* |
| **UC vs CD** | | | | CARD15 | | | Radford-Smith et al 2007, Gastroenterology 132(7): 2313-9. |
| **UC vs CD** | | | | | (P)ASCA | | Li X et al., World J Gastroenterol. 2008 Sep 7;14(33):5115-24. |

FIG. 14

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| Hyperplastic polyp versus normal | | | SLC6A14 | | | | Galamb et al., 2008, Cancer Epidemiol Biomarkers Prev, 17(10): 2835-45 |
| Hyperplastic polyp versus normal | | | ARHGEF10 | | | | Galamb et al., *supra.* |
| Hyperplastic polyp versus normal | | | ALS2 | | | | Galamb et al., *supra.* |
| Hyperplastic polyp versus normal | | | IL1RN | | | | Galamb et al., *supra.* |
| Hyperplastic polyp versus normal | | | SPRY4 | | | | Galamb et al., *supra.* |
| Hyperplastic polyp versus normal | | | PTGER3 | | | | Galamb et al., *supra.* |
| Hyperplastic polyp versus normal | | | TRIM29 | | | | Galamb et al., *supra.* |
| Hyperplastic polyp versus normal | | | SERPINB5 | | | | Galamb et al., *supra.* |
| Hyperplastic polyp versus normal | | | 1560327_at | | | | Galamb et al., *supra.* |
| Hyperplastic polyp versus normal | | | ZAK | | | | Galamb et al., *supra.* |
| Hyperplastic polyp versus normal | | | BAG4 | | | | Galamb et al., *supra.* |
| Hyperplastic polyp versus normal | | | TRIB3 | | | | Galamb et al., *supra.* |
| Hyperplastic polyp versus normal | | | TTL | | | | Galamb et al., *supra.* |
| Hyperplastic polyp versus normal | | | FOXQ1 | | | | Galamb et al., *supra.* |

FIG. 15

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| Adenoma with low grade dysplasia versus normal | | | UGT2A3 | | | | Galamb et al., 2008, Dis Markers, 25(1): 1-16. |
| Adenoma with low grade dysplasia versus normal | | | KLK11 | | | | Galamb et al., *supra.* |
| Adenoma with low grade dysplasia versus normal | | | KIAA1199 | | | | Galamb et al., *supra.* |
| Adenoma with low grade dysplasia versus normal | | | FOXQ1 | | | | Galamb et al., *supra.* |
| Adenoma with high grade dysplasia versus normal | | | CLDN8 | | | | Galamb et al., *supra.* |
| Adenoma with high grade dysplasia versus normal | | | ABCA8 | | | | Galamb et al., *supra.* |
| Adenoma with high grade dysplasia versus normal | | | PYY | | | | Galamb et al., *supra.* |

FIG. 16

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Adenoma versus normal** | | | KIAA1199 | | | | Galamb et al., 2008, Dis Markers, 25(1): 1-16. |
| **Adenoma versus normal** | | | FOXQ1 | | | | Galamb et al., *supra.* |
| **Adenoma versus normal** | | | CA7 | | | | Galamb et al., *supra.* |
| **Adenoma versus normal** | | | | | Clusterin | | Chen X et al., Proc Natl Acad Sci U S A. 2003 Aug 5;100(16):9530-5. |

FIG. 17

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| CRC versus normal | | | VWF | | | | Galamb et al., 2008, Dis Markers, 25(1): 1-16 |
| CRC versus normal | | | IL8 | | | | Galamb et al., *supra.* |
| CRC versus normal | | | CHI3L1 | | | | Galamb et al., *supra.* |
| CRC versus normal | | | S100A8 | | | | Galamb et al., *supra.* |
| CRC versus normal | | | GREM1 | | | | Galamb et al., *supra.* |
| CRC versus normal | | | ODC | | | | Hu HY et al., World J Gastroenterol. 2005 Apr 21;11(15):2244-8. |
| CRC versus normal | | | | KRAS | | | Amado RG et al., J Clin Oncol, 2008.26(10): p. 1626-34; De Roock W et al., Ann Oncol, 2008. 19(3): p. 508-15. |
| CRC versus normal | | | | BRAF | | | Ogino S et al., Gut. 2008 Oct 2; Matos P et al., Gastroenterology. 2008 Sep;135(3):899-906. |
| CRC versus normal | | | | APC | | | Conlin A et al., Gut, 2005. 54(9): p. 1283-6. |
| CRC versus normal | | | | MSH2 | | | Davidson NO, Keio J Med. 2007 Mar;56(1):14-20. |
| CRC versus normal | | | | MLH1 | | | Davidson NO, Keio *supra.* |
| CRC versus normal | | | | | cytokeratin 13 | | Madoz-Gúrpide J et al., Molecular & Cellular Proteomics 6:2150-2164, 2007. |
| CRC versus normal | | | | | calcineurin | | Madoz-Gúrpide J et al., *supra.* |
| CRC versus normal | | | | | CHK1 | | Madoz-Gúrpide J et al., *supra.* |
| CRC versus normal | | | | | clathrin light chain | | Madoz-Gúrpide J et al., *supra.* |
| CRC versus normal | | | | | phospho-ERK | | Madoz-Gúrpide J et al., *supra.* |
| CRC versus normal | | | | | phospho-PTK2 | | Madoz-Gúrpide J et al., *supra.* |
| CRC versus normal | | | | | MDM2 | | Madoz-Gúrpide J et al., *supra.* |

FIG. 18

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Benign Prostatic Hyperplasia** | | | | | Intact Fibronectin | | Janković MM, Kosanović MM, Dis Markers, 2008;25(1):49-58. |

FIG. 19a

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Prostate** | | | | | FASLG | | Huber et al., 2005, Gastroenterol Nurs 28(6): 510-1. |
| **Prostate** | | | | | TNFSF10 | | Huber et al., 2005, *supra.* |
| **Prostate** | | | | | FASLG | | Adreola et al., JEM 195:10 1303-1316 (2002) |
| **Prostate** | | | | | TNFSF10 | | Adreola et al., *supra.* |
| **Prostate** | | | | | FASLG | | Abusamra et al., 2005, Blood Cells Mol Dis, 35(2): 169-73 |
| **Prostate** | | | | | TNFSF10 | | Abusamra et al., 2005, *supra.* |
| **Prostate** | | | | | FASLG | | Kim et al., Int J Cancer. 2008 Dec 1;123(11):2587-93. |
| **Prostate** | | | | | TNFSF10 | | Kim et al., *supra.* |
| **Prostate** | | | | | FASLG | | Taylor et al., 2003, Int J Oncol 22(6): 1311-7 |
| **Prostate** | | | | | TNFSF10 | | Taylor et al., *supra.* |
| **Prostate** | | let-7a | | | | | Porkka et al., 2007, Cancer Res, 67(13): 6130-5 |
| **Prostate** | | let-7b | | | | | Porkka et al., *supra.* |
| **Prostate** | | let-7c | | | | | Porkka et al., *supra.* |
| **Prostate** | | let-7d | | | | | Porkka et al., *supra.* |
| **Prostate** | | let-7g | | | | | Porkka et al., *supra.* |
| **Prostate** | | miR-16 | | | | | Porkka et al., *supra.* |
| **Prostate** | | miR-23a | | | | | Porkka et al., *supra.* |
| **Prostate** | | miR-23b | | | | | Porkka et al., *supra.* |
| **Prostate** | | miR-26a | | | | | Porkka et al., *supra.* |
| **Prostate** | | miR-92 | | | | | Porkka et al., *supra.* |
| **Prostate** | | miR-99a | | | | | Porkka et al., *supra.* |
| **Prostate** | | miR-103 | | | | | Porkka et al., *supra.* |
| **Prostate** | | miR-125a | | | | | Porkka et al., *supra.* |
| **Prostate** | | miR-125b | | | | | Porkka et al., *supra.* |
| **Prostate** | | miR-143 | | | | | Porkka et al., *supra.* |
| **Prostate** | | miR-145 | | | | | Porkka et al., *supra.* |
| **Prostate** | | miR-195 | | | | | Porkka et al., *supra.* |
| **Prostate** | | miR-199 | | | | | Porkka et al., *supra.* |
| **Prostate** | | miR-221 | | | | | Porkka et al., *supra.* |
| **Prostate** | | miR-222 | | | | | Porkka et al., *supra.* |
| **Prostate** | | miR-497 | | | | | Porkka et al., *supra.* |
| **Prostate** | | let-7f | | | | | Porkka et al., *supra.* |
| **Prostate** | | miR-19b | | | | | Porkka et al., *supra.* |
| **Prostate** | | miR-22 | | | | | Porkka et al., *supra.* |
| **Prostate** | | miR-26b | | | | | Porkka et al., *supra.* |
| **Prostate** | | miR-27a | | | | | Porkka et al., *supra.* |

FIG. 19b

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Prostate** | | miR-27b | | | | | Porkka et al., *supra.* |
| **Prostate** | | miR-29a | | | | | Porkka et al., *supra.* |
| **Prostate** | | miR-29b | | | | | Porkka et al., *supra.* |
| **Prostate** | | miR-30_5p | | | | | Porkka et al., *supra.* |
| **Prostate** | | miR-30c | | | | | Porkka et al., *supra.* |
| **Prostate** | | miR-100 | | | | | Porkka et al., *supra.* |
| **Prostate** | | miR-141 | | | | | Porkka et al., *supra.* |
| **Prostate** | | miR-148a | | | | | Porkka et al., *supra.* |
| **Prostate** | | miR-205 | | | | | Porkka et al., *supra.* |
| **Prostate** | miR-202 | | | | | | Porkka et al., *supra.* |
| **Prostate** | miR-210 | | | | | | Porkka et al., *supra.* |
| **Prostate** | miR-296 | | | | | | Porkka et al., *supra.* |
| **Prostate** | miR-320 | | | | | | Porkka et al., *supra.* |
| **Prostate** | miR-370 | | | | | | Porkka et al., *supra.* |
| **Prostate** | miR-373 | | | | | | Porkka et al., *supra.* |
| **Prostate** | miR-498 | | | | | | Porkka et al., *supra.* |
| **Prostate** | miR-503 | | | | | | Porkka et al., *supra.* |
| **Prostate** | miR-184 | | | | | | Porkka et al., *supra.* |
| **Prostate** | miR-198 | | | | | | Porkka et al., *supra.* |
| **Prostate** | miR-302c | | | | | | Porkka et al., *supra.* |
| **Prostate** | miR-345 | | | | | | Porkka et al., *supra.*5 |
| **Prostate** | miR-491 | | | | | | Porkka et al., *supra.* |
| **Prostate** | miR-513 | | | | | | Porkka et al., *supra.* |
| **Prostate** | miR-32 | | | | | | Ambs et al., 2008, Cancer Res, 68(15): 6162-70 |
| **Prostate** | miR-182 | | | | | | Ambs et al., *supra.* |
| **Prostate** | miR-31 | | | | | | Ambs et al., *supra.* |
| **Prostate** | miR-26a-1/2 | | | | | | Ambs et al., *supra.*-70 |
| **Prostate** | miR-200c | | | | | | Ambs et al., *supra.* |
| **Prostate** | miR-375 | | | | | | Ambs et al., *supra.* |
| **Prostate** | miR-196a-1/2 | | | | | | Ambs et al., *supra.* |
| **Prostate** | miR-370 | | | | | | Ambs et al., *supra.* |
| **Prostate** | miR-425 | | | | | | Ambs et al., *supra.* |
| **Prostate** | miR-425 | | | | | | Ambs et al., *supra.* |
| **Prostate** | miR-194-1/2 | | | | | | Ambs et al., *supra.* |
| **Prostate** | miR-181a-1/2 | | | | | | Ambs et al., *supra.* |
| **Prostate** | miR-34b | | | | | | Ambs et al., *supra.* |

FIG. 19c

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Prostate** | let-7i | | | | | | Ambs et al., *supra.* |
| **Prostate** | miR-188 | | | | | | Ambs et al., *supra.* |
| **Prostate** | miR-25 | | | | | | Ambs et al., *supra.* |
| **Prostate** | miR-106b | | | | | | Ambs et al., *supra.* |
| **Prostate** | miR-449 | | | | | | Ambs et al., *supra.* |
| **Prostate** | miR-99b | | | | | | Ambs et al., *supra.* |
| **Prostate** | miR-93 | | | | | | Ambs et al., *supra.* |
| **Prostate** | miR-92-1/2 | | | | | | Ambs et al., *supra.* |
| **Prostate** | miR-125a | | | | | | Ambs et al., *supra.* |
| **Prostate** | | miR-520h | | | | | Ambs et al., *supra.* |
| **Prostate** | | miR-494 | | | | | Ambs et al., *supra.* |
| **Prostate** | | miR-490 | | | | | Ambs et al., *supra.* |
| **Prostate** | | miR-133a-1 | | | | | Ambs et al., *supra.* |
| **Prostate** | | miR-1-2 | | | | | Ambs et al., *supra.* |
| **Prostate** | | miR-218-2 | | | | | Ambs et al., *supra.* |
| **Prostate** | | miR-220 | | | | | Ambs et al., *supra.* |
| **Prostate** | | miR-128a | | | | | Ambs et al., *supra.* |
| **Prostate** | | miR-221 | | | | | Ambs et al., *supra.* |
| **Prostate** | | miR-499 | | | | | Ambs et al., *supra.* |
| **Prostate** | | miR-329 | | | | | Ambs et al., *supra.* |
| **Prostate** | | miR-340 | | | | | Ambs et al., *supra.* |
| **Prostate** | | miR-345 | | | | | Ambs et al., *supra.* |
| **Prostate** | | miR-410 | | | | | Ambs et al., *supra.* |
| **Prostate** | | miR-126 | | | | | Ambs et al., *supra.* |
| **Prostate** | | miR-205. | | | | | Ambs et al., *supra.* |
| **Prostate** | | miR-7-1/2 | | | | | Ambs et al., *supra.* |
| **Prostate** | | miR-145 | | | | | Ambs et al., *supra.* |
| **Prostate** | | miR-34a | | | | | Ambs et al., *supra.* |
| **Prostate** | | miR-487 | | | | | Ambs et al., *supra.* |
| **Prostate** | | let-7b | | | | | Ambs et al., *supra.* |
| **Prostate** | | | | | | U50 | Dong et al., 2008, Prostate 68(4): 381-99. |
| **Prostate** | | | AR | | | | |
| **Prostate** | miR-141 | | | | | | Mitchell et al. PNAS 2008 |
| **Prostate** | | | PCA3 | | | | Marks et. Al, Urology 69: 532-535, 2007. |

FIG. 20a

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Melanoma** | | | | | Alix | | Mears et al., 2004, Proteomics 4(12): 4019-31. |
| **Melanoma** | | | | | hsp70 | | Mears et al., *supra.* |
| **Melanoma** | | | | | Gib2 | | Mears et al., *supra.* |
| **Melanoma** | | | | | Gia | | Mears et al., *supra.* |
| **Melanoma** | | | | | moesin | | Mears et al., *supra.* |
| **Melanoma** | | | | | GAPDH | | Mears et al., *supra.* |
| **Melanoma** | | | | | malate dehydro-genase | | Mears et al., *supra.* |
| **Melanoma** | | | | | p120 catenin | | Mears et al., *supra.* |
| **Melanoma** | | | | | PGRL | | Mears et al., *supra.* |
| **Melanoma** | | | | | syntaxin-binding protein 1 & 2 | | Mears et al., *supra.* |
| **Melanoma** | | | | | septin-2 | | Mears et al., *supra.* |
| **Melanoma** | | | | | WD-repeat containing protein 1 | | Mears et al., *supra.* |
| **Melanoma** | | miR-9 | | | | | Schultz et al., 2008, Cell Res 18(5): 549-57. |
| **Melanoma** | | miR-15a | | | | | Schultz et al., *supra.* |
| **Melanoma** | | miR-17-3p | | | | | Schultz et al., *supra.* |
| **Melanoma** | miR-19a | | | | | | Schultz et al., *supra.* |
| **Melanoma** | | miR-23b | | | | | Schultz et al., *supra.* |
| **Melanoma** | | miR-27a | | | | | Schultz et al., *supra.* |
| **Melanoma** | | miR-28 | | | | | Schultz et al., *supra.* |
| **Melanoma** | | miR-29b | | | | | Schultz et al., *supra.* |
| **Melanoma** | | miR-30b | | | | | Schultz et al., *supra.* |
| **Melanoma** | | miR-31 | | | | | Schultz et al., *supra.* |
| **Melanoma** | | miR-34b | | | | | Schultz et al., *supra.* |
| **Melanoma** | | m1R-34c | | | | | Schultz et al., *supra.* |
| **Melanoma** | | miR-95 | | | | | Schultz et al., *supra.* |
| **Melanoma** | | miR-96 | | | | | Schultz et al., *supra.* |
| **Melanoma** | | miR-100 | | | | | Schultz et al., *supra.* |
| **Melanoma** | | miR-104 | | | | | Schultz et al., *supra.* |
| **Melanoma** | | miR-105 | | | | | Schultz et al., *supra.* |
| **Melanoma** | | miR-106a | | | | | Schultz et al., *supra.* |
| **Melanoma** | | miR-107 | | | | | Schultz et al., *supra.* |
| **Melanoma** | | miR-122a | | | | | Schultz et al., *supra.* |
| **Melanoma** | | miR-124a | | | | | Schultz et al., *supra.* |

FIG. 20b

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Melanoma** | | miR-125b | | | | | Schultz et al., *supra.* |
| **Melanoma** | | miR-127 | | | | | Schultz et al., *supra.* |
| **Melanoma** | | miR-128a | | | | | Schultz et al., *supra.* |
| **Melanoma** | | miR-128b | | | | | Schultz et al., *supra.* |
| **Melanoma** | | miR-129 | | | | | Schultz et al., *supra.* |
| **Melanoma** | | miR-135a | | | | | Schultz et al., *supra.* |
| **Melanoma** | | miR-135b | | | | | Schultz et al., *supra.* |
| **Melanoma** | | miR-137 | | | | | Schultz et al., *supra.* |
| **Melanoma** | | miR-138 | | | | | Schultz et al., *supra.* |
| **Melanoma** | | miR-139 | | | | | Schultz et al., *supra.* |
| **Melanoma** | | miR-140 | | | | | Schultz et al., *supra.* |
| **Melanoma** | | miR-141 | | | | | Schultz et al., *supra.* |
| **Melanoma** | miR-144 | | | | | | Schultz et al., *supra.* |
| **Melanoma** | | miR-149 | | | | | Schultz et al., *supra.* |
| **Melanoma** | | miR-154 | | | | | Schultz et al., *supra.* |
| **Melanoma** | | miR-154#3 | | | | | Schultz et al., *supra.* |
| **Melanoma** | | miR-181a | | | | | Schultz et al., *supra.* |
| **Melanoma** | | miR-182 | | | | | Schultz et al., *supra.* |
| **Melanoma** | | miR-183 | | | | | Schultz et al., *supra.* |
| **Melanoma** | | miR-184 | | | | | Schultz et al., *supra.* |
| **Melanoma** | | miR-185 | | | | | Schultz et al., *supra.* |
| **Melanoma** | | miR-189 | | | | | Schultz et al., *supra.* |
| **Melanoma** | | miR-190 | | | | | Schultz et al., *supra.* |
| **Melanoma** | | miR-199 | | | | | Schultz et al., *supra.* |
| **Melanoma** | | miR-199b | | | | | Schultz et al., *supra.* |
| **Melanoma** | | miR-200a | | | | | Schultz et al., *supra.* |
| **Melanoma** | | miR-200b | | | | | Schultz et al., *supra.* |
| **Melanoma** | miR-200c | | | | | | Schultz et al., *supra.* |
| **Melanoma** | | miR-204 | | | | | Schultz et al., *supra.* |
| **Melanoma** | miR-211 | | | | | | Schultz et al., *supra.* |
| **Melanoma** | | miR-213 | | | | | Schultz et al., *supra.* |
| **Melanoma** | | miR-215 | | | | | Schultz et al., *supra.* |
| **Melanoma** | | miR-216 | | | | | Schultz et al., *supra.* |
| **Melanoma** | | miR-219 | | | | | Schultz et al., *supra.* |
| **Melanoma** | | miR-222 | | | | | Schultz et al., *supra.* |
| **Melanoma** | | miR-224 | | | | | Schultz et al., *supra.* |
| **Melanoma** | | miR-299 | | | | | Schultz et al., *supra.* |
| **Melanoma** | | miR-302a | | | | | Schultz et al., *supra.* |
| **Melanoma** | | miR-302b | | | | | Schultz et al., *supra.* |
| **Melanoma** | | miR-302c | | | | | Schultz et al., *supra.* |
| **Melanoma** | | miR-302d | | | | | Schultz et al., *supra.* |
| **Melanoma** | | miR-323 | | | | | Schultz et al., *supra.* |

FIG. 20c

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Melanoma** | miR-324-5p | | | | | | Schultz et al., *supra.* |
| **Melanoma** | | miR-325 | | | | | Schultz et al., *supra.* |
| **Melanoma** | miR-331 | | | | | | Schultz et al., *supra.* |
| **Melanoma** | miR-374 | | | | | | Schultz et al., *supra.* |
| **Melanoma** | | let-7a | | | | | Schultz et al., *supra.* |
| **Melanoma** | | let-7b | | | | | Schultz et al., *supra.* |
| **Melanoma** | | let-7d | | | | | Schultz et al., *supra.* |
| **Melanoma** | | let-7e | | | | | Schultz et al., *supra.* |
| **Melanoma** | | let-7g | | | | | Schultz et al., *supra.* |
| **Melanoma** | | | | CDK4 | | | Castelli et al., J Cell Physiology 182(3)323-31, 2000. |
| **Melanoma** | | | MUM-1 | | | | Castelli et al., *supra.* |
| **Melanoma** | | | beta-catenin | | | | Castelli et al., *supra.* |
| **Melanoma** | | | Nop/5/Sik | | | | Nakamoto et al., American Journal of Pathology 159(4), 2001. |
| **Melanoma** | | | | | | H/ACA (U107f) | Luo and Li, 2007, J Ind Microbiol Biotechnol 34(2): 117-22. |
| **Melanoma** | | | | | | SNO RA11D | Yang et al., nar 34:5112-5123, 2006 |
| **Melanoma** | | | | | DUSP-1 | | |

FIG. 21a

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Pancreatic** | miR-221 | | | | | | Bloomston et al., 2008, J Gastrointest Surg. Dec;11(12):1680-5. |
| **Pancreatic** | miR-181a | | | | | | Bloomston et al., *supra.* |
| **Pancreatic** | miR-155 | | | | | | Bloomston et al., *supra* |
| **Pancreatic** | miR-210 | | | | | | Bloomston et al., *supra* |
| **Pancreatic** | miR-213 | | | | | | Bloomston et al., *supra.* |
| **Pancreatic** | miR-181b | | | | | | Bloomston et al., *supra* |
| **Pancreatic** | miR-222 | | | | | | Bloomston et al., *supra.* |
| **Pancreatic** | miR-181b-2 | | | | | | Bloomstom et al., *supra.* |
| **Pancreatic** | miR-21 | | | | | | Bloomstom et al., *supra.* |
| **Pancreatic** | miR-181b-1 | | | | | | Bloomstom et al., *supra.* |
| **Pancreatic** | miR-181c | | | | | | Bloomstom et al., *supra.* |
| **Pancreatic** | miR-220 | | | | | | Bloomstom et al., *supra.* |
| **Pancreatic** | miR-181d | | | | | | Bloomstom et al., *supra.* |
| **Pancreatic** | miR-223 | | | | | | Bloomstom et al., *supra.* |
| **Pancreatic** | miR-100-1/2 | | | | | | Bloomstom et al., *supra.* |
| **Pancreatic** | miR-125a | | | | | | Bloomstom et al., *supra.* |
| **Pancreatic** | miR-143 | | | | | | Bloomstom et al., *supra.* |
| **Pancreatic** | miR-10a | | | | | | Bloomstom et al., *supra.* |
| **Pancreatic** | mi R-146 | | | | | | Bloomstom et al., *supra.* |
| **Pancreatic** | miR-99 | | | | | | Bloomstom et al., *supra.* |
| **Pancreatic** | miR-100 | | | | | | Bloomstom et al., *supra.* |
| **Pancreatic** | miR-199a-1 | | | | | | Bloomstom et al., *supra.* |
| **Pancreatic** | miR-10b | | | | | | Bloomstom et al., *supra.* |
| **Pancreatic** | miR-199a-2 | | | | | | Bloomstom et al., *supra.* |
| **Pancreatic** | miR-107 | | | | | | Bloomstom et al., *supra.* |
| **Pancreatic** | miR-103-2 | | | | | | Bloomstom et al., *supra.* |
| **Pancreatic** | miR-125b-1 | | | | | | Bloomstom et al., *supra.* |
| **Pancreatic** | miR-205 | | | | | | Bloomstom et al., *supra.* |
| **Pancreatic** | miR-23a | | | | | | Bloomstom et al., *supra.* |
| **Pancreatic** | | miR-148a | | | | | Bloomstom et al., *supra.* |
| **Pancreatic** | | mIR-148b | | | | | Bloomstom et al., *supra.* |
| **Pancreatic** | | miR-375 | | | | | Bloomstom et al., *supra.* |
| **Pancreatic** | miR-221 | | | | | | Lee et al., 2006, J Biol Chem 281(5): 2649-53. |
| **Pancreatic** | miR-424 | | | | | | Lee at al., *supra.* |

FIG. 21b

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Pancreatic** | miR-301 | | | | | | Lee at al., *supra.* |
| **Pancreatic** | miR-100 | | | | | | Lee at al., *supra.* |
| **Pancreatic** | miR-376a | | | | | | Lee at al., *supra.* |
| **Pancreatic** | miR-125b-1 | | | | | | Lee at al., *supra.* |
| **Pancreatic** | miR-21 | | | | | | Lee at al., *supra.* |
| **Pancreatic** | | miR-345 | | | | | Lee at al., *supra.* |
| **Pancreatic** | miR-16-1 | | | | | | Lee at al., *supra.* |
| **Pancreatic** | miR-181a | | | | | | Lee at al., *supra.* |
| **Pancreatic** | miR-181c | | | | | | Lee at al., *supra.* |
| **Pancreatic** | miR-92 | | | | | | Lee at al., *supra.* |
| **Pancreatic** | miR-15 | | | | | | Lee at al., *supra.* |
| **Pancreatic** | | miR-142 | | | | | Lee at al., *supra.* |
| **Pancreatic** | miR-155 | | | | | | Lee at al., *supra.* |
| **Pancreatic** | let-7f-1 | | | | | | Lee at al., *supra.* |
| **Pancreatic** | miR-212 | | | | | | Lee at al., *supra.* |
| **Pancreatic** | miR-107 | | | | | | Lee at al., *supra.* |
| **Pancreatic** | miR-024-1/2 | | | | | | Lee at al., *supra.* |
| **Pancreatic** | let-7d | | | | | | Lee at al., *supra.* |
| **Pancreatic** | | miR-139 | | | | | Lee at al., *supra.* |
| **Pancreatic** | | | | KRAS | | | Shibata D et al., Baillieres Clin Gastroenterol. 1990 Mar;4(1):151-69. |
| **Pancreatic** | | | | CTNNLB1 | | | Shi C et al., Adv Anat Pathol. 2008 Jul;15(4):185-95. |
| **Pancreatic** | | | | AKT | | | Kang SP and Siaf MW, JOP. J Pancreas (Online) 2008; 9(3):251-266. |
| **Pancreatic** | | | | NCOA3 | | | Kang SP and Siaf MW, *supra.* |
| **Pancreatic** | | | | B-RAF | | | Kang SP and Siaf MW, *supra* |
| **Pancreatic** | | | PSCA | | | | Koorstra JB et al., Pancreatology. 2008;8(2)110-25. Epub 2008 Apr 1. |
| **Pancreatic** | | | Meso-thelin | | | | Koorstra JB et al., *supra.* |
| **Pancreatic** | | | Osteo-pontin | | | | Koorstra JB et al., *supra.* |

FIG. 22

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Brain** | miR-21 | | | | | | Mathupala et al., 2007, DNA Cell Biol, 26(5): 301-10 |
| **Brain** | miR-10b | | | | | | Ciafre et al., 2005, Biochem Biophys Res 2005 Sep 9;334(4):1351. |
| **Brain** | miR-130a | | | | | | Ciafre et al., *supra.* |
| **Brain** | miR-221 | | | | | | Ciafre et al., *supra.* |
| **Brain** | miR-125b-1 | | | | | | Ciafre et al., *supra.* |
| **Brain** | miR-125b-2 | | | | | | Ciafre et al., *supra.* |
| **Brain** | miR-9-2 | | | | | | Ciafre et al., *supra.* |
| **Brain** | miR-21 | | | | | | Ciafre et al., *supra.* |
| **Brain** | miR-25 | | | | | | Ciafre et al., *supra.* |
| **Brain** | miR-23 | | | | | | Ciafre et al., *supra.* |
| **Brain** | | miR-128a | | | | | Ciafre et al., *supra.* |
| **Brain** | | miR-181c | | | | | Ciafre et al., *supra.* |
| **Brain** | | miR-181a | | | | | Ciafre et al., *supra.* |
| **Brain** | | miR-181b | | | | | Ciafre et al., *supra.* |
| **Brain** | | | MGMT | | | | Blank M et al., JBC May 11; 276(19)16464-8, 2001 |
| **Brain** | | | | | EGFR | | Hicke et al., J. Biol. Chem. 276, 48644-48654, 2001; Daniels et al., PNAS 100, 15416-15421, 2003 |

FIG. 23a

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Psoriasis** | miR-146b | | | | | | Sonkoly et al., 2007, PLoS ONE, 2(7): e610 |
| **Psoriasis** | miR-20a | | | | | | Sonkoly et al., *supra.* |
| **Psoriasis** | miR-146a | | | | | | Sonkoly et al., *supra.* |
| **Psoriasis** | miR-31 | | | | | | Sonkoly et al., *supra.* |
| **Psoriasis** | miR-200a | | | | | | Sonkoly et al., *supra.* |
| **Psoriasis** | miR-17-5p | | | | | | Sonkoly et al., *supra.* |
| **Psoriasis** | miR-30e-5p | | | | | | Sonkoly et al., *supra.* |
| **Psoriasis** | miR-141 | | | | | | Sonkoly et al., *supra.* |
| **Psoriasis** | miR-203 | | | | | | Sonkoly et al., *supra.* |
| **Psoriasis** | miR-142-3p | | | | | | Sonkoly et al., *supra.* |
| **Psoriasis** | miR-21 | | | | | | Sonkoly et al., *supra.* |
| **Psoriasis** | miR-106a | | | | | | Sonkoly et al., *supra.* |
| **Psoriasis** | | miR-125b | | | | | Sonkoly et al., *supra.* |
| **Psoriasis** | | miR-99b | | | | | Sonkoly et al., *supra.* |
| **Psoriasis** | | miR-122a | | | | | Sonkoly et al., *supra.* |
| **Psoriasis** | | miR-197 | | | | | Sonkoly et al., *supra.* |
| **Psoriasis** | | miR-100 | | | | | Sonkoly et al., *supra.* |
| **Psoriasis** | | miR-381 | | | | | Sonkoly et al., *supra.* |
| **Psoriasis** | | miR-518b | | | | | Sonkoly et al., *supra.* |
| **Psoriasis** | | miR-524 | | | | | Sonkoly et al., *supra.* |
| **Psoriasis** | | let-7e | | | | | Sonkoly et al., *supra.* |
| **Psoriasis** | | miR-30c | | | | | Sonkoly et al., *supra.* |
| **Psoriasis** | | miR-365 | | | | | Sonkoly et al., *supra.* |
| **Psoriasis** | | miR-133b | | | | | Sonkoly et al., *supra.* |
| **Psoriasis** | | miR-10a | | | | | Sonkoly et al., *supra.* |
| **Psoriasis** | | miR-133a | | | | | Sonkoly et al., *supra.* |
| **Psoriasis** | | miR-22 | | | | | Sonkoly et al., *supra.* |
| **Psoriasis** | | miR-326 | | | | | Sonkoly et al., *supra.* |
| **Psoriasis** | | miR-215 | | | | | Sonkoly et al., *supra.* |
| **Psoriasis** | | | IL-20 | | | | Stenderup K et al., Ann N Y Acad Sci. 2007 Sep;1110:368-81. |
| **Psoriasis** | | | VEGFR-1 | | | | Man XY et al., J Cell Mol Med. 2008 Apr;12(2):649-60 |
| **Psoriasis** | | | VEGFR-2 | | | | Man XY et al., *supra.* |
| **Psoriasis** | | | VEGFR-3 | | | | Man XY et al., *supra.* |

FIG. 23b

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Psoriasis** | | | EGR1 | | | | Fang M et al., Genomic Med. 2007;1(1-2):75-85. Epub 2007 Jul 25 |
| **Psoriasis** | | | | MGST2 | | | Yan KL et al., J Invest Dermatol. 2006 May;126(5):1003-5. |

FIG. 24a

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Cardiovascular Disease** | | | | | CK-MB | | Wu AH et al., 1996, Clin Chem, 42(4): 651-2 |
| **Cardiovascular Disease** | | | | | cTnI (cardiac troponin) | | Wu AH et al., *supra.* |
| **Cardiovascular Disease** | | | | | C-reactive protein | | Rifai N and Ridker PM, Clin Chem. 2001 Mar;47(3):403-11. |
| **Cardiovascular Disease** | | | | | cardiac Troponin (cTn) | | O'Brien PJ, Toxicology. 2008 Mar 20;245(3):206-18. |
| **Cardiovascular Disease** | | | | | IL-6 | | Ikonomidis I et al., Atherosclerosis. 2008 Jul;199(1):3-11. |
| **Cardiovascular Disease** | | | | | MCSF | | Ikonomidis I et al., *supra.* |
| **Cardiovascular Disease** | | | | | BNP | | Wang TJ et al., N Engl J Med. 350 (7): 655-63 |
| **Cardiovascular Disease** | | miR-1 | | | | | van Rooij et al., 2008, Circ. Res, 103(9): 919-28 |
| **Cardiovascular Disease** | miR-195 | | | | | | van Rooij et al., *supra.* |
| **Cardiovascular Disease** | miR-208 | | | | | | van Rooij et al., *supra.* |
| **Cardiovascular Disease** | | miR-1 | | | | | Ikeda et al., 2007, Physiol Genomics 31(3): 367-73. |
| **Cardiovascular Disease** | miR-214 | | | | | | Ikeda et al., 2007, *supra.* |
| **Cardiovascular Disease** | let-7b | | | | | | Ikeda et al., *supra.* |
| **Cardiovascular Disease** | let-7c | | | | | | Ikeda et al., *supra.* |
| **Cardiovascular Disease** | let-7e | | | | | | Ikeda et al., *supra.* |
| **Cardiovascular Disease** | | miR-10a | | | | | Ikeda et al., *supra.* |
| **Cardiovascular Disease** | miR-15b | | | | | | Ikeda et al., *supra.* |
| **Cardiovascular Disease** | | miR-17-5p | | | | | Ikeda et al., *supra.* |
| **Cardiovascular Disease** | | miR-19a | | | | | Ikeda et al., *supra.* |
| **Cardiovascular Disease** | | miR-19b | | | | | Ikeda et al., *supra.* |
| **Cardiovascular Disease** | | miR-20a | | | | | Ikeda et al., *supra.* |
| **Cardiovascular Disease** | | miR-20b | | | | | Ikeda et al., *supra.* |

FIG. 24b

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| Cardiovascular Disease | miR-23a | | | | | | Ikeda et al., *supra.* |
| Cardiovascular Disease | miR-24 | | | | | | Ikeda et al., *supra.* |
| Cardiovascular Disease | | miR-26b | | | | | Ikeda et al., *supra.* |
| Cardiovascular Disease | miR-27a | | | | | | Ikeda et al., *supra.* |
| Cardiovascular Disease | miR-27b | | | | | | Ikeda et al., *supra.* |
| Cardiovascular Disease | | miR-28 | | | | | Ikeda et al., *supra.* |
| Cardiovascular Disease | | miR-30e-5p | | | | | Ikeda et al., *supra.* |
| Cardiovascular Disease | miR-93 | | | | | | Ikeda et al., *supra.* |
| Cardiovascular Disease | miR-99b | | | | | | Ikeda et al., *supra.* |
| Cardiovascular Disease | miR-100 | | | | | | Ikeda et al., *supra.* |
| Cardiovascular Disease | | miR-101 | | | | | Ikeda et al., *supra.* |
| Cardiovascular Disease | miR-103 | | | | | | Ikeda et al., *supra.* |
| Cardiovascular Disease | | miR-106a | | | | | Ikeda et al., *supra.* |
| Cardiovascular Disease | miR-125b | | | | | | Ikeda et al., *supra.* |
| Cardiovascular Disease | | miR-126 | | | | | Ikeda et al., *supra.* |
| Cardiovascular Disease | miR-140 | | | | | | Ikeda et al., *supra.* |
| Cardiovascular Disease | miR-145 | | | | | | Ikeda et al., *supra.* |
| Cardiovascular Disease | miR-181a | | | | | | Ikeda et al., *supra.* |
| Cardiovascular Disease | miR-191 | | | | | | Ikeda et al., *supra.* |
| Cardiovascular Disease | miR-195 | | | | | | Ikeda et al., *supra.* |
| Cardiovascular Disease | miR-199a | | | | | | Ikeda et al., *supra.* |
| Cardiovascular Disease | | miR-222 | | | | | Ikeda et al., *supra.* |
| Cardiovascular Disease | miR-320 | | | | | | Ikeda et al., *supra.* |
| Cardiovascular Disease | miR-342 | | | | | | Ikeda et al., *supra.* |

FIG. 24c

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Cardiovascular Disease** | | miR-374 | | | | | Ikeda et al., *supra.* |
| **Cardiovascular Disease** | | miR-422b | | | | | Ikeda et al., *supra.* |
| **Cardiovascular Disease** | | miR-423 | | | | | Ikeda et al., *supra.* |
| **Cardiovascular Disease** | miR-451 | | | | | | Ikeda et al., *supra.* |
| **Cardiovascular Disease** | miR-499 | | | | | | Ikeda et al., *supra.* |
| **Cardiovascular Disease** | | | | MYH7 | | | Buvoli M et al., Trends Cardiovasc Med. 2008 May;18(4):141-9. |
| **Cardiovascular Disease** | | | | SCN5A | | | Makita N et al., J Clin Invest. 2008 Jun;118(6):2219-29,. |
| **Cardiovascular Disease** | | | | CHRM2 | | | Zhang L et al., Circ Res. 2008 Jun 6;102(11):1426-32. Epub 2008 May 1. |
| **Cardiovascular Disease** | | | MRP14 | | | | Healy AM et al., Circulation 113:2278-2284, 2006. |
| **Cardiovascular Disease** | | | CD69 | | | | Healy AM et al., *supra.* |
| **Cardiovascular Disease** | | | | | CRP | | Moura LM et al., Expert Rev Cardiovasc Ther. 2008 Aug;6(7):945-54. |
| **Cardiovascular Disease** | | | | | BPN | | Moura LM et al., *supra.* |
| **Cardiovascular Disease** | | | | | CD40 & CD4OL | | Ferroni P and Guadagni F, Cardiovasc Hematol Disord Drug Targets. 2008 Sep;8(3):194-202. |

FIG. 25

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Hematological malignancies – TALL** | | | HOX11 | | | | Fernando et al., Cancer Cell, 1: 75-87, 2002. |
| **Hematological malignancies – TALL** | | | TAL1 | | | | Fernando et al., Cancer Cell, 1: 75-87, 2002. |
| **Hematological malignancies – TALL** | | | LY1 | | | | Fernando et al., Cancer Cell, 1: 75-87, 2002. |
| **Hematological malignancies – TALL** | | | LMO1 | | | | Fernando et al., Cancer Cell, 1: 75-87, 2002. |
| **Hematological malignancies – TALL** | | | LMO2 | | | | Fernando et al., Cancer Cell, 1: 75-87, 2002. |
| **Hematological malignancies** | | | | c-kit | | | Ravandi F et al., Clin Cancer Res. 2003 Feb;9(2):535-52 |
| **Hematological malignancies** | | | | PDGFR | | | Ravandi F et al., Clin Cancer Res. 2003 Feb;9(2):535-53 |
| **Hematological malignancies** | | | | ABL | | | Ravandi F et al., Clin Cancer Res. 2003 Feb;9(2):535-54 |

FIG. 26a

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **B-Cell Chronic Lymphocytic Leukemias** | | miR-213 | | | | | Calin et al., 2004, Proc Natl Acad Sci U S A 101(32): 11755-60. |
| **B-Cell Chronic Lymphocytic Leukemias** | miR-183-prec | | | | | | Calin et al., *supra.* |
| **B-Cell Chronic Lymphocytic Leukemias** | miR-190 | | | | | | Calin et al., *supra.* |
| **B-Cell Chronic Lymphocytic Leukemias** | miR-24-1-prec | | | | | | Calin et al., *supra.* |
| **B-Cell Chronic Lymphocytic Leukemias** | miR-33 | | | | | | Calin et al., *supra.* |
| **B-Cell Chronic Lymphocytic Leukemias** | miR-19a | | | | | | Calin et al., *supra.* |
| **B-Cell Chronic Lymphocytic Leukemias** | miR-140 | | | | | | Calin et al., *supra.* |
| **B-Cell Chronic Lymphocytic Leukemias** | miR-123 | | | | | | Calin et al., *supra.* |
| **B-Cell Chronic Lymphocytic Leukemias** | miR-10b | | | | | | Calin et al., *supra.* |
| **B-Cell Chronic Lymphocytic Leukemias** | miR-15b-prec | | | | | | Calin et al., *supra.* |
| **B-Cell Chronic Lymphocytic Leukemias** | miR-92-1 | | | | | | Calin et al., *supra.* |
| **B-Cell Chronic Lymphocytic Leukemias** | miR-188 | | | | | | Calin et al., *supra.* |
| **B-Cell Chronic Lymphocytic Leukemias** | miR-154 | | | | | | Calin et al., *supra.* |
| **B-Cell Chronic Lymphocytic Leukemias** | | miR-220 | | | | | Calin et al., *supra.* |
| **B-Cell Chronic Lymphocytic Leukemias** | miR-217 | | | | | | Calin et al., *supra.* |
| **B-Cell Chronic Lymphocytic Leukemias** | miR-101 | | | | | | Calin et al., *supra.* |
| **B-Cell Chronic Lymphocytic Leukemias** | miR-141-prec | | | | | | Calin et al., *supra.* |
| **B-Cell Chronic Lymphocytic Leukemias** | miR-153-prec | | | | | | Calin et al., *supra.* |
| **B-Cell Chronic Lymphocytic Leukemias** | miR-196-2 | | | | | | Calin et al., *supra.* |
| **B-Cell Chronic Lymphocytic Leukemias** | miR-134 | | | | | | Calin et al., *supra.* |
| **B-Cell Chronic Lymphocytic Leukemias** | miR-141 | | | | | | Calin et al., *supra.* |
| **B-Cell Chronic Lymphocytic Leukemias** | miR-132 | | | | | | Calin et al., *supra.* |
| **B-Cell Chronic Lymphocytic Leukemias** | miR-192 | | | | | | Calin et al., *supra.* |

FIG. 26b

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **B-Cell Chronic Lymphocytic Leukemias** | miR-181b-prec | | | | | | Calin et al., *supra.* |
| **B-Cell Chronic Lymphocytic Leukemias** | | | ZAP70 | IGHV | | | Plass C et al., 2007 British Journal of Haematology, 139, 744-752, " |
| **B-Cell Chronic Lymphocytic Leukemias** | | | | P53 | | | Plass C et al., *supra.* |
| **B-Cell Chronic Lymphocytic Leukemias** | | | | ATM | | | Plass C et al., *supra.* |
| **B-Cell Chronic Lymphocytic Leukemias** | | | AdipoR1 | | | | Molica S et al., 2008 Sep 27, Leuk Lymphoma 49(1): 62-7. |

FIG. 27

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **B-cell lymphoma** | | | | | | U50 | Tanaka et al., Genes Cells 5(4)277-87, 2000. |
| **B-cell lymphoma** | miR-17-92 polycistron | | | | | | Inomata M et al., Blood. 2008 Oct 21. |
| **B-cell lymphoma-DLBCL** | miR-155 | | | | | | Lawrie CH et al., Br J Haematol. 2008 May;141(5):672-5. |
| **B-cell lymphoma-DLBCL** | miR-210 | | | | | | Lawrie CH et al., Br J Haematol. 2008 May;141(5):672-5. |
| **B-cell lymphoma-DLBCL** | miR-21 | | | | | | Lawrie CH et al., Br J Haematol. 2008 May;141(5):672-5. |

FIG. 28

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **B-cell lymphoma-DLBCL-germinal center-like** | | | A-myb | | | | Rosenwald et al., 2002, Semin Oncol 29(3): 258-63. |
| **B-cell lymphoma-DLBCL-germinal center-like** | | | LMO2 | | | | Rosenwald et al., *supra.* |
| **B-cell lymphoma-DLBCL-germinal center-like** | | | JNK3 | | | | Rosenwald et al., *supra* |
| **B-cell lymphoma-DLBCL-germinal center-like** | | | CD10 | | | | Rosenwald et al., *supra* |
| **B-cell lymphoma-DLBCL-germinal center-like** | | | bcl-6 | | | | Rosenwald et al., *supra* |
| **B-cell lymphoma-DLBCL-activated B-cell-like** | | | Cyclin D2 | | | | Rosenwald et al., *supra* |
| **B-cell lymphoma-DLBCL-activated B-cell-like** | | | IRF4 | | | | Rosenwald et al., *supra.* |
| **B-cell lymphoma-DLBCL-activated B-cell-like** | | | Flip | | | | Rosenwald et al., *supra* |
| **B-cell lymphoma-DLBCL-activated B-cell-like** | | | CD44 | | | | Rosenwald et al., *supra* |
| **B-cell lymphoma-DLBCL** | miR-155 | | | | | | Lawrie CH et al., Br J Haematol. 2008 May;141(5):672-5. |
| **B-cell lymphoma-DLBCL** | miR-210 | | | | | | Lawrie CH et al., *supra.* |
| **B-cell lymphoma-DLBCL** | miR-21 | | | | | | Lawrie CH et al., *supra.* |

FIG. 29

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Burkitt's lymphoma** | | pri-miR-155 | | | | | Kluiver J et al., Oncogene. 2007 May 31;26(26):3769-76. |
| **Burkitt's lymphoma** | | | | | BCL6 | | Rosenwald, A & G. Ott, Ann Oncol. 2008 Jun;19 Suppl 4:iv67-9. |
| **Burkitt's lymphoma** | | | | | KI-67 | | Rosenwald, A & G. Ott, *supra.* |
| **Burkitt's lymphoma** | | | MYC | | | | Dave SS et al., N Engl J Med. 2006 Jun 8;354(23):2431-42. |
| **Burkitt's lymphoma** | | | TERT | | | | Dave et al., *supra.* |
| **Burkitt's lymphoma** | | | NS | | | | Dave et al., *supra.* |
| **Burkitt's lymphoma** | | | NP | | | | Dave et al., *supra.* |
| **Burkitt's lymphoma** | | | MAZ | | | | Dave et al., *supra.* |
| **Burkitt's lymphoma** | | | RCF3 | | | | Dave et al., *supra.* |
| **Burkitt's lymphoma** | | | BYSL | | | | Dave et al., *supra.* |
| **Burkitt's lymphoma** | | | IDES | | | | Dave et al., *supra.* |
| **Burkitt's lymphoma** | | | CDC7 | | | | Dave et al., *supra.* |
| **Burkitt's lymphoma** | | | TCL1A | | | | Dave et al., *supra.* |
| **Burkitt's lymphoma** | | | AUTS2 | | | | Dave et al., *supra.* |
| **Burkitt's lymphoma** | | | MYBL1 | | | | Dave et al., *supra.* |
| **Burkitt's lymphoma** | | | BMP7 | | | | Dave et al., *supra.* |
| **Burkitt's lymphoma** | | | ITPR3 | | | | Dave et al., *supra.* |
| **Burkitt's lymphoma** | | | CDC2 | | | | Dave et al., *supra.* |
| **Burkitt's lymphoma** | | | BACK2 | | | | Dave et al., *supra.* |
| **Burkitt's lymphoma** | | | TTK | | | | Dave et al., *supra.* |
| **Burkitt's lymphoma** | | | MME | | | | Dave et al., *supra.* |
| **Burkitt's lymphoma** | | | ALOX5 | | | | Dave et al., *supra.* |
| **Burkitt's lymphoma** | | | TOP1 | | | | Dave et al., *supra.* |

FIG. 30a

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Hepatocellular Carcinoma** | | let-7a-1 | | | | | Gramantieri et al., 2007, Cancer Res 67(13): 6092-9 |
| **Hepatocellular Carcinoma** | | let-7a-2 | | | | | Gramantieri et al., *supra.* |
| **Hepatocellular Carcinoma** | | let-7a-3 | | | | | Gramantieri et al., *supra.* |
| **Hepatocellular Carcinoma** | | let-7b | | | | | Gramantieri et al., *supra.* |
| **Hepatocellular Carcinoma** | | let-7c | | | | | Gramantieri et al., *supra.* |
| **Hepatocellular Carcinoma** | | let-7d | | | | | Gramantieri et al., *supra.* |
| **Hepatocellular Carcinoma** | | let-7e | | | | | Gramantieri et al., *supra.* |
| **Hepatocellular Carcinoma** | | let-7f-2 | | | | | Gramantieri et al., *supra.* |
| **Hepatocellular Carcinoma** | | let-fg | | | | | Gramantieri et al., *supra.* |
| **Hepatocellular Carcinoma** | | miR-122a | | | | | Gramantieri et al., *supra.* |
| **Hepatocellular Carcinoma** | | miR-124a-2 | | | | | Gramantieri et al., *supra.* |
| **Hepatocellular Carcinoma** | | miR-130a | | | | | Gramantieri et al., *supra.* |
| **Hepatocellular Carcinoma** | | miR-132 | | | | | Gramantieri et al., *supra.* |
| **Hepatocellular Carcinoma** | | miR-136 | | | | | Gramantieri et al., *supra.* |
| **Hepatocellular Carcinoma** | | miR-141 | | | | | Gramantieri et al., *supra.* |
| **Hepatocellular Carcinoma** | | miR-142 | | | | | Gramantieri et al., *supra.* |
| **Hepatocellular Carcinoma** | | miR-143 | | | | | Gramantieri et al., *supra.* |
| **Hepatocellular Carcinoma** | | miR-145 | | | | | Gramantieri et al., *supra.* |
| **Hepatocellular Carcinoma** | | miR-146 | | | | | Gramantieri et al., *supra.* |
| **Hepatocellular Carcinoma** | | miR-150 | | | | | Gramantieri et al., *supra.* |
| **Hepatocellular Carcinoma** | | miR-155(BIC) | | | | | Gramantieri et al., *supra.* |
| **Hepatocellular Carcinoma** | | miR-181a-1 | | | | | Gramantieri et al., *supra.* |
| **Hepatocellular Carcinoma** | | miR-181a-2 | | | | | Gramantieri et al., *supra.* |

FIG. 30b

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Hepatocellular Carcinoma** | | miR-181c | | | | | Gramantieri et al., *supra.* |
| **Hepatocellular Carcinoma** | | miR-195 | | | | | Gramantieri et al., *supra.* |
| **Hepatocellular Carcinoma** | | miR-199a-1-5p | | | | | Gramantieri et al., *supra.* |
| **Hepatocellular Carcinoma** | | miR-199a-2-5p | | | | | Gramantieri et al., *supra.* |
| **Hepatocellular Carcinoma** | | miR-199b | | | | | Gramantieri et al., *supra.* |
| **Hepatocellular Carcinoma** | | miR-200b | | | | | Gramantieri et al., *supra.* |
| **Hepatocellular Carcinoma** | | miR-214 | | | | | Gramantieri et al., *supra.* |
| **Hepatocellular Carcinoma** | miR-221 | | | | | | Gramantieri et al., *supra.* |
| **Hepatocellular Carcinoma** | | miR-223 | | | | | Gramantieri et al., *supra.* |
| **Hepatocellular Carcinoma** | | pre-mIR-594 | | | | | Gramantieri et al., *supra.* |
| **Hepatocellular Carcinoma** | | | FAT10 | | | | Lukasiak S et al., Methods Mol Biol. 2008;429:59-72. |

FIG. 31

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Cervical Cancer** | | | HPV E6 | | | | Liang et al., Clin Oncol 134(8)899-907, 2008, "Galectin-9 |
| **Cervical Cancer** | | | HPV E7 | | | | |
| **Cervical Cancer** | | | p53 | | | | |

FIG. 32

| **Cancer Lineage, Group Comparison, Other Significant Disease State** | **Up-regulated miRs** | **Down-regulated miRs** | **mRNAs** | **Mutational Analysis** | **Proteins, Ligands, Peptides** | **snoRNA** | **Select Reference(s)** |
|---|---|---|---|---|---|---|---|
| **Endometrial Cancer** | miR-185 | miR-71 | | | | N/A | Boren T et al., Gynecologic Oncology 110 (2008) 206-215. |
| **Endometrial Cancer** | miR-106a | miR-221 | | | | | Boren et al., *supra.* |
| **Endometrial Cancer** | miR-181a | miR-193 | | | | | Boren et al., *supra.* |
| **Endometrial Cancer** | miR-210 | miR-152 | | | | | Boren et al., *supra.* |
| **Endometrial Cancer** | miR-423 | miR-30c | | | | | Boren et al., *supra.* |
| **Endometrial Cancer** | miR-103 | | | | | | Boren et al., *supra.* |
| **Endometrial Cancer** | miR-107 | | | | | | Boren et al., *supra.* |
| **Endometrial Cancer** | let-7c | | | | | | Boren et al., *supra.* |
| **Endometrial Cancer** | | | | PTEN | | | Doll A et al., J Steroid Biochem Mol Biol. 2008 Feb;108(3-5):221-9. |
| **Endometrial Cancer** | | | | K-RAS | | | Doll et al., *supra.* |
| **Endometrial Cancer** | | | | B-catenin | | | Doll et al., *supra.* |
| **Endometrial Cancer** | | | | p53 | | | Doll et al., *supra.* |
| **Endometrial Cancer** | | | | Her2/neu | | | Doll et al., *supra.* |
| **Endometrial Cancer** | | | | | NLRP7 | | Ohno S et al., Anticancer Res. 2008 Jul-Aug;28(4C): 2493-7. |
| **Endometrial Cancer** | | | | | AlphaV Beta6 integrin | | Hecht JL et al., Appl Immunohistochem Mol Morphol. 2008 Aug 11. |

FIG. 33a

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Head and Neck Cancer** | | | HPV E6 | | | N/A | Ragin CC et al., J Dent Res. 2007 Feb;86(2):104-14 |
| **Head and Neck Cancer** | | | HPV E7 | | | | Ragin CC et al., *supra.* |
| **Head and Neck Cancer** | | | p53 | | | | van Houten VM et al., J Pathol. 2002 Dec;198(4):476-86. |
| **Head and Neck Cancer** | miR-21 | miR-494 | | | | | Chang SS et al., Int J Cancer. 2008 Sep 16;123(12):2791¬2797. |
| **Head and Neck Cancer** | let-7 | | | | | | Chang SS et al., *supra.* |
| **Head and Neck Cancer** | miR-18 | | | | | | Chang SS et al., *supra.* |
| **Head and Neck Cancer** | miR-29c | | | | | | Chang SS et al., *supra.* |
| **Head and Neck Cancer** | miR-142-3p | | | | | | Chang SS et al., *supra.* |
| **Head and Neck Cancer** | miR-155 | | | | | | Chang SS et al., *supra.* |
| **Head and Neck Cancer** | miR-146b | | | | | | Chang SS et al., *supra.* |
| **Head and Neck Cancer** | miR-205 | | | | | | Tran N et al., Biochem Biophys Res Commun. 2007 Jun 22;358(1):12-7. |
| **Head and Neck Cancer** | miR-21 | | | | | | Tran N et at, *supra.* |
| **Head and Neck Cancer** | | | | GSTM1 | | | Rusin P et al., Postepy Hg Med Dosw (Online). 2008 Sep 23;62:490-501. |
| **Head and Neck Cancer** | | | | GSTT1 | | | Rusin P et al., Postepy Hig Med Dosw (Online). 2008 Sep 23;62:490-501. |
| **Head and Neck Cancer** | | | | GSTP1 | | | Rusin P et al., *supra.* |
| **Head and Neck Cancer** | | | | OGG1 | | | Rusin P et al., *supra.* |
| **Head and Neck Cancer** | | | | XRCC1 | | | Rusin P et al., *supra.* |
| **Head and Neck Cancer** | | | | XPD | | | Rusin P et al., *supra.* |
| **Head and Neck Cancer** | | | | RAD51 | | | Rusin P et al., *supra.* |

FIG. 33b

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Head and Neck Cancer** | | | IL-8 | | | | Palka KT et al., 2008, Semin Oncol 35(3): 198-210. |
| **Head and Neck Cancer** | | | SAT | | | | Palka KT et al., *supra.* |
| **Head and Neck Cancer** | | | H3FA3 | | | | Palka KT et al., *supra.* |
| **Head and Neck Cancer** | | | EGFR | EGFR | EGFR | | Sheikh Ali MA et al., Cancer Sci. 2008 Aug;99(8):1589-94 |
| **Head and Neck Cancer** | | | | p53 | | | Kanatas A and Harris A , Tumori 94(3): 444; author reply 444. |
| **Head and Neck Cancer** | | | | | | | Ferris RL and Grandis JR, Clinical Cancer Research 13, 5663-5664, October 1, 2007." |
| **Head and Neck Cancer** | | | | | EphB4 | | Yavrouian EJ et al., Arch Otolaryngol Head Neck Surg. 2008 Sep;134(9):985-91. |
| **Head and Neck Cancer** | | | | | EphrinB2 | | Yavrouian EJ et al., *supra.* |

FIG. 34

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Irritable Bowel Disease** | | | | | Il-16 | | Seegert D, et al., 2001, Gut, 48(3): 326-32 |
| **Irritable Bowel Disease** | | | | | Il-1 beta | | Seegert D, et al., *supra.* |
| **Irritable Bowel Disease** | | | | | Il-12 | | Seegert D, et al., *supra* |
| **Irritable Bowel Disease** | | | | | TNF-alpha | | Seegert D, et al., *supra* |
| **Irritable Bowel Disease** | | | | | interferon gamma | | Seegert D, et al., *supra* |
| **Irritable Bowel Disease** | | | | | Il-6 | | Seegert D, et al., *supra* |
| **Irritable Bowel Disease** | | | | | Rantes | | Seegert D, et al., *supra* |
| **Irritable Bowel Disease** | | | | | MCP-1 | | Seegert D, et al., *supra* |
| **Irritable Bowel Disease** | | | | CARD 15 | | | Li X et al., World J Gastroenterol. 2008 Sep 7;14(33):5115-24. |
| **Irritable Bowel Disease** | | | | | Resistin | | Li X et al., *supra.* |
| **Irritable Bowel Disease** | | | Trypsinogen IV | | | | Kerckhoffs AP et al., Neurogastroenterol Motil. 2008 Aug;20(8):900-7.." |
| **Irritable Bowel Disease** | | | | | 5-HT | | Kerckhoffs AP et al., *supra.* |

FIG. 35

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Diabetes** | | | IL-8 | | | | Nair S et al., Diabetologia. 2005 September; 48(9): 1784-1788. |
| **Diabetes** | | | CTSS | | | | Nair S et al., *supra.* |
| **Diabetes** | | | ITGB2 | | | | Nair S et al., *supra.* |
| **Diabetes** | | | HLA-DRA | | | | Nair S et al., *supra.* |
| **Diabetes** | | | CD53 | | | | Nair S et al., *supra.* |
| **Diabetes** | | | PLAG27 | | | | Nair S et al., *supra.* |
| **Diabetes** | | | MMP9 | | | | Nair S et al., *supra.* |
| **Diabetes** | | | | | RBP4 | | Nair S et al., *supra.* |

FIG. 36

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Barrett's Esophagus** | | | | p53 | p53 | | Hamelin R, et al., 1994, Gastroenterology, 107(4): 1012-8 |
| **Barrett's Esophagus** | miR-21 | | | | | | Watson DI, et al., 2007, World J Surg 31(3): 447-9. |
| **Barrett's Esophagus** | miR-143 | | | | | | Watson DI, et al., *supra*.. |
| **Barrett's Esophagus** | miR-145 | | | | | | Watson DI, et al., *supra*.. |
| **Barrett's Esophagus** | miR-194 | | | | | | Watson DI, et al., *supra*.. |
| **Barrett's Esophagus** | miR-215 | | | | | | Watson DI, et al., *supra*.. |
| **Barrett's Esophagus** | | | | | MUC1 | | Burjonrappa SC et al., Indian J Cancer. 2007 Jan-Mar;44(1):1-5. |
| **Barrett's Esophagus** | | | | | MUC2 | | Burjonrappa SC et al., *supra.* |
| **Barrett's Esophagus** | | | | | MUC6 | | Glickman JN et al., Am J Surg Pathol. 2003 Oct;27(10):1357- 65 |
| **Barrett's Esophagus** | | | S100A2 | | | | Lee OJ et al., Neoplasia. 2006 Oct;8(10):843-50 |
| **Barrett's Esophagus** | | | S100A4 | | | | Lee OJ et al., *supra.* |

FIG. 37

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| Fibromyalgia | | | NR2D | | | | Kim SH et al., J Rheumatol. 2006 Apr;33(4):785-8. |

FIG. 38

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Stroke** | | | MMP9 | | | | Sharp FR et al., Stroke. 2007 Feb;38(2 Suppl):691-3. |
| **Stroke** | | | S100-P | | | | Sharp FR et al., *supra.* |
| **Stroke** | | | S100A12 | | | | Sharp FR et al., *supra.* |
| **Stroke** | | | S100A9 | | | | Sharp FR et al., *supra.* |
| **Stroke** | | | coag factor V | | | | Sharp FR et al., *supra.* |
| **Stroke** | | | Arginasel | | | | Sharp FR et al., *supra.* |
| **Stroke** | | | CA-IV | | | | Sharp FR et al., *supra.* |
| **Stroke** | | | monocarboxylic acid transporter | | | | Sharp FR et al., *supra.* |
| **Stroke** | | | ets-2 | | | | Sharp FR et al., *supra.* |
| **Stroke** | | | EIF2alpha | | | | Sharp FR et al., *supra.* |
| **Stroke** | | | cytoskeleton associated protein 4 | | | | Sharp FR et al., *supra.* |
| **Stroke** | | | N-formylpeptide receptor | | | | Sharp FR et al., *supra.* |
| **Stroke** | | | Ribonuclease2 | | | | Sharp FR et al., *supra.* |
| **Stroke** | | | N-acetylneuraminate pyruvate lyase | | | | Sharp FR et al., *supra.* |
| **Stroke** | | | BCL-6 | | | | Sharp FR et al., *supra.* |
| **Stroke** | | | Glycogen phosphorylase | | | | Sharp FR et al., *supra.* |
| **Stroke** | | | | | Lp-PLA2 | | http://www.doctorslounge.com/neurology/news/stroke_lp-pla2_crp.shtml; Gorelick PB, Am J Cardiol. 2008 Jun 16;101(12A):34F-40F |
| **Stroke** | | | | | hs-CRP | | http://www.doctorslounge.com/neurology/news/stroke_lp-pla2_crp.shtml |

FIG. 39

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Multiple Sclerosis** | | | IL-6 | | | | Kinter J et al., Int MS J. 2008 Jun;15(2):51-8. |
| **Multiple Sclerosis** | | | IL-17 | | | | Tajouri L et al., Curr Genomics. 2007 May:8(3):181-9.. |
| **Multiple Sclerosis** | | | PAR-3 | | | | Tajouri L et al., *supra.* |
| **Multiple Sclerosis** | | | IL-17 | | | | Tajouri L et al., *supra* |
| **Multiple Sclerosis** | | | T1/ST2 | | | | Tajouri L et al., *supra* |
| **Multiple Sclerosis** | | | JunD | | | | Tajouri L et al., *supra* |
| **Multiple Sclerosis** | | | 5-LO | | | | Tajouri L et al., *supra* |
| **Multiple Sclerosis** | | | LTA4H | | | | Tajouri L et al., *supra* |
| **Multiple Sclerosis** | | | MBP | | | | Tajouri L et al., *supra* |
| **Multiple Sclerosis** | | | PLP | | | | Tajouri L et al., *supra* |
| **Multiple Sclerosis** | | | alpha-beta crystallin | | | | Tajouri L et al., *supra* |

FIG. 40a

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Parkinsons Disease** | | miR-133b | | | | | Kim J. et al., Science. 2007 Aug 31;317(5842):1220-4. |
| **Parkinsons Disease** | | | | FGF20 | | | Wang G. et al., 2008, FEBS Lett 582 (25-26): 3663-8 |
| **Parkinsons Disease** | | | | alpha-synuclein | | | Mizuta I. et al., 2008, Hum Genet, 124(1): 89-94 |
| **Parkinsons Disease** | | | | FGF20 | | | Mizuta I. et al., *supra.* |
| **Parkinsons Disease** | | | | NDUFV2 | | | Mizuta I. et al., *supra.* |
| **Parkinsons Disease** | | | | FGF2 | | | Mizuta I. et al., *supra.* |
| **Parkinsons Disease** | | | | CALB1 | | | Mizuta I. et al., *supra.v* |
| **Parkinsons Disease** | | | | B2M | | | Mizuta I. et al., *supra.* |
| **Parkinsons Disease** | | | Nurr1 | | | | Altar CA, Neuropsychopharm. 2008 Oct 15. |
| **Parkinsons Disease** | | | BDNF | | | | Altar CA, *supra.* |
| **Parkinsons Disease** | | | TrkB | | | | Altar CA, *supra.* |
| **Parkinsons Disease** | | | gstml | | | | Altar CA, *supra.* |
| **Parkinsons Disease** | | | S100 beta | | | | Altar CA, *supra.* |
| **Parkinsons Disease** | | | | | apo-H | | Shi M et al., Neurobiol Dis. 2008 Sep 26. |
| **Parkinsons Disease** | | | | | Ceruloplas min | | Shi M et al., *supra.* |
| **Parkinsons Disease** | | | | | BDNF | | Zhang et al., 2008 Am. J. Clin. Pathol. 129, 526-9. |
| **Parkinsons Disease** | | | | | IL-8 | | Zhang et al., *supra.* |
| **Parkinsons Disease** | | | | | Beta2-microglobul in | | Zhang et al., *supra* |
| **Parkinsons Disease** | | | | | apoAII | | Zhang et al., *supra* |
| **Parkinsons Disease** | | | | | tau | | Zhang et al., *supra* |
| **Parkinsons Disease** | | | | | ABeta1-42 | | Zhang et al., *supra* |

FIG. 40b

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Parkinsons Disease** | | | | | DJ-1 | | Waragai et al., 2007 Neurosci. Lett. 425, 18¬22 & Waragai et al 2006 Biochem. Biophys. Res. Commun. 345, 967-72. |

FIG. 41

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Rheumatic Disease** | miR-146a | | | | | | Pauley KM et al., Arthritis Res Ther. 2008 Aug 29;10(4):R101. [Epub ahead of print]; Stanczyk J et al., Arthritis Rheum. 2008 Apr;58(4):1001-9. |
| **Rheumatic Disease** | miR-155 | | | | | | Pauley KM et al., *supra.*; Stanczyk J et al., *supra.* |
| **Rheumatic Disease** | mIR-132 | | | | | | Pauley KM et al., *supra.*; Stanczyk J et al., *supra.* |
| **Rheumatic Disease** | mIR-16 | | | | | | Pauley KM et al., *supra.*;Stanczyk J et al., *supra.* |
| **Rheumatic Disease** | miR-181 | | | | | | TiNat Clin Pract Rheumatol. 2008 Oct;4(10):534- 41. Epub 2008 Aug 26.ii E et al., |
| **Rheumatic Disease** | | | HOXD10 | | | | Galligan CL et al., Genes Immun. 2007 Sep;6(6):480-91. Epub 2007 Jun 14 . |
| **Rheumatic Disease** | | | HOXD11 | | | | Galligan CL et al., *supra.* |
| **Rheumatic Disease** | | | HOXD13 | | | | Galligan CL et al., *supra* |
| **Rheumatic Disease** | | | CCL8 | | | | Galligan CL et al., *supra* |
| **Rheumatic Disease** | | | LIM homeobox2 | | | | Galligan CL et al., *supra* |
| **Rheumatic Disease** | | | CENP-E | | | | Kullmann F et al., Arthritis Res. 1999;1(1):71-80. Epub 1999 Oct 26. |
| **Rheumatic Disease** | | | | | | | Anderson AK et al., Arthritis Res Ther. 2008;10(2):204. Epub 2008 Mar 14. |
| **Rheumatic Disease** | | | | | TNFalpha | | Anderson AK et al., *supra.* |

FIG. 42a

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Alzheimers Disease** | | | | APP | | | Vassar et al., 2005 Subcell. Biochem. 38, pp. 79–103. |
| **Alzheimers Disease** | | | | presenilin1 | | | Vassar et al., *supra.* |
| **Alzheimers Disease** | | | | presenilin2 | | | Vassar et al., *supra.* |
| **Alzheimers Disease** | | miR-107 | | | | | Wang WX et al., 2008, FEBS Lett. 582(25-26): 3663-8 |
| **Alzheimers Disease** | | miR-29a | | | | | Hebert SS et al., 2008, Proc Natl Aced Sci U.S.A., 105(17): 6415-20 |
| **Alzheimers Disease** | | miR-29b-1 | | | | | Hebert SS et al., *supra.* |
| **Alzheimers Disease** | | miR-9 | | | | | Hebert SS et al., *supra.* |
| **Alzheimers Disease** | | | | | BACE1 | | Hebert SS et al., *supra.* |
| **Alzheimers Disease** | | | HIF-1alpha | | | | Zhang et al., 2008 Am. J. Clin. Pathol. 129, 526-9. |
| **Alzheimers Disease** | | | BACE1 | | | | Zhang et al., *supra.* |
| **Alzheimers Disease** | | | | APOE4 | | | Thomas P and Fenech M, Mutagenesis. 2007 Jan;22(1):15-33. Epub 2006 Dec 8 |
| **Alzheimers Disease** | | | Reelin | | Reelin | | Botella-Lopez A et al., Proc Nail Acad Sci U S A. 2006 Apr 4;103(14):5573-8. Epub 2006 Mar 27 |
| **Alzheimers Disease** | | | CHRNA7 | | | | Altar CA, Neuropsychopharmacology. 2008 Oct 15. |
| **Alzheimers Disease** | | | 3Rtau/4Rtau | | | | Altar CA, *supra.* |
| **Alzheimers Disease** | | | | | Cystatin C | | Simonsen et al., 2008 Neurobiol. Aging. 29, 961-8 |
| **Alzheimers Disease** | | | | | Truncated Cystatin C | | Simonsen et al., *supra.* |
| **Alzheimers Disease** | | | | | Amyloid Beta | | Simonsen et al., *supra.* |
| **Alzheimers Disease** | | | | | C3a | | Simonsen et al., *supra.* |

FIG. 42b

| **Cancer Lineage, Group Comparison, Other Significant Disease State** | **Up-regulated miRs** | **Down-regulated miRs** | **mRNAs** | **Mutational Analysis** | **Proteins, Ligands, Peptides** | **snoRNA** | **Select Reference(s)** |
|---|---|---|---|---|---|---|---|
| **Alzheimers Disease** | | | | | t-Tau | | Simonsen et al., *supra.* |
| **Alzheimers Disease** | | | | | Complement factor H | | Hye et al., 2006 Brain. 129, 3042-50 |
| **Alzheimers Disease** | | | | | Alpha-2-macroglobulin | | Hye et al., *supra.* |

FIG. 43

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Prion Diseases** | | | | | PrP© | | Takemura K et al., Exp Biol Med (Maywood) Feb;231(2)204-14, 2006 |
| **Prion Diseases** | | | | | 14-3-3 | | Kubler E et al , British Medical Bulletin 66:267-279, 2003 |
| **Prion Diseases** | | | | | NSE | | Kubler E et al , British Medical Bulletin 66:267-279, 2003 |
| **Prion Diseases** | | | | | S-100 | | Kubler E et al , British Medical Bulletin 66:267-279, 2003 |
| **Prion Diseases** | | | | | Tau | | Kubler E et al , British Medical Bulletin 66:267-279, 2003 |
| **Prion Diseases** | | | | | AQP-4 | | Kubler E et al , British Medical Bulletin 66:267-279, 2003 |
| **Prion Diseases** | | | Amyloid B4 | | | | Tamguney G et al., J Gen Virol. 2008 Jul;89(Pt 7):1777-88 |
| **Prion Diseases** | | | App | | | | Tamguney G et al., J Gen Virol. 2008 Jul;89(Pt 7):1777-88 |
| **Prion Diseases** | | | IL-1R1 | | | | Tamguney G et al., J Gen Virol. 2008 Jul;89(Pt 7):1777-88 |
| **Prion Diseases** | | | SOD1 | | | | Tamguney G et al., J Gen Virol. 2008 Jul;89(Pt 7):1777-88 |

FIG. 44

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Sepsis** | | | 15-Hydroxy-PG dehydrogenase (up) | | | | Tang MP et al., Am J Respir Crit Care Med 176:676-684, 2007 |
| **Sepsis** | | | LAIR1 (up) | | | | Tang MP et al., *supra.* |
| **Sepsis** | | | NFKB1A (up) | | | | Tang MP et al., *supra.* |
| **Sepsis** | | | TLR2 | | | | Johnson SB et al., Annals of Surgery 245,Number 4, April 2007, 245(4): 611-21. |
| **Sepsis** | | | PGLYPRI | | | | Johnson SB et al., *supra.* |
| **Sepsis** | | | TLR4 | | | | Johnson SB et al., *supra.* |
| **Sepsis** | | | MD2 | | | | Johnson SB et al., *supra.* |
| **Sepsis** | | | TLR5 | | | | Johnson SB et al., *supra.* |
| **Sepsis** | | | IFNAR2 | | | | Johnson SB et al., *supra.* |
| **Sepsis** | | | IRAK2 | | | | Johnson SB et al., *supra.* |
| **Sepsis** | | | IRAK3 | | | | Johnson SB et al., *supra.* |
| **Sepsis** | | | IRAK4 | | | | Johnson SB et al., *supra.* |
| **Sepsis** | | | PI3K | | | | Johnson SB et al., *supra.* |
| **Sepsis** | | | PI3KCB | | | | Johnson SB et al., *supra.* |
| **Sepsis** | | | MAP2K6 | | | | Johnson SB et al., *supra.* |
| **Sepsis** | | | MAPK14 | | | | Johnson SB et al., *supra.* |
| **Sepsis** | | | NFKBIA | | | | Johnson SB et al., *supra.* |
| **Sepsis** | | | NFKB1 | | | | Johnson SB et al., *supra.* |
| **Sepsis** | | | IL1R1 | | | | Johnson SB et al., *supra.* |
| **Sepsis** | | | MAP2K1IP1 | | | | Johnson SB et al., *supra.* |
| **Sepsis** | | | MKNK1 | | | | Johnson SB et al., *supra.* |
| **Sepsis** | | | FAS | | | | Johnson SB et al., *supra.* |
| **Sepsis** | | | CASP4 | | | | Johnson SB et al., *supra.* |
| **Sepsis** | | | GADD45B | | | | Johnson SB et al., *supra.* |
| **Sepsis** | | | SOCS3 | | | | Johnson SB et al., *supra.* |
| **Sepsis** | | | TNFSF10 | | | | Johnson SB et al., *supra.* |
| **Sepsis** | | | TNFSF13B | | | | Johnson SB et al., *supra.* |
| **Sepsis** | | | OSM | | | | Johnson SB et al., *supra.* |
| **Sepsis** | | | HGF | | | | Johnson SB et al., *supra.* |
| **Sepsis** | | | IL18R1 | | | | Johnson SB et al., *supra.* |

FIG. 45

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| Chronic Neuropathic Pain | | | ICAM-1 (rodent) | | | | Rodriguez Parkitna J et al., J Physiol Pharmacol. 2006 Sep;57(3):401-14. |
| Chronic Neuropathic Pain | | | CGRP (rodent) | | | | Rodriguez Parkitna J et al., J Physiol Pharmacol. 2006 Sep;57(3):401-14. |
| Chronic Neuropathic Pain | | | TIMP-1 (rodent) | | | | Rodriguez Parkitna J et al., J Physiol Pharmacol. 2006 Sep;57(3):401-14. |
| Chronic Neuropathic Pain | | | CLR-1 (rodent) | | | | Rodriguez Parkitna J et al., J Physiol Pharmacol. 2006 Sep;57(3):401-14. |
| Chronic Neuropathic Pain | | | HSP-27 (rodent) | | | | Kim DS et al., Neuroreport. 2001 Oct 29;12(15):3401-5 |
| Chronic Neuropathic Pain | | | FABP (rodent) | | | | Kim DS et al., Neuroreport. 2001 Oct 29;12(15):3401-5 |
| Chronic Neuropathic Pain | | | Apolipo-protein D (rodent) | | | | Kim DS et al., Neuroreport. 2001 Oct 29;12(15):3401-5 |
| Chronic Neuropathic Pain | | | | | Chemokines | | White FA et al., Proc Natl Acad Sci U S A. 2007 Dec 18;104(51):20151-8 |
| Chronic Neuropathic Pain | | | | | Chemokine receptor (CCR2/4) | | White FA et al., Proc Natl Acad Sci U S A. 2007 Dec 18;104(51):20151-8 |

FIG. 46

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Periperhal Neuropathic Pain** | | | | | OX42 (rodent) | | Blackbeard J et al., J Neurosci Methods. 2007 Aug 30;164(2):207-17 |
| **Periperhal Neuropathic Pain** | | | | | ED9 (rodent) | | Blackbeard J et al., J Neurosci Methods. 2007 Aug 30;164(2):207-17 |

FIG. 47

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Schizophrenia** | | | IFITM3 | | ATP5B | | Altar CA, Neuropsychopharm. 2008 Oct 15. |
| **Schizophrenia** | | | SERPINA3 | | ATP5H | | Altar CA, *supra.* |
| **Schizophrenia** | | | GLS | | ATP6V1B | | Altar CA, *supra.* |
| **Schizophrenia** | | | ALDH7A1B ASP1 | | DNM1 | | Altar CA, *supra.* |
| **Schizophrenia** | | | | | NDUFV2 | | Altar CA, *supra.* |
| **Schizophrenia** | | | | | NSF | | Altar CA, *supra.* |
| **Schizophrenia** | | | | | PDHB | | Altar CA, *supra.* |
| **Schizophrenia** | miR-181b | | | | | | Beveridge NJ et al., Hum Moi Genet. 2008 Apr 15;17(8):1156-68. Epub 2008 Jan 9 |
| **Schizophrenia** | | miR-7 | | | | | Perkins DO et al., Genome Biol. 2007;8(2):R27. |
| **Schizophrenia** | | miR-24 | | | | | Perkins DO et al., *supra.* |
| **Schizophrenia** | | miR-26b | | | | | Perkins DO et al., *supra* |
| **Schizophrenia** | | miR-29b | | | | | Perkins DO et al., *supra* |
| **Schizophrenia** | | miR-30b | | | | | Perkins DO et al., *supra* |
| **Schizophrenia** | | miR-30e | | | | | Perkins DO et al., *supra* |
| **Schizophrenia** | | miR-92 | | | | | Perkins DO et al., *supra* |
| **Schizophrenia** | | miR-195 | | | | | Perkins DO et al., *supra* |
| **Schizophrenia** | | | | DISCI | | | Millar JK et al., J Physiol. 2007 Oct 15;584(Pt 2):401-5. |
| **Schizophrenia** | | | | dysbindin | | | Chen XW et al., J Cell Biol. 2008 Jun 2;181(5):791-801 |
| **Schizophrenia** | | | | neuregulin-1 | | | Harrison PJ, Novartis Found Symp. 2007;288:246-55; discussion 255-9, 276-81 |
| **Schizophrenia** | | | | seratonin 2a receptor | | | Erdmann J et al., Volume 97, Number 5 / March, 1996 614-619 |
| **Schizophrenia** | | | | NURR1 | | | Buervenich Set al., Volume 96 Issue 6, Pages 808- 813 |

FIG. 48

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Bipolar Disorder** | | | FGF2 | | | | Altar CA, Neuropsychopharm. 2008 Oct 15. |
| **Bipolar Disorder** | | | ALDH7A1 | | | | Altar CA, *supra.* |
| **Bipolar Disorder** | | | AGXT2L1 | | | | Altar CA, *supra.* |
| **Bipolar Disorder** | | | AQP4 | | | | Altar CA, *supra.* |
| **Bipolar Disorder** | | | PCNT2 | | | | Anitha A et al., Biol Psychiatry. 2008 Apr 1;63(7):678-85. Epub 2007 Sep 20 |
| **Bipolar Disorder** | | | | Dysbindin | | | Goes FS et al., Curr Psychiatry Rep. 2008 Apr;10(2):178-89 "The genetics of psychotic bipolar disorder." |
| **Bipolar Disorder** | | | | DAOA/G30 | | | Goes FS et al., Curr Psychiatry Rep. 2008 Apr;10(2):178-89. |
| **Bipolar Disorder** | | | | DISCI | | | Goes FS et al., Curr Psychiatry Rep. 2008 Apr;10(2):178-89. |
| **Bipolar Disorder** | | | | neuregulin-1 | | | Goes FS et al., Curr Psychiatry Rep, 2008 Apr;10(2):178-89. |

FIG. 49

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Depression** | | | FGFR1 | | | | Altar CA, Neuropsychopharinacology. 2008 Oct 15. |
| **Depression** | | | FGFR2 | | | | Altar CA, Neuropsychopharmacology. 2008 Oct 15. |
| **Depression** | | | FGFR3 | | | | Altar CA, Neuropsychopharmacology. 2008 Oct 15. |
| **Depression** | | | AQP4 | | | | Altar CA, Neuropsychopharmacology. 2008 Oct 15. |

FIG. 50

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **GIST** | | | | | PDGFRA | | Yang J et al., Cancer. 2008 Oct 1;113(7):1532-43 |
| **GIST** | | | | | c-kit | | Yang J et al., *supra.* |
| **GIST** | | | DOG-1 | | | | Espinosa F et al., Am J Surg Pathol Feb;32(2)210-8, 2008 |
| **GIST** | | | PKC-theta | PKC-theta | | | Blay P et al., CM Cancer Res. 2004 Jun 15;10(12 Pt 1):4089-95 |
| **GIST** | | | KIT | | | | Allander SV et al., Cancer Res. 2001 Dec 15;61(24):8624-8. |
| **GIST** | | | GPR20 | | | | Allander SV et al., *supra.* |
| **GIST** | | | PRKCQ | | | | Allander SV et al., *supra* |
| **GIST** | | | KCNK3 | | | | Allander SV et al., *supra* |
| **GIST** | | | KCNH2 | | | | Allander SV et al., *supra* |
| **GIST** | | | SCG2 | | | | Allander SV et al., *supra* |
| **GIST** | | | TNFRSF 6B | | | | Allander SV et al., *supra* |
| **GIST** | | | CD34 | | | | Allander SV et al., *supra* |

FIG. 51a

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **RCC** | | Mir-141 | | | | | Nakada C et al., J Pathol. 2008 Aug 28 |
| **RCC** | | Mir200c | | | | | Nakada C et al., *supra.* |
| **RCC** | | | laminin receptor 1 | | | | Ohno Y et al., Oncol Rep. 2008 Sep;20(3):501-9. |
| **RCC** | | | betaig-h3 | | | | Ohno Y et al., *supra.* |
| **RCC** | | | | VHL | | | Nickerson ML et al., Clin Cancer Res. 2008 Aug 1;14(15):4726-34 |
| **RCC** | | | | | HIF1alpha | | Rathmell WK, Chen S, Expert Rev Anticancer Ther. 2008 Jan;8(1):63-73. |
| **RCC** | | | | | VEGF | | Rathmell WK, Chen S, *supra.* |
| **RCC** | | | | | PDGFRA | | Rathmell WK, Chen S, *supra.* |
| **RCC** | | | Galectin-1 | | | | Young AN, Am J Pathol. 2001 May;158(5):1639-51. |
| **RCC** | | | a-2 Macroglobulin | | | | Young AN, *supra.* |
| **RCC** | | | Adipophilin | | | | Young AN, *supra.* |
| **RCC** | | | Angiopoietin 2 | | | | Young AN, *supra.* |
| **RCC** | | | Caldesmon 1 | | | | Young AN, *supra.* |
| **RCC** | | | Class II MHC-associated invariant chain (CD74) | | | | Young AN, *supra.* |
| **RCC** | | | Collagen IV-a1 | | | | Young AN, *supra.* |
| **RCC** | | | Complement component | | | | Young AN, *supra.* |
| **RCC** | | | Complement component 3 | | | | Young AN, *supra.* |

FIG. 51b

| **Cancer Lineage, Group Comparison, Other Significant Disease State** | **Up-regulated miRs** | **Down-regulated miRs** | **mRNAs** | **Mutational Analysis** | **Proteins, Ligands, Peptides** | **snoRNA** | **Select Reference(s)** |
|---|---|---|---|---|---|---|---|
| **RCC** | | | Cytochrome P450, subfamily IIJ polypeptide 2 | | | | Young AN, *supra.* |
| **RCC** | | | Delta sleep-Inducing peptide | | | | Young AN, *supra.* |
| **RCC** | | | Fc g receptor illa (CD16) | | | | Young AN, *supra.* |
| **RCC** | | | HLA-B | | | | Young AN, *supra.* |
| **RCC** | | | HLA-DR a | | | | Young AN, *supra.* |
| **RCC** | | | HLA-DR b | | | | Young AN, *supra.* |
| **RCC** | | | HLA-SB | | | | Young AN, *supra.* |
| **RCC** | | | IFN-induced transmembrane protein 3 | | | | Young AN, *supra.* |
| **RCC** | | | IFN-induced transmembrane protein 1 | | | | Young AN, *supra.* |
| **RCC** | | | Lysyl Oxidase | | | | Young AN, *supra.* |

FIG. 52

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Cirrhosis** | | | NLT | | | | Simonson GD et al., Journal of Cell Science 107, 1065-1072 (1994) |
| **Cirrhosis** | | | | | NLT | | Simonson GD et al., *supra.* |
| **Cirrhosis** | | | | | HBsAg | | Wang, W. et al., Hepatology. 1991 Jul;14(1):29-37. |
| **Cirrhosis** | | | | | AST | | Wai CT, et al. Hepatology. 2003;38:518-526. |
| **Cirrhosis** | | | | | YKL-40 | | Patel K, et al., Gastroenterology. 2004;126 (suppl 2):A-708. [S1645] |
| **Cirrhosis** | | | | | Hyaluronic acid | | Patel K, et al., *supra.* |
| **Cirrhosis** | | | | | TIMP-1 | | Patel K, et al., *supra.* |
| **Cirrhosis** | | | | | alpha 2 macroglobulin | | Patel K, et al., *supra.* |
| **Cirrhosis** | | | | | a-1-antitrypsin PI Z allele | | *Hum Hered* 1992;42:235-241 |
| **Cirrhosis** | | | | | haptoglobin | | *Hum Hered* 1992;42:235-241 |
| **Cirrhosis** | | | | | acid phosphatase ACP AC | | *Hum Hered* 1992;42:235-241 |

FIG. 53

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Esphageal cancer (adeno)** | miR-192 | miR-27b | | | | | Feber A et al., J Thorac Cardiovasc Surg. 2008 Feb;135(2):255-60 |
| **Esphageal cancer (adeno)** | miR-194 | miR-205 | | | | | Feber A et al., *supra.* |
| **Esphageal cancer (adeno)** | miR-21 | miR-203 | | | | | Feber A et al., *supra.* |
| **Esphageal cancer (adeno)** | miR-200c | miR-342 | | | | | Feber A et al., *supra.* |
| **Esphageal cancer (adeno)** | miR-93 | let-7c | | | | | Feber A et al., *supra.* |
| **Esphageal cancer (adeno)** | | miR-125b | | | | | Feber A et al., *supra.* |
| **Esphageal cancer (adeno)** | | miR-100 | | | | | Feber A et al., *supra.* |
| **Esphageal cancer (adeno)** | | miR-152 | | | | | Feber A et al., *supra.* |
| **Esphageal cancer (squamous)** | miR-342 | miR-192 | | | | | Feber A et al., *supra.* |
| **Esphageal cancer (squamous)** | miR-152 | miR-194 | | | | | Feber A et al., *supra.* |
| **Esphageal cancer (squamous)** | miR-93 | miR-27b | | | | | Feber A et al., *supra.* |
| **Esphageal cancer (squamous)** | | miR-205 | | | | | Feber A et al., *supra.* |
| **Esphageal cancer (squamous)** | | miR-203 | | | | | Feber A et al., *supra.* |
| **Esphageal cancer (squamous)** | | miR-200c | | | | | Feber A et al., *supra.* |
| **Esphageal cancer (squamous)** | | let-7c | | | | | Feber A et al., *supra.* |
| **Esphageal cancer (squamous)** | | miR-100 | | | | | Feber A et al., *supra.* |
| **Esphageal cancer** | miR-25 | miR-100 | | | | | Guo Y et al., Cancer Res. 2008 Jan 1;68(1):26-33. |
| **Esphageal cancer** | miR-424 | miR-99a | | | | | Guo Y et al., *supra.* |
| **Esphageal cancer** | miR-151 | miR-29c | | | | | Guo Y et al., *supra.* |
| **Esphageal cancer** | | miR-140 | | | | | Guo Y et al., *supra.* |
| **Esphageal cancer** | | miR-103 | | | | | Guo Y et al., *supra.* |
| **Esphageal cancer** | | miR-107 | | | | | Guo Y et al., *supra.* |
| **Esphageal cancer** | | | MTHFR | | | | Höfler H et al., Adv Exp Med Biol. 2006;587:115-20. |

FIG. 54

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Gastric cancer** | miR-106a | | | | | | Xiao B et al., Clin Chim Acta. 2008 Oct 30. |
| **Gastric cancer** | miR-21 | | | | | | Zhang Z et al., Lab Invest. 2008 Sep 15. |
| **Gastric cancer** | | let-7a | | | | | Zhang HH et al., World J Gastroenterol. 2007 May 28;13(20):2883-8. |
| **Gastric cancer** | miR-21 | | | | | | Volinia S et al., Proc Natl Acad Sci U S A. 2006 Feb 14;103(7):2257-61. |
| **Gastric cancer** | miR-191 | | | | | | Volinia S et al., Proc Natl Acad Sci U S A. 2006 Feb 14;103(7):2257-61. |
| **Gastric cancer** | miR-223 | | | | | | Volinia S et al., Proc Natl Acad Sci U S A. 2006 Feb 14;103(7):2257-61. |
| **Gastric cancer** | miR-24-1 | | | | | | Volinia S et al., Proc Natl Acad Sci U S A. 2006 Feb 14;103(7):2257-61. |
| **Gastric cancer** | miR-24-2 | | | | | | Volinia S et al., Proc Natl Acad Sci U S A. 2006 Feb 14;103(7):2257-61. |
| **Gastric cancer** | miR-107 | | | | | | Volinia S et al., Proc Natl Acad Sci U S A. 2006 Feb 14;103(7):2257-61. |
| **Gastric cancer** | miR-92-2 | | | | | | Volinia S et al., Proc Natl Acad Sci U S A. 2006 Feb 14;103(7):2257-61. |
| **Gastric cancer** | miR-214 | | | | | | Volinia S et al., Proc Natl Acad Sci U S A. 2006 Feb 14;103(7):2257-61. |
| **Gastric cancer** | miR-25 | | | | | | Volinia S et al., Proc Natl Acad Sci U S A. 2006 Feb 14;103(7):2257-61. |
| **Gastric cancer** | miR-221 | | | | | | Volinia S et al., Proc Natl Acad Sci U S A. 2006 Feb 14;103(7):2257-61. |
| **Gastric cancer** | | | RRM2 | | | | Kolesar J et al., Cancer Chemother Pharmacol. 2008 Oct 22. |
| **Gastric cancer** | | | EphA4 | | EphA4 | | Oki M et al., World J Gastroenterol. 2008 Oct 7;14(37):5650-6 |
| **Gastric cancer** | | | survivin | | | | Yie SM et al., Ann Surg Oncol. 2008 Nov;15(11):3073-82. |
| **Gastric cancer** | | | | APC | | | Lea IA et al., Carcinogenesis. 2007 September;28(9): 1851–1858. |

FIG. 55

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Autism** | | | | | GM1 | | Lekman et al., Acta Paediatrica 1995, vol. 84, no7, pp. 787-790. |
| **Autism** | | | | | GDIa | | Lekman et al., *supra.* |
| **Autism** | | | | | GDIb | | Lekman et al., *supra* |
| **Autism** | | | | | GTIb | | Lekman et al., *supra* |
| **Autism** | miR-484 | | | | | | Ablu-Elneel, Liu et al., Neurogenetics (2008) 9:153-161 |
| **Autism** | miR-21 | | | | | | Ablu-Elneel, Liu et al., *supra.* |
| **Autism** | miR-212 | | | | | | Ablu-Elneel, Liu et al., *supra.* |
| **Autism** | miR-23a | | | | | | Ablu-Elneel, Liu et al., *supra.* |
| **Autism** | miR-598 | | | | | | Ablu-Elneel, Liu et al., *supra.* |
| **Autism** | miR-95 | | | | | | Ablu-Elneel, Liu et al., *supra.* |
| **Autism** | miR-129 | | | | | | Ablu-Elneel, Liu et al., *supra.* |
| **Autism** | miR-431 | | | | | | Ablu-Elneel, Liu et al., *supra.* |
| **Autism** | miR-7 | | | | | | Ablu-Elneel, Liu et al., *supra.* |
| **Autism** | miR-15a | | | | | | Ablu-Elneel, Liu et al., *supra.* |
| **Autism** | miR-27a | | | | | | Ablu-Elneel, Liu et al., *supra.* |
| **Autism** | miR-15b | | | | | | Ablu-Elneel, Liu et al., *supra.* |
| **Autism** | miR-148b | | | | | | Ablu-Elneel, Liu et al., *supra.* |
| **Autism** | miR-132 | | | | | | Ablu-Elneel, Liu et al., *supra.* |
| **Autism** | miR-128 | | | | | | Ablu-Elneel, Liu et al., *supra.* |
| **Autism** | | miR-93 | | | | | Ablu-Elneel, Liu et al., *supra.* |
| **Autism** | | miR-106a | | | | | Ablu-Elneel, Liu et al., *supra.* |
| **Autism** | | miR-539 | | | | | Ablu-Elneel, Liu et al., *supra.* |
| **Autism** | | miR-652 | | | | | Ablu-Elneel, Liu et al., *supra.* |
| **Autism** | | miR-550 | | | | | Ablu-Elneel, Liu et al., *supra.* |
| **Autism** | | miR-432 | | | | | Ablu-Elneel, Liu et al., *supra.* |
| **Autism** | | miR-193b | | | | | Ablu-Elneel, Liu et al., *supra.* |
| **Autism** | | miR-181d | | | | | Ablu-Elneel, Liu et al., *supra.* |
| **Autism** | | miR-146b | | | | | Ablu-Elneel, Liu et al., *supra.* |
| **Autism** | | miR-140 | | | | | Ablu-Elneel, Liu et al., *supra.* |
| **Autism** | | miR-381 | | | | | Ablu-Elneel, Liu et al., *supra.* |
| **Autism** | | miR-320a | | | | | Ablu-Elneel, Liu et al., *supra.* |
| **Autism** | | miR-106b | | | | | Ablu-Elneel, Liu et al., *supra.* |

FIG. 56

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Organ Rejection** | | | | | matrix metallo-protein-9 | | American Physiological Society (2006, November 4). Proteins May Predict Lung Transplant Rejection. ScienceDaily. Retrieved |
| **Organ Rejection** | | | | | proteinase 3 | | American Physiological Society, *supra.* |
| **Organ Rejection** | | | | | HNP | | American Physiological Society, *supra.* |
| **Organ Rejection** | miR-658 | | | | | | W. Sui et al., Transplant Immunology 19 (2008) 81-85 |
| **Organ Rejection** | miR-125a | | | | | | W. Sui et al.., *supra.* |
| **Organ Rejection** | miR-320 | | | | | | W. Sui et al.., *supra.* |
| **Organ Rejection** | miR-381 | | | | | | W. Sui et al.., *supra.* |
| **Organ Rejection** | miR-628 | | | | | | W. Sui et al.., *supra.* |
| **Organ Rejection** | miR-602 | | | | | | W. Sui et al.., *supra.* |
| **Organ Rejection** | miR-629 | | | | | | W. Sui et al.., *supra.* |
| **Organ Rejection** | miR-125a | | | | | | W. Sui et al.., *supra.* |
| **Organ Rejection** | | miR-324-3p | | | | | W. Sui et al.., *supra.* |
| **Organ Rejection** | | miR-611 | | | | | W. Sui et al.., *supra.* |
| **Organ Rejection** | | miR-654 | | | | | W. Sui et al.., *supra.* |
| **Organ Rejection** | | miR-330_MM1 | | | | | W. Sui et al.., *supra.* |
| **Organ Rejection** | | miR-524 | | | | | W. Sui et al.., *supra.* |
| **Organ Rejection** | | miR-17-3p_MM1 | | | | | W. Sui et al.., *supra.* |
| **Organ Rejection** | | miR-483 | | | | | W. Sui et al.., *supra.* |
| **Organ Rejection** | | miR-663 | | | | | W. Sui et al.., *supra.* |
| **Organ Rejection** | | miR-516-5p | | | | | W. Sui et al.., *supra.* |
| **Organ Rejection** | | miR-326 | | | | | W. Sui et al.., *supra.* |
| **Organ Rejection** | | miR-197_MM2 | | | | | W. Sui et al.., *supra.* |
| **Organ Rejection** | | miR-346 | | | | | W. Sui et al.., *supra.* |

FIG. 57

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **methicillin-resistant Staphylococcus aureus** | | | | | ETA | | M. Ben Nejma et al.., Diagnostic Microbiology and Infectious Disease 55 (2006) 21– 25 |
| **methicillin-resistant Staphylococcus aureus** | | | | | ETB | | M. Ben Nejma et al. / Diagnostic Microbiology and Infectious Disease 55 (2006) 21– 26 |
| **methicillin-resistant Staphylococcus aureus** | | | | | TSST-1 | | M. Ben Nejma et al. / Diagnostic Microbiology and Infectious Disease 55 (2006) 21– 27 |
| **methicillin-resistant Staphylococcus aureus** | | | | | leukocidins | | M. Ben Nejma et al. / Diagnostic Microbiology and Infectious Disease 55 (2006) 21– 28 |
| **methicillin-resistant Staphylococcus aureus** | | | | mecA | | | M. Ben Nejma et al. / Diagnostic Microbiology and Infectious Disease 55 (2006) 21– 29 |
| **methicillin-resistant Staphylococcus aureus** | | | | Protein A SNPs | | | Frénay HM et al., J Clin Microbiol. 1994 Mar;32(3):846-7. |
| **methicillin-resistant Staphylococcus aureus** | | | TSST-1 | | | | Chini V et al., Lett Appl Microbiol. 2007 Nov;45(5):479-84. |

FIG. 58

| Cancer Lineage, Group Comparison, Other Significant Disease State | Up-regulated miRs | Down-regulated miRs | mRNAs | Mutational Analysis | Proteins, Ligands, Peptides | snoRNA | Select Reference(s) |
|---|---|---|---|---|---|---|---|
| **Vulnerable plaque** | | | | | IL-6 | | Maier W et al., 2005 Circulation 111:1355-1361. |
| **Vulnerable plaque** | | | | | MMP-9 | | Blankenberg S et al., 2003 Circulation 107:1579-1585. |
| **Vulnerable plaque** | | | | | PAPP-A | | Elesber AA et al., 2006 Eur Heart J 27:1678-1684. |
| **Vulnerable plaque** | | | | | D-dimer | | Danesh j et al., JAMA 2005, 294:1799-1809, Danesh J, Circulation 2001, 103:2323-2327 |
| **Vulnerable plaque** | | | | | fibrinogen | | Danesh et al. 2005, Danesh et al. 2001 |
| **Vulnerable plaque** | | | | | Lp-PLA2 | | Zalewski A et al., Arterioscler Thromb Vasc Biol. 2005;25:923-931 |
| **Vulnerable plaque** | | | | | SCD40L | | Koenig W and Khuseyinova N, Arterioscler Thromb Vasc Biol. 2007;27:15-26. |
| **Vulnerable plaque** | | | | | IL-18 | | Koenig W and Khuseyinova N, Arterioscler Thromb Vasc Biol. 2007;27:15-26. |
| **Vulnerable plaque** | | | | | oxLDL | | Koenig W and Khuseyinova N, Arterioscler Thromb Vasc Biol. 2007;27:15-26. |
| **Vulnerable plaque** | | | | | GPx-1 | | Koenig W and Khuseyinova N, Arterioscler Thromb Vasc Biol. 2007;27:15-26. |
| **Vulnerable plaque** | | | | | MCP-1 | | Koenig W and Khuseyinova N, Arterioscler Thromb Vasc Biol. 2007;27:15-26. |
| **Vulnerable plaque** | | | | | PIGF | | Koenig W and Khuseyinova N, Arterioscler Thromb Vasc Biol. 2007;27:15-26. |
| **Vulnerable plaque** | | | | | CRP | | Koenig W and Khuseyinova N, Arterioscler Thromb Vasc Biol. 2007;27:15-26. |

FIG. 59a

| 5' Upstream Fusion Gene Partner | 3' downstream Fusion Gene Partner | Cancer Lineage |
|---|---|---|
| ACSL3 | ETV1 | Prostate cancer |
| AKAP9 | BRAF | Papillary thyroid carcinoma |
| Alpha | TFEB | Renal cell carcinoma |
| ARHGAP20 | BRWD3 | B-cell chronic lymphocytic leukemia (B-CLL) |
| ASPSCR1 | TFE3 | Renal-cell carcinoma |
| ATIC | ALK | Anaplastic large cell lymphoma (ALCL) |
| BCL11B | TLX3 | T-cell acute lymphoblastic / lymphocytic leukemia (T-ALL) |
| BCL3 | MYC | B-cell chronic lymphocytic leukemia (B-CLL) |
| BCL7A | MYC | B-cell chronic lymphocytic leukemia (B-CLL) |
| BCR | ABL1 | Chronic myelogenous leukemia (CML) |
| BCR | FGFR1 | CML-like Myeoproliferative disorder (MPD) |
| BCR | JAK2 | Chronic myelogenous leukemia (CML) |
| BCR | PDGFRA | Atypical CML |
| BIRC3 | MALT1 | B-cell non Hodgkin lymphoma, MALT-lymphomas |
| BRD4 | NUT | Poorly differenitated epithelial carcinoma (Aggressive midline carcinoma) |
| BRWD3 | ARHGAP20 | B-cell chronic lymphocytic leukemia (B-CLL) |
| BTG1 | MYC | B-cell chronic lymphocytic leukemia (B-CLL) |
| CARS | ALK | Inflammatory myofibroblastic tumor |
| CANT1 | ETV4 | Prostate cancer |
| CBFB | MYH11 | Acute myelogenous leukemia (AML) |
| CCDC6 | PDGFRB | Philadelphia chr negative Myeoproliferative disorder (MPD) |
| CCDC6 | RET | Pappilary thyroid carcinoma |
| CCND1 | FSTL3 | Chronic myelogenous leukemia (CML) |
| CD74 | ROS1 | Non small cell lung carcinoma (NSCLC) |
| CDH11 | USP6 | Aneurysmal bone cyst |
| CDK6 | EVI1 | Myeolid leukemia |
| CDK6 | MLL | Acute lymphoblastic / lymphocytic leukemia (ALL) |
| CDK6 | TLX3 | Acute lymphoblastic / lymphocytic leukemia (ALL) |
| CEP110 | FGFR1 | Myeloproliferative disorder (Myeoproliferative disorder (MPD)) |
| CHCHD7 | PLAG1 | Pleomorphic salivary gland adenomas (PA) (Head and Neck) |
| CHIC2 | ETV6 | Acute myelogenous leukemia (AML) |
| CIITA | BCL6 | Diffuse large B-cell lymphoma (DLBCL) |
| CLTC | ALK | Diffuse large B-cell lymphoma (DLBCL) |
| CLTC | TFE3 | Pediatric renal adenocarcinoma |
| C15ORF21 | ETV1 | Prostate cancer |
| COL1A1 | PDGFB | Dermatofibrosarcoma protuberans |
| COL1A1 | USP6 | Aneurysmal bone cyst |
| COL1A2 | PLAG1 | Lipoblastoma |

FIG. 59b

| 5' Upstream Fusion Gene Partner | 3' downstream Fusion Gene Partner | Cancer Lineage |
|---|---|---|
| CRC1 | MAML2 | Mucoepidermoid carcinoma |
| CRTC1 | MAML2 | Mucoepidermoid carcinomas , Warthin's tumor |
| CRTC3 | MAML2 | Mucoepidermoid carcinoma |
| CTNNB1 | PLAG1 | Pleomorphic salivary gland adenomas (PA) (Head and Neck) |
| DDX5 | ETV4 | Prostate cancer |
| EIF4A2 | BCL6 | Non-Hodgkin lymphoma (NHL) |
| EML1 | ABL1 | T-cell acute lymphoblastic / lymphocytic leukemia (T-ALL) |
| EML4 | ALK | Non small cell lung carcinoma (NSCLC) |
| EPC1 | PHF1 | Endometiral stromal sarcoma |
| ERC1 | RET | Papillary thyroid carcinoma |
| ETV6 | ABL1 | Chronic myelogenous leukemia (CML), Acute myelogenous leukemia (AML), Acute lymphoblastic / lymphocytic leukemia (ALL) |
| ETV6 | ABL2 | T-cell acute lymphoblastic / lymphocytic leukemia (T-ALL), Acute myelogenous leukemia (AML) |
| ETV6 | ACSL6 | Polycythemia vera |
| ETV6 | ARNT | Acute myelogenous leukemia (AML) |
| ETV6 | CDX2 | Acute myelogenous leukemia (AML) |
| ETV6 | EVI1 | Chronic myelogenous leukemia (CML) |
| ETV6 | FGFR3 | Peripheral T-cell lymphoma |
| ETV6 | FLT3 | ALL, Myeoproliferative disorder (MPD) |
| ETV6 | HLXB9 | Acute myelogenous leukemia (AML) |
| ETV6 | JAK2 | Philadelphia chr negative Myeoproliferative disorder (MPD), B cell malignancies |
| ETV6 | MDS2 | Myelodisplastic syndrome |
| ETV6 | MN1 | Chronic myelogenous leukemia (CML) |
| ETV6 | NTRK3 | Secretory breast cancer |
| ETV6 | PDGFRB | Chronic myelomonocytic leukemia (CMML) |
| ETV6 | PER1 | Acute myelogenous leukemia (AML) |
| ETV6 | RUNX1 | Acute lymphoblastic / lymphocytic leukemia (ALL) |
| ETV6 | SYK | Myelodisplastic syndrome |
| ETV6 | TCBA1 | Chronic myelogenous leukemia (CML) |
| ETV6 | TTL | Acute lymphoblastic / lymphocytic leukemia (ALL) |
| EWSR1 | ATF1 | Soft tissue sarcoma |
| EWSR1 | DDIT3 | Myxoid liposarcoma |
| EWSR1 | ERG | Ewing sarcomas |
| EWSR1 | ETV1 | Ewing sarcomas |
| EWSR1 | ETV4 | Ewing sarcomas |
| EWSR1 | FEV | Ewing sarcomas |
| EWSR1 | FLI1 | Ewing sarcomas |

FIG. 59c

| 5' Upstream Fusion Gene Partner | 3' downstream Fusion Gene Partner | Cancer Lineage |
|---|---|---|
| EWSR1 | NR4A3 | Malignant tumor of soft tissue origin |
| EWSR1 | POU5F1 | Undifferentiated bone tumor |
| EWSR1 | TEC | Ewing sarcomas |
| EWSR1 | WT1 | Soft tissue sarcoma |
| EWSR1 | ZNF278 | Small round cell sarcoma |
| EWSR1 | ZNF384 | Acute lymphoblastic leukemia |
| FGFR1OP | FGFR1 | Stem-cell myeloproliferative disorder characterized by myeloid hyperplasia, T -cell lymphoblastic leukemia/lymphoma and peripheral blood eosinophilia, and it generally progresses to acute myeloid leukemia; |
| FGFR1OP2 | FGFR1 | Myeoproliferative disorder (MPD) is characterized by myeloid hyperplasia, eosinophilia and T-cell or B-cell lymphoblastic lymphoma |
| FHIT | HMGA2 | Pleomorphic salivary gland adenomas (PA) (Head and Neck) |
| FIP1L1 | PDGFRA | Hypereosinophilia |
| FLT3 | ETV6 | Hypereosinophilia |
| FLJ35294 | ETV1 | Prostate cancer |
| FUS | ATF1 | Angiomatoid fibrous histiocytoma (AFH) |
| FUS | CREB3L1 | Fibromyxoid sarcoma |
| FUS | CREB3L2 | Low-grade fibromyxoid sarcoma (LGFMS) |
| FUS | DDIT3 | Myxoid liposarcoma |
| FUS | DDIT3 | The Myxoid/Round Cell Liposarcoma |
| FUS | ERG | Ewing sarcomas |
| GAPDH | BCL6 | B-cell non hodgkin lymphoma (B-NHL), Diffuse large B-cell lymphoma (DLBCL) |
| GOLGA5 | RET | Papillary thyroid carcinoma |
| GOPC | ROS1 | Glioblastoma |
| HAS2 | PLAG1 | Lipoblastoma |
| HERV | ETV1 | Prostate cancer |
| HIP1 | PDGFRB | Chronic myelomonocytic leukemia (CMML) |
| HIST1H4I | BCL6 | B-cell Non-Hodgkin lymphoma (NHL) (NHL) |
| HMGA1 | LAMA4 | Pulmonary chondroid hamartoma |
| HMGA2 | CCNB1IP1 | Benign mesenchymal tumors |
| HMGA2 | COX6C | Uterine leiomyoma |
| HMGA2 | CXCR7 | Lipoma |
| HMGA2 | FHIT | Pleomorphic salivary gland adenomas (PA) (Head andNeck) |
| HMGA2 | LHFP | Solitary lipomas |
| HMGA2 | LPP | Lipoma, parosteal lipoma, and pulmonary chondroid hamartoma |
| HMGA2 | NFIB | Pleomorphic salivary gland adenomas (PA) (Head and Neck) |
| HMGA2 | RAD51L1 | Uterine leiomyomata |

FIG. 59d

| 5' Upstream Fusion Gene Partner | 3' downstream Fusion Gene Partner | Cancer Lineage |
|---|---|---|
| HNRPA2B1 | ETV1 | Prostate cancer |
| HOOK3 | RET | Pappilary thyroid carcinoma |
| HRH4 | RET | Pappilary thyroid carcinoma |
| HSP90AA1 | BCL6 | B cell Non-Hodgkin lymphoma (NHL) (B-NHL) |
| HSP90AB1 | BCL6 | B-cell tumors |
| IGH | MYC | Burkitt's lymphoma |
| IKZF1 | BCL6 | Diffuse large B-cell lymphoma (DLBCL) |
| IL2 | TNFRSF17 | T-cell acute lymphoblastic leukemia (T-ALL) |
| IL21R | BCL6 | Diffuse large B-cell lymphoma (DLBCL) |
| ITK | SYK | Unspecified peripheral T-cell lymphoma |
| JAZF1 | PHF1 | Endometrial stromal sarcomas |
| JAZF1 | SUZ12 | endometrial stromal tumors and endometrial stromal sarcoma |
| KIAA1509 | PDGFRA | Chronic eosinophilic leukemia (CEL) |
| KIAA1618 | ALK | Anaplastic large-cell lymphoma (ALCL) |
| KLK2 | ETV4 | Prostate cancer |
| KTN1 | RET | Papillary thyroid carcinoma |
| LCP1 | BCL6 | Non Hodgkin follicular, Burkitt lymphomas |
| LIFR | PLAG1 | Pleomorphic salivary gland adenomas (PA) (Head and Neck) |
| MALAT1 | TFEB | Pediatric renal neoplasm |
| MEF2D | DAZAP1 | Acute myelogenous leukemia (AML) |
| MLL | ABI1 | acute non lymphoblastic leukemia |
| MLL | AFF1 | Acute lymphoblastic / lymphocytic leukemia (ALL), Acutemyelogenous leukemia (AML) |
| MLL | AFF3 | Acute lymphoblastic / lymphocytic leukemia (ALL) |
| MLL | AFF4 | Acute lymphoblastic / lymphocytic leukemia (ALL) |
| MLL | ARHGAP26 | Acute monocytic leukemia (Acute myelogenous leukemia (AML) (M5b) |
| MLL | ARHGEF12 | Acute myelogenous leukemia (AML) |
| MLL | CASC5 | Acute myelogenous leukemia (AML) |
| MLL | CBL | Acute myelogenous leukemia (AML) |
| MLL | CLP1 | Monoblastic leukemia |
| MLL | CREBBP | Acute myelogenous leukemia (AML) |
| MLL | CXXC6 | Acute lymphoblastic / lymphocytic leukemia (ALL) |
| MLL | DAB2IP | Acute myelogenous leukemia (AML) |
| MLL | ELL | Acute myelogenous leukemia (AML) |
| MLL | EP300 | Acute myelogenous leukemia (AML) |
| MLL | EPS15 | Acute myelogenous leukemia (AML) |
| MLL | FNBP1 | Acute myelogenous leukemia (AML) |
| MLL | FOXO3A | Acute myelogenous leukemia (AML) |

FIG. 59e

| 5' Upstream Fusion Gene Partner | 3' downstream Fusion Gene Partner | Cancer Lineage |
|---|---|---|
| MLL | GAS7 | Acute lymphoblastic / lymphocytic leukemia (ALL) |
| MLL | GMPS | Acute myelogenous leukemia (AML) |
| MLL | GPHN | Acute myelogenous leukemia (AML) |
| MLL | LASP1 | Infant acute myeloid leukemia Acute myelogenous leukemia (AML)-M4 |
| MLL | LPP | Secondary acute leukemia |
| MLL | MAPRE1 | Pro-B acute lymphoblastic leukemia |
| MLL | MLL | Acute myeloid and lymphoid leukemia |
| MLL | MLLT1 | Acute myelogenous leukemia (AML) |
| MLL | MLLT10 | Pediatric acute megakaryoblastic leukemia AND acute monoblastic leukemia |
| MLL | MLLT11 | Acute myelogenous leukemia (AML) |
| MLL | MLLT3 | Acute myelogenous leukemia (AML) |
| MLL | MLLT4 | M4/M5 ANLL |
| MLL | MLLT6 | Acute myelogenous leukemia (AML) |
| MLL | MLLT7 | Acute leukemias |
| MLL | MYO1F | Acute myelogenous leukemia (AML) |
| MLL | PICALM | Acute myelogenous leukemia (AML) |
| MLL | RARA | M5 acute non lymphocytic leukemia (ANLL) |
| MLL | SEPT11 | Chronic neutrophilic leukemia |
| MLL | SEPT2 | Acute myelogenous leukemia (AML), therapy-related myelodysplastic syndrome |
| MLL | SEPT5 | De novo acute non lymphocytic leukemia |
| MLL | SEPT6 | Acute myelogenous leukemia (AML) |
| MLL | SEPT9 | Myeloid neoplasia |
| MLL | SH3GL1 | Acute leukemia |
| MLL | SORBS2 | Acute myelogenous leukemia (AML) |
| MLL | ZFYVE19 | Acute myelogenous leukemia (AML) |
| MSI2 | HOXA9 | Chronic myelogenous leukemia (CML) |
| MSN | ALK | Anaplastic large cell lymphoma (ALCL) |
| MYC | BCL7A | High-grade B cell Non-Hodgkin lymphoma (NHL) |
| MYC | BTG1 | B-cell chronic lymphocytic leukemia (B-CLL) |
| MYH9 | ALK | Anaplastic large cell lymphoma (ALCL) |
| MYST3 | ASXL2 | Therapy-related myelodysplastic syndrome |
| MYST3 | CREBBP | Acute myelogenous leukemia (AML) |
| MYST3 | EP300 | Acute myelomonocytic or monocytic leukaemia (M4 or M5 Acute myelogenous leukemia (AML)) |
| MYST3 | NCOA2 | Acute leukemia |
| MYST4 | CREBBP | Acute myelogenous leukemia (AML) |
| NACA | BCL6 | Non-Hodgkin lymphoma (NHL) |

FIG. 59f

| 5' Upstream Fusion Gene Partner | 3' downstream Fusion Gene Partner | Cancer Lineage |
|---|---|---|
| NCOA4 | RET | Papillary thyroid carcinoma |
| NIN | PDGFRB | Chronic myeloprolifetrative disorder with eosinophilia |
| NONO | TFE3 | Renal cell carcinoma |
| NPM1 | ALK | Anaplastic large-cell lymphomas (ALCL) |
| NPM1 | MLF1 | Acute myelogenous leukemia (AML) |
| NPM1 | RARA | Acute promyelocytic leukemia (APML) |
| NUMA1 | RARA | Atypical M3 acute non lyphoblastic leukemia (ANLL) |
| NUP214 | ABL1 | T-cell acute lymphoblastic / lymphocytic leukemia (T-ALL) |
| NUP214 | DEK | Acute myelogenous leukemia (AML) and myelodysplastic syndrome |
| NUP214 | SET | Acute undifferentiated leukemia (AUL) |
| NUP98 | ADD3 | T-cell acute lymphoblastic leukemia with biphenotipic characteristics (T/myeloid) |
| NUP98 | CCDC28A | Acute megakaryoblastic leukemia, AND T cell acute lymphoblastic leukaemia (T-ALL) |
| NUP98 | DDX10 | De novo or secondary myeloid malignancies |
| NUP98 | HOXA11 | Juvenile myelomonocytic leukemia (JMML) |
| NUP98 | HOXA13 | Acute myelogenous leukemia (AML) |
| NUP98 | HOXA9 | Acute myelogenous leukemia (AML) |
| NUP98 | HOXC11 | Acute myelogenous leukemia (AML) |
| NUP98 | HOXC13 | Acute myelogenous leukemia (AML) |
| NUP98 | HOXD11 | Acute myelomonocytic leukaemia |
| NUP98 | HOXD13 | Acute myelogenous leukemia (AML) |
| NUP98 | JARID1A | Acute leukemia |
| NUP98 | NSD1 | Childhood acute myelogenous leukemia (AML) |
| NUP98 | PRRX1 | M2-ANLL, Non hodgkin lymphoma (NHL) |
| NUP98 | PRRX2 | Acute myelogenous leukemia (AML) |
| NUP98 | PSIP1 | Acute non lymphoblastic leukemia |
| NUP98 | RAP1GDS1 | T acute lymphoblastic leukaemia |
| NUP98 | TOP1 | Acute myelogenous leukemia (AML) |
| NUP98 | WHSC1L1 | Acute myelogenous leukemia (AML) |
| NUT | BRD4 | Midline carcinoma |
| OMD | USP6 | Aneurysmal bone cyst |
| PAX3 | FOXO1 | Rhabdomyosarcoma |
| PAX5 | ETV6 | Acute lymphoblastic / lymphocytic leukemia (ALL) |
| PAX7 | FOXO1 | Alveolar rhabdomyosarcomas |
| PAX8 | PPARy | Follicular thyroid carcinoma |
| PCM1 | JAK2 | Myeloproliferative disorder (MPD) and acute erythroid leukemia |
| PCM1 | RET | Papillary thyroid carcinoma |
| PDE4DIP | PDGFRB | Chronic eosinophilic leukemia (CEL) |

FIG. 59g

| 5' Upstream Fusion Gene Partner | 3' downstream Fusion Gene Partner | Cancer Lineage |
|---|---|---|
| PICALM | MLLT10 | CML, Acute myelogenous leukemia (AML) |
| PIM1 | BCL6 | Diffuse large B-cell lymphoma (DLBCL) |
| PML | RARA | Acute promyelocytic leukemia (APML) |
| POU2AF1 | BCL6 | Non-Hodgkin lymphoma (NHL) |
| PRCC | TFE3 | Renal cell carcinoma |
| PRDM16 | EVI1 | MDS and Acute myelogenous leukemia (AML) |
| PRKAR1A | RET | Papillary thyroid carcinoma |
| RABEP1 | PDGFRB | Myeloproliferative disorder (MPD) and Acute myelogenousleukemia (AML), |
| RANBP2 | ALK | Infammatory myofibroblastic tumors (IMT) |
| RBM15 | MKL1 | Acute myelogenous leukemia (AML) |
| RFG | RET | Papillary thyroid carcinoma |
| RFG9 | RET | Papillary thyroid carcinoma |
| RHOH | BCL6 | Follicular centrocytic-centroblastic lymphoma. |
| Ria | RET | Papillary thyroid carcinoma |
| RLF | MYCL1 | Small-cell lung cancer (SCLC) |
| RPN1 | EVI1 | Acute non lymphocytic leukemia (ANLL), Myelodysplastic syndrome |
| RUNX1 | CBFA2T3 | Myeloid malignancies. |
| RUNX1 | EVI1 | Acute myelogenous leukemia (AML), therapy-related MDS and chronic myeloid leukemia in blastic phase |
| RUNX1 | MDS1 | Acute myelogenous leukemia (AML), therapy-related MDS and chronic myeloid leukemia in blastic phase |
| RUNX1 | RPL22 | Acute myelogenous leukemia (AML) |
| RUNX1 | RUNX1T1 | Acute myelogenous leukemia (AML) |
| RUNX1 | SH3D19 | Acute myelogenous leukemia (AML) |
| RUNX1 | USP42 | Acute myelogenous leukemia (AML) |
| RUNX1 | YTHDF2 | Acute myelogenous leukemia (AML) |
| RUNX1 | ZNF687 | Acute myelogenous leukemia (AML) |
| SEC31A | ALK | Diffuse large B-cell lymphoma (DLBCL) |
| SENP6 | TCBA1 | T-cell lymphoma |
| SFPQ | TFE3 | Renal cell carcinoma |
| SFRS3 | BCL6 | Follicular lymphoma |
| SLC5A3 | ERG | Prostate cancer |
| SLC45A3 | ETV1 | Prostate cancer |
| SLC45A3 | ETV5 | Prostate cancer |
| SPECC1 | PDGFRB | Juvenile myelomonocytic leukemia |
| SS18 | SSX1 | Synovial sarcoma |
| SS18 | SSX2 | Synovial sarcoma |
| SS18 | SSX4 | Synovial sarcoma |

FIG. 59h

| 5' Upstream Fusion Gene Partner | 3' downstream Fusion Gene Partner | Cancer Lineage |
|---|---|---|
| SS18L1 | SSX1 | Synovial sarcoma |
| STAT5B | RARA | Acute promyelocytic leukemia (APML) |
| TAF15 | NR4A3 | Ewing's sarcoma/primitive neuroectodermal tumor |
| TAF15 | TEC | Ewing sarcomas |
| TAF15 | ZNF384 | Acute myelogenous leukemia (AML) |
| TAL1 | STIL | T-cell malignancies (T-ALL) |
| TCBA1 | ETV6 | Acute lymphoblastic / lymphocytic leukemia (ALL) |
| TCEA1 | PLAG1 | Pleomorphic salivary gland adenomas (PA) (Head and Neck) |
| TCF12 | NR4A3 | Extraskeletal myxoid chondrosarcoma |
| TCF12 | TEC | Extraskeletal myxoid chondrosarcoma |
| TCF3 | HLF | pre-B-cell acute lymphoblastic leukemia |
| TCF3 | PBX1 | Acute lymphoblastic / lymphocytic leukemia (ALL) |
| TCF3 | TFPT | Acute lymphoblastic / lymphocytic leukemia (ALL) |
| TFG | ALK | Anaplastic large cell lymphoma (ALCL), Non small cell lung carcinoma (NSCLC) |
| TFG | NR4A3 | Extraskeletal myxoid chondrosarcoma |
| TFG | NTRK1 | Papillary thyroid carcinoma |
| TFRC | BCL6 | B-cell non hodgkin lymphoma (B-NHL), Diffuse large B-cell lymphoma (DLBCL) |
| THRAP3 | USP6 | Aneurysmal bone cysts |
| TIAF1 | FGFR1 | Myeoproliferative disorder (MPD) |
| TMPRSS2 | ERG | Prostate cancer |
| TMPRSS2 | ETV1 | Prostate cancer |
| TMPRSS2 | ETV4 | Prostate cancer |
| TMPRSS2 | ETV5 | Prostate cancer |
| TP53BP1 | PDGFRB | CML-like disorder associated with eosinophilia |
| TPM3 | ALK | Anaplastic large cell lymphoma (ALCL) |
| TPM3 | NTRK1 | Papillary thyroid carcinoma |
| TPM3 | PDGFRB | Chronic eosinophilic leukemia (CEL) |
| TPM3 | TPR | Papillary thyroid carcinoma |
| TPM4 | ALK | Inflammatory Myofibroblastic Tumors |
| TPR | MET | Papillary thyroid carcinoma |
| TPR | NTRK1 | Papillary thyroid carcinoma |
| TRIM24 | FGFR1 | Myeoproliferative disorder (MPD) |
| TRIM24 | RARA | Myeoproliferative disorder (MPD) |
| TRIM24 | RET | Papillary thyroid carcinoma |
| TRIM27 | RET | Papillary thyroid carcinoma |
| TRIM33 | RET | Papillary thyroid carcinoma |
| TRIP11 | PDGFRB | Acute myelogenous leukemia (AML) |

FIG. 59i

| 5' Upstream Fusion Gene Partner | 3' downstream Fusion Gene Partner | Cancer Lineage |
|---|---|---|
| TTL | ETV6 | Acute lymphoblastic / lymphocytic leukemia (ALL) |
| ZBTB16 | RARA | Acute promyelocytic leukemia (APML) |
| ZMYM2 | FGFR1 | Stem cell leukemia lymphoma syndrome (SCLL). |

FIG. 60a

| Gene | miRNA Associated with Gene |
|---|---|
| Androgen receptor | miR-124a, miR-130a, miR-130b,miR-143, miR-149, miR-194, miR-29b, miR-29c, miR-301, miR-30a-5p, miR-30d, miR-30e-5p, miR-337, miR-342, miR-368, miR-488, miR-493-5p, miR-506, miR-512-5p, miR-644, miR-768-5p, miR-801 |
| DNMT3B | miR-618, miR-1253, miR-765, miR-561, miR-330-5p, miR-326, miR-188, miR-203, miR-221, miR-222, miR-26a, miR-26b, miR-29a, miR-29b, miR-29c, miR-370, miR-379, miR-429, miR-519e*, miR-598, miR-618, miR-635 |
| GART | miR-101, miR-141, miR-144, miR-182, miR-189, miR-199a , miR-199b, miR-200a, miR-200b, miR-202, miR-203, miR-223, miR-329, miR-383, miR-429, miR-433, miR-485-5p, miR-493-5p, miR-499, miR-519a, miR-519b, miR-519c, miR-569, miR-591, miR-607, miR-627, miR-635, miR-659 |
| MGMT | miR-122a, miR-142-3p, miR-17-3p, miR-181a, miR-181b, miR-181c, miR-181d, miR-199b, miR-200a*, miR-217, miR-302b*, miR-32, miR-324-3p, miR-34a, miR-371, miR-425-5p, miR-496, miR-514, miR-515-3p, miR-516-3p, miR-574, miR-597, miR-603, miR-653, miR-655, miR-92, miR-92b, miR-99a |
| Top2B | miR-548f, miR-548a-3p, miR-548g, miR-513a-3p, miR-548c-3p, miR-101, miR-653, miR-548d-3p, miR-575, miR-297, miR-576-3p, miR-548b-3p, miR-624, miR-548n, miR-758, miR-1253, miR-1324, miR-23b, miR-320a, miR-320b, miR-1183, miR-1244, miR-23a, miR-451, miR-568, miR-1276 , miR-548e, miR-590-3p, miR-1, miR-101, miR-126, miR-126*, miR-129, miR-136, miR-140, miR-141, miR-144, miR-147, miR-149, miR-18, miR-181b, miR-181c, miR-182, miR-184 , miR-186, miR-189, miR-191, miR-19a, miR-19b, miR-200a, miR-206, miR-210, miR-218, miR-223, miR-23a, miR-23b , miR-24, miR-27a, miR-302, miR-30a, miR-31, miR-320, miR, 23, miR-362, miR-374, miR-383, miR-409-3p, miR-451, miR-489, miR-493-3p, miR-514, miR-542-3p, miR-544, miR-548a, miR-548b, miR-548c, miR-548d, miR-559, miR-568, miR-575, miR-579, miR-585, miR-591, miR-598, miR-613, miR-649, miR-651, miR-758, miR-768-3p, miR-9* |
| HSP90 | miR-1, miR-513a-3p, miR-548d-3, miR-642, miR-206, miR-450b-3p, miR-152, miR-148, miR-148b, miR-188-3p, miR-23a, miR-23b, miR-578, miR-653, miR-1206, miR-192, miR-215, miR-181b, miR-181d, miR-223, miR-613, miR-769-3p, miR-99a, miR-100, miR-454, miR-548n, miR-640, miR-99b, miR-150, miR-181a, miR-181c, miR-522, miR-624, miR-1, miR-130a, miR-130b, miR-146, miR-148a, miR-148b, miR-152, miR-181a, miR-181b, miR-181c, miR-204, miR-206, miR-211, miR-212, miR-215, miR-223, miR-23a, miR-23b, miR-301, miR-31, miR-325, miR-363*, miR-566, miR-9, miR-99b |
| ASPM | miR-1, miR-122a, miR-135a, miR-135b, miR-137, miR-153, miR-190, miR-206, miR-320, miR-380-3p, miR-382, miR-433, miR-453, miR-493-5p, miR-496, miR-499, miR-507, miR-517b, miR-548a, miR-548c, miR-567, miR-568, miR-580, miR-602, miR-651, miR-653, miR-758, miR-9* |
| SPARC | miR-768-5p, miR-203, miR-196, miR-569, miR-187, miR-641, miR-1275, miR-432, miR-622, miR-296-3p, miR-646, miR-96b, miR-499-5p, miR-590-5p, miR-495, miR-625, miR-1244, miR-512-5p, miR-1206, miR-1303, miR-186, miR-302d, miR-494, miR-562, miR-573, miR-10a, miR-203, miR-204, miR-211, miR-29a, miR-29b, miR-29c, miR-29c, miR-339, miR-433, miR-452, miR-515-5p, miR-517a, miR-517b, miR-517c, miR-592, miR-96 |

FIG. 60b

| Gene | miRNA Associated with Gene |
|---|---|
| PFKB3 | miR-513a-3p, miR-1286, miR-488, miR-539, miR-658, miR-524-5p, miR-1258, miR-150, miR-216b, miR-377, miR-135a, miR-26a, miR-548a-5p, miR-26b, miR-520d-5p , miR-224, miR-1297, miR-1197, miR-182, miR-452, miR-509-3-5p, miR-548m, miR-625, miR-509-5p, miR-1266, miR-135b , miR-190b, miR-496, miR-616, miR-621, miR-650, miR-105, miR-19a, miR-346, miR-620, miR-637, miR-651, miR-1283, miR-590-3p, miR-942, miR-1185, miR-577, miR-602, miR-1305, miR-220c, miR-1270, miR-1282, miR-432, miR-491-5p, miR-548n, miR-765, miR-768-3p, miR-924 |
| HMMR | miR-936, miR-656, miR-105, miR-361-5p, miR-194, miR-374a, miR-590-3p, miR-186, miR-769-5p, miR-892a, miR-380, miR-875-3p, miR-208a, miR-208b, miR-586, miR-125a-3p, miR-630, miR-374b, miR-411, miR-629, miR-1286, miR-1185, miR-16, miR-200b, miR-671-5p, miR-95, miR-421, miR-496, miR-633, miR-1243, miR-127-5p, miR-143, miR-15b, miR-200c, miR-24, miR-34c-3p |
| CENPF | miR-30c, miR-30b, miR-190, miR-508-3p, miR-384, miR-512-5p, miR-548p, miR-297, miR-520f, miR-376a, miR-1184, miR-577, miR-708, miR-205, miR-376b, miR-520g, miR-520h, miR-519d, miR-596, miR-768-3p, miR-340, miR-620, miR-539, miR-567, miR-671-5, miR-1183, miR-129-3p, miR-636, miR-106a, miR-1301, miR-17, miR-20a, miR-570, miR-656, miR-1263, miR-1324, miR-142-5p, miR-28-5p, miR-302b, miR-452, miR-520d-3p, miR-548o, miR-892b, miR-302d, miR-875-3p, miR-106b, miR-1266, miR-1323, miR-20b, miR-221, miR-520e, miR-664, miR-920, miR-922, miR-93, miR-1228, miR-1271, miR-30e, miR-483-3p, miR-509-3-5p, miR-515-3p, miR-519e, miR-520b, miR-520c-3p, miR-582-3p |
| NCAPG2 | miR-876-5p, miR-1260, miR-1246, miR-548c-3p, miR-1224-3p, miR-619, miR-605, miR-490-5p, miR-186, miR-448, miR-129-5p, miR-188-3p, miR-516b, miR-342-3p, miR-127, miR-548k, miR-654-3p, miR-1290, miR-656, miR-34b, miR-520g, miR-1231, miR-1289, miR-1229, miR-23a, miR-23b, miR-616, miR-620 |
| EGFR | miR-105, miR-128a, miR-128b, miR-140, miR-141, miR-146a, miR-146b, miR-27a, miR-27b, miR-302a, miR-302d, miR-370, miR-548c,miR-574, miR-587, miR-7 |
| SSTR3 | miR-125a, miR-125b, miR-133a, miR-133b, miR-136, miR-150, miR-21, miR-380-5p, miR-504,miR-550, miR-671, miR-766, miR-767-3p |

FIG. 63

| Protein Name | vcap average | lncap average | normalaverage |
|---|---|---|---|
| Biotin | 33236 | 40207 | 52224 |
| bcl-XL | 19205 | 24857 | 9458 |
| Estriol | 16066 | 23435 | 16560 |
| Heat Shock Protein 27/hsp27 | 10172 | 22822 | 43471 |
| CD45RO | 15037 | 20251 | 10114 |
| CNPase | 11269 | 19646 | 11675 |
| ERCC1 | 15292 | 19036 | 1597 |
| Keratin 15 | 13459 | 17580 | 9325 |
| CD81/TAPA-1 | 4967 | 17031 | 194 |
| Laminin B1/b1 | 4609 | 14848 | 10241 |
| MyoD1 | 7144 | 12472 | 15022 |
| HPV 16 | 12742 | 11185 | 15094 |
| Gai1 | 4163 | 10716 | 1361 |
| CD9 | 7009 | 10146 | 191 |
| Epithelial Specific Antigen | 10850 | 9754 | 1275 |
| Cyclin E | 5111 | 9068 | 6280 |
| MHC II (HLA-DP and DR) | 6936 | 8943 | 4757 |
| E2F-2 | 2890 | 8801 | 3094 |
| CD63 | 4591 | 8501 | 2783 |
| Amyloid Beta (APP) | 4663 | 7896 | 5893 |
| Streptavidin | 6348 | 7658 | 7909 |
| Mast Cell Chymase | 1818 | 7582 | 433 |
| AIF (Apoptosis Inducing Factor) | 4263 | 7322 | 7686 |
| CD42b | 1717 | 6787 | 10836 |
| MHC II (HLA-DP and DR) | 6936 | 8943 | 4757 |
| Calmodulin | 3353 | 4722 | 1861 |

Screening Scheme

5 × 20 = 100
Detection   Capture   Combinations
Antibodies  Antibodies  Screened CD63    CD9      Rab
CD9     PSCA     IgG
CD81    TNFR     CD81
B7H3    CD63 2X  STEAP
EpCam   B7H3     PCSA
        HER2     PSM
        MFG-E8   5T4
        Epcam 2X
        CD63 black: exosome antibodies
red: prostate antibodies
green: Colon antibodies
blue: Cancer antibodies
orange: Control

FIG. 73A

| | Sensitivity | Specificity | Confidence |
|---|---|---|---|
| EpCam vs CD63 | 87.5% | 80% | 99% |
| CD63 vs CD81 | 90% | 100% | 99% |
| CD63 vs CD63 | 60% | 80% | 99% |
| CD9 vs CD63 | 60% | 80% | 99% |

FIG. 73B-E

B. EpCam vs. CD63

| | | | |
|---|---|---|---|
| True Positive | 7 | 8 | True Negative |
| False Negative | 1 | 2 | False Positive |

C. CD81 vs. CD63

| | | | |
|---|---|---|---|
| True Positive | 4 | 10 | True Negative |
| False Negative | 1 | 0 | False Positive |

D. CD63 vs. CD63

| | | | |
|---|---|---|---|
| True Positive | 3 | 8 | True Negative |
| False Negative | 2 | 2 | False Positive |

E. CD9 vs. CD63

| | | | |
|---|---|---|---|
| True Positive | 3 | 8 | True Negative |
| False Negative | 2 | 2 | False Positive |

FIG. 74A

| Detector vs Capture | Sensitivity | Specificity | Confidence |
|---|---|---|---|
| Epcam vs CD63 | 95% | ND | 99% |
| Epcam vs CD9 | 90% | ND | 99% |
| CD63 vs CD63 | 100% | ND | 99% |
| CD9 vs CD63 | 100% | ND | 99% |
| CD66 vs CD9 | 85% | ND | 99% |

FIG. 74 B-F

B. EpCam vs. CD63

| | | | |
|---|---|---|---|
| True Positive | 19 | 6 | True Negative |
| False Negative | 1 | ND | False Positive |

C. CD81 vs. CD63

| | | | |
|---|---|---|---|
| True Positive | 18 | 6 | True Negative |
| False Negative | 2 | ND | False Positive |

D. CD63 vs. CD63

| | | | |
|---|---|---|---|
| True Positive | 20 | 6 | True Negative |
| False Negative | 0 | ND | False Positive |

E. CD9 vs. CD63

| | | | |
|---|---|---|---|
| True Positive | 20 | 6 | True Negative |
| False Negative | 0 | ND | False Positive |

F. CD66 vs. CD63

| | | | |
|---|---|---|---|
| True Positive | 17 | 6 | True Negative |
| False Negative | 3 | ND | False Positive |

FIG. 76B

| | VCAP Exosomes avg CT | Normal Plasma Exosomes avg ct |
|---|---|---|
| miR-629 | 30.63 | |
| miR-141 | 25.69 | 38.78 |
| miR-671-3p | 31.31 | 36.93 |
| miR-9 | 28.72 | 38.69 |
| miR-491 | 27.89 | 37.47 |
| miR-182 | 26.83 | 36.3 |
| miR-125a-3p | 31.26 | 38.51 |
| miR-324-5p | 27.74 | 35.98 |
| miR-148b | 29.11 | 36.51 |
| miR-222 | 24.06 | 31.33 |

miR 21 Expression with CD-9 Bead Capture

FIG. 79

| Exosome | Prostate | Cancer-1 | Cancer-2 | Cancer-3 | QC-1 | QC-2 | Sensitivity With BPH | Specificity With BPH | Sensitivity Without BPH | Specificity Without BPH |
|---|---|---|---|---|---|---|---|---|---|---|
| 3000 | 100 | na | 200 | na | 4000 | na | 85.70% | 58.00% | 85.70% | 71.40% |
| 3000 | 100 | 350 | 100 | na | 4000 | na | 85.70% | 74.10% | 85.70% | 85.70% |
| 3000 | 100 | 125 | 125 | 50 | 4000 | na | 71.40% | 83.00% | 71.40% | 90.40% |
| 3000 | 100 | 100 | 100 | 50 | 4000 | 8000 | 71.40% | 87.00% | 71.40% | 90.40% |
| 3000 | 100 | 100 | 150 | 50 | 4000 | na | 64.30% | 90.30% | 64.20% | 90.40% |
| 3000 | 100 | 100 | 150 | 150 | 4000 | na | 35.70% | 93.40% | 35.70% | 95.20% |

METHODS AND SYSTEMS OF USING EXOSOMES FOR DETERMINING PHENOTYPES

CROSS-REFERENCE

This application is a continuation of U.S. patent application Ser. No. 12/658,452, filed Feb. 5, 2010, which is a continuation of U.S. patent application Ser. No. 12/591,226 filed Nov. 12, 2009, now U.S. Pat. No. 7,897,356, which claims the benefit of U.S. Provisional Application Nos. 61/114,045, filed Nov. 12, 2008; 61/114,058, filed Nov. 12, 2008; 61/114,065, filed Nov. 13, 2008; 61/151,183, filed Feb. 9, 2009; 61/278,049, filed Oct. 2, 2009; 61/250,454, filed Oct. 9, 2009; and 61/253,027 filed Oct. 19, 2009. This application is also related to U.S. patent application Ser. No. 13/009,393, filed on Jan. 19, 2011, and U.S. application Ser. No. 12/609,847, filed Oct. 30, 2009, which claims the benefit of U.S. Provisional Application Nos. 61/109,742, filed Oct. 30, 2008; 61/112,571, filed Nov. 7, 2008, as well as the provisional applications referenced with respect to U.S. application Ser. No. 12/591,226. The entire content of these applications is hereby incorporated by reference.

BACKGROUND

A critical need for disease detection, prognostic prediction, monitoring, and therapeutic decisions is improved assay sensitivity and specificity. At present, biomarkers (proteins, peptides, lipids, RNAs, DNA and modifications thereof for disease-associated molecular alterations) for conditions and diseases, such as cancer, rely almost exclusively on obtaining samples from tissue to identify the condition or disease. Methods to obtain these tissues of interest for analysis are often invasive, costly and pose complication risks for the patient. Furthermore, use of bodily fluids to isolate or detect biomarkers often significantly dilutes a biomarker resulting in readouts that lack requisite sensitivity. Additionally, most biomarkers are produced in low or moderate amounts in normal tissues other than the diseased tissue and thus this lack of specificity can also be problematic.

The identification of specific biomarkers, such as DNA, RNA and proteins can provide bio-signatures that are used for the diagnosis, prognosis, or theranosis of a condition or disease. Exosomes are a good source for assessing one or more biomarkers that are present in or on the surface of an exosome. Furthermore, identifying particular characteristics of an exosome (e.g., size, surface antigens, cell-of-origin) can itself provide a diagnostic, prognostic or theranostic readout.

The secretion of exosomes by cancerous cells, other diseased cells, or at certain times of a physiological process (e.g., pregnancy), can be leveraged to aid in diagnosis as well as individualized treatment decisions. Exosomes have been found in a number of body fluids, including blood plasma, breast milk, bronchoalveolar lavage fluid and urine. Exosomes also take part in the communication between cells, as transport vehicles for proteins, RNAs, DNAs, viruses, and prions.

The present inventions provide an improvement to prior art assays. Products and process are provided for improved assay sensitivity and specificity, allowing for disease detection, prognostic prediction, disease monitoring, disease staging, and therapeutic decision-making, as well as physiological state identification. Products and processes include cell-of-origin specific selection of exosomes and analysis of their protein composition, RNA composition, DNA composition, lipid profile, and relevant metabolic and/or epigenetic modifications of these analytes. Also provided herein are methods of determining biomarkers and bio-signatures for exosomes without prior concentration or purification of the exosomes from a sample.

SUMMARY

Disclosed herein are methods and compositions for characterizing a phenotype by analyzing an exosome. Characterizing a phenotype for a subject or individual may include, but is not limited to, the diagnosis of a disease or condition, the prognosis of a disease or condition, the determination of a disease stage or a condition stage, a drug efficacy, a physiological condition, organ distress or organ rejection, disease or condition progression, therapy-related association to a disease or condition, or a specific physiological or biological state.

The method can include determining a bio-signature of an exosome in a biological sample from a subject and characterizing a phenotype in said subject based on the bio-signature. Characterizing can also be based on determining the amount of exosomes in a biological sample. The characterization of the phenotype can be performed with at least 70, 80 or 90% sensitivity, specificity, or both.

The exosome can be isolated or concentrated prior to determining an exosomal bio-signature. The bio-signature can comprise an expression level, presence, absence, mutation, copy number variation, truncation, duplication, insertion, modification, sequence variation, or molecular association of a biomarker. The bio-signature can also comprise quantification of isolated exosomes, temporal evaluation of the variation in exosomal half-life, circulating exosomal half-life, exosomal metabolic half-life, or the activity of an exosome.

The exosome can be a cell-of-origin specific exosome. The exosome can be derived from a tumor or cancer cell. The cell-of-origin for an exosome can be a lung, pancreas, stomach, intestine, bladder, kidney, ovary, testis, skin, colorectal, breast, prostate, brain, esophagus, liver, placenta, or fetal cell.

One or more biomarkers of an exosome can be assessed for characterizing a phenotype. The biomarker can be a nucleic acid, peptide, protein, lipid, antigen, carbohydrate or proteoglycan, such as DNA or RNA. The RNA can be mRNA, miRNA, snoRNA, snRNA, rRNAs, tRNAs, siRNA, hnRNA, or shRNA. The biomarker can be an antigen selected from FIG. 1, or a biomarker selected from a table listed in FIG. 3-60. One or more biomarkers can be assessed and used to characterize a phenotype. The bio-signature can comprise one or more miRNAs selected from the group consisting of: miR-9, miR-629, miR-141, miR-671-3p, miR-491, miR-182, miR-125a-3p, miR-324-5p, miR-148b, and miR-222. The bio-signature can be used to characterize a phenotype, such as prostate cancer. Other biomarkers can be selected from the group consisting of: CD9, PSCA (prostate stem cell antigen), TNFR, CD63, MFG-E8, EpCam, Rab, CD81, STEAP, PCSA (prostate cell surface antigen), PSM (or PSMA, prostate specific membrane antigen), 5T4, CD59, CD66, CD24 and B7H3. Detecting a plurality of biomarkers can provide greater sensitivity or specificity as compared to detecting less than a plurality of biomarkers.

Methods of multiplexing, or multiplex analysis of, a plurality of exosomes are also provided. Multiplexing a plurality of exosomes can comprise applying said plurality of exosomes to a plurality of particles, wherein each particle of a subset of the plurality of particles is coupled to a different capture agent, capturing a subset of said plurality of exosomes; and, detecting one or more biomarkers of the captured exosomes. Multiplexing can also be performed using an array, wherein the capture agents are attached to an array instead of particles or beads.

Also provided herein are isolated exosomes. The isolated exosome can comprise any one or more biomarkers disclosed herein, such as a specific combination of biomarkers. Compositions comprising the one or more isolated exosomes are also provided. The composition can comprise a substantially enriched population of exosomes. The population of exosomes can be substantially homogeneous for one or more specific biomarkers, for a particular bio-signature, or derived from a specific cell type.

Detection systems, microfluidic devices, and kits for assessing one or more exosomes, such as for the isolation, separation, or detection of one or more exosomes, are also provided.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

FIG. 1(*a*)-(*g*) represents a table which lists exemplary cancers by lineage, group comparisons of cells/tissue, and specific disease states and antigens specific to those cancers, group cell/tissue comparisons and specific disease states. Furthermore, the antigen can be a biomarker. The one or more biomarkers can be present or absent, underexpressed or overexpressed, mutated, or modified, such as epigentically modified or post-translationally modified.

FIG. 2(*a*)-(*f*) represents a table which lists exemplary cancers by lineage, group comparisons of cells/tissue, and specific disease states and binding agents specific to those cancers, group cell/tissue comparisons and specific disease states.

FIG. 3(*a*)-(*b*) represents a table which lists exemplary breast cancer biomarkers that can be derived and analyzed from exosomes specific to breast cancer to create a breast cancer specific exosome bio-signature. Furthermore, the one or more biomarkers can be present or absent, underexpressed or overexpressed, mutated, or modified, such as epigentically modified or post-translationally modified.

FIG. 4(*a*)-(*b*) represents a table which lists exemplary ovarian cancer biomarkers that can be derived from and analyzed from exosomes specific to ovarian cancer to create an ovarian cancer specific exosome bio-signature. Furthermore, the one or more biomarkers can be present or absent, underexpressed or overexpressed, mutated, or modified, such as epigentically modified or post-translationally modified.

FIG. 5 represents a table which lists exemplary lung cancer biomarkers that can be derived from and analyzed from exosomes specific to lung cancer to create a lung cancer specific exosome bio-signature. Furthermore, the one or more biomarkers can be present or absent, underexpressed or overexpressed, mutated, or modified, such as epigentically modified or post-translationally modified.

FIG. 6(*a*)-(*d*) represents a table which lists exemplary colon cancer biomarkers that can be derived from and analyzed from exosomes specific to colon cancer to create a colon cancer specific exosome bio-signature. Furthermore, the one or more biomarkers can be present or absent, underexpressed or overexpressed, mutated, or modified, such as epigentically modified or post-translationally modified.

FIG. 7 represents a table which lists exemplary biomarkers specific to an adenoma versus a hyperplastic polyp that can be derived and analyzed from exosomes specific to adenomas versus hyperplastic polyps. Furthermore, the one or more biomarkers can be present or absent, underexpressed or overexpressed, mutated, or modified, such as epigentically modified or post-translationally modified.

FIG. 8 is a table which lists exemplary biomarkers specific to inflammatory bowel disease (IBD) versus normal tissue that can be derived and analyzed from exosomes specific to inflammatory bowel disease versus normal tissue. Furthermore, the one or more biomarkers can be present or absent, underexpressed or overexpressed, mutated, or modified, such as epigentically modified or post-translationally modified.

FIG. 9(*a*)-(*c*) represents a table which lists exemplary biomarkers specific to an adenoma versus colorectal cancer (CRC) that can be derived and analyzed from exosomes specific to adenomas versus colorectal cancer. Furthermore, the one or more biomarkers can be present or absent, underexpressed or overexpressed, mutated, or modified, such as epigentically modified or post-translationally modified.

FIG. 10 represents a table which lists exemplary biomarkers specific to IBD versus CRC that can be derived and analyzed from exosomes specific to IBD versus CRC. Furthermore, the one or more biomarkers can be present or absent, underexpressed or overexpressed, mutated, or modified, such as epigentically modified or post-translationally modified.

FIG. 11(*a*)-(*b*) represents a table which lists exemplary biomarkers specific to CRC Dukes B versus Dukes C-D that can be derived and analyzed from exosomes specific to CRC Dukes B versus Dukes C-D. Furthermore, the one or more biomarkers can be present or absent, underexpressed or overexpressed, mutated, or modified, such as epigentically modified or post-translationally modified.

FIG. 12(*a*)-(*d*) represents a table which lists exemplary biomarkers specific to an adenoma with low grade dysplasia versus an adenoma with high grade dysplasia that can be derived and analyzed from exosomes specific to an adenoma with low grade dysplasia versus an adenoma with high grade dysplasia. Furthermore, the one or more biomarkers can be present or absent, underexpressed or overexpressed, mutated, or modified, such as epigentically modified or post-translationally modified.

FIG. 13(*a*)-(*b*) represents a table which lists exemplary biomarkers specific to ulcerative colitis (UC) versus Crohn's Disease (CD) that can be derived and analyzed from exosomes specific to UC versus CD. Furthermore, the one or more biomarkers can be present or absent, underexpressed or overexpressed, mutated, or modified, such as epigentically modified or post-translationally modified.

FIG. 14 represents a table which lists exemplary biomarkers specific to a hyperplastic polyp versus normal tissue that can be derived and analyzed from exosomes specific to a hyperplastic polyp versus normal tissue. Furthermore, the one or more biomarkers can be present or absent, underexpressed or overexpressed, mutated, or modified, such as epigentically modified or post-translationally modified.

FIG. 15 is a table which lists exemplary biomarkers specific to an adenoma with low grade dysplasia versus normal tissue that can be derived and analyzed from exosomes specific to an adenoma with low grade dysplasia versus normal tissue. Furthermore, the one or more biomarkers can be present or absent, underexpressed or overexpressed, mutated, or modified, such as epigentically modified or post-translationally modified.

FIG. 16 is a table which lists exemplary biomarkers specific to an adenoma versus normal tissue that can be derived and analyzed from exosomes specific to an adenoma versus normal tissue. Furthermore, the one or more biomarkers can be present or absent, underexpressed or overexpressed, mutated, or modified, such as epigentically modified or post-translationally modified.

FIG. 17 represents a table which lists exemplary biomarkers specific to CRC versus normal tissue that can be derived and analyzed from exosomes specific to CRC versus normal tissue. Furthermore, the one or more biomarkers can be present or absent, underexpressed or overexpressed, mutated, or modified, such as epigentically modified or post-translationally modified.

FIG. 18 is a table which lists exemplary biomarkers specific to benign prostatic hyperplasia that can be derived from and analyzed from exosomes specific to benign prostatic hyperplasia. Furthermore, the one or more biomarkers can be present or absent, underexpressed or overexpressed, mutated, or modified, such as epigentically modified or post-translationally modified.

FIG. 19(*a*)-(*c*) represents a table which lists exemplary prostate cancer biomarkers that can be derived from and analyzed from exosomes specific to prostate cancer to create a prostate cancer specific exosome bio-signature. Furthermore, the one or more biomarkers can be present or absent, underexpressed or overexpressed, mutated, or modified, such as epigentically modified or post-translationally modified.

FIG. 20(*a*)-(*c*) represents a table which lists exemplary melanoma biomarkers that can be derived from and analyzed from exosomes specific to melanoma to create a melanoma specific exosome bio-signature. Furthermore, the one or more biomarkers can be present or absent, underexpressed or overexpressed, mutated, or modified, such as epigentically modified or post-translationally modified.

FIG. 21(*a*)-(*b*) represents a table which lists exemplary pancreatic cancer biomarkers that can be derived from and analyzed from exosomes specific to pancreatic cancer to create a pancreatic cancer specific exosome bio-signature. Furthermore, the one or more biomarkers can be present or absent, underexpressed or overexpressed, mutated, or modified, such as epigentically modified or post-translationally modified.

FIG. 22 is a table which lists exemplary biomarkers specific to brain cancer that can be derived from and analyzed from exosomes specific to brain cancer to create a brain cancer specific exosome bio-signature. Furthermore, the one or more biomarkers can be present or absent, underexpressed or overexpressed, mutated, or modified, such as epigentically modified or post-translationally modified.

FIG. 23(*a*)-(*b*) represents a table which lists exemplary psoriasis biomarkers that can be derived from and analyzed from exosomes specific to psoriasis to create a psoriasis specific exosome bio-signature. Furthermore, the one or more biomarkers can be present or absent, underexpressed or overexpressed, mutated, or modified, such as epigentically modified or post-translationally modified.

FIG. 24(*a*)-(*c*) represents a table which lists exemplary cardiovascular disease biomarkers that can be derived from and analyzed from exosomes specific to cardiovascular disease to create a cardiovascular disease specific exosome bio-signature. Furthermore, the one or more biomarkers can be present or absent, underexpressed or overexpressed, mutated, or modified, such as epigentically modified or post-translationally modified.

FIG. 25 is a table which lists exemplary biomarkers specific to hematological malignancies that can be derived from and analyzed from exosomes specific to hematological malignancies to create a specific exosome bio-signature for hematological malignancies. Furthermore, the one or more biomarkers can be present or absent, underexpressed or overexpressed, mutated, or modified, such as epigentically modified or post-translationally modified.

FIG. 26(*a*)-(*b*) represents a table which lists exemplary biomarkers specific to B-Cell Chronic Lymphocytic Leukemias that can be derived from and analyzed from exosomes specific to B-Cell Chronic Lymphocytic Leukemias to create a specific exosome bio-signature for B-Cell Chronic Lymphocytic Leukemias. Furthermore, the one or more biomarkers can be present or absent, underexpressed or overexpressed, mutated, or modified, such as epigentically modified or post-translationally modified.

FIG. 27 is a table which lists exemplary biomarkers specific to B-Cell Lymphoma and B-Cell Lymphoma-DLBCL that can be derived from and analyzed from exosomes specific to B-Cell Lymphoma and B-Cell Lymphoma-DLBCL. Furthermore, the one or more biomarkers can be present or absent, underexpressed or overexpressed, mutated, or modified, such as epigentically modified or post-translationally modified.

FIG. 28 represents a table which lists exemplary biomarkers specific to B-Cell Lymphoma-DLBCL-germinal center-like and B-Cell Lymphoma-DLBCL-activated B-cell-like and B-cell lymphoma-DLBCL that can be derived from and analyzed from exosomes specific to B-Cell Lymphoma-DLBCL-germinal center-like and B-Cell Lymphoma-DLBCL-activated B-cell-like and B-cell lymphoma-DLBCL. Furthermore, the one or more biomarkers can be present or absent, underexpressed or overexpressed, mutated, or modified, such as epigentically modified or post-translationally modified.

FIG. 29 represents a table which lists exemplary Burkitt's lymphoma biomarkers that can be derived from and analyzed from exosomes specific to Burkitt's lymphoma to create a Burkitt's lymphoma specific exosome bio-signature. Furthermore, the one or more biomarkers can be present or absent, underexpressed or overexpressed, mutated, or modified, such as epigentically modified or post-translationally modified.

FIG. 30(*a*)-(*b*) represents a table which lists exemplary hepatocellular carcinoma biomarkers that can be derived from and analyzed from exosomes specific to hepatocellular carcinoma to create a specific exosome bio-signature for hepatocellular carcinoma. Furthermore, the one or more biomarkers can be present or absent, underexpressed or overexpressed, mutated, or modified, such as epigentically modified or post-translationally modified.

FIG. 31 is a table which lists exemplary biomarkers for cervical cancer that can be derived from and analyzed from exosomes specific to cervical cancer. Furthermore, the one or more biomarkers can be present or absent, underexpressed or overexpressed, mutated, or modified, such as epigentically modified or post-translationally modified.

FIG. 32 represents a table which lists exemplary biomarkers for endometrial cancer that can be derived from and analyzed from exosomes specific to endometrial cancer to create a specific exosome bio-signature for endometrial cancer. Furthermore, the one or more biomarkers can be present or absent, underexpressed or overexpressed, mutated, or modified, such as epigentically modified or post-translationally modified.

FIG. 33(*a*)-(*b*) represents a table which lists exemplary biomarkers for head and neck cancer that can be derived from and analyzed from exosomes specific to head and neck cancer to create a specific exosome bio-signature for head and neck cancer. Furthermore, the one or more biomarkers can be present or absent, underexpressed or overexpressed, mutated, or modified, such as epigentically modified or post-translationally modified.

FIG. 34 represents a table which lists exemplary biomarkers for inflammatory bowel disease (IBD) that can be derived from and analyzed from exosomes specific to IBD to create a specific exosome bio-signature for IBD. Furthermore, the one or more biomarkers can be present or absent, underexpressed or overexpressed, mutated, or modified, such as epigentically modified or post-translationally modified.

FIG. 35 is a table which lists exemplary biomarkers for diabetes that can be derived from and analyzed from exosomes specific to diabetes to create a specific exosome bio-signature for diabetes. Furthermore, the one or more biomarkers can be present or absent, underexpressed or overexpressed, mutated, or modified, such as epigentically modified or post-translationally modified.

FIG. 36 is a table which lists exemplary biomarkers for Barrett's Esophagus that can be derived from and analyzed from exosomes specific to Barrett's Esophagus to create a specific exosome bio-signature for Barrett's Esophagus. Furthermore, the one or more biomarkers can be present or absent, underexpressed or overexpressed, mutated, or modified, such as epigentically modified or post-translationally modified.

FIG. 37 is a table which lists exemplary biomarkers for fibromyalgia that can be derived from and analyzed from exosomes specific to fibromyalgia. Furthermore, the one or more biomarkers can be present or absent, underexpressed or overexpressed, mutated, or modified, such as epigentically modified or post-translationally modified.

FIG. 38 represents a table which lists exemplary biomarkers for stroke that can be derived from and analyzed from exosomes specific to stroke to create a specific exosome bio-signature for stroke. Furthermore, the one or more biomarkers can be present or absent, underexpressed or overexpressed, mutated, or modified, such as epigentically modified or post-translationally modified.

FIG. 39 is a table which lists exemplary biomarkers for Multiple Sclerosis (MS) that can be derived from and analyzed from exosomes specific to MS to create a specific exosome bio-signature for MS. Furthermore, the one or more biomarkers can be present or absent, underexpressed or overexpressed, mutated, or modified, such as epigentically modified or post-translationally modified.

FIG. 40(*a*)-(*b*) represents a table which lists exemplary biomarkers for Parkinson's Disease that can be derived from and analyzed from exosomes specific to Parkinson's Disease to create a specific exosome bio-signature for Parkinson's Disease. Furthermore, the one or more biomarkers can be present or absent, underexpressed or overexpressed, mutated, or modified, such as epigentically modified or post-translationally modified.

FIG. 41 represents a table which lists exemplary biomarkers for Rheumatic Disease that can be derived from and analyzed from exosomes specific to Rheumatic Disease to create a specific exosome bio-signature for Rheumatic Disease. Furthermore, the one or more biomarkers can be present or absent, underexpressed or overexpressed, mutated, or modified, such as epigentically modified or post-translationally modified.

FIG. 42(*a*)-(*b*) represents a table which lists exemplary biomarkers for Alzheimers Disease that can be derived from and analyzed from exosomes specific to Alzheimers Disease to create a specific exosome bio-signature for Alzheimers Disease. Furthermore, the one or more biomarkers can be present or absent, underexpressed or overexpressed, mutated, or modified, such as epigentically modified or post-translationally modified.

FIG. 43 is a table which lists exemplary biomarkers for Prion Diseases that can be derived from and analyzed from exosomes specific to Prion Diseases to create a specific exosome bio-signature for Prion Diseases. Furthermore, the one or more biomarkers can be present or absent, underexpressed or overexpressed, mutated, or modified, such as epigentically modified or post-translationally modified.

FIG. 44 represents a table which lists exemplary biomarkers for sepsis that can be derived from and analyzed from exosomes specific to sepsis to create a specific exosome bio-signature for sepsis. Furthermore, the one or more biomarkers can be present or absent, underexpressed or overexpressed, mutated, or modified, such as epigentically modified or post-translationally modified.

FIG. 45 is a table which lists exemplary biomarkers for chronic neuropathic pain that can be derived from and analyzed from exosomes specific to chronic neuropathic pain. Furthermore, the one or more biomarkers can be present or absent, underexpressed or overexpressed, mutated, or modified, such as epigentically modified or post-translationally modified.

FIG. 46 is a table which lists exemplary biomarkers for peripheral neuropathic pain that can be derived from and analyzed from exosomes specific to peripheral neuropathic pain. Furthermore, the one or more biomarkers can be present or absent, underexpressed or overexpressed, mutated, or modified, such as epigentically modified or post-translationally modified.

FIG. 47 represents a table which lists exemplary biomarkers for Schizophrenia that can be derived from and analyzed from exosomes specific to Schizophrenia to create a specific exosome bio-signature for Schizophrenia. Furthermore, the one or more biomarkers can be present or absent, underexpressed or overexpressed, mutated, or modified, such as epigentically modified or post-translationally modified.

FIG. 48 is a table which lists exemplary biomarkers for bipolar disorder or disease that can be derived from and analyzed from exosomes specific to bipolar disorder to create a specific exosome bio-signature for bipolar disorder. Furthermore, the one or more biomarkers can be present or absent, underexpressed or overexpressed, mutated, or modified, such as epigentically modified or post-translationally modified.

FIG. 49 is a table which lists exemplary biomarkers for depression that can be derived from and analyzed from exosomes specific to depression to create a specific exosome bio-signature for depression. Furthermore, the one or more biomarkers can be present or absent, underexpressed or overexpressed, mutated, or modified, such as epigentically modified or post-translationally modified.

FIG. 50 is a table which lists exemplary biomarkers for gastrointestinal stromal tumor (GIST) that can be derived from and analyzed from exosomes specific to GIST to create a specific exosome bio-signature for GIST. Furthermore, the one or more biomarkers can be present or absent, underexpressed or overexpressed, mutated, or modified, such as epigentically modified or post-translationally modified.

FIG. 51(*a*)-(*b*) represent sa table which lists exemplary biomarkers for renal cell carcinoma (RCC) that can be derived from and analyzed from exosomes specific to RCC to create a specific exosome bio-signature for RCC. Furthermore, the one or more biomarkers can be present or absent, underexpressed or overexpressed, mutated, or modified, such as epigentically modified or post-translationally modified.

FIG. 52 is a table which lists exemplary biomarkers for cirrhosis that can be derived from and analyzed from exosomes specific to cirrhosis to create a specific exosome bio-signature for cirrhosis. Furthermore, the one or more biomarkers can be present or absent, underexpressed or overexpressed, mutated, or modified, such as epigentically modified or post-translationally modified.

FIG. 53 is a table which lists exemplary biomarkers for esophageal cancer that can be derived from and analyzed from exosomes specific to esophageal cancer to create a specific exosome bio-signature for esophageal cancer. Furthermore, the one or more biomarkers can be present or absent, underexpressed or overexpressed, mutated, or modified, such as epigentically modified or post-translationally modified.

FIG. 54 is a table which lists exemplary biomarkers for gastric cancer that can be derived from and analyzed from exosomes specific to gastric cancer to create a specific exosome bio-signature for gastric cancer. Furthermore, the one or more biomarkers can be present or absent, underexpressed or overexpressed, mutated, or modified, such as epigentically modified or post-translationally modified.

FIG. 55 is a table which lists exemplary biomarkers for autism that can be derived from and analyzed from exosomes specific to autism to create a specific exosome bio-signature for autism. Furthermore, the one or more biomarkers can be present or absent, underexpressed or overexpressed, mutated, or modified, such as epigentically modified or post-translationally modified.

FIG. 56 is a table which lists exemplary biomarkers for organ rejection that can be derived from and analyzed from exosomes specific to organ rejection to create a specific exosome bio-signature for organ rejection. Furthermore, the one or more biomarkers can be present or absent, underexpressed or overexpressed, mutated, or modified, such as epigentically modified or post-translationally modified.

FIG. 57 is a table which lists exemplary biomarkers for methicillin-resistant *staphylococcus aureus* that can be derived from and analyzed from exosomes specific to methicillin-resistant *staphylococcus aureus* to create a specific exosome bio-signature for methicillin-resistant *staphylococcus aureus*. Furthermore, the one or more biomarkers can be present or absent, underexpressed or overexpressed, mutated, or modified, such as epigentically modified or post-translationally modified.

FIG. 58 is a table which lists exemplary biomarkers for vulnerable plaque that can be derived from and analyzed from exosomes specific to vulnerable plaque to create a specific exosome bio-signature for vulnerable plaque. Furthermore, the one or more biomarkers can be present or absent, underexpressed or overexpressed, mutated, or modified, such as epigentically modified or post-translationally modified.

FIG. 59(*a*)-(*i*) is a table which lists exemplary gene fusions that can be derived from, or analyzed from exosomes. The gene fusion can be biomarker, and can be present or absent, underexpressed or overexpressed, or modified, such as epigentically modified or post-translationally modified.

FIG. 60(*a*)-(*b*) is a table of genes and their associated miRNAs, of which the gene, such as the mRNA of the gene, their associated miRNAs, or any combination thereof, can be used as one or more biomarkers that can be analyzed from exosomes. Furthermore, the one or more biomarkers can be present or absent, underexpressed or overexpressed, mutated, or modified.

FIG. 63 illustrates results obtained from screening for proteins on exosomes, which can be used a biomarkers for the exosomes and antibodies to the proteins can be used as binding agents. Examples of the proteins identified include Bcl-XL, ERCC1, Keratin 15, CD81/TAPA-1, CD9, Epithelial Specific Antigen (ESA), and Mast Cell Chymase. The one or more biomarkers can be present or absent, underexpressed or overexpressed, mutated, or modified.

FIG. 73: illustrates (A) the sensitivity and specificity, and the confidence level, for detecting prostate cancer using antibodies to the listed proteins listed as the detector and capture antibodies. CD63, CD9, and CD81 are general exosome markers and EpCam is a cancer marker. The individual results are depicted in (B) for EpCam versus CD63, with 99% confidence, 100% (n=8) cancer patient samples were different from the Generalized Normal Distribution and with 99% confidence, 77% (n=10) normal patient samples were not different from the Generalized Normal Distribution; (C) for CD81 versus CD63, with 99% confidence, 90% (n=5) cancer patient samples were different from the Generalized Normal Distribution; with 99% confidence, 77% (n=10) normal patient samples were not different from the Generalized Normal Distribution; (D) for CD63 versus CD63, with 99% confidence, 60% (n=5) cancer patient samples were different from the Generalized Normal Distribution; with 99% confidence, 80% (n=10) normal patient samples were not different from the Generalized Normal Distribution; (E) for CD9 versus CD63, with 99% confidence, 90% (n=5) cancer patient samples were different from the Generalized Normal Distribution; with 99% confidence, 77% (n=10) normal patient samples were not different from the Generalized Normal Distribution.

FIG. 74 illustrates (A) the sensitivity and the confidence level for detecting colon cancer using antibodies to the listed proteins listed as the detector and capture antibodies. CD63, CD9 are general exosome markers, EpCam is a cancer marker, and CD66 is a colon marker. The individual results are depicted in (B) for EpCam versus CD63, with 99% confidence, 95% (n=20) cancer patient samples were different from the Generalized Normal Distribution; with 99% confidence, 100% (n=6) normal patient samples were not different from the Generalized Normal Distribution; (C) for EpCam versus CD9, with 99% confidence, 90% (n=20) cancer patient samples were different from the Generalized Normal Distribution; with 99% confidence, 77% (n=6) normal patient samples were not different from the Generalized Normal Distribution; (D) for CD63 versus CD63, with 99% confidence, 60% (n=20) cancer patient samples were different from the Generalized Normal Distribution; with 99% confidence, 80% (n=6) normal patient samples were not different from the Generalized Normal Distribution; (E) for CD9 versus CD63, with 99% confidence, 90% (n=20) cancer patient samples were different from the Generalized Normal Distribution; with 99% confidence, 77% (n=6) normal patient samples were not different from the Generalized Normal Distribution; (F) for CD66 versus CD9, with 99% confidence, 90% (n=20) cancer patient samples were different from the Generalized Normal Distribution; with 99% confidence, 77% (n=6) normal patient samples were not different from the Generalized Normal Distribution.

FIG. 79 depicts a table of the sensitivity and specificity for different prostate signatures. "Exosome" lists the threshold value or reference value of exosome levels, "Prostate" lists the threshold value or reference value used for prostate exosomes, "Cancer-1," "Cancer-2," and "Cancer-3" lists the threshold values or reference values for the three different bio-signatures for prostate cancer, the "QC-1" and "QC-2" columns list the threshold values or reference values for quality control, or reliability, and the last four columns list the specificities and sensitivities for benign prostate hyperplasia (BPH).

DETAILED DESCRIPTION

Figure 61:
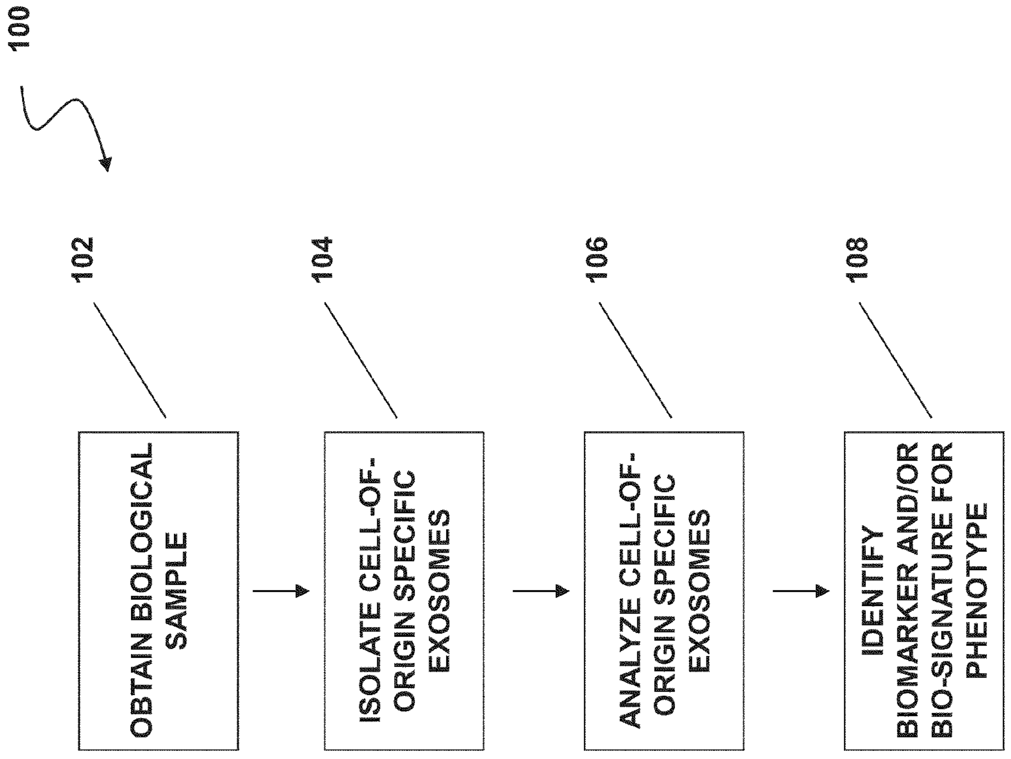
FIG. 61 is a flow chart of an exemplary method disclosed herein.

Disclosed herein are products and processes for characterizing a phenotype of an individual by analyzing exosomes. A phenotype can be any observable characteristic or trait of a subject, such as a disease or condition, a disease stage or condition stage, susceptibility to a disease or condition, prognosis of a disease stage or condition, a physiological state; or response to therapeutics. A phenotype can result from a subject's gene expression as well as the influence of environmental factors and the interactions between the two, as well as from epigenetic modifications to nucleic acid sequences A phenotype in a subject can be characterized by obtaining a biological sample from said subject and analyzing one or more exosomes from the sample. For example, characterizing a phenotype for a subject or individual may include detecting a disease or condition (including pre-symptomatic early stage detecting), determining the prognosis, diagnosis, or theranosis of a disease or condition, or determining the stage or progression of a disease or condition. Characterizing a phenotype can also include identifying appropriate treatments or treatment efficacy for specific diseases, conditions, disease stages and condition stages, predictions and likelihood analysis of disease progression, particularly disease recurrence, metastatic spread or disease relapse. A phenotype can also be a clinically distinct type or subtype of a condition or disease, such as a cancer or tumor. Phenotype determination can also be a determination of a physiological condition, or an assessment of organ distress or organ rejection, such as post-transplantation. The products and processes described herein allow assessment of a subject on an individual basis, which can provide benefits of more efficient and economical decisions in treatment.

The phenotype can be a disease or condition such as listed in Table 1. For example, the phenotype can be a tumor, neoplasm, or cancer. A cancer detected or assessed by products or processes described herein includes, but is not limited to, breast cancer, ovarian cancer, lung cancer, colon cancer, hyperplastic polyp, adenoma, colorectal cancer, high grade dysplasia, low grade dysplasia, prostatic hyperplasia, prostate cancer, melanoma, pancreatic cancer, brain cancer (such as a glioblastoma), hematological malignancy, hepatocellular carcinoma, cervical cancer, endometrial cancer, head and neck cancer, esophageal cancer, gastrointestinal stromal tumor (GIST), renal cell carcinoma (RCC) or gastric cancer. The colorectal cancer can be CRC Dukes B or Dukes C-D. The hematological malignancy can be B-Cell Chronic Lymphocytic Leukemia, B-Cell Lymphoma-DLBCL, B-Cell Lymphoma-DLBCL-germinal center-like, B-Cell Lymphoma-DLBCL-activated B-cell-like, and Burkitt's lymphoma. The phenotype may also be a premalignant condition, such as Barrett's Esophagus.

The phenotype can also be an inflammatory disease, immune disease, or autoimmune disease. For example, the disease may be inflammatory bowel disease (IBD), Crohn's disease (CD), ulcerative colitis (UC), pelvic inflammation, vasculitis, psoriasis, diabetes, autoimmune hepatitis, Multiple Sclerosis, Myasthenia Gravis, Type I diabetes, Rheumatoid Arthritis, Psoriasis, Systemic Lupus Erythematosis (SLE), Hashimoto's Thyroiditis, Grave's disease, Ankylosing Spondylitis Sjogrens Disease, CREST syndrome, Scleroderma, Rheumatic Disease, organ rejection, Primary Sclerosing Cholangitis, or sepsis.

The phenotype can also be a cardiovascular disease, such as atherosclerosis, congestive heart failure, vulnerable plaque, stroke, or ischemia. The cardiovascular disease or condition can be high blood pressure, stenosis, vessel occlusion or a thrombotic event.

The phenotype can also be a neurological disease, such as Multiple Sclerosis (MS), Parkinson's Disease (PD), Alzheimer's Disease (AD), schizophrenia, bipolar disorder, depression, autism, Prion Disease, Pick's disease, dementia, Huntington disease (HD), Down's syndrome, cerebrovascular disease, Rasmussen's encephalitis, viral meningitis, neurospsychiatric systemic lupus erythematosus (NPSLE), amyotrophic lateral sclerosis, Creutzfeldt-Jacob disease, Gerstmann-Straussler-Scheinker disease, transmissible spongiform encephalopathy, ischemic reperfusion damage (e.g. stroke), brain trauma, microbial infection, or chronic fatigue syndrome. The phenotype may also be a condition such as fibromyalgia, chronic neuropathic pain, or peripheral neuropathic pain.

The phenotype may also be an infectious disease, such as a bacterial, viral or yeast infection. For example, the disease or condition may be Whipple's Disease, Prion Disease, cirrhosis, methicillin-resistant *staphylococcus aureus*, HIV, hepatitis, syphilis, meningitis, malaria, tuberculosis, or influenza. Viral proteins, such as HIV or HCV-like particles can be assessed in an exosome, to characterize a viral condition.

The phenotype can also be a perinatal or pregnancy related condition (e.g. preeclampsia or preterm birth), metabolic disease or condition, such as a metabolic disease or condition associated with iron metabolism. For example, hepcidin can be assayed in an exosome to characterize an iron deficiency. The metabolic disease or condition can also be diabetes, inflammation, or a perinatal condition.

Subject

One or more phenotypes of a subject can be determined by analyzing exosomes in a biological sample obtained from the subject. A subject or patient can include, but is not limited to, mammals such as bovine, avian, canine, equine, feline, ovine, porcine, or primate animals (including humans and non-human primates). A subject may also include mammals of importance due to being endangered, such as Siberian tigers; or economic importance, such as animals raised on farms for consumption by humans, or animals of social importance to humans such as animals kept as pets or in zoos. Examples of such animals include but are not limited to: carnivores such as cats and dogs; swine including pigs, hogs and wild boars; ruminants or ungulates such as cattle, oxen, sheep, giraffes, deer, goats, bison, camels or horses. Also included are birds that are endangered or kept in zoos, as well as fowl and more particularly domesticated fowl, i.e. poultry, such as turkeys and chickens, ducks, geese, guinea fowl. Also included are domesticated swine and horses (including race horses). In addition, any animal species connected to commercial activities are also included such as those animals connected to agriculture and aquaculture and other activities in which disease monitoring, diagnosis, and therapy selection are routine practice in husbandry for economic productivity and/or safety of the food chain.

The subject can have a pre-existing disease or condition, such as cancer. Alternatively, the subject may not have any known pre-existing condition. The subject may also be non-responsive to an existing or past treatment, such as a treatment for cancer.

Samples

The biological sample obtained from the subject may be any bodily fluid. For example, the biological sample can be peripheral blood, sera, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen (including prostatic fluid), Cowper's fluid or pre-ejaculatory fluid, female ejaculate, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates or other lavage fluids. A biological sample may also include the blastocyl cavity, umbilical cord blood, or maternal circulation which may be of fetal or maternal origin. The biological sample may also be a tissue sample or biopsy, from which exosomes may be obtained. For example, if the sample is a solid sample, cells from the sample can be cultured and exosome product induced (see for example, Example 1).

Table 1 provides a list of examples of diseases, conditions, or biological states and a corresponding list of biological samples from which exosomes may be analyzed.

TABLE 1

Examples of Biological Samples for Exosome Analysis for Various Diseases, Conditions, or Biological States

| Disease, Condition or Biological State | Biological Samples |
|---|---|
| Cancers/neoplasms affecting the following tissue types/bodily systems: breast, lung, ovarian, colon, rectal, prostate, pancreatic, brain, bone, connective tissue, glands, skin, lymph, nervous system, endocrine, germ cell, genitourinary, hematologic/blood, bone marrow, muscle, eye, esophageal, fat tissue, thyroid, pituitary, spinal cord, bile duct, heart, gall bladder, bladder, testes, cervical, endometrial, renal, ovarian, digestive/gastrointestinal, stomach, head and neck, liver, leukemia, respiratory/thorasic, cancers of unknown primary | Blood, serum, cerebrospinal fluid (CSF), urine, sputum, ascites, synovial fluid, semen, nipple aspirates, saliva, bronchoalveolar lavage fluid, tears, oropharyngeal washes, feces, peritoneal fluids, pleural effusion, sweat, tears, aqueous humor, pericardial fluid, lymph, chyme, chyle, bile, stool water, amniotic fluid, breast milk, pancreatic juice, cerumen, Cowper's fluid or pre-ejaculatory fluid, female ejaculate, interstitial fluid, menses, mucus, pus, sebum, vaginal lubrication, vomit |
| Neurodegenerative/neurological disorders: Parkinson's disease, Alzheimer's Disease and multiple sclerosis, Schizophrenia, and bipolar disorder, spasticity disorders, epilepsy | Blood, serum, CSF, urine |
| Cardiovascular Disease: atherosclerosis, cardiomyopathy, endocarditis, vunerable plaques, infection | Blood, serum, CSF, urine |
| Stroke: ischemic, intracerebral hemorrhage, subarachnoid hemorrhage, transient ischemic attacks (TIA) | Blood, serum, CSF, urine |
| Pain disorders: peripheral neuropathic pain and chronic neuropathic pain, and fibromyalgia, | Blood, serum, CSF, urine |
| Autoimmune disease: systemic and localized diseases, rheumatic disease, Lupus, Sjogren's syndrome | Blood, serum, CSF, urine, synovial fluid |

TABLE 1-continued

Examples of Biological Samples for Exosome Analysis for Various Diseases, Conditions, or Biological States

| Disease, Condition or Biological State | Biological Samples |
|---|---|
| Digestive system abnormalities: Barrett's esophagus, irritable bowel syndrome, ulcerative colitis, Crohn's disease, Diverticulosis and Diverticulitis, Celiac Disease | Blood, serum, CSF, urine |
| Endocrine disorders: diabetes mellitus, various forms of Thyroiditis,, adrenal disorders, pituitary disorders | Blood, serum, CSF, urine |
| Diseases and disorders of the skin: psoriasis | Blood, serum, CSF, urine, synovial fluid, tears |
| Urological disorders: benign prostatic hypertrophy (BPH), polycystic kidney disease, interstitial cystitis | Blood, serum, urine |
| Hepatic disease/injury: Cirrhosis, induced hepatotoxicity (due to exposure to natural or synthetic chemical sources) | Blood, serum, urine |
| Kidney disease/injury: acute, sub-acute, chronic conditions, Podocyte injury, focal segmental glomerulosclerosis | Blood, serum, urine |
| Endometriosis | Blood, serum, urine, vaginal fluids |
| Osteoporosis | Blood, serum, urine, synovial fluid |
| Pancreatitis | Blood, serum, urine, pancreatic juice |
| Asthma | Blood, serum, urine, sputum, bronchiolar lavage fluid |
| Allergies | Blood, serum, urine, sputum, bronchiolar lavage fluid |
| Prion-related diseases | Blood, serum, CSF, urine |
| Viral Infections: HIV/AIDS | Blood, serum, urine |
| Sepsis | Blood, serum, urine, tears, nasal lavage |
| Organ rejection/transplantation | Blood, serum, urine, various lavage fluids |
| Differentiating conditions: adenoma versus hyperplastic polyp, irritable bowel syndrome (IBS) versus normal, classifying Dukes stages A, B, C, and/or D of colon cancer, adenoma with low-grade hyperplasia versus high-grade hyperplasia, adenoma versus normal, colorectal cancer versus normal, IBS versus. ulcerative colitis (UC) versus Crohn's disease (CD), | Blood, serum, urine, sputum, feces, colonic lavage fluid |
| Pregnancy related physiological states, conditions, or affiliated diseases: genetic risk, adverse pregnancy outcomes | Maternal serum, amniotic fluid, cord blood |

The biological samples may be obtained through a third party, such as a party not performing the analysis of the exosome. For example, the sample may be obtained through a clinician, physician, or other health care manager of a subject from which the sample is derived. Alternatively, the biological sample may obtained by the same party analyzing the exosomes.

The volume of the biological sample used for analyzing an exosome can be in the range of between 0.1-20 mL, such as less than about 20, 15, 10, 9, 8, 7, 6, 5, 4, 3, 2, 1 or 0.1 mL.

Furthermore, analysis of one or more exosomes in a biological sample can be used to determine whether an additional biological sample should be obtained for analysis. For example, analysis of one or more exosomes in a serum sample can be used to determine whether a biopsy should be obtained.

Exosomes

The exosomes from a biological sample for analysis are used to determine a phenotype. Exosomes are small vesicles that are released into the extracellular environment from a variety of different cells such as but not limited to, cells that originate from, or are derived from, the ectoderm, endoderm, or mesoderm including any such cells that have undergone genetic, environmental, and/or any other variations or alterations (e.g. Tumor cells or cells with genetic mutations). An exosome is typically created intracellularly when a segment of the cell membrane spontaneously invaginates and is ultimately exocytosed (see for example, Keller et al., *Immunol. Lett.* 107 (2): 102-8 (2006)). Exosomes can have, but not be limited to, a diameter of greater than about 10, 20, or 30 nm. They can have a diameter of about 30-1000 nm, about 30-800 nm, about 30-200 nm, or about 30-100 nm. In some embodiments, the exosomes can have, but not be limited to, a diameter of less than about 10,000 nm, 1000 nm, 800 nm, 500 nm, 200 nm, 100 nm or 50 nm. As used throughout, the term "about," when referring to a value or to an amount is meant to encompass variations in some embodiments±10% from the specified amount, as such variations are appropriate.

Exosomes may also be referred to as microvesicles, nanovesicles, vesicles, dexosomes, bleb, blebby, prostasomes, microparticles, intralumenal vesicles, endosomal-like vesicles or exocytosed vehicles. As used herein, exosomes can also include any shed membrane bound particle that is derived from either the plasma membrane or an internal membrane. Exosomes can also include cell-derived structures bounded by a lipid bilayer membrane arising from both herniated evagination (blebbing) separation and sealing of portions of the plasma membrane or from the export of any intracellular membrane-bounded vesicular structure containing various membrane-associated proteins of tumor origin, including surface-bound molecules derived from the host circulation that bind selectively to the tumor-derived proteins together with molecules contained in the exosome lumen, including but not limited to tumor-derived microRNAs or intracellular proteins. Blebs and blebbing are further described in Charras et al., *Nature Reviews Molecular and Cell Biology, Vol.* 9, No. 11, p. 730-736 (2008). Exosomes can also include membrane fragments. Circulating tumor-derived exosomes (CTEs) as referenced herein are exosomes that are shed into circulation or bodily fluids from tumor cells. CTEs, as with cell-of-origin specific exosomes, typically have unique biomarkers that permit their isolation from bodily fluids in a highly specific manner.

Exosomes can be directly assayed from the biological samples, such that the level of exosomes is determined or the one or more biomarkers of the exosomes is determined without prior isolation, purification, or concentration of the exosomes. Alternatively, exosomes may be isolated, purified, or concentrated from a sample prior to analysis.

Isolation of Exosomes

An exosome may be purified or concentrated prior to analysis. Analysis of an exosome can include quantitating the amount one or more exosome populations of a biological sample. For example, a heterogeneous population of exosomes can be quantitated, or a homogeneous population of exosomes, such as a population of exosomes with a particular biomarker profile, a particular bio-signature, or derived from a particular cell type (cell-of-origin specific exosomes) can be isolated from a heterogeneous population of exosomes and quantitated. Analysis of an exosome can also include detecting, quantitatively or qualitatively, a particular biomarker profile or a bio-signature, of an exosome, as described below.

An exosome can be stored and archived, such as in a bio-fluid bank and retrieved for analysis as necessary. An exosome may also be isolated from a biological sample that has been previously harvested and stored from a living or deceased subject. In addition, an exosome may be isolated from a biological sample which has been collected as described in King et al., *Breast Cancer Res* 7(5): 198-204 (2005). An exosome may be isolated from an archived or stored sample. Alternatively, an exosome may be isolated from a biological sample and analyzed without storing or archiving of the sample. Furthermore, a third party may obtain or store the biological sample, or obtain or store the exosomes for analysis.

An enriched population of exosomes can be obtained from a biological sample. For example, exosomes may be concentrated or isolated from a biological sample using size exclusion chromatography, density gradient centrifugation, differential centrifugation, nanomembrane ultrafiltration, immunoabsorbent capture, affinity purification, microfluidic separation, or combinations thereof.

Size exclusion chromatography, such as gel permeation columns, centrifugation or density gradient centrifugation, and filtration methods can be used. For example, exosomes can be isolated by differential centrifugation, anion exchange and/or gel permeation chromatography (for example, as described in U.S. Pat. Nos. 6,899,863 and 6,812,023), sucrose density gradients, organelle electrophoresis (for example, as described in U.S. Pat. No. 7,198,923), magnetic activated cell sorting (MACS), or with a nanomembrane ultrafiltration concentrator. Various combinations of isolation or concentration methods can be used.

Highly abundant proteins, such as albumin and immunoglobulin, may hinder isolation of exosomes from a biological sample. For example, exosomes may be isolated from a biological sample using a system that utilizes multiple antibodies that are specific to the most abundant proteins found in blood. Such a system can remove up to several proteins at once, thus unveiling the lower abundance species such as cell-of-origin specific exosomes.

This type of system can be used for isolation of exosomes from biological samples such as blood, cerebrospinal fluid or urine. The isolation of exosomes from a biological sample may also be enhanced by high abundant protein removal methods as described in Chromy et al. *J. Proteome Res* 2004; 3:1120-1127. In another embodiment, the isolation of exosomes from a biological sample may also be enhanced by removing serum proteins using glycopeptide capture as described in Zhang et al, *Mol Cell Proteomics* 2005; 4:144-155. In addition, exosomes from a biological sample such as urine may be isolated by differential centrifugation followed by contact with antibodies directed to cytoplasmic or anti-cytoplasmic epitopes as described in Pisitkun et al., *Proc Natl Acad Sci USA,* 2004; 101:13368-13373.

Isolation or enrichment of exosomes from biological samples can also be enhanced by use of sonication (for example, by applying ultrasound), or the use of detergents, other membrane-active agents, or any combination thereof. For example, ultrasonic energy can be applied to a potential tumor site, and without being bound by theory, release of exosomes from the tissue can be increased, allowing an enriched population of exosomes that can be analyzed or assessed from a biological sample using one or more methods disclosed herein.

Binding Agents

A binding agent is an agent that binds to an exosomal component, such as a biomarker of an exosome. The binding agent can be a capture agent. A capture agent captures the exosome by binding to an exosomal target, such as a biomarker on the exosome. For example, the capture agent can be a capture antibody that binds to an antigen on the exosome. The capture agent can be coupled to a substrate and used to isolate the exosome, such as described herein.

A binding agent can be used after exosomes are concentrated or isolated from a biological sample. For example, exosomes can first be isolated from a biological sample before exosomes with a specific biomarker are isolated using a binding agent for the biomarker. Thus, exosomes with the specific biomarker is isolated from a heterogeneous population of exosomes. Alternatively, a binding agent may be used on a biological sample comprising exosomes without a prior isolation step or concentration of exosomes. For example, a binding agent is used to isolate an exosome with a specific biomarker from a biological sample.

A binding agent can be DNA, RNA, monoclonal antibodies, polyclonal antibodies, Fabs, Fab', single chain antibodies, synthetic antibodies, aptamers (DNA/RNA), peptoids, zDNA, peptide nucleic acids (PNAs), locked nucleic acids (LNAs), lectins, synthetic or naturally occurring chemical compounds (including but not limited to drugs, labeling reagents), dendrimers, or combinations thereof. For example, the binding agent can be a capture antibody.

In some instances, a single binding agent can be employed to isolate an exosome. In other instances, a combination of different binding agents may be employed to isolate an exosome. For example, at least 2, 3, 4, 5, 6, 7, 8, 9, 10, 11, 12, 13, 14, 15, 16, 17, 18, 19, 20, 25, 50, 75 or 100 different binding agents may be used to isolate an exosome from a biological sample. Furthermore, the one or more different binding agents for an exosome can form the bio-signature of the exosome, further described below.

Different binding agents can also be used for multiplexing. For example, isolation of more than one population of exosomes (for example, exosomes from specific cell types) can be performed by isolating each exosome population with a different binding agent. Different binding agents can be bound to different particles, wherein the different particles are labeled. In another embodiment, an array comprising different binding agents can be used for multiplex analysis, wherein the different binding agents are differentially labeled or can be ascertained based on the location of the binding agent on the array. Multiplexing can be accomplished up to the resolution capability of the labels or detection method, such as described below.

The binding agent can be an antibody. For example, an exosome may be isolated using one or more antibodies specific for one or more antigens present on the exosome. For example, an exosome can have CD63 on its surface, and an antibody, or capture antibody, for CD63 can be used to isolate the exosome. Alternatively, an exosome derived from a tumor cell can express EpCam, the exosome can be isolated using an antibody for EpCam and CD63. Other antibodies for isolating exosomes can include an antibody, or capture antibody, to CD9, PSCA, TNFR, CD63, B7H3, MFG-E8, EpCam, Rab, CD81, STEAP, PCSA, PSMA, or 5T4.

The antibodies disclosed herein can be immunoglobulin molecules or immunologically active portions of immunoglobulin molecules, i.e., molecules that contain an antigen binding site that specifically binds an antigen and synthetic antibodies. The immunoglobulin molecules can be of any class (e.g., IgG, IgE, IgM, IgD or IgA) or subclass of immunoglobulin molecule. Antibodies include, but are not limited to, polyclonal, monoclonal, bispecific, synthetic, humanized and chimeric antibodies, single chain antibodies, Fab fragments and $F(ab')_2$ fragments, Fv or Fv' portions, fragments produced by a Fab expression library, anti-idiotypic (anti-Id) antibodies, or epitope-binding fragments of any of the above. An antibody, or generally any molecule, "binds specifically" to an antigen (or other molecule) if the antibody binds preferentially to the antigen, and, e.g., has less than about 30%, 20%, 10%, 5% or 1% cross-reactivity with another molecule.

The binding agent can also be a polypeptide or peptide. Polypeptide is used in its broadest sense and may include a sequence of subunit amino acids, amino acid analogs, or peptidomimetics. The subunits may be linked by peptide bonds. The polypeptides may be naturally occurring, processed forms of naturally occurring polypeptides (such as by enzymatic digestion), chemically synthesized or recombinantly expressed. The polypeptides for use in the methods of the present invention may be chemically synthesized using standard techniques. The polypeptides may comprise D-amino acids (which are resistant to L-amino acid-specific proteases), a combination of D- and L-amino acids, β amino acids, or various other designer or non-naturally occurring amino acids (e.g., (β-methyl amino acids, Cα-methyl amino acids, and Nα-methyl amino acids, etc.) to convey special properties. Synthetic amino acids may include ornithine for lysine, and norleucine for leucine or isoleucine. In addition, the polypeptides can have peptidomimetic bonds, such as ester bonds, to prepare polypeptides with novel properties. For example, a polypeptide may be generated that incorporates a reduced peptide bond, i.e., $R_1—CH_2—NH—R_2$, where $R_1$ and $R_2$ are amino acid residues or sequences. A reduced peptide bond may be introduced as a dipeptide subunit. Such a polypeptide would be resistant to protease activity, and would possess an extended half-live in vivo. Polypeptides can also include peptoids (N-substituted glycines), in which the side chains are appended to nitrogen atoms along the molecule's backbone, rather than to the α-carbons, as in amino acids. Polypeptides and peptides are intended to be used interchangeably throughout this application, i.e. where the term peptide is used, it may also include polypeptides and where the term polypeptides is used, it may also include peptides.

An exosome may be isolated using a known binding agent. For example, the binding agent can be an agent that binds exosomal "housekeeping proteins," or general exosome biomarkers, such as CD63, CD9, CD81, CD82, CD37, CD53, or Rab-5b. The binding agent can also be an agent that binds to exosomes derived from specific cell types, such as tumor cells (e.g. binding agent for EpCam) or specific cell-of-origins, such as described below. For example, the binding agent used to isolate an exosome may be a binding agent for an antigen selected from FIG. 1. The binding agent for an exosome can also be selected from those listed in FIG. 2. For example, the binding agent can be for an antigen such as 5T4, B7H3, caveolin, CD63, CD9, E-Cadherin, MFG-E8, PSCA, PSMA, Rab-5B, STEAP, TNFR1, CD81, EpCam, CD59, or CD66. One or more binding agents, such as one or more binding agents for two or more of the antigens, can be used for isolating an exosome. The binding agent used can be selected based on the desire of isolating exosomes derived from particular cell types, or cell-of-origin specific exosomes.

A binding agent can also be linked directly or indirectly to a solid surface or substrate. A solid surface or substrate can be any physically separable solid to which a binding agent can be directly or indirectly attached including, but not limited to, surfaces provided by microarrays and wells, particles such as beads, columns, optical fibers, wipes, glass and modified or functionalized glass, quartz, mica, diazotized membranes (paper or nylon), polyformaldehyde, cellulose, cellulose acetate, paper, ceramics, metals, metalloids, semiconductive materials, quantum dots, coated beads or particles, other chromatographic materials, magnetic particles; plastics (including acrylics, polystyrene, copolymers of styrene or other materials, polypropylene, polyethylene, polybutylene, polyurethanes, TEFLON™, etc.), polysaccharides, nylon or nitrocellulose, resins, silica or silica-based materials including silicon and modified silicon, carbon, metals, inorganic glasses, plastics, ceramics, conducting polymers (including polymers such as polypyrole and polyindole); micro or nanostructured surfaces such as nucleic acid tiling arrays, nanotube, nanowire, or nanoparticulate decorated surfaces; or porous surfaces or gels such as methacrylates, acrylamides, sugar polymers, cellulose, silicates, or other fibrous or stranded polymers. In addition, as is known the art, the substrate may be coated using passive or chemically-derivatized coatings with any number of materials, including polymers, such as dextrans, acrylamides, gelatins or agarose. Such coatings can facilitate the use of the array with a biological sample.

For example, an antibody used to isolate an exosome can be bound to a solid substrate such as a well, such as commercially available plates (e.g. from Nunc, Milan Italy). Each well can be coated with the antibody. In some embodiments, the antibody used to isolate an exosome can be bound to a solid substrate such as an array. The array can have a predetermined spatial arrangement of molecule interactions, binding islands, biomolecules, zones, domains or spatial arrangements of binding islands or binding agents deposited within discrete boundaries. Further, the term array may be used herein to refer to multiple arrays arranged on a surface, such as would be the case where a surface bore multiple copies of an array. Such surfaces bearing multiple arrays may also be referred to as multiple arrays or repeating arrays.

A binding agent can also be bound to particles such as beads or microspheres. For example, an antibody specific for an exosomal component can be bound to a particle, and the antibody-bound particle is used to isolate exosomes from a biological sample. In some embodiments, the microspheres may be magnetic or fluorescently labeled. In addition, a binding agent for isolating exosomes can be a solid substrate itself. For example, latex beads, such as aldehyde/sulfate beads (Interfacial Dynamics, Portland, Oreg.) can be used.

A binding agent bound to a magnetic bead can also be used to isolate an exosome. For example, a biological sample such as serum from a patient can be collected for colon cancer screening. The sample can be incubated with anti-CCSA-3 (Colon Cancer-Specific Antigen) coupled to magnetic microbeads. A low-density microcolumn can be placed in the magnetic field of a MACS Separator and the column is then washed with a buffer solution such as Tris-buffered saline. The magnetic immune complexes can then be applied to the column and unbound, non-specific material can be discarded. The CCSA-3 selected exosomes can be recovered by removing the column from the separator and placing it on a collection tube. A buffer can be added to the column and the magnetically labeled exosomes can be released by applying the plunger supplied with the column. The isolated exosomes can be diluted in IgG elution buffer and the complex can then be centrifuged to separate the microbeads from the exosomes. The pelleted isolated cell-of-origin specific exosomes can be resuspended in buffer such as phosphate-buffered saline and quantitated. Alternatively, due to the strong adhesion force between the antibody captured cell-of-origin specific exosomes and the magnetic microbeads, a proteolytic enzyme such as trypsin can be used for the release of captured exosomes without the need for centrifugation. The proteolytic enzyme can be incubated with the antibody captured cell-of-origin specific exosomes for at least a time sufficient to release the exosomes.

A binding agent, such as an antibody, for isolating an exosome is preferably contacted with the biological sample comprising the exosome of interest for at least a time sufficient for the binding agent to bind to an exosomal component. For example, an antibody may be contacted with a biological sample for various intervals ranging from seconds days, including but not limited to, about 10 minutes, 30 minutes, 1 hour, 3 hours, 5 hours, 7 hours, 10 hours, 15 hours, 1 day, 3 days, 7 days or 10 days.

A binding agent, such as an antibody specific to an antigen listed in FIG. 1, or a binding agent listed in FIG. 2, can be labeled with, including but not limited to, a magnetic label, a fluorescent moiety, an enzyme, a chemiluminescent probe, a metal particle, a non-metal colloidal particle, a polymeric dye particle, a pigment molecule, a pigment particle, an electrochemically active species, semiconductor nanocrystal or other nanoparticles including quantum dots or gold particles. The label can be, but not be limited to, fluorophores, quantum dots, or radioactive labels. For example, the label can be a radioisotope (radionuclides), such as $^{3}H$, $^{11}C$, $^{14}C$, $^{18}F$, $^{32}P$, $^{35}S$, $^{64}Cu$, $^{68}Ga$, $^{86}Y$, $^{99}Tc$, $^{111}In$, $^{123}I$, $^{124}I$, $^{125}I$, $^{131}I$, $^{133}Xe$, $^{177}Lu$, $^{211}At$, or $^{213}Bi$. The label can be a fluorescent label, such as a rare earth chelate (europium chelate), fluorescein type, such as, but not limited to, FITC, 5-carboxyfluorescein, 6-carboxy fluorescein; a rhodamine type, such as, but not limited to, TAMRA; dansyl; Lissamine; cyanines; phycoerythrins; Texas Red; and analogs thereof.

A binding agent can be directly or indirectly labeled, e.g., the label is attached to the antibody through biotin-streptavidin. Alternatively, an antibody is not labeled, but is later contacted with a second antibody that is labeled after the first antibody is bound to an antigen of interest.

For example, various enzyme-substrate labels are available or disclosed (see for example, U.S. Pat. No. 4,275,149). The enzyme generally catalyzes a chemical alteration of a chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRP), alkaline phosphatase (AP), β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Examples of enzyme-substrate combinations include, but are not limited to, horseradish peroxidase (HRP) with hydrogen peroxidase as a substrate, wherein the hydrogen peroxidase oxidizes a dye precursor (e.g., orthophenylene diamine (OPD) or 3,3',5,5'-tetramethylbenzidine hydrochloride (TMB)); alkaline phosphatase (AP) with para-nitrophenyl phosphate as chromogenic substrate; and β-D-galactosidase ((β-D-Gal) with a chromogenic substrate (e.g., p-nitrophenyl-(β-D-galactosidase) or fluorogenic substrate 4-methylumbelliferyl-β-D-galactosidase.

Depending on the method of isolation used, the binding agent may be linked to a solid surface or substrate, such as arrays, particles, wells and other substrates described above. Methods for direct chemical coupling of antibodies, to the cell surface are known in the art, and may include, for example, coupling using glutaraldehyde or maleimide activated antibodies. Methods for chemical coupling using multiple step procedures include biotinylation, coupling of trinitrophenol (TNP) or digoxigenin using for example succinimide esters of these compounds. Biotinylation can be accomplished by, for example, the use of D-biotinyl-N-hydroxysuccinimide. Succinimide groups react effectively with amino groups at pH values above 7, and preferentially between about pH 8.0 and about pH 8.5. Biotinylation can be accomplished by, for example, treating the cells with dithiothreitol followed by the addition of biotin maleimide.

Flow Cytometry

Isolation of exosomes using particles such as beads or microspheres can also be performed using flow cytometry. Flow cytometry can be used for sorting microscopic particles suspended in a stream of fluid. As particles pass through they can be selectively charged and on their exit can be deflected into separate paths of flow. It is therefore possible to separate populations from an original mix, such as a biological sample, with a high degree of accuracy and speed. Flow cytometry allows simultaneous multiparametric analysis of the physical and/or chemical characteristics of single cells flowing through an optical/electronic detection apparatus. A beam of light, usually laser light, of a single frequency (color) is directed onto a hydrodynamically focused stream of fluid. A number of detectors are aimed at the point where the stream passes through the light beam; one in line with the light beam (Forward Scatter or FSC) and several perpendicular to it (Side Scatter or SSC) and one or more fluorescent detectors.

Each suspended particle passing through the beam scatters the light in some way, and fluorescent chemicals in the particle may be excited into emitting light at a lower frequency than the light source. This combination of scattered and fluorescent light is picked up by the detectors, and by analyzing fluctuations in brightness at each detector (one for each fluorescent emission peak), it is possible to deduce various facts about the physical and chemical structure of each individual particle. FSC correlates with the cell size and SSC depends on the inner complexity of the particle, such as shape of the nucleus, the amount and type of cytoplasmic granules or the membrane roughness. Some flow cytometers have eliminated the need for fluorescence and use only light scatter for measurement.

Flow cytometers can analyze several thousand particles every second in "real time" and can actively separate out and isolate particles having specified properties. They offer high-throughput automated quantification, and separation, of the set parameters for a high number of single cells during each analysis session. Modern instruments have multiple lasers and fluorescence detectors, for example up to 4 lasers and 18 fluorescence detectors, allowing multiple labels to be used to more precisely specify a target population by their phenotype.

The data resulting from flow-cytometers can be plotted in 1 dimension to produce histograms or seen in 2 dimensions as dot plots or in 3 dimensions with newer software. The regions on these plots can be sequentially separated by a series of subset extractions which are termed gates. Specific gating protocols exist for diagnostic and clinical purposes especially in relation to hematology. The plots are often made on logarithmic scales. Because different fluorescent dye's emission spectra overlap, signals at the detectors have to be compensated electronically as well as computationally. Fluorophores for labeling biomarkers may include those described in Ormerod, *Flow Cytometry* 2nd ed., Springer-Verlag, New York (1999), and in Nida et al., *Gynecologic Oncology* 2005; 4 889-894 which is incorporated herein by reference.

Multiplexing

Different binding agents can be used for multiplexing different exosome populations. Different exosome populations can be isolated or detected using different binding agents. Each exosome population in a biological sample can be labeled with a different signaling label, such as fluorophores, quantum dots, or radioactive labels, such as described above. The label can be directly conjugated to a binding agent or indirectly used to detect a binding agent. The number of populations detected in a multiplexing assay is dependent on the resolution capability of the labels and the summation of signals, as more than two differentially labeled exosome populations that bind two or more affinity elements can produce summed signals.

Multiplexing of at least 2, 3, 4, 5, 6, 7, 8, 9, 10, 11, 12, 13, 14, 15, 16, 17, 18, 19, 20, 25, 50, 75 or 100 different exosome populations may be performed. For example, one population of exosomes specific to a cell-of-origin can be assayed along with a second population of exosomes specific to a different cell-of-origin, where each population is labeled with a different label. Alternatively, a population of exosomes with a particular biomarker or bio-signature can be assayed along with a second population of exosomes with a different biomarker or bio-signature.

In one embodiment, multiplex analysis is performed by applying a plurality of exosomes comprising more than one population of exosomes to a plurality of substrates, such as beads. Each bead is coupled to one or more capture agents. The plurality of beads is divided into subsets, where beads with the same capture agent or combination of capture agents form a subset of beads, such that each subset of beads has a different capture agent or combination of capture agents than another subset of beads. The beads can then be used to capture exosomes that comprises a component that binds to the capture agent. The different subsets can be used to capture different populations of exosomes. The captured exosomes can then be analyzed by detecting one or more biomarkers of the exosomes.

Flow cytometry can be used in combination with a particle-based or bead based assay. Multiparametric immunoassays or other high throughput detection assays using bead coatings with cognate ligands and reporter molecules with specific activities consistent with high sensitivity automation can be used. For example, beads in each subset can be differentially labeled from another subset. For example, in a particle based assay system, a binding agent or capture agent for an exosome, such as a capture antibody, can be immobilized on addressable beads or microspheres. Each binding agent for each individual binding assay (such as an immunoassay when the binding agent is an antibody) can be coupled to a distinct type of microsphere (i.e., microbead) and the binding assay reaction takes place on the surface of the microspheres. Microspheres can be distinguished by different labels, for example, a microsphere with a specific capture agent would have a different signaling label as compared to another microsphere with a different capture agent. For example, microspheres can be dyed with discrete fluorescence intensities such that the fluorescence intensity of a microsphere with a specific binding agent is different than that of another microsphere with a different binding agent.

The microsphere can be labeled or dyed with at least 2 different labels or dyes. In some embodiments, the microsphere is labeled with at least 3, 4, 5, 6, 7, 8, 9, or 10 different labels. Different microspheres in a plurality of microspheres can have more than one label or dye, wherein various subsets of the microspheres have various ratios and combinations of the labels or dyes permitting detection of different microspheres with different binding agents. For example, the various ratios and combinations of labels and dyes can permit different fluorescent intensities. Alternatively, the various ratios and combinations may be used to generate different detection patters to identify the binding agent. The microspheres can be labeled or dyed externally or may have intrinsic fluorescence or signaling labels. Beads can be loaded separately with their appropriate binding agents and thus, different exosome populations can be isolated based on the different binding agents on the differentially labeled microspheres to which the different binding agents are coupled.

In another embodiment, multiplex analysis can be performed using a planar substrate, wherein the said substrate comprises a plurality of capture agents. The plurality of capture agents can capture one or more populations of exosomes, and one or more biomarkers of the captured exosomes detected. The planar substrate can be a microarray or other substrate as further described herein.

Novel Binding Agents

An exosome may be isolated using a binding agent for a novel component of an exosome, such as an antibody for a novel antigen specific to an exosome of interest. Novel antigens that are specific to exosomes of interest may be isolated or identified using different test compounds of known composition bound to a substrate, such as an array or a plurality of particles, which can allow a large amount of chemical/structural space to be adequately sampled using only a small fraction of the space. The novel antigen identified can also serve as a biomarker for the exosome. For example, a novel antigen identified for a cell-of-origin specific exosome can be a biomarker for that particular cell-of-origin specific exosome.

A binding agent can be identified by screening either a homogeneous or heterogeneous exosome population against test compounds. Since the composition of each test compound on the substrate surface is known, this constitutes a screen for affinity elements. For example, a test compound array comprises test compounds at specific locations on the substrate addressable locations, and can be used to identify one or more binding agents for an exosome. The test compounds can all be unrelated or related based on minor variations of a core sequence or structure. The different test compounds may include variants of a given test compound (such as polypeptide isoforms), test compounds that are structurally or compositionally unrelated, or a combination thereof.

Test compounds can be peptoids, polysaccharides, organic compounds, inorganic compounds, polymers, lipids, nucleic acids, polypeptides, antibodies, proteins, polysaccharides, or other compounds. The test compounds can be natural or synthetic. The test compounds can comprise or consist of linear or branched heteropolymeric compounds based on any of a number of linkages or combinations of linkages (e.g., amide, ester, ether, thiol, radical additions, metal coordination, etc.), dendritic structures, circular structures, cavity structures or other structures with multiple nearby sites of attachment that serve as scaffolds upon which specific additions are made. These test compounds can be spotted on the substrate or synthesized in situ, using standard methods in the art. In addition, the test compounds can be spotted or synthesized in situ in combinations in order to detect useful interactions, such as cooperative binding.

The test compounds can be polypeptides with known amino acid sequences, thus, detection a test compound binding with an exosome can lead to identification of a polypeptide of known amino sequence that can be used as a binding agent. For example, a homogenous population of exosomes can be applied to a spotted array on a slide containing between a few and 1,000,000 test polypeptides having a length of variable amino acids. The polypeptides can be attached to the surface through the C-terminus. The sequence of the polypeptides can be generated randomly from 19 amino acids, excluding cysteine. The binding reaction can include a non-specific competitor, such as excess bacterial proteins labeled with another dye such that the specificity ratio for each polypeptide binding target can be determined. The polypeptides with the highest specificity and binding can be selected. The identity of the polypeptide on each spot is known, and thus can be readily identified. Once the novel antigens specific to the homogeneous exosome population, such as a cell-of-origin specific exosome is identified, such cell-of-origin specific exosomes may subsequently be isolated using such antigens in methods described hereafter.

Arrays can also be used for identifying antibodies for isolating exosomes. Test antibodies can be attached to an array and screened against a heterogeneous population of exosomes to identify antibodies that can be used to isolate, and identify, an exosome. A homogeneous population of exosomes, such as cell-of-origin specific exosomes, can also be screened with an antibody array. Other than identifying antibodies to isolate the homogeneous population of exosomes, one or more protein biomarkers specific to the homogenous exosome population can be identified. Commercially available platforms with test antibodies pre-selected, or custom selection of test antibodies attached to the array, can be used. For example, an antibody array from Full Moon Biosystems can be screened using prostate cancer cell derived exosomes, identifying antibodies to Bcl-XL, ERCC1, Keratin 15, CD81/TAPA-1, CD9, Epithelial Specific Antigen (ESA), and Mast Cell Chymase as binding agents (see for example, FIG. 63), and the proteins identified can be used as biomarkers for the exosomes.

An antibody or synthetic antibody to be used as a binding agent can also be identified through a peptide array. Another method is the use of synthetic antibody generation through antibody phage display. M13 bacteriophage libraries of antibodies (e.g. Fabs) are displayed on the surfaces of phage particles as fusions to a coat protein. Each phage particle displays a unique antibody and also encapsulates a vector that contains the encoding DNA. Highly diverse libraries can be constructed and represented as phage pools, which can be used in antibody selection for binding to immobilized antigens. Antigen-binding phages are retained by the immobilized antigen, and the nonbinding phages are removed by washing. The retained phage pool can be amplified by infection of an *Escherichia coli* host and the amplified pool can be used for additional rounds of selection to eventually obtain a population that is dominated by antigen-binding clones. At this stage, individual phase clones can be isolated and subjected to DNA sequencing to decode the sequences of the displayed antibodies. Through the use of phase display and other methods known in the art, high affinity designer antibodies for exosomes can be generated.

Bead-based assays can also be used to identify novel binding agents to isolate exosomes. A test antibody or peptide can be conjugated to a particle. For example, a bead can be conjugated to an antibody or peptide and used to detect and quantify the proteins expressed on the surface of a population of exosomes in order to discover and specifically select for novel antibodies that can target exosomes from specific tissue or tumor types. Any molecule of organic origin can be successfully conjugated to a polystyrene bead through use of a commercially available kit according to manufacturer's instructions. Each bead set can be colored a certain detectable wavelength and each can be linked to a known antibody or peptide which can be used to specifically measure which beads are linked to exosomal proteins matching the epitope of previously conjugated antibodies or peptides. The beads can be dyed with discrete fluorescence intensities such that each bead with a different intensity has a different binding agent as described above.

For example, a purified exosome preparation can be diluted in assay buffer to an appropriate concentration according to empirically determined dynamic range of assay. A sufficient volume of coupled beads can be prepared and approximately 1 μl of the antibody-coupled beads can be aliqouted into a well and adjusted to a final volume of approximately 50 μl. Once the antibody-conjugated beads have been added to a vacuum compatible plate, the beads can be washed to ensure proper binding conditions: An appropriate volume of exosomal preparation can then be added to each well being tested and the mixture incubated, such as for 15-18 hours. A sufficient volume of detection antibodies using detection antibody diluent solution can be prepared and incubated with the mixture for 1 hour or for as long as necessary. The beads can then be washed before the addition of detection antibody (biotin expressing) mixture composed of streptavidin phycoereythin. The beads can then be washed and vacuum aspirated several times before analysis on a suspension array system using software provided with an instrument. The identity of antigens that can be used to selectively extract the exosomes can then be elucidated from the analysis.

Assays using imaging systems can be utilized to detect and quantify proteins expressed on the surface of an exosome in order to discover and specifically select for and enrich exosomes from specific tissue or tumor types. Antibodies, peptides or cells conjugated to multiple well multiplex carbon coated plates can be used. Simultaneous measurement of many analytes in a well can be achieved through the use of capture antibodies arrayed on the patterned carbon working surface. Analytes can then be detected with antibodies labeled with reagents in electrode wells with an enhanced electro-chemiluminescent plate. Any molecule of organic origin can be successfully conjugated to the carbon coated plate. Proteins expressed on the surface of exosomes can be identified from this assay and can be used as targets to specifically select for and enrich exosomes from specific tissue or tumor types.

The binding agent can also be a novel aptamer. An aptamer for a target can be identified using systematic evolution of ligands by exponential enrichment (SELEX) (Tuerk & Gold, *Science* 249:505-510, 1990; Ellington & Szostak, *Nature* 346:818-822, 1990), such as described in U.S. Pat. No. 5,270,163. A library of nucleic acids can be contacted with a target exosome, and those nucleic acids specifically bound to the target are partitioned from the remainder of nucleic acids in the library which do not specifically bind the target. The partitioned nucleic acids are amplified to yield a ligand-enriched pool. Multiple cycles of binding, partitioning, and amplifying (i.e., selection) result in identification of one or more aptamers with the desired activity. Another method for identifying an aptamer to isolate exosomes is described in U.S. Pat. No. 6,376,19, which describes increasing or decreasing frequency of nucleic acids in a library by their binding to a chemically synthesized peptide. Modified methods, such as Laser SELEX or deSELEX as described in U.S. Patent Publication No. 20090264508 can also be used.

Microfluidics

The methods for isolating or identifying exosomes can be used in combination with microfluidic devices. The methods of isolating exosomes disclosed herein can be performed using microfluidic devices. Microfluidic devices, which may also be referred to as "lab-on-a-chip" systems, biomedical micro-electro-mechanical systems (bioMEMs), or multicomponent integrated systems, can be used for isolating, and analyzing, exosomes. Such systems miniaturize and compartmentalize processes that allow for binding of exosomes, detection of exosomal biomarkers, and other processes.

A microfluidic device can also be used for isolation of an exosome through size differential or affinity selection. For example, a microfluidic device can use one more channels for isolating an exosome from a biological sample based on size, or by using one or more binding agents for isolating an exosome, from a biological sample. A biological sample can be introduced into one or more microfluidic channels, which selectively allows the passage of exosomes. The selection can be based on a property of the exosomes, for example, size, shape, deformability, biomarker profile, or bio-signature.

Alternatively, a heterogeneous population of exosomes can be introduced into a microfluidic device, and one or more different homogeneous populations of exosomes can be obtained. For example, different channels can have different size selections or binding agents to select for different exosome populations. Thus, a microfluidic device can isolate a plurality of exosomes, wherein at least a subset of the plurality of exosomes comprises a different bio-signature from another subset of said plurality of exosomes. For example, the microfluidic device can isolate at least 2, 3, 4, 5, 6, 7, 8, 9, 10, 15, 20, 25, 30, 40, 50, 60, 70, 80, 90, or 100 different subsets of exosomes, wherein each subset of exosomes comprises a different bio-signature.

In some embodiments, the microfluidic device can comprise one or more channels that permit further enrichment or selection of exosomes. A population of exosomes that has been enriched after passage through a first channel can be introduced into a second channel, which allows the passage of the desired exosome population to be further enriched, such as through binding agents present in the second channel.

Array-based assays and bead-based assays can be used with microfluidic device. For example, the binding agent can be coupled to beads and the binding reaction between the beads and exosomes can be performed in a microfluidic device. Multiplexing can also be performed using a microfluidic device. Different compartments can comprise different binding agents for different populations of exosomes, where each population is of a different cell-of-origin specific exosome population or each population has a different bio-signature. The hybridization reaction between the microspheres and exosomes can be performed in a microfluidic device and the reaction mixture can be delivered to a detection device. The detection device, such as a dual or multiple laser detection system can be part of the microfluidic system and can use a laser to identify each bead or microsphere by its color-coding, and another laser can detect the hybridization signal associated with each bead.

Examples of microfluidic devices that may be used, or adapted for use with exosomes, include but are not limited to those described in U.S. Pat. Nos. 7,591,936, 7,581,429, 7,579,136, 7,575,722, 7,568,399, 7,552,741, 7,544,506, 7,541,578, 7,518,726, 7,488,596, 7,485,214, 7,467,928, 7,452,713, 7,452,509, 7,449,096, 7,431,887, 7,422,725, 7,422,669, 7,419,822, 7,419,639, 7,413,709, 7,411,184, 7,402,229, 7,390,463, 7,381,471, 7,357,864, 7,351,592, 7,351,380, 7,338,637, 7,329,391, 7,323,140, 7,261,824, 7,258,837, 7,253,003, 7,238,324, 7,238,255, 7,233,865, 7,229,538, 7,201,881, 7,195,986, 7,189,581, 7,189,580, 7,189,368, 7,141,978, 7,138,062, 7,135,147, 7,125,711, 7,118,910, and 7,118,661.

Cell-of-Origin and Disease-Specific Exosomes

The bindings agents disclosed herein can be used to isolate a heterogeneous population of exosomes from a sample or can be used to isolate or identify a homogeneous population of exosomes, such as cell-of-origin specific exosomes or exosomes with specific bio-signatures. A homogeneous population of exosomes, such as cell-of-origin specific exosomes, can be analyzed and used to characterize a phenotype for a subject. Cell-of-origin specific exosomes are exosomes derived from specific cell types, which can include, but are not limited to, cells of a specific tissue, cells from a specific tumor of interest or a diseased tissue of interest, circulating tumor cells, or cells of maternal or fetal origin. The exosomes may be derived from tumor cells or lung, pancreas, stomach, intestine, bladder, kidney, ovary, testis, skin, colorectal, breast, prostate, brain, esophagus, liver, placenta, or fetal cells. The isolated exosomes can also be from a particular sample type, such as urinary exosomes.

Cell-of-origin specific exosomes from a biological sample can be isolated using one or more binding agents that are specific to a cell-of-origin. Exosomes for analysis of a disease or condition can be isolated using one or more binding agents specific for biomarkers for that disease or condition.

The exosomes can be concentrated prior to isolation of cell-of-origin specific exosomes, such as through centrifugation, chromatography, or filtration, as described above, to produce a heterogeneous population of exosomes prior to isolation of cell-of-origin specific exosomes. Alternatively, the exosomes are not concentrated, or the biological sample is not enriched for exosomes, prior to isolation of cell-of-origin exosomes.

FIG. 61 illustrates a flowchart which depicts one method 100 for isolating or identifying cell-of-origin specific exosomes. First, a biological sample is obtained from a subject in step 102. The sample can be obtained from a third party or from the same party performing the analysis. Next, cell-of-origin specific exosomes are isolated from the biological sample in step 104. The isolated cell-of-origin specific exosomes are then analyzed in step 106 and a biomarker or bio-signature for a particular phenotype is identified in step 108. The method may be used for a number of phenotypes. In some embodiments, prior to step 104, exosomes are concentrated or isolated from a biological sample to product a heterogeneous population of exosomes. For example, heterogeneous population of exosomes may be isolated using centrifugation, chromatography, filtration, or other methods as described above, prior to use of one or more binding agents specific for isolating or identifying exosomes derived from specific cell types, or cell-of-origin specific exosomes.

Cell-of-origin specific exosomes can be isolated from a biological sample of a subject by employing one or more binding agents that bind with high specificity to the cell-of-origin specific exosomes. In some instances, a single binding agent can be employed to isolate cell-of-origin specific exosomes. In other instances, a combination of binding agents may be employed to isolate cell-of-origin specific exosomes. For example, at least 2, 3, 4, 5, 6, 7, 8, 9, 10, 11, 12, 13, 14, 15, 16, 17, 18, 19, 20, 25, 50, 75, or 100 different binding agents may be used to isolate cell-of-origin exosomes. Therefore, an exosome population (e.g., exosomes having the same binding agent profile) can be identified by utilizing a single or a plurality of binding agents.

One or more binding agents can be selected based on their specificity for a target antigen(s) that is specific to a cell-of-origin, tumor or disease. Non-limiting examples of antigens which may be used singularly, or in combination, to isolate a cell-of-origin specific exosome, disease specific exosome, or tumor specific exosome is shown in FIG. 1 and are also described below. The antigen may be membrane bound antigens which are accessible to binding agents. The antigen can also be a biomarker for the phenotype.

Breast Cancer

An exosome derived from a breast cancer cell can be isolated using a binding agent (e.g., antibody), that is specific for an antigen that is associated with a cell of breast cancer origin (e.g., cells of glandular or stromal origin). An exosome derived from a breast cancer cell can be isolated using an antigen including, but not limited to, BCA-225, hsp70, MART1, ER, VEGFA, Class III b-tubulin, HER2/neu (for Her2+BC), GPR30, ErbB4 (JM) isoform, MPR8, MISIIR, fragments thereof, any combination thereof, or any combination of antigens that are specific for a breast cancer cell.

Ovarian Cancer

An exosome derived from an ovarian cancer cell can be isolated using an antibody, or any other binding agent, for an antigen that is specific for a cell of ovarian cancer origin including, but not limited to, CA125, VEGFR2, HER2, MISIIR, VEGFA, CD24, fragments thereof, any combination thereof, or any combination of antigens that is specific for an ovarian cancer cell.

Lung Cancer

An exosome derived from a lung cancer cell can be isolated using an antibody, or any other binding agent, for an antigen that is specific for a cell of lung cancer origin including, but not limited to, CYFRA21-1, TPA-M, TPS, CEA, SCC-Ag, XAGE-1b, HLA Class 1, TA-MUC1, KRAS, hENT1, kinin B1 receptor, kinin B2 receptor, TSC403, HTI56, DC-LAMP, fragments thereof, any combination thereof, or any combination of antigens that is specific for a lung cancer cell.

Colon Cancer

An exosome derived from a colon cancer cell can be isolated using an antibody, or any other binding agent, for an antigen that is specific for a cell of colon cancer origin including, but not limited to, CEA, MUC2, GPA33, CEACAM5, ENFB1, CCSA-3, CCSA-4, ADAM10, CD44, NG2, ephrin B1, plakoglobin, galectin 4, RACK1, tetraspanin-8, FASL, A33, CEA, EGFR, dipeptidase 1, PTEN, Na(+)-dependent glucose transporter, UDP-glucuronosyltransferase 1A, fragments thereof, any combination thereof, or any combination of antigens that is specific for a colon cancer cell.

Prostate Cancer

An exosome derived from a prostate cancer cell can be isolated using an antibody, or any other binding agent, for an antigen that is specific for a cell of prostate cancer origin including, but not limited to, PSA, TMPRSS2, FASLG, TNFSF10, PSMA, NGEP, Il-7RI, CSCR4, CysLT1R, TRPM8, Kv1.3, TRPV6, TRPM8, PSGR, MISIIR, galectin-3, PCA3, TMPRSS2:ERG, fragments thereof, any combination thereof, or any combination of antigens that is specific for a prostate cancer cell.

Brain Cancer

An exosome derived from brain cancer cell can be isolated using an antibody, or any other binding agent, for an antigen that is specific for a cell of brain cancer origin including, but not limited to, PRMT8, BDNF, EGFR, DPPX, Elk, Densin-180, BAI2, BAI3, fragments thereof, any combination thereof, or any combination of antigens that is specific for a brain cancer cell.

Blood Cancer

An exosome derived from a hematological malignancy cell can be isolated using an antibody, or any other binding agent, for an antigen that is specific for a cell of hematological malignancy origin including, but not limited to, CD44, CD58, CD31, CD11a, CD49d, GARP, BTS, Raftlin, fragments thereof, any combination thereof, or any combination of antigens that is specific for a hematological malignancy cell.

Melanoma

An exosome derived from a melanoma cell can be isolated using an antibody, or any other binding agent, for an antigen that is specific for a cell of melanoma origin including, but not limited to, DUSP1, TYRP1, SILV, MLANA, MCAM, CD63, Alix, hsp70, meosin, p120 catenin, PGRL, syntaxin binding protein 1 &2, caveolin, fragments thereof, any combination thereof, or any combination of antigens that is specific for a melanoma cell.

Liver Cancer

An exosome derived from a hepatocellular carcinoma cell can be isolated using an antibody, or any other binding agent, for an antigen that is specific for a cell of hepatocellular carcinoma origin including, but not limited to, HBxAg, HBsAg, NLT, fragments thereof, any combination thereof, or any combination of antigens that is specific for a hepatocellular carcinoma cell.

Cervical Cancer

An exosome derived from a cervical cancer cell can be isolated using an antibody, or any other binding agent, for an antigen that is specific for a cell of cervical cancer origin including, but not limited to, MCT-1, MCT-2, MCT-4, fragments thereof, any combination thereof, or any combination of antigens that is specific for a cervical cancer cell.

Endometrial Cancer

An exosome derived from an endometrial cancer cell can be isolated using an antibody, or any other binding agent, for an antigen that is specific for a cell of endometrial cancer origin including, but not limited to, Alpha V Beta 6 integrin, fragments thereof, any combination thereof, or any combination of antigens that is specific for an endometrial cancer cell.

Psoriasis

An exosome for characterizing psoriasis can be isolated using an antibody, or any other binding agent, for an antigen that is specific for psoriasis including, but not limited to, flt-1, VPF receptors, kdr, fragments thereof, any combination thereof, or any combination of antigens that is specific to psoriasis.

Autoimmune Disease

An exosome for characterizing an autoimmune disease can be isolated using an antibody, or any other binding agent, for an antigen that is specific for an autoimmune disease including, but not limited to, Tim-2, fragments thereof, or any combination of antigens that is specific to an autoimmune disease.

Irritable Bowel Disease

An exosome for characterizing irritable bowel disease (IBD) or syndrome (IBS) can be isolated using an antibody, or any other binding agent, for an antigen that is specific for IBD or IBS including, but not limited to, IL-16, IL-1beta, IL-12, TNF-alpha, interferon-gamma, IL-6, Rantes, Il-12, MCP-1, 5HT, fragments thereof, or any combination of antigens that is specific to IBD or IBS.

Diabetes

An exosome derived from a pancreatic cell can be isolated using an antibody, or any other binding agent, for an antigen that is specific for a cell of pancreatic origin including, but not limited to, IL-6, CRP, RBP4, fragments thereof, any combination thereof, or any combination of antigens that is specific for a pancreatic cell.

Barrett's Esophagus

An exosome for characterizing Barrett's Esophagus can be isolated using an antibody, or any other binding agent, for an antigen that is specific for Barrett's Esophagus including, but not limited to, p53, MUC1, MUC6, fragments thereof, any combination thereof, or any combination of antigens that is specific to Barrett's Esophagus.

Fibromyalgia

An exosome for characterizing fibromyalgia can be isolated using an antibody, or any other binding agent, for an antigen that is specific for fibromyalgia including, but not limited to, neopterin, gp130, fragments thereof, any combination thereof, or any combination of antigens that is specific to fibromyalgia.

Prostatic Hyperplasia

An exosome derived from a benign prostatic hyperplasia (BPH) cell can be isolated using an antibody, or any other binding agent, for an antigen that is specific for a cell of BPH origin including, but not limited to, KIA1, intact fibronectin, fragments thereof, any combination thereof, or any combination of antigens that is specific for a BPH cell.

Multiple Sclerosis

An exosome for characterizing multiple sclerosis (MS) can be isolated using an antibody, or any other binding agent, for an antigen that is specific for MS including, but not limited to, B7, B7-2, CD-95 (fas), Apo-1/Fas, fragments thereof, any combination thereof, or any combination of antigens that is specific to MS.

Parkinson's Disease

An exosome for characterizing Parkinson's disease can be isolated using an antibody, or any other binding agent, for an antigen that is specific for Parkinson's disease including, but not limited to, PARK2, ceruloplasmin, VDBP, tau, DJ-1, fragments thereof, any combination thereof, or any combination of antigens that is specific to Parkinson's disease.

Rheumatic Disease

An exosome for characterizing rheumatic disease can be isolated using an antibody, or any other binding agent, for an antigen that is specific for rheumatic disease including, but not limited to, Citrulinated fibrin a-chain, CD5 antigen-like fibrinogen fragment D, CD5 antigen-like fibrinogen fragment B, TNF alpha, fragments thereof, any combination thereof, or any combination of antigens that is specific to rheumatic disease.

Alzheimer's Disease

An exosome derived from a neuron of a patient suffering from Alzheimer's disease can be further isolated using an antibody, or any other binding agent, for an antigen that including, but not limited to, APP695, APP751 or APP770, BACE1, cystatin C, amyloid β, T-tau, complement factor H or alpha-2-macroglobulin, fragments thereof, any combination thereof, or any combination of antigens that are specific for Alzheimer's.

Head and Neck Cancer

An exosome derived from a head and neck cancer cell can be isolated using an antibody, or any other binding agent, for an antigen that is specific for a cell of head and neck cancer origin including, but not limited to, EGFR, EphB4 or Ephrin B2, fragments thereof, any combination thereof, or any combination of antigens that is specific for a head and neck cancer cell.

Gastrointestinal Stromal Tumor

An exosome derived from a gastrointestinal stromal tumor (GIST) cell can be isolated using an antibody, or any other binding agent, for an antigen that is specific for a cell of GIST origin including, but not limited to, c-kit PDGFRA, NHE-3, fragments thereof, any combination thereof, or any combination of antigens that is specific for a GIST cell.

Renal Cell Carcinoma

An exosome derived from a renal cell carcinomas (RCC) cell can be isolated using an antibody, or any other binding agent, for an antigen that is specific for a cell of RCC origin including, but not limited to, c PDGFRA, VEGF, HIF 1 alpha, fragments thereof, any combination thereof, or any combination of antigens that is specific for a RCC cell.

Schizophrenia

An exosome for characterizing schizophrenia can be isolated using an antibody, or any other binding agent, for an antigen that is specific for schizophrenia including, but not limited to, ATP5B, ATP5H, ATP6V1B, DNM1, fragments thereof, any combination thereof, or any combination of antigens that is specific to schizophrenia.

Peripheral Neuropathic Pain

An exosome derived from a nerve cell of a patient suffering from peripheral neuropathic pain can be isolated using an antibody, or any other binding agent, for an antigen that is specific for peripheral neuropathic pain including, but not limited to, OX42, ED9, fragments thereof, any combination thereof, or any combination of antigens that is specific for peripheral neuropathic pain.

Chronic Neuropathic Pain

An exosome derived from a nerve cell of a patient suffering from chronic neuropathic pain can be isolated using an antibody, or any other binding agent, for an antigen that is specific for chronic neuropathic pain including, but not limited to, chemokine receptor (CCR2/4), fragments thereof, or any combination of antigens that is specific for chronic neuropathic pain.

Prion Disease

An exosome derived from a cell of a patient suffering from prion disease can be isolated using an antibody, or any other binding agent, for an antigen that is specific for prion disease including, but not limited to, PrPSc, 14-3-3 zeta, S-100, AQP4, fragments thereof, or any combination of antigens that is specific for prion disease.

Stroke

An exosome for characterizing stroke can be isolated using an antibody, or any other binding agent, for an antigen that is specific for stroke including, but not limited to, S-100, neuron specific enolase, PARK7, NDKA, ApoC-I, ApoC-III, SAA or AT-III fragment, Lp-PLA2, hs-CRP, fragments thereof, any combination thereof, or any combination of antigens that is specific to stroke.

Cardiovascular Disease

An exosome for characterizing a cardiovascular disease can be isolated using an antibody, or any other binding agent, for an antigen that is specific for a cardiovascular disease including, but not limited to, FATP6, fragments thereof, or any combination of antigens that is specific to a cardiovascular disease or cardiac cell.

Esophageal Cancer

An exosome derived from an esophageal cancer cell can be isolated using an antibody, or any other binding agent, for an antigen that is specific for a cell of esophageal cancer origin including, but not limited to, CaSR, fragments thereof, or any combination of antigens that is specific for an esophageal cancer cell.

Tuberculosis

An exosome for characterizing tuberculosis (TB) can be isolated using an antibody, or any other binding agent, for an antigen that is specific for TB including, but not limited to, antigen 60, HSP, Lipoarabinomannan, Sulfolipid, antigen of acylated trehalose family, DAT, TAT, Trehalose 6,6-dimycolate (cord-factor) antigen, fragments thereof, any combination thereof, or any combination of antigens that is specific to TB.

HIV

An exosome for characterizing HIV can be isolated using an antibody, or any other binding agent, for an antigen that is specific for HIV including, but not limited to, gp41, gp120, fragments thereof, any combination thereof, or any combination of antigens that is specific to HIV.

Autism

An exosome for characterizing autism can be isolated using an antibody, or any other binding agent, for an antigen that is specific for autism including, but not limited to, VIP, PACAP, CGRP, NT3, fragments thereof, any combination thereof, or any combination of antigens that is specific to autism.

Asthma

An exosome for characterizing asthma can be isolated using an antibody, or any other binding agent, for an antigen that is specific for asthma including, but not limited to, YKL-40, S-nitrosothiols, SSCA2, PAI, amphiregulin, periostin, fragments thereof, any combination thereof, or any combination of antigens that is specific to asthma.

Lupus

An exosome for characterizing lupus can be isolated using an antibody, or any other binding agent, for an antigen that is specific for lupus including, but not limited to, TNFR, fragments thereof, or any combination of antigens that is specific to lupus.

Cirrhosis

An exosome for characterizing cirrhosis can be isolated using an antibody, or any other binding agent, for an antigen that is specific for cirrhosis including, but not limited to, NLT, HBsAg, fragments thereof, any combination thereof, or any combination of antigens that is specific to cirrhosis.

Influenza

An exosome for characterizing influenza can be isolated using an antibody, or any other binding agent, for an antigen that is specific for influenza including, but not limited to, hemagglutinin, neurominidase, fragments thereof, any combination thereof, or any combination of antigens that is specific to influenza.

Vulnerable Plaque

An exosome for characterizing vulnerable plaque can be isolated using an antibody, or any other binding agent, for an antigen that is specific for vulnerable plaque including, but not limited to, Alpha v. Beta 3 integrin, MMP9, fragments thereof, any combination thereof, or any combination of antigens that is specific to vulnerable plaque.

A cell-of-origin specific exosome may be isolated using novel binding agents, using methods as described above. Furthermore, a cell-of-origin specific exosome can also be isolated from a biological sample using isolation methods based on cellular binding partners or binding agents of such exosomes. Such cellular binding partners can include but are not limited to peptides, proteins, RNA, DNA, apatmers, cells or serum-associated proteins that only bind to such exosomes when one or more specific biomarkers are present. Isolation of a cell-of-origin specific exosome can be carried out with a single binding partner or binding agent, or a combination of binding partners or binding agents whose singular application or combined application results in cell-of-origin specific isolation. Non-limiting examples of such binding agents are provided in FIG. 2. For example, an exosome for characterizing breast cancer can be isolated with one or more binding agents including, but not limited to, estrogen, progesterone, Herceptin (Trastuzumab), CCND1, MYC PNA, IGF-1 PNA, MYC PNA, SC4 aptamer (Ku), AII-7 aptamer (ERB2), Galectin-3, mucin-type O-glycans, L-PHA, Galectin-9, or any combination thereof.

A binding agent may also be used for isolating the cell-of-origin specific exosome based on i) the presence of antigens specific for cell-of-origin specific exosomes cells, ii) the absence of markers specific for cell-of-origin specific exosomes, or iii) expression levels of biomarkers specific for cell-of-origin specific exosomes. A heterogeneous population of exosomes is applied to a surface coated with specific binding agents designed to rule out or identify the cell-of-origin characteristics of the exosomes. Various binding agents, such as antibodies, can be arrayed on a solid surface or substrate and the heterogeneous population of exosomes is allowed to contact the solid surface or substrate for a sufficient time to allow interactions to take place. Specific binding or non-binding to given antibody locations on the array surface or substrate can then serve to identify antigen specific characteristics of the exosome population that are specific to a given cell-of-origin.

A cell-of-origin specific exosome can be enriched or isolated using one or more binding agents using a magnetic capture method, fluorescence activated cell sorting or laser cytometry as described above. Magnetic capture methods can include, but are not limited to, the use of magnetically activated cell sorter (MACS) microbeads or magnetic columns. Examples of immunoaffinity and magnetic particle methods that can be used is described in U.S. Pat. No. 4,551,435, 4,795,698, 4,925,788, 5,108,933, 5,186,827, 5,200,084 or 5,158,871. A cell-of-origin specific exosome can also be isolated following the general methods described in U.S. Pat. No. 7,399,632, by using combination of antigens specific to an exosome.

Any other method for isolating or otherwise enriching the cell-of-origin specific exosomes with respect to a biological sample may also be used in combination with the present invention. For example, size exclusion chromatography such as gel permeation columns, centrifugation or density gradient centrifugation, and filtration methods can be used in combination with the antigen selection methods described herein. The cell-of-origin specific exosomes may also be isolated following the methods described in Koga et al., *Anticancer Research,* 25:3703-3708 (2005), Taylor et al., *Gynecologic Oncology,* 110:13-21 (2008), Nanjee et al., *Clin Chem,* 2000; 46:207-223 or U.S. Pat. No. 7,232,653.

Exosome Assessment

A phenotype can be characterized for a subject by analyzing a biological sample from the subject and determining the level, amount, or concentration of one or more populations of exosomes in the sample. An exosome can be purified or concentrated prior to determining the amount of exosomes. Alternatively, the amount of exosomes can be directly assayed from a sample, without prior purification or concentration. The exosomes can be cell-of-origin specific exosomes or exosomes with a specific biomarker or combination of biomarkers. The amount of exosomes can be used to characterize a phenotype, such as a diagnosis, theranosis or prognosis of a condition or disease. The amount may be used to determine a physiological or biological state, such as pregnancy or the stage of pregnancy. The amount of exosomes can also be used to determine treatment efficacy, stage of a disease or condition, or progression of a disease or condition. For example, the amount of exosomes can be proportional to an increase in disease stage or progression.

The exosomes can be evaluated by comparing the level of exosomes with a reference level or value of exosomes. The reference value can be particular to physical or temporal endpoint. For example, the reference value can be from the same subject from whom a sample is assessed for an exosome, or the reference value can be from a representative population of samples (e.g., samples from normal subjects not exhibiting a symptom of disease). Therefore, a reference value can provide a threshold measurement which is compared to a subject sample's readout for one or more exosome populations assayed in a given sample. Such reference values may be set according to data pooled from groups of sample corresponding to a particular cohort, including but not limited to age (e.g., newborns, infants, adolescents, young, middle-aged adults, seniors and adults of varied ages), racial/ethnic groups, normal versus diseased subjects, smoker v. non-smoker, subject receiving therapy versus untreated subject, different time points of treatment for a particular individual or group of subjects similarly diagnosed or treated or combinations thereof.

A reference value may be based on samples assessed from the same subject so to provide individualized tracking. Frequent testing of a patient may provide better comparisons to the reference values previously established for a particular patient and would allow a physician to more accurately assess the patient's disease stage or progression, and to inform a better decision for treatment. The reduced intraindividual variance of exosomes levels would allow a more specific and individualized threshold to be defined for the patient. Temporal intrasubject variation allows each individual to serve as a longitudinal control for optimum analysis of disease or physiological state.

Reference values can be established for unaffected individuals (of varying ages, ethnic backgrounds and sexes) without a particular phenotype by determining the amount of exosomes in an unaffected individual. For example, a reference value for a reference population can be utilized as a baseline for detection of one or more exosome populations in a test subject. If a sample from a subject has a level or value that is similar to the reference, the subject can be identified to not have the disease, or of having a low likelihood of developing a disease.

Alternatively, reference values or levels can be established for individuals with a particular phenotype by determining the amount of one or more populations of exosomes in an individual with the phenotype. In addition, an index of values can be generated for a particular phenotype. For example, different disease stages can have different values, such as obtained from individuals with the different disease stages. A subject's value can be compared to the index and a diagnosis or prognosis of the disease can be determined, such as the disease stage or progression. In other embodiments, an index of values is generated for therapeutic efficacies. For example, the level of exosomes of individuals with a particular disease can be generated and noted what treatments were effective for the individual. The levels can be used to generate values of which is a subject's value is compared, and a treatment or therapy can be selected for the individual.

For example, a reference value can be determined for individuals unaffected with a particular cancer, by isolating exosomes with an antigen that specifically targets for the particular cancer. For example, individuals with varying stages of colorectal cancer and noncancerous polyps can be surveyed using the same techniques described for unaffected individuals and the levels of circulating exosomes for each group defined as means±standard deviations from at least two separate experiments performed in triplicate. Comparisons between these groups can be made using statistical applications such as one-way ANOVA, followed by Tukey's multiple comparisons post-test comparing each population.

Reference values can also be established for disease recurrence monitoring (or exacerbation phase in MS), or for therapeutic response monitoring.

The values can be a quantitative or qualitative value. The values can be a direct measurement of the level of exosomes (example, mass per volume), or an indirect measure, such as the amount of a specific exosomal marker. The values can be a quantitative, such as a numerical value. In other embodiments, the value is qualitative, such as no exosomes, low level of exosomes, medium level, or high level of exosomes, or variations thereof.

The reference values can be stored in a database and used as a reference for the diagnosis, prognosis, or theranosis of a disease or condition based on the level or amount of exosomes, such as total amount of exosomes, or the amount of a specific population of exosomes, such as cell-of-origin specific exosomes or exosomes with one or more specific biomarkers.

Exosome levels may be characterized using mass spectrometry or flow cytometry. Analysis may also be carried out on exosomes by immunocytochemical staining, Western blotting, electrophoresis, chromatography or x-ray crystallography in accordance with procedures well known in the art. Exosomes may be characterized and quantitatively measured using flow cytometry as described in Clayton et al., *Journal of Immunological Methods* 2001; 163-174, which is herein incorporated by reference in its entirety. Exosome levels may be determined using binding agents as described above. For example, a binding agent to exosomes can be labeled and the label detected and used to determine the amount of exosomes in a sample. The binding agent can be bound to a substrate, such as arrays or particles, such as described above. Alternatively, the exosomes may be labeled directly.

Electrophoretic tags or eTags can also be used to determine the amount of exosomes. eTags are small fluorescent molecules linked to nucleic acids or antibodies and are designed to bind one specific nucleic acid sequence or protein, respectively. After the eTag binds its target, an enzyme is used to cleave the bound eTag from the target. The signal generated from the released eTag, called a "reporter," is proportional to the amount of target nucleic acid or protein in the sample. The eTag reporters can be identified by capillary electrophoresis. The unique charge-to-mass ratio of each eTag reporter—that is, its electrical charge divided by its molecular weight—makes it show up as a specific peak on the capillary electrophoresis readout. Thus by targeting a specific biomarker of an exosome with an eTag, the amount or level of exosomes can be determined.

The exosome levels can determined from a heterogeneous population of exosomes, such as the total population of exosomes in a sample. Alternatively, the exosomes level is determined from a homogenous population, or substantially homogenous population of exosomes, such as the level of specific cell-of-origin exosomes, such as exosomes from prostate cancer cells. In yet other embodiments, the level is determined for exosomes with a particular biomarker or combination of biomarkers, such as a biomarker specific for prostate cancer. Determining the level of exosome can be performed in conjunction with determining the biomarker or combination of biomarkers of an exosome. Alternatively, determining the amount of exosome may be performed prior to or subsequent to determining the biomarker or combination of biomarkers of the exosomes.

Determining the amount of exosomes can be assayed in a multiplexed manner. For example, determining the amount of more than one population of exosomes, such as different cell-of-origin specific exosomes or exosomes with different biomarkers or combination of biomarkers, can be performed, such as those disclosed herein.

Specificity and Sensitivity

The level of exosomes as determined using one or more processes disclosed herein can be used to characterize a phenotype with increased sensitivity and the specificity. The sensitivity can be determined by: (number of true positives)/(number of true positives+number of false negatives). The specificity can be determined by: (number of true negatives)/(number of true negatives+number of false positives).

The level of exosomes as determined using one or more processes disclosed herein can be used to characterize a phenotype with at least 60, 61, 62, 63, 64, 65, 66, 67, 68, 69, or 70% sensitivity, such as with at least 71, 72, 73, 74, 75, 76, 77, 78, 79, 80, 81, 82, 83, 84, 85, 86, or 87% sensitivity. For example, the phenotype can be characterized with at least 87.1, 87.2, 87.3, 87.4, 87.5, 87.6, 87.7, 87.8, 87.9, 88.0, or 89% sensitivity, such as with at least 90% sensitivity. The phenotype can be characterized with at least 91, 92, 93, 94, 95, 96, 97, 98, 99 or 100% sensitivity.

The phenotype of a subject can also be characterized with at least 70, 71, 72, 73, 74, 75, 76, 77, 78, 79, 80, 81, 82, 83, 84, 85, 86, 87, 88, 89, 90, 91, 92, 93, 94, 95, 96, or 97% specificity, such as with at least 97.1, 97.2, 97.3, 97.4, 97.5, 97.6, 97.7, 97.8, 97.8, 97.9, 98.0, 98.1, 98.2, 98.3, 98.4, 98.5, 98.6, 98.7, 98.8, 98.9, 99.0, 99.1, 99.2, 99.3, 99.4, 99.5, 99.6, 99.7, 99.8, 99.9 or 100% specificity.

The phenotype can also be characterized with at least 70% sensitivity and at least 80, 90, 95, 99, or 100% specificity; at least 75% sensitivity and at least 80, 90, 95, 99, or 100% specificity; at least 80% sensitivity and at least 80, 85, 90, 95, 99, or 100% specificity; at least 85% sensitivity and at least 80, 85, 90, 95, 99, or 100% specificity; at least 86% sensitivity and at least 80, 85, 90, 95, 99, or 100% specificity; at least 87% sensitivity and at least 80, 85, 90, 95, 99, or 100% specificity; at least 88% sensitivity and at least 80, 85, 90, 95, 99, or 100% specificity; at least 89% sensitivity and at least 80, 85, 90, 95, 99, or 100% specificity; at least 90% sensitivity and at least 80, 85, 90, 95, 99, or 100% specificity; at least 95% sensitivity and at least 80, 85, 90, 95, 99, or 100% specificity; at least 99% sensitivity and at least 80, 85, 90, 95, 99, or 100% specificity; or at least 100% sensitivity and at least 80, 85, 90, 95, 99, or 100% specificity.

Furthermore, the confidence level for determining the specificity, sensitivity, or both, may be with at least 90, 91, 92, 93, 94, 95, 96, 97, 98, or 99% confidence.

Bio-Signatures

A bio-signature of an exosome from a subject can be used to characterize a phenotype. A bio-signature can reflect the particular antigens or biomarkers that are present on an exosome. In addition, a bio-signature can also reflect one or more biomarkers that are carried in an exosome. Alternatively, a bio-signature can comprise a combination of one or more antigens or biomarkers that are present on an exosome with one or more biomarkers that are detected in the exosome.

The exosome can be purified or concentrated prior to determining the bio-signature of the exosome. Alternatively, the bio-signature of the exosome can be directly assayed from a sample, without prior purification or concentration. An exosome can also be isolated prior to assaying. For example, a cell-of-origin specific exosome can be isolated and its bio-signature determined. The bio-signature is used to determine a diagnosis, prognosis, or theranosis of a disease or condition. Therefore, a bio-signature can also be used to determine treatment efficacy, stage of a disease or condition, or progression of a disease or condition. Furthermore, a bio-signature may be used to determine a physiological state, such as pregnancy.

An exosomal characteristic in and of itself can be assessed to determine a bio-signature. The exosomal characteristic can be used to diagnose, detect or determine a disease stage or progression, the therapeutic implications of a disease or condition, or characterize a physiological state. An exosomal characteristic can include, but is not limited to, the level or amount of exosomes, temporal evaluation of the variation in exosomal half-life, circulating exosomal half-life or exosomal metabolic half-life, or the activity of an exosome.

In addition, a bio-signature can also correspond to an expression level, presence, absence, mutation, variant, copy number variation, truncation, duplication, modification, or molecular association of one or more biomarkers. A biomarker may be any exosomal component and can form its own signature. For example, the biomarker may be the RNA content of the exosome, such that the RNA signature includes one or more RNA species, such as, but not limited to, mRNA, miRNA, snoRNA, snRNA, rRNAs, tRNAs, siRNA, hnRNA, shRNA, or a combination thereof. Therefore, an exosome can be assayed to determine a RNA signature.

Other biomarkers include, but are not limited to, one or more proteins or peptides (e.g., providing a protein signature), nucleic acids (e.g. RNA signature as described, or a DNA signature), lipids (e.g. lipid signature), or combinations thereof. In some embodiments, the bio-signature can also comprise the type or amount of drug or drug metabolite present in an exosome (e.g. drug signature), as such drug may be taken by a subject from which the biological sample is obtained from, resulting in an exosome carrying such drug, or metabolites of such drug.

An RNA signature or DNA signature can also include a mutational, epigenetic modification, or genetic variant analysis of the RNA or DNA present in the exosome. In addition, a protein signature can include, but is not limited to, the mutation, modification, overexpression, underexpression, presence or absence of antigens, peptides, proteins or combinations thereof.

A bio-signature of an exosome can comprise one or more miRNA signatures combined with one or more additional signatures including, but not limited to, an mRNA signature, DNA signature, protein signature, peptide signature, antigen signature, or any combination thereof. For example, the bio-signature can comprise one or more miRNA biomarkers with one or more DNA biomarkers, one or more mRNA biomarkers, one or more snoRNA biomarkers, one or more protein biomarkers, one or more peptide biomarkers, one or more antigen biomarkers, one or more antigen biomarkers, one or more lipid biomarkers, or any combination thereof.

A bio-signature can comprise a combination of one or more antigens or binding agents (such as ability to bind one or more binding agents), such as listed in FIGS. 1 and 2, respectively. The bio-signature can further comprise one or more other biomarkers, such as, but not limited to, miRNA, DNA (e.g. single stranded DNA, complementary DNA, or noncoding DNA), or mRNA. For example, the bio-signature of an exosome can comprise a combination of one or more antigens, such as shown in FIG. 1, one or more binding agents, such as shown in FIG. 2, and one or more biomarkers for a condition or disease, such as listed in FIGS. 3-60. The bio-signature can comprise one or more biomarkers, for example miRNA, with one or more antigens specific for a cancer cell (for example, as shown in FIG. 1).

An exosome can have a bio-signature that is specific to the cell-of-origin and, as such, can be utilized to derive disease-specific or biological state specific diagnostic, prognostic or therapy-related bio-signatures representative of the cell-of-origin. An exosome may also have a bio-signature that is specific to a given disease or physiological condition that may be different from the bio-signature of the cell-of-origin, but no less important to the diagnosis, prognosis, staging, therapy-related determinations or physiological state characterization.

The bio-signature of an exosome, such as a cell-of-origin specific exosome described herein, can be used clinically in making decisions concerning treatment modalities, including therapeutic intervention, diagnostic criteria such as disease staging, disease monitoring, and disease stratification, and surveillance for detection, metastasis or recurrence or progression of disease. The bio-signature of an exosome, such as an isolated cell-of-origin specific exosome can further be used clinically to make treatment decisions, including whether to perform surgery or what treatment standards should be utilized along with surgery (e.g., either pre-surgery or post-surgery).

An exosome bio-signature can also be used in therapy related diagnostics to provide tests useful to diagnose a disease or choose the correct treatment regimen, as well as monitor a subject's response. Therapy related tests are useful to predict and assess drug response in individual subjects, i.e., to provide personalized medicine. Therapy related tests are also useful to select a subject for treatment who is particularly likely to benefit from the treatment or to provide an early and objective indication of treatment efficacy in an individual subject. For example, a treatment can be altered without the great expense of delaying beneficial treatment as well as the great financial cost of administering an ineffective drug(s).

Therapy related diagnostics are also useful in clinical diagnosis and management of a variety of diseases and disorders, which include, but are not limited to cardiovascular disease, cancer, infectious diseases, sepsis, neurological diseases, central nervous system related diseases, endovascular related diseases, and autoimmune related diseases or the prediction of drug toxicity, drug resistance or drug response. Therapy related tests may be developed in any suitable diagnostic testing format, which include, but are not limited to, e.g., immunohistochemical tests, clinical chemistry, immunoassay, cell-based technologies, nucleic acid tests or body imaging methods. Therapy related tests can further include but are not limited to, testing that aids in the determination of therapy, testing that monitors for therapeutic toxicity, or response to therapy testing. For example, a bio-signature can determine whether a particular disease or condition is resistant to a drug, and therefore, a physician need not waste valuable time with hit-and-miss treatment. Instead, to obtain early validation of a drug choice or treatment regimen, a bio-signature is determined for an exosome obtained from a subject, which then determines whether the particular subject's disease has the biomarker associated with drug resistance. Therefore, such a determination enables doctors to devote critical time as well as the patient's financial resources to effective treatments.

Moreover, an exosome bio-signature may be used to assess whether a subject is afflicted with disease, is at risk for developing disease or to assess the stage or progression of the disease. For example, a bio-signature can be used to assess whether a subject has prostate cancer (for example, FIG. 68, 73) or colon cancer (for example, FIG. 69, 74). Furthermore, a bio-signature can be used to determine a stage of a disease or condition, such as colon cancer (for example, FIGS. 71, 72).

Furthermore, determining the amount of exosomes, such a heterogeneous population of exosomes, and the amount of one or more homogeneous population of exosomes, such as a population of exosomes with the same bio-signature, can be used to characterize a phenotype. For example, determination of the total amount of exosomes in a sample (i.e. not cell-type specific) and determining the presence of one or more different cell-of-origin specific exosomes (such as cell-of-origin specific exosomes) can be used to characterize a phenotype. Threshold values, or reference values or amounts can be determined based on comparisons of normal subjects and subjects with the phenotype of interest, as further described below, and criteria based on the threshold or reference values determined. The different criteria can be used to characterize a phenotype.

For example, one criterion can be based on the amount of a heterogeneous population of exosomes in a sample. If the amount is lower than a threshold value or reference value, the criterion is met. Alternatively, the criterion can be based on whether the amount of exosomes is higher than a threshold or reference value. Another criterion can be the amount of exosomes with a specific bio-signature or biomarker. If the amount of exosomes with the specific bio-signature or biomarker is lower, or higher, than a threshold or reference value, the criterion is met. A criterion can also be based on the amount of exosomes derived from a particular cell type. If the amount is lower, or higher, than a threshold or reference value, the criterion is met. Another criterion can be based on whether the amount of exosomes derived from a cancer cell or comprising one or more cancer specific biomarkers. If the amount is lower, or higher, than a threshold or reference value, the criterion is met. A criterion can also be the reliability of the result, such as meeting a quality control measure or value.

A phenotype for a subject can be characterized based on meeting at least 1, 2, 3, 4, 5, 6, 7, 8, 9, or 10 criteria. For example, for the characterizing of a cancer, a number of different criteria can be used: 1) if the amount of exosomes in a sample from a subject is higher than a reference value; 2) if the amount of a cell type (ie. derived from a specific tissue or organ) specific exosomes is higher than a reference value; and 3) if the amount of exosomes with one or more cancer specific biomarkers is higher than a reference value, the subject is diagnosed with a cancer. The method can further include a quality control measure, such that the results are provided for the subject if the samples meet the quality control measure.

A bio-signature can be determined by comparing the amount of exosomes, the structure of an exosome, (using transmission electron microscopy, see for example, Hansen et al., *Journal of Biomechanics* 31, *Supplement* 1: 134-134(1) (1998), or scanning electron microscopy), or any other exosomal characteristic. Various combinations of methods and techniques or analyzing one or more exosomes can be used to determine a phenotype for a subject.

An exosome characteristic can include, but is not limited to the presence or absence, copy number, expression level, or activity level of a biomarker. The presence of a mutation (e.g., mutations which affect activity of the biomarker, such as substitution, deletion, or insertion mutations), variant, or post-translation modification of a biomarker, such as a protein biomarker, can include, but not be limited to, acylation, acetylation, phosphorylation, ubiquitination, deacetylation, alkylation, methylation, amidation, biotinylation, gamma-carboxylation, glutamylation, glycosylation, glycyation, hydroxylation, covalent attachment of heme moiety, iodination, isoprenylation, lipoylation, prenylation, GPI anchor formation, myristoylation, farnesylation, geranylgeranylation, covalent attachment of nucleotides or derivatives thereof, ADP-ribosylation, flavin attachment, oxidation, palmitoylation, pegylation, covalent attachment of phosphatidylinositol, phosphopantetheinylation, polysialylation, pyroglutamate formation, racemization of proline by prolyl isomerase, tRNA-mediation addition of amino acids such as arginylation, sulfation, the addition of a sulfate group to a tyrosine, or selenoylation of the biomarker can also be an exosomal characteristic.

The methods described above can be used to identify an exosome bio-signature that is associated with a disease, condition or physiological state.

The bio-signature can also be utilized to determine if a subject is afflicted with cancer or is at risk for developing cancer. A subject at risk of developing cancer can include those who may be predisposed or who have pre-symptomatic early stage disease.

A bio-signature can also be utilized to provide a diagnostic or theranostic determination for other diseases including but not limited to autoimmune diseases, inflammatory bowel diseases, Alzheimer's disease, Parkinson's disease, Multiple Sclerosis, sepsis or pancreatitis or any disease, conditions or symptoms listed in FIGS. 3-58.

The bio-signature can also be used to identify a given pregnancy state from the peripheral blood, umbilical cord blood, or amniotic fluid (e.g. miRNA signature specific to Downs Syndrome) or adverse pregnancy outcome such as pre-eclampsia, pre-term birth, premature rupture of membranes, intrauterine growth restriction or recurrent pregnancy loss. The bio-signature can also be used to indicate the health of the mother, the fetus at all developmental stages, the pre-implantation embryo or a newborn.

A bio-signature can be utilized for pre-symptomatic diagnosis. Furthermore, the bio-signature can be utilized to detect disease, determine disease stage or progression, determine the recurrence of disease, identify treatment protocols, determine efficacy of treatment protocols or evaluate the physiological status of individuals related to age and environmental exposure.

Monitoring the bio-signature of an exosome can also be used to identify toxic exposures in a subject including, but not limited to, situations of early exposure or exposure to an unknown or unidentified toxic agent. Without being bound by any one specific theory for mechanism of action, exosomes are shed from damaged cells and in the process compartmentalize specific contents of the cell including both membrane components and engulfed cytoplasmic contents. Cells exposed to toxic agents/chemicals may increase exosome shedding to expel toxic agents or metabolites thereof, thus resulting in increased exosome levels. Thus, monitoring an exosome and/or bio-signature allows assessment of an individual's response to potential toxic agent(s).

Furthermore, an exosome can be used to identify states of drug-induced toxicity or the organ injured, by detecting one or more specific antigen, binding agent, biomarker, or any combination thereof of the exosome. Therefore, the exosome, or exosome bio-signature can be used to monitor an individual for acute, chronic, or occupational exposures to any number of toxic agents including, but not limited to, drugs, antibiotics, industrial chemicals, toxic antibiotic metabolites, herbs, household chemicals, and chemicals produced by other organisms, either naturally occurring or synthetic in nature.

In addition, an exosome bio-signature can be used to identify conditions or diseases, including cancers of unknown origin, also known as cancers of unknown primary (CUP). For example, an exosome may be isolated from a biological sample as previously described to arrive at a heterogeneous population of exosomes. The heterogeneous population of exosomes can then be applied to surfaces coated with specific binding agents designed to rule out or identify antigen specific characteristics of the exosome population that are specific to a given cell-of-origin. Further, as described above, the bio-signature of a specific cell-of-origin exosome can correlate with the cancerous state of cells. Compounds that inhibit cancer in a subject may cause a change, e.g., a change in bio-signature of specific cell-of-origin exosome, which can be monitored by serial isolation of a cell-of-origin exosome over time and treatment course.

Alternatively, an exosome bio-signature can be used to assess the efficacy of a therapy, e.g., chemotherapy, radiation therapy, surgery, or any other therapeutic approach useful for inhibiting cancer in a subject. In addition, an exosome bio-signature can be used in a screening assay to identify candidate or test compounds or agents (e.g., proteins, peptides, peptidomimetics, peptoids, small molecules or other drugs) that have a modulatory effect on the bio-signature of a specific cell-of-origin exosome. Compounds identified via such screening assays may be useful, for example, for modulating, e.g., inhibiting, ameliorating, treating, or preventing conditions or diseases.

For example, a bio-signature for an exosome can be obtained from a patient who is undergoing successful treatment for a particular cancer. Cells from a cancer patient not being treated with the same drug can be cultured and exosomes from the cultures obtained for determining bio-signatures. The cells can be treated with test compounds and the bio-signature of the exosomes from the cultures can be compared to the bio-signature of the exosomes obtained from the patient undergoing successful treatment. The test compounds that results in exosome bio-signatures that are similar to those of the patient undergoing successful treatment can be selected for further studies.

The bio-signature of a specific cell-of-origin exosome can also be used to monitor the influence of an agent (e.g., drug compounds) on the bio-signature in clinical trials. Monitoring an exosome bio-signature can also be used in a method of assessing the efficacy of a test compound, such as a test compound for inhibiting cancer cells.

An exosome bio-signature can also be used to determine the effectiveness of a particular therapeutic intervention (pharmaceutical or non-pharmaceutical) and to alter the intervention to 1) reduce the risk of developing adverse outcomes, 2) enhance the effectiveness of the intervention or 3) identify resistant states. Thus, in addition to diagnosing or confirming the presence of or risk for developing a disease, condition or a syndrome, the methods and compositions disclosed herein also provide a system for optimizing the treatment of a subject having such a disease, condition or syndrome. For example, a therapy-related approach to treating a disease, condition or syndrome by integrating diagnostics and therapeutics to improve the real-time treatment of a subject can be determined by identifying the bio-signature of an exosome.

Tests that identify an exosome bio-signature can be used to identify which patients are most suited to a particular therapy, and provide feedback on how well a drug is working, so as to optimize treatment regimens. For example, in pregnancy-induced hypertension and associated conditions, therapy-related diagnostics can flexibly monitor changes in important parameters (e.g., cytokine and/or growth factor levels) over time, to optimize treatment.

Within the clinical trial setting of investigational agents as defined by the FDA, MDA, EMA, USDA, and EMEA, therapy-related diagnostics as determined by a bio-signature disclosed herein, can provide key information to optimize trial design, monitor efficacy, and enhance drug safety. For instance, for trial design, therapy-related diagnostics can be used for patient stratification, determination of patient eligibility (inclusion/exclusion), creation of homogeneous treatment groups, and selection of patient samples that are optimized to a matched case control cohort. Such therapy-related diagnostic can therefore provide the means for patient efficacy enrichment, thereby minimizing the number of individuals needed for trial recruitment. For example, for efficacy, therapy-related diagnostics are useful for monitoring therapy and assessing efficacy criteria. Alternatively, for safety, therapy-related diagnostics can be used to prevent adverse drug reactions or avoid medication error and monitor compliance with the therapeutic regimen.

Therefore, an exosomal bio-signature can be used to monitor drug efficacy, determine response or resistance to a given drug, and thereby enhance drug safety. For example, in colon cancer, exosomes are typically shed from colon cancer cells and can be isolated from the peripheral blood and used to isolate one or more biomarkers (e.g., KRAS mRNA). In the case of mRNA biomarkers, the mRNA can be reverse transcribed into cDNA and sequenced (e.g., by Sanger sequencing) to determine if there are mutations present that confer resistance to a drug (e.g., cetuximab or panitumimab).

In another example, exosomes that are specifically shed from lung cancer cells are isolated from a biological sample and used to isolate a lung cancer biomarker, e.g., EGFR mRNA. The EGFR mRNA is processed to cDNA and sequenced to determine if there are EGFR mutations present that show resistance or response to specific drugs or treatments for lung cancer.

One or more exosome bio-signatures can be grouped so that information obtained about the set of bio-signatures in a particular group provides a reasonable basis for making a clinically relevant decision, such as but not limited to a diagnosis, prognosis, or management of treatment, such as treatment selection.

As with most diagnostic markers, it is often desirable to use the fewest number of markers sufficient to make a correct medical judgment. This prevents a delay in treatment pending further analysis as well inappropriate use of time and resources.

Also disclosed herein are methods of conducting retrospective analysis on samples (e.g., serum and tissue biobanks) for the purpose of correlating qualitative and quantitative properties, such as exosome bio-signatures, with clinical outcomes in terms of disease state, disease stage, progression, prognosis; therapeutic efficacy or selection; or physiological conditions. Furthermore, methods and compositions disclosed herein are utilized for conducting prospective analysis on a sample (e.g., serum and/or tissue collected from individuals in a clinical trial) for the purpose of correlating qualitative and quantitative exosome bio-signatures with clinical outcomes in terms of disease state, disease stage, progression, prognosis; therapeutic efficacy or selection; or physiological conditions can also be performed. As used herein, exosome bio-signatures can be to cell-of-origin specific exosomes. Furthermore, bio-signatures can be determined based on an exosome surface marker profile and/or exosome contents (e.g., biomarkers).

An exosome bio-signature can comprise at least 2, 3, 4, 5, 6, 7, 8, 9, 10, 11, 12, 13, 14, 15, 16, 17, 18, 19, 20, 25, 30, 40, 50, 75, or 100 characteristics. A bio-signature with more than one exosomal characteristic, such as at least 2, 3, 4, 5, 6, 7, 8, 9, 10, 11, 12, 13, 14, 15, 16, 17, 18, 19, 20, 25, 30, 40, 50, 75, or 100 characteristics, may provide higher sensitivity, specificity, or both, in determining a phenotype. For example, assessing a plurality of exosomal characteristics can provide increased sensitivity, specificity, or both, as compared to assessing less than a plurality of exosomal characteristics.

A bio-signature comprising more than one exosomal characteristic can be used to characterize a phenotype with at least 60, 61, 62, 63, 64, 65, 66, 67, 68, 69, or 70% sensitivity, such as with at least 71, 72, 73, 74, 75, 76, 77, 78, 79, 80, 81, 82, 83, 84, 85, 86, or 87% sensitivity. For example, the phenotype can be characterized with at least 87.1, 87.2, 87.3, 87.4, 87.5, 87.6, 87.7, 87.8, 87.9, 88.0, or 89% sensitivity, such as at least 90% sensitivity. The phenotype can be characterized with at least 91, 92, 93, 94, 95, 96, 97, 98, 99 or 100% sensitivity.

The bio-signature can be used to characterize a phenotype of a subject with at least 70, 71, 72, 73, 74, 75, 76, 77, 78, 79, 80, 81, 82, 83, 84, 85, 86, 87, 88, 89, 90, 91, 92, 93, 94, 95, 96, or 97% specificity, such as with at least 97.1, 97.2, 97.3, 97.4, 97.5, 97.6, 97.7, 97.8, 97.8, 97.9, 98.0, 98.1, 98.2, 98.3, 98.4, 98.5, 98.6, 98.7, 98.8, 98.9, 99.0, 99.1, 99.2, 99.3, 99.4, 99.5, 99.6, 99.7, 99.8, 99.9 or 100% specificity.

The phenotype can also be characterized using a bio-signature with at least 70% sensitivity and at least 80, 90, 95, 99, or 100% specificity; at least 75% sensitivity and at least 80, 90, 95, 99, or 100% specificity; at least 80% sensitivity and at least 80, 85, 90, 95, 99, or 100% specificity; at least 85% sensitivity and at least 80, 85, 90, 95, 99, or 100% specificity; at least 86% sensitivity and at least 80, 85, 90, 95, 99, or 100% specificity; at least 87% sensitivity and at least 80, 85, 90, 95, 99, or 100% specificity; at least 88% sensitivity and at least 80, 85, 90, 95, 99, or 100% specificity; at least 89% sensitivity and at least 80, 85, 90, 95, 99, or 100% specificity; at least 90% sensitivity and at least 80, 85, 90, 95, 99, or 100% specificity; at least 95% sensitivity and at least 80, 85, 90, 95, 99, or 100% specificity; at least 99% sensitivity and at least 80, 85, 90, 95, 99, or 100% specificity; or at least 100% sensitivity and at least 80, 85, 90, 95, 99, or 100% specificity.

Furthermore, the confidence level for determining the specificity, sensitivity, or both, may be with at least 90, 91, 92, 93, 94, 95, 96, 97, 98, or 99% confidence.

Bio-Signatures: Exosomal Biomarkers

An exosome bio-signature can comprise one or more biomarkers. An exosomal biomarker can be any component present in an exosome or on the exosome, such as any nucleic acid (e.g. RNA or DNA); protein, peptide, polypeptide, antigen, lipid, carbohydrate, or proteoglycan.

The bio-signature can include the presence or absence, expression level, mutational state, genetic variant state, or any modification (such as epigentic modification, post-translation modification) of a biomarker (e.g. any one or more biomarker listed in FIGS. 1, 3-60). The expression level of a biomarker can be compared to a control or reference, to determine the overexpression or underexpression (or upregulation or downregulation) of a biomarker in a sample. The control or reference level can be the amount of a biomarker, such as a miRNA in a control sample, such as a sample from a subject that does not have or exhibit the condition or disease, and further described below.

The nucleic acid can be any RNA or DNA species. For example, the biomarker can be mRNA, miRNA, small nucleolar RNAs (snoRNA), small nuclear RNAs (snRNA), ribosomal RNAs (rRNA), heterogeneous nuclear RNA (hnRNA), ribosomal RNAS (rRNA), siRNA, transfer RNAs (tRNA), or shRNA. The DNA can be double-stranded DNA, single stranded DNA, complementary DNA, or noncoding DNA.

In addition, the biomarker can be a polypeptide, peptides or protein, such as the modification state, truncations, mutations, expression level (such as overexpression or underexpression as compared to a reference level), and post-translational modifications, such as described above.

An exosome bio-signature may include a number of the same type of biomarkers (e.g., two different mRNAs, each corresponding to a different gene) or one or more of different types of biomarkers (e.g. mRNAs, miRNAs, proteins, peptides, ligands, and antigens).

One or more exosome bio-signatures can comprise at least one biomarker selected from those listed in FIGS. 1, 3-60. A specific cell-of-origin bio-signature may include one or more biomarkers. FIGS. 3-58 depict tables which lists a number of disease or condition specific biomarkers that can be derived and analyzed from an exosome. The biomarker can also beCD24, midkine, hepcidin, TMPRSS2-ERG, PCA-3, PSA, EGFR, EGFRvIII, BRAF variant, MET, cKit, PDGFR, Wnt, beta-catenin, K-ras, H-ras, N-ras, Raf, N-myc, c-myc, IGFR, PI3K, Akt, BRCA1, BRCA2, PTEN, VEGFR-2, VEGFR-1, Tie-2, TEM-1, CD276, HER-2, HER-3, or HER-4. The biomarker can also be annexin V, CD63, Rab-5b, or caveolin, or a miRNA, such as let-7a; miR-15b; miR-16; miR-19b; miR-21; miR-26a; miR-27a; miR-92; miR-93; miR-320 or miR-20. The biomarker can also be of any gene or fragment thereof as disclosed in PCT Publication No. WO2009/100029, such as those listed in Tables 3-15.

Other biomarkers useful for assessment in methods and compositions disclosed herein can include those associated with conditions or physiological states as disclosed in Rajendran et al., *Proc Natl Acad Sci USA* 2006; 103:11172-11177, Taylor et al., *Gynecol Oncol* 2008; 110:13-21, Zhou et al., *Kidney Int* 2008; 74:613-621, Buning et al., *Immunology* 2008, Prado et al. *J Immunol* 2008; 181:1519-1525, Vella et al. (2008) *Vet Immunol Immunopathol* 124(3-4): 385-93, Gould et al. (2003). *Proc Natl Acad Sci USA* 100(19): 10592-7, Fang et al. (2007). *PLoS Biol* 5(6): e158, Chen, B. J. and R. A. Lamb (2008). *Virology* 372(2): 221-32, Bhatnagar, S, and J. S. Schorey (2007). *J Biol Chem* 282(35): 25779-89, Bhatnagar et al. (2007) *Blood* 110(9): 3234-44, Yuyama, et al. (2008). *J Neurochem* 105(1): 217-24, Gomes et al. (2007). *Neurosci Lett.* 428(1): 43-6, Nagahama et al. (2003). *Autoimmunity* 36(3): 125-31, Taylor, D. D., S. Akyol, et al. (2006). *J Immunol* 176(3): 1534-42, Peche, et al. (2006). *Am J Transplant* 6(7): 1541-50, Iero, M., M. Valenti, et al. (2008). *Cell Death and Differentiation* 15: 80-88, Gesierich, S., I. Berezoversuskiy, et al. (2006), *Cancer Res* 66(14): 7083-94, Clayton, A., A. Turkes, et al. (2004). *Faseb J* 18(9): 977-9, Skriner., K. Adolph, et al. (2006). *Arthritis Rheum* 54(12): 3809-14, Brouwer, R., G. J. Pruijn, et al. (2001). *Arthritis Res* 3(2): 102-6, Kim, S. H., N. Bianco, et al. (2006). *Mol Ther* 13(2): 289-300, Evans, C. H., S. C. Ghivizzani, et al. (2000). *Clin Orthop Relat Res* (379 Suppl): S300-7, Zhang, H. G., C. Liu, et al. (2006). *J Immunol* 176(12): 7385-93, Van Niel, G., J. Mallegol, et al. (2004). *Gut* 52: 1690-1697, Fiasse, R. and O. Dewit (2007). *Expert Opinion on Therapeutic Patents* 17(12): 1423-1441(19).

A biomarker that can be derived and analyzed from an exosome includes, but is not limited to, the presence or absence, expression level, mutations (for example genetic mutations, such as deletions, translocations, duplications, nucleotide or amino acid substitutions, and the like) of miRNA (miR) and miRNA*nonsense (miR*), and other RNAs (including, but not limited to, mRNA, preRNA, preRNA, hnRNA, snRNA, siRNA, shRNA), DNA, proteins, peptides, and ligands. Any epigenetic modulation or copy number variation of a biomarker can also be analyzed. A miRNA biomarker includes not only its miRNA and microRNA*nonsense, but its precursor molecules: pri-microRNAs (pri-miRs) and pre-microRNAs (pre-miRs) are also included as biomarkers. The sequence of a miRNA can be obtained from publicly available databases such as http://www.mirbase.org/, http://www.microrna.org/, or any others available.

The one or more biomarkers analyzed from an exosome can be indicative of a particular tissue or cell of origin, disease, or physiological state, as further described below. Furthermore, the presence, absence or expression level of one or more of the biomarkers described herein can be correlated to a phenotype of a subject, including a disease, condition, prognosis or drug efficacy. The specific biomarker and bio-signature set forth below constitute non-inclusive examples for each of the diseases, condition comparisons, conditions, and/or physiological states. Furthermore, the one or more biomarker assessed for a phenotype can be a cell-of-origin specific exosome, such as those described above.

The one or more miRNAs used to characterize a phenotype may be selected from those disclosed in PCT Publication No. WO2009/036236. For example, one or more miRNAs listed in Tables I-VI (FIGS. 6-11) can be used to characterize colon adenocarcinoma, colorectal cancer, prostate cancer, lung cancer, breast cancer, b-cell lymphoma, pancreatic cancer, diffuse large BCL cancer, CLL, bladder cancer, renal cancer, hypoxia-tumor, uterine leiomyomas, ovarian cancer, hepatitis C virus-associated hepatocellular carcinoma, ALL, Alzheimer's disease, myelofibrosis, myelofibrosis, polycythemia vera, thrombocythemia, HIV, or HIV-I latency, as further described herein.

The one or more miRNAs can be detected in plasma exosomes. The one or more miRNAs can be miR-223, miR-484, miR-191, miR-146a, miR-016, miR-026a, miR-222, miR-024, miR-126, and miR-32. One or more miRNAs can also be detected in PBMC. The one or more miRNAs can be miR-223, miR-150, miR-146b, miR-016, miR-484, miR-146a, miR-191, miR-026a, miR-019b, or miR-020a. The one or more miRNAs can be used to characterize a particular disease or condition. For example, for the disease bladder cancer, one or more miRNAs can be detected, such as miR-223, miR-26b, miR-221, miR-103-1, miR-185, miR-23b, miR-203, miR-17-5p, miR-23a, miR-205 or any combination thereof. The one or more miRNAs may be upregulated or overexpressed.

In some embodiments, the one or more miRNAs is used to characterize hypoxia-tumor. The one or more miRNA may be miR-23, miR-24, miR-26, miR-27, miR-103, miR-107, miR-181, miR-210, or miR-213, and may be upregulated. One or more miRNAs can also be used to characterize uterine leiomyomas. For example, the one or more miRNAs used to characterize a uterine leiomyoma may be a let-7 family member, miR-21, miR-23b, miR-29b, or miR-197. The miRNA can be upregulated.

Myelofibrosis can also be characterized by one or more miRNAs, such as miR-190, which can be upregulated; miR-31, miR-150 and miR-95, which can be downregulated, or any combination thereof. Furthermore, myelofibrosis, polycythemia vera or thrombocythemia can also be characterized by detecting one or more miRNAs, such as, but not limited to, miR-34a, miR-342, miR-326, miR-105, miR-149, miR-147, or any combination thereof. The one or more miRNAs may be down-regulated.

Other examples of phenotypes that can be characterized by assessing an exosome for one or more biomarkers are further described herein.

The one or more biomarkers can be detected by a probe. A probe can comprise of an oligonucleotide, such as DNA or RNA, an aptamer, monoclonal antibody, polyclonal antibody, Fabs, Fab', single chain antibody, synthetic antibody, peptoid, zDNA, peptide nucleic acid (PNA), locked nucleic acid (LNA), lectin, synthetic or naturally occurring chemical compound (including but not limited to a drug or labeling reagent), dendrimer, or any combination thereof. The probe can be directly detected, for example by being directly labeled, or be indirectly detected, such as through a labeling reagent. The probe can selectively hybridize to a biomarker. For example, a probe that is an oligonucleotide can selectively hybridize to a miRNA biomarker.

Breast Cancer

Breast cancer specific biomarkers can include one or more (for example, 2, 3, 4, 5, 6, 7, 8, or more) overexpressed miRs, underexpressed miRs, mRNA, genetic mutations, proteins, ligands, peptides, snoRNA, or any combination thereof, such as listed in FIG. 3.

One or more breast cancer specific biomarker can be assessed to provide a breast cancer specific exosome bio-signature. For example, the bio-signature can comprise one or more overexpressed miRs, including but not limited to, miR-21, miR-155, miR-206, miR-122a, miR-210, miR-21, miR-21, miR-155, miR-206, miR-122a, miR-210, or miR-21, or any combination thereof.

The bio-signature can also comprise one or more underexpressed miRs such as, but not limited to, let-7, miR-10b, miR-125a, miR-125b, miR-145, miR-143, miR-145, miR-16, let-7, let-7, let-7, miR-10b, miR-125a, miR-125b, or miR-145, or any combination thereof.

The mRNAs that may be analyzed can include, but are not limited to, ER, PR, HER2, MUC1, or EGFR, or any combination thereof. Mutations including, but not limited to, those related to KRAS, B-Raf, or CYP2D6, or any combination thereof can also be used as specific biomarkers from exosomes for breast cancer. In addition, a protein, ligand, or peptide that can be used as biomarkers from exosomes that are specific to breast cancer includes, but are not limited to, hsp70, MART-1, TRP, HER2, hsp70, MART-1, TRP, HER2, ER, PR, Class III b-tubulin, or VEGFA, or any combination thereof. Furthermore the snoRNA that can be used as an exosomal biomarker for breast cancer include, but are not limited to, GAS5. The gene fusion ETV6-NTRK3 can also be used a biomarker for breast cancer.

Also provided herein is an isolated exosome comprising one or more breast cancer specific biomarkers, such as ETV6-NTRK3, or biomarkers listed in FIG. 3 and in FIG. 1 for breast cancer. A composition comprising the isolated exosome is also provided. Accordingly, in some embodiments, the composition comprises a population of exosomes comprising one or more breast cancer specific biomarkers, such as ETV6-NTRK3, or biomarkers listed in FIG. 3 and in FIG. 1 for breast cancer. The composition can comprise a substantially enriched population of exosomes, wherein the population of exosomes is substantially homogeneous for breast cancer specific exosomes or exosomes comprising one or more breast cancer specific biomarkers, such as ETV6-NTRK3, or biomarkers listed in FIG. 3 and in FIG. 1 for breast cancer.

One or more breast cancer specific biomarkers, such as ETV6-NTRK3, or biomarkers listed in FIG. 3 and in FIG. 1 for breast cancer can also be detected by one or more systems disclosed herein, for characterizing a breast cancer. For example, a detection system can comprise one or more probes to detect one or more breast cancer specific biomarkers, such as ETV6-NTRK3, or biomarkers listed in FIG. 3 and in FIG. 1 for breast cancer, of one or more exosomes of a biological sample.

Ovarian Cancer

Ovarian cancer specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 4, and can be used to create a ovarian cancer specific exosome bio-signature. For example, the bio-signature can comprise one or more overexpressed miRs, such as, but not limited to, miR-200a, miR-141, miR-200c, miR-200b, miR-21, miR-141, miR-200a, miR-200b, miR-200c, miR-203, miR-205, miR-214, miR-199*, or miR-215, or any combination thereof. The bio-signature can also comprise one or more underexpressed miRs such as, but not limited to, miR-199a, miR-140, miR-145, miR-100, miR-let-7 cluster, or miR-125b-1, or any combination thereof. The one or more mRNAs that may be analyzed can include, but are not limited to, ERCC1, ER, TOPO1, TOP2A, AR, PTEN, HER2/neu, CD24 or EGFR, or any combination thereof.

A biomarker mutation for ovarian cancer that can be assessed in an exosome includes, but is not limited to, a mutation of KRAS, mutation of B-Raf, or any combination of mutations specific for ovarian cancer. The protein, ligand, or peptide that can be assessed in an exosome can include, but is not limited to, VEGFA, VEGFR2, or HER2, or any combination thereof. Furthermore, an exosome isolated or assayed can be ovarian cancer cell specific, or derived from ovarian cancer cells.

Also provided herein is an isolated exosome comprising one or more ovarian cancer specific biomarkers, such as CD24, those listed in FIG. 4 and in FIG. 1 for ovarian cancer. A composition comprising the isolated exosome is also provided. Accordingly, in some embodiments, the composition comprises a population of exosomes comprising one or more ovarian cancer specific biomarkers, such as CD24, those listed in FIG. 4 and in FIG. 1 for ovarian cancer. The composition can comprise a substantially enriched population of exosomes, wherein the population of exosomes is substantially homogeneous for ovarian cancer specific exosomes or exosomes comprising one or more ovarian cancer specific biomarkers, such as CD24, those listed in FIG. 4 and in FIG. 1 for ovarian cancer.

One or more ovarian cancer specific biomarkers, such as CD24, those listed in FIG. 4 and in FIG. 1 for ovarian cancer can also be detected by one or more systems disclosed herein, for characterizing an ovarian cancer. For example, a detection system can comprise one or more probes to detect one or more ovarian cancer specific biomarkers, such as CD24, those listed in FIG. 4 and in FIG. 1 for ovarian cancer, of one or more exosomes of a biological sample.

Lung Cancer

Lung cancer specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 5, and can be used to create a lung cancer specific exosome bio-signature.

The bio-signature can comprise one or more overexpressed miRs, such as, but not limited to, miR-21, miR-205, miR-221 (protective), let-7a (protective), miR-137 (risky), miR-372 (risky), or miR-122a (risky), or any combination thereof. The bio-signature can comprise one or more upregulated or overexpressed miRNAs, such as miR-17-92, miR-19a, miR-21, miR-92, miR-155, miR-191, miR-205 or miR-210; one or more downregulated or underexpressed miRNAs, such as miR-let-7, or any combination thereof.

The one or more mRNAs that may be analyzed can include, but are not limited to, EGFR, PTEN, RRM1, RRM2, ABCB1, ABCG2, LRP, VEGFR2, VEGFR3, class III b-tubulin, or any combination thereof.

A biomarker mutation for lung cancer that can be assessed in an exosome includes, but is not limited to, a mutation of EGFR, KRAS, B-Raf, UGT1A1, or any combination of mutations specific for lung cancer. The protein, ligand, or peptide that can be assessed in an exosome can include, but is not limited to, KRAS, hENT1, or any combination thereof.

The biomarker can also be midkine (MK or MDK). Furthermore, an exosome isolated or assayed can be lung cancer cell specific, or derived from lung cancer cells.

Also provided herein is an isolated exosome comprising one or more lung cancer specific biomarkers, such as RLF-MYCL1, TGF-ALK, or CD74-ROS1, or those listed in FIG. 5 and in FIG. 1 for lung cancer. A composition comprising the isolated exosome is also provided. Accordingly, in some embodiments, the composition comprises a population of exosomes comprising one or more lung cancer specific biomarkers, such as RLF-MYCL1, TGF-ALK, or CD74-ROS1, or those listed in FIG. 5 and in FIG. 1 for lung cancer. The composition can comprise a substantially enriched population of exosomes, wherein the population of exosomes is substantially homogeneous for lung cancer specific exosomes or exosomes comprising one or more lung cancer specific biomarkers, such as RLF-MYCL1, TGF-ALK, or CD74-ROS1, or those listed in FIG. 5 and in FIG. 1 for lung cancer.

One or more lung cancer specific biomarkers, such as RLF-MYCL1, TGF-ALK, or CD74-ROS1, or those listed in FIG. 5 and in FIG. 1 for lung cancer can also be detected by one or more systems disclosed herein, for characterizing a lung cancer. For example, a detection system can comprise one or more probes to detect one or more lung cancer specific biomarkers, such as RLF-MYCL1, TGF-ALK, or CD74-ROS1, or those listed in FIG. 5 and in FIG. 1 for lung cancer, of one or more exosomes of a biological sample.

Colon Cancer

Colon cancer specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 6, and can be used to create a colon cancer specific exosome bio-signature. For example, the bio-signature can comprise one or more overexpressed miRs, such as, but not limited to, miR-24-1, miR-29b-2, miR-20a, miR-10a, miR-32, miR-203, miR-106a, miR-17-5p, miR-30c, miR-223, miR-126, miR-128b, miR-21, miR-24-2, miR-99b, miR-155, miR-213, miR-150, miR-107, miR-191, miR-221, miR-20a, miR-510, miR-92, miR-513, miR-19a, miR-21, miR-20, miR-183, miR-96, miR-135b, miR-31, miR-21, miR-92, miR-222, miR-181b, miR-210, miR-20a, miR-106a, miR-93, miR-335, miR-338, miR-133b, miR-346, miR-106b, miR-153a, miR-219, miR-34a, miR-99b, miR-185, miR-223, miR-211, miR-135a, miR-127, miR-203, miR-212, miR-95, or miR-17-5p, or any combination thereof. The bio-signature can also comprise one or more underexpressed miRs such as miR-143, miR-145, miR-143, miR-126, miR-34b, miR-34c, let-7, miR-9-3, miR-34a, miR-145, miR-455, miR-484, miR-101, miR-145, miR-133b, miR-129, miR-124a, miR-30-3p, miR-328, miR-106a, miR-17-5p, miR-342, miR-192, miR-1, miR-34b, miR-215, miR-192, miR-301, miR-324-5p, miR-30a-3p, miR-34c, miR-331, or miR-148b, or any combination thereof.

The one or more biomarker can be an upregulated or overexpressed miRNA, such as miR-20a, miR-21, miR-106a, miR-181b or miR-203, for characterizing a colon adenocarcinoma. The one or more biomarker can be used to characterize a colorectal cancer, such as an upregulated or overexpressed miRNA selected from the group consisting of: miR-19a, miR-21, miR-127, miR-31, miR-96, miR-135b and miR-183, a downregulated or underexpressed miRNA, such as miR-30c, miR-133a, mirl43, miR-133b or miR-145, or any combination thereof.

The one or more mRNAs that may be analyzed can include, but are not limited to, EFNB1, ERCC1, HER2, VEGF, or EGFR, or any combination thereof. A biomarker mutation for colon cancer that can be assessed in an exosome includes, but is not limited to, a mutation of EGFR, KRAS, VEGFA, B-Raf, APC, or p53, or any combination of mutations specific for colon cancer. The protein, ligand, or peptide that can be assessed in an exosome can include, but is not limited to, AFRs, Rabs, ADAM10, CD44, NG2, ephrin-B1, MIF, b-catenin, Junction, plakoglobin, glalectin-4, RACK1, tetrspanin-8, FasL, TRAIL, A33, CEA, EGFR, dipeptidase 1, hsc-70, tetraspanins, ESCRT, TS, PTEN, or TOPO1, or any combination thereof. Furthermore, an exosome isolated or assayed can be colon cancer cell specific, or derived from colon cancer cells.

Also provided herein is an isolated exosome comprising one or more colon cancer specific biomarkers, such as listed in FIG. 6 and in FIG. 1 for colon cancer. A composition comprising the isolated exosome is also provided. Accordingly, in some embodiments, the composition comprises a population of exosomes comprising one or more colon cancer specific biomarkers, such as listed in FIG. 6 and in FIG. 1 for colon cancer. The composition can comprise a substantially enriched population of exosomes, wherein the population of exosomes is substantially homogeneous for colon cancer specific exosomes or exosomes comprising one or more colon cancer specific biomarkers, such as listed in FIG. 6 and in FIG. 1 for colon cancer.

One or more colon cancer specific biomarkers, such as listed in FIG. 6 and in FIG. 1 for colon cancer can also be detected by one or more systems disclosed herein, for characterizing a colon cancer. For example, a detection system can comprise one or more probes to detect one or more colon cancer specific biomarkers, such as listed in FIG. 6 and in FIG. 1 for colon cancer, of one or more exosomes of a biological sample.

Adenoma Versus Hyperplastic Polyp

Adenoma versus hyperplastic polyp specific biomarkers from exosomes can include one or more (for example, 2, 3, 4, 5, 6, 7, 8, or more) overexpressed miRs, underexpressed miRs, mRNAs, genetic mutations, proteins, ligands, peptides, or any combination thereof, such as listed in FIG. 7, and can be used to create an adenoma versus hyperplastic polyp specific exosome bio-signature. For example, the one or more mRNAs that may be analyzed can include, but are not limited to, ABCA8, KIAA1199, GCG, MAMDC2, C2orf32, 229670_at, IGF1, PCDH7, PRDX6, PCNA, COX2, or MUC6, or any combination thereof.

A biomarker mutation to distinguish for adenoma versus hyperplastic polyp that can be assessed in an exosome includes, but is not limited to, a mutation of KRAS, mutation of B-Raf, or any combination of mutations specific for distinguishing between adenoma versus hyperplastic polyp. The protein, ligand, or peptide that can be assessed in an exosome can include, but is not limited to, hTERT.

Also provided herein is an isolated exosome comprising one or more specific biomarkers for distinguishing between an adenoma and a hyperplastic polyp, such as listed in FIG. 7. A composition comprising the isolated exosome is also provided. Accordingly, in some embodiments, the composition comprises a population of exosomes comprising one or more specific biomarkers for distinguishing between an adenoma and a hyperplastic polyp, such as listed in FIG. 7. The composition can comprise a substantially enriched population of exosomes, wherein the population of exosomes is substantially homogeneous for having one or more specific biomarkers for distinguishing between an adenoma and a hyperplastic polyp, such as listed in FIG. 7.

One or more specific biomarkers for distinguishing between an adenoma and a hyperplastic polyp, such as listed in FIG. 7 can also be detected by one or more systems disclosed herein, for distinguishing between an adenoma and a hyperplastic polyp. For example, a detection system can comprise one or more probes to detect one or more specific biomarkers for distinguishing between an adenoma and a hyperplastic polyp, such as listed in FIG. 7, of one or more exosomes of a biological sample.

Irritable Bowel Disease (IBD)

IBD versus normal biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 8, and can be used to create a IBD versus normal specific exosome bio-signature. For example, the one or more mRNAs that may be analyzed can include, but are not limited to, REG1A, MMP3, or any combination thereof.

Also provided herein is an isolated exosome comprising one or more specific biomarkers for distinguishing between IBD and a normal sample, such as listed in FIG. 8. A composition comprising the isolated exosome is also provided. Accordingly, in some embodiments, the composition comprises a population of exosomes comprising one or more specific biomarkers for distinguishing between IBD and a normal sample, such as listed in FIG. 8. The composition can comprise a substantially enriched population of exosomes, wherein the population of exosomes is substantially homogeneous for having one or more specific biomarkers for distinguishing between IBD and a normal sample, such as listed in FIG. 8.

One or more specific biomarkers for distinguishing between IBD and a normal sample, such as listed in FIG. 8 can also be detected by one or more systems disclosed herein, for distinguishing between IBD and a normal sample. For example, a detection system can comprise one or more probes to detect one or more specific biomarkers for distinguishing between IBD and a normal sample, such as listed in FIG. 8, of one or more exosomes of a biological sample.

Adenoma Versus Colorectal Cancer (CRC)

Adenoma versus CRC specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 9, and can be used to create a Adenoma versus CRC specific exosome bio-signature. For example, the one or more mRNAs that may be analyzed can include, but are not limited to, GREM1, DDR2, GUCY1A3, TNS1, ADAMTS1, FBLN1, FLJ38028, RDX, FAM129A, ASPN, FRMD6, MCC, RBMS1, SNA12, MEIS1, DOCK10, PLEKHC1, FAM126A, TBC1D9, VWF, DCN, ROBO1, MSRB3, LATS2, MEF2C, IGFBP3, GNB4, RCN3, AKAP12, RFTN1, 226834_at, COL5A1, GNG2, NR3C1*, SPARCL1, MAB21L2, AXIN2, 236894_at, AEBP1, AP1S2, C10orf56, LPHN2, AKT3, FRMD6, COL15A1, CRYAB, COL14A1, LOC286167, QKI, WWTR1, GNG11, PAPPA, or ELDT1, or any combination thereof.

Also provided herein is an isolated exosome comprising one or more specific biomarkers for distinguishing between an adenoma and a CRC, such as listed in FIG. 9. A composition comprising the isolated exosome is also provided. Accordingly, in some embodiments, the composition comprises a population of exosomes comprising one or more specific biomarkers for distinguishing between an adenoma and a CRC, such as listed in FIG. 9. The composition can comprise a substantially enriched population of exosomes, wherein the population of exosomes is substantially homogeneous for having one or more specific biomarkers for distinguishing between an adenoma and a CRC, such as listed in FIG. 9.

One or more specific biomarkers for distinguishing between an adenoma and a CRC, such as listed in FIG. 9 can also be detected by one or more systems disclosed herein, for distinguishing between an adenoma and a CRC. For example, a detection system can comprise one or more probes to detect one or more specific biomarkers for distinguishing between an adenoma and a CRC, such as listed in FIG. 9, of one or more exosomes of a biological sample.

IBD Versus CRC

IBD versus CRC specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 10, and can be used to create a IBD versus CRC specific exosome bio-signature. For example, the one or more mRNAs that may be analyzed can include, but are not limited to, 227458_at, INDO, CXCL9, CCR2, CD38, RARRES3, CXCL10, FAM26F, TNIP3, NOS2A, CCRL1, TLR8, IL18BP, FCRL5, SAMD9L, ECGF1, TNFSF13B, GBPS, or GBP1, or any combination thereof.

Also provided herein is an isolated exosome comprising one or more specific biomarkers for distinguishing between IBD and a CRC, such as listed in FIG. 10. A composition comprising the isolated exosome is also provided. Accordingly, in some embodiments, the composition comprises a population of exosomes comprising one or more specific biomarkers for distinguishing between IBD and a CRC, such as listed in FIG. 10. The composition can comprise a substantially enriched population of exosomes, wherein the population of exosomes is substantially homogeneous for having one or more specific biomarkers for distinguishing between IBD and a CRC, such as listed in FIG. 10.

One or more specific biomarkers for distinguishing between IBD and a CRC, such as listed in FIG. 10 can also be detected by one or more systems disclosed herein, for distinguishing between IBD and a CRC. For example, a detection system can comprise one or more probes to detect one or more specific biomarkers for distinguishing between IBD and a CRC, such as listed in FIG. 10, of one or more exosomes of a biological sample.

CRC Dukes B Versus Dukes C-D

CRC Dukes B versus Dukes C-D specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 11, and can be used to create a CRC D-B versus C-D specific exosome bio-signature. For example, the one or more mRNAs that may be analyzed can include, but are not limited to, TMEM37*, IL33, CA4, CCDC58, CLIC6, VERSUSNL1, ESPN, APCDD1, C13orf18, CYP4X1, ATP2A3, LOC646627, MUPCDH, ANPEP, C1orf115, HSD3B2, GBA3, GABRB2, GYLTL1B, LYZ, SPC25, CDKN2B, FAM89A, MOGAT2, SEMA6D, 229376_at, TSPAN5, IL6R, or SLC26A2, or any combination thereof.

Also provided herein is an isolated exosome comprising one or more specific biomarkers for distinguishing between CRC Dukes B and a CRC Dukes C-D, such as listed in FIG. 11. A composition comprising the isolated exosome is also provided. Accordingly, in some embodiments, the composition comprises a population of exosomes comprising one or more specific biomarkers for distinguishing between CRC Dukes B and a CRC Dukes C-D, such as listed in FIG. 11. The composition can comprise a substantially enriched population of exosomes, wherein the population of exosomes is substantially homogeneous for having one or more specific biomarkers for distinguishing between CRC Dukes B and a CRC Dukes C-D, such as listed in FIG. 11.

One or more specific biomarkers for distinguishing between CRC Dukes B and a CRC Dukes C-D, such as listed in FIG. 11 can also be detected by one or more systems disclosed herein, for distinguishing between CRC Dukes B and a CRC Dukes C-D. For example, a detection system can comprise one or more probes to detect one or more specific biomarkers for distinguishing between CRC Dukes B and a CRC Dukes C-D, such as listed in FIG. 11, of one or more exosomes of a biological sample.

Adenoma with Low Grade Dysplasia Versus Adenoma with High Grade Dysplasia

Adenoma with low grade dysplasia versus adenoma with high grade dysplasia specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 12, and can be used to create an adenoma low grade dysplasia versus adenoma high grade dysplasia specific exosome bio-signature. For example, the one or mRNAs that may be analyzed can include, but are not limited to, SI, DMBT1, CFI*, AQP1, APOD, TNFRSF17, CXCL10, CTSE, IGHA1, SLC9A3, SLC7A1, BATF2, SOCS1, DOCK2, NOS2A, HK2, CXCL2, IL15RA, POU2AF1, CLEC3B, ANI3BP, MGC13057, LCK*, C4BPA, HOXC6, GOLT1A, C2orf32, IL10RA, 240856_at, SOCS3, MEIS3P1, HIPK1, GLS, CPLX1, 236045_x_at, GALC, AMN, CCDC69, CCL28, CPA3, TRIB2, HMGA2, PLCL2, NR3C1, EIF5A, LARP4, RP5-1022P6.2, PHLDB2, FKBP1B, INDO, CLDN8, CNTN3, PBEF1, SLC16A9, CDC25B, TPSB2, PBEF1, ID4, GJB5, CHN2, LIMCH1, or CXCL9, or any combination thereof.

Also provided herein is an isolated exosome comprising one or more specific biomarkers for distinguishing between adenoma with low grade dysplasia and adenoma with high grade dysplasia, such as listed in FIG. 12. A composition comprising the isolated exosome is also provided. Accordingly, in some embodiments, the composition comprises a population of exosomes comprising one or more specific biomarkers for distinguishing between adenoma with low grade dysplasia and adenoma with high grade dysplasia, such as listed in FIG. 12. The composition can comprise a substantially enriched population of exosomes, wherein the population of exosomes is substantially homogeneous for having one or more specific biomarkers for distinguishing between adenoma with low grade dysplasia and adenoma with high grade dysplasia, such as listed in FIG. 12.

One or more specific biomarkers for distinguishing between adenoma with low grade dysplasia and adenoma with high grade dysplasia, such as listed in FIG. 12 can also be detected by one or more systems disclosed herein, for distinguishing between adenoma with low grade dysplasia and adenoma with high grade dysplasia. For example, a detection system can comprise one or more probes to detect one or more specific biomarkers for distinguishing between adenoma with low grade dysplasia and adenoma with high grade dysplasia, such as listed in FIG. 12, of one or more exosomes of a biological sample.

Ulcerative Colitis (UC) Versus Crohn's Disease (CD)

Ulcerative colitis (UC) versus Crohn's disease (CD) specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 13, and can be used to create a UC versus CD specific exosome bio-signature. For example, the one or more mRNAs that may be analyzed can include, but are not limited to, IFITM1, IFITM3, STAT1, STAT3, TAP1, PSME2, PSMB8, HNF4G, KLF5, AQP8, APT2B1, SLC16A, MFAP4, CCNG2, SLC44A4, DDAH1, TOB1, 231152_at, MKNK1, CEACAM7*, 1562836_at, CDC42SE2, PSD3, 231169_at, IGL@*, GSN, GPM6B, CDV3*, PDPK1, ANP32E, ADAM9, CDH1, NLRP2, 215777_at, OSBPL1, VNN1, RABGAP1L, PHACTR2, ASH1L, 213710_s_at, CDH1, NLRP2, 215777_at, OSBPL1, VNN1, RABGAP1L, PHACTR2, ASH1, 213710_s_at, ZNF3, FUT2, IGHA1, EDEM1, GPR171, 229713_at, LOC643187, FLVCR1, SNAP23*, ETNK1, LOC728411, POSTN, MUC12, HOXA5, SIGLEC1, LARP5, PIGR, SPTBN1, UFM1, C6orf62, WDR90, ALDH1A3, F2RL1, IGHV1-69, DUOX2, RAB5A, or CP, or any combination thereof can also be used as specific biomarkers from exosomes for UC versus CD.

A biomarker mutation for distinguishing UC versus CD that can be assessed in an exosome includes, but is not limited to, a mutation of CARD15, or any combination of mutations specific for distinguishing UC versus CD. The protein, ligand, or peptide that can be assessed in an exosome can include, but is not limited to, (P)ASCA.

Also provided herein is an isolated exosome comprising one or more specific biomarkers for distinguishing between UC and CD, such as listed in FIG. 13. A composition comprising the isolated exosome is also provided. Accordingly, in some embodiments, the composition comprises a population of exosomes comprising one or more specific biomarkers for distinguishing between UC and CD, such as listed in FIG. 13. The composition can comprise a substantially enriched population of exosomes, wherein the population of exosomes is substantially homogeneous for having one or more specific biomarkers for distinguishing between UC and CD, such as listed in FIG. 13.

One or more specific biomarkers for distinguishing between UC and CD, such as listed in FIG. 13 can also be detected by one or more systems disclosed herein, for distinguishing between UC and CD. For example, a detection system can comprise one or more probes to detect one or more specific biomarkers for distinguishing between UC and CD, such as listed in FIG. 13, of one or more exosomes of a biological sample.

Hyperplastic Polyp

Hyperplastic polyp versus normal specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 14, and can be used to create a hyperplastic polyp versus normal specific exosome bio-signature. For example, the one or more mRNAs that may be analyzed can include, but are not limited to, SLC6A14, ARHGEF10, ALS2, IL1RN, SPRY4, PTGER3, TRIM29, SERPINB5, 1560327 at, ZAK, BAG4, TRIB3, TTL, FOXQ1, or any combination.

Also provided herein is an isolated exosome comprising one or more hyperplastic polyp specific biomarkers, such as listed in FIG. 14. A composition comprising the isolated exosome is also provided. Accordingly, in some embodiments, the composition comprises a population of exosomes comprising one or more hyperplastic polyp specific biomarkers, such as listed in FIG. 14. The composition can comprise a substantially enriched population of exosomes, wherein the population of exosomes is substantially homogeneous for hyperplastic polyp specific exosomes or exosomes comprising one or more hyperplastic polyp specific biomarkers, such as listed in FIG. 14.

One or more hyperplastic polyp specific biomarkers, such as listed in FIG. 14 can also be detected by one or more systems disclosed herein, for characterizing a hyperplastic polyp. For example, a detection system can comprise one or more probes to detect one or more listed in FIG. 14. One or more hyperplastic specific biomarkers, such as listed in FIG. 14, of one or more exosomes of a biological sample.

Adenoma with Low Grade Dysplasia Versus Normal

Adenoma with low grade dysplasia versus normal specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 15, and can be used to create an adenoma low grade dysplasia versus normal specific exosome bio-signature. For example, the RNAs that may be analyzed can include, but are not limited to, UGT2A3, KLK11, KIAA1199, FOXQ1, CLDN8, ABCA8, or PYY, or any combination thereof and can be used as specific biomarkers from exosomes for Adenoma low grade dysplasia versus normal. Furthermore, the snoRNA that can be used as an exosomal biomarker for adenoma low grade dysplasia versus normal can include, but is not limited to, GAS5.

Also provided herein is an isolated exosome comprising one or more specific biomarkers for distinguishing between adenoma with low grade dysplasia and normal, such as listed in FIG. 15. A composition comprising the isolated exosome is also provided. Accordingly, in some embodiments, the composition comprises a population of exosomes comprising one or more specific biomarkers for distinguishing between adenoma with low grade dysplasia and normal, such as listed in FIG. 15. The composition can comprise a substantially enriched population of exosomes, wherein the population of exosomes is substantially homogeneous for having one or more specific biomarkers for distinguishing between adenoma with low grade dysplasia and normal, such as listed in FIG. 15.

One or more specific biomarkers for distinguishing between adenoma with low grade dysplasia and normal, such as listed in FIG. 15 can also be detected by one or more systems disclosed herein, for distinguishing between adenoma with low grade dysplasia and normal. For example, a detection system can comprise one or more probes to detect one or more specific biomarkers for distinguishing between adenoma with low grade dysplasia and normal, such as listed in FIG. 15, of one or more exosomes of a biological sample.

Adenoma Versus Normal

Adenoma versus normal specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 16, and can be used to create an Adenoma versus normal specific exosome bio-signature. For example, the one or more mRNAs that may be analyzed can include, but are not limited to, KIAA1199, FOXQ1, or CA7, or any combination thereof. The protein, ligand, or peptide that can be used as a biomarker from exosomes that is specific to adenoma versus. normal can include, but is not limited to, Clusterin.

Also provided herein is an isolated exosome comprising one or more specific biomarkers for distinguishing between adenoma and normal, such as listed in FIG. 16. A composition comprising the isolated exosome is also provided. Accordingly, in some embodiments, the composition comprises a population of exosomes comprising one or more specific biomarkers for distinguishing between adenoma and normal, such as listed in FIG. 16. The composition can comprise a substantially enriched population of exosomes, wherein the population of exosomes is substantially homogeneous for having one or more specific biomarkers for distinguishing between adenoma and normal, such as listed in FIG. 16.

One or more specific biomarkers for distinguishing between adenoma and normal, such as listed in FIG. 16 can also be detected by one or more systems disclosed herein, for distinguishing between adenoma and normal. For example, a detection system can comprise one or more probes to detect one or more specific biomarkers for distinguishing between adenoma and normal, such as listed in FIG. 16, of one or more exosomes of a biological sample.

CRC Versus Normal

CRC versus normal specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 17, and can be used to create a CRC versus normal specific exosome bio-signature. For example, the one or mRNAs that may be analyzed can include, but are not limited to, VWF, IL8, CHI3L1, S100A8, GREM1, or ODC, or any combination thereof and can be used as specific biomarkers from exosomes for CRC versus normal.

A biomarker mutation for CRC versus normal that can be assessed in an exosome includes, but is not limited to, a mutation of KRAS, BRAF, APC, MSH2, or MLH1, or any combination of mutations specific for distinguishing between CRC versus normal. The protein, ligand, or peptide that can be assessed in an exosome can include, but is not limited to, cytokeratin 13, calcineurin, CHK1, clathrin light chain, phospho-ERK, phospho-PTK2, or MDM2, or any combination thereof.

Also provided herein is an isolated exosome comprising one or more specific biomarkers for distinguishing between CRC and normal, such as listed in FIG. 17. A composition comprising the isolated exosome is also provided. Accordingly, in some embodiments, the composition comprises a population of exosomes comprising one or more specific biomarkers for distinguishing between CRC and normal, such as listed in FIG. 17. The composition can comprise a substantially enriched population of exosomes, wherein the population of exosomes is substantially homogeneous for having one or more specific biomarkers for distinguishing between CRC and normal, such as listed in FIG. 17.

One or more specific biomarkers for distinguishing between CRC and normal, such as listed in FIG. 17 can also be detected by one or more systems disclosed herein, for distinguishing between CRC and normal. For example, a detection system can comprise one or more probes to detect one or more specific biomarkers for distinguishing between CRC and normal, such as listed in FIG. 17, of one or more exosomes of a biological sample.

Benign Prostatic Hyperplasia (BPH)

Benign prostatic hyperplasia (BPH) specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 18, and can be used to create a BPH specific exosome bio-signature. The protein, ligand, or peptide that can be assessed in an exosome can include, but is not limited to, intact fibronectin.

Also provided herein is an isolated exosome comprising one or more BPH specific biomarkers, such as listed in FIG. 18 and in FIG. 1 for BPH. A composition comprising the isolated exosome is also provided. Accordingly, in some embodiments, the composition comprises a population of exosomes comprising one or more BPH specific biomarkers, such as listed in FIG. 18 and in FIG. 1 for BPH. The composition can comprise a substantially enriched population of exosomes, wherein the population of exosomes is substantially homogeneous for BPH specific exosomes or exosomes comprising one or more BPH specific biomarkers, such as listed in FIG. 18 and in FIG. 1 for BPH.

One or more BPH specific biomarkers, such as listed in FIG. 18 and in FIG. 1 for BPH, can also be detected by one or more systems disclosed herein, for characterizing a BPH. For example, a detection system can comprise one or more probes to detect one more BPH specific biomarkers, such as listed in FIG. 18 and in FIG. 1 for BPH, of one or more exosomes of a biological sample.

Prostate Cancer

Prostate cancer specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 19, and can be used to create a prostate cancer specific exosome bio-signature. For example, a bio-signature for prostate cancer can comprise miR-9, miR-21, miR-141, miR-370, miR-200b, miR-210, miR-155, or miR-196a. In some embodiments, the bio-signature can comprise one or more overexpressed miRs, such as, but not limited to, miR-202, miR-210, miR-296, miR-320, miR-370, miR-373, miR-498, miR-503, miR-184, miR-198, miR-302c, miR-345, miR-491, miR-513, miR-32, miR-182, miR-31, miR-26a-1/2, miR-200c, miR-375, miR-196a-1/2, miR-370, miR-425, miR-425, miR-194-1/2, miR-181a-1/2, miR-34b, let-71, miR-188, miR-25, miR-106b, miR-449, miR-99b, miR-93, miR-92-1/2, miR-125a, or miR-141, or any combination thereof.

The bio-signature can also comprise one or more underexpressed miRs such as, but not limited to, let-7a, let-7b, let-7c, let-7d, let-7g, miR-16, miR-23a, miR-23b, miR-26a, miR-92, miR-99a, miR-103, miR-125a, miR-125b, miR-143, miR-145, miR-195, miR-199, miR-221, miR-222, miR-497, let-7f, miR-19b, miR-22, miR-26b, miR-27a, miR-27b, miR-29a, miR-29b, miR-30_5p, miR-30c, miR-100, miR-141, miR-148a, miR-205, miR-520h, miR-494, miR-490, miR-133a-1, miR-1-2, miR-218-2, miR-220, miR-128a, miR-221, miR-499, miR-329, miR-340, miR-345, miR-410, miR-126, miR-205, miR-7-1/2, miR-145, miR-34a, miR-487, or let-7b, or any combination thereof. The bio-signature can comprise upregulated or overexpressed miR-21, downregulated or underexpressed miR-15a, miR-16-1, miR-143 or miR-145, or any combination thereof.

The one or more mRNAs that may be analyzed can include, but are not limited to, AR, PCA3, or any combination thereof and can be used as specific biomarkers from exosomes for prostate cancer.

The protein, ligand, or peptide that can be assessed in an exosome can include, but is not limited to, FASLG or TNFSF10 or any combination thereof. Furthermore, an exosome isolated or assayed can be prostate cancer cell specific, or derived from prostate cancer cells. Furthermore, the snoRNA that can be used as an exosomal biomarker for prostate cancer can include, but is not limited to, U50. Examples of prostate cancer bio-signatures are further described below.

Also provided herein is an isolated exosome comprising one or more prostate cancer specific biomarkers, such as ACSL3-ETV1, C15ORF21-ETV1, FLJ35294-ETV1, HERV-ETV1, TMPRSS2-ERG, TMPRSS2-ETV1/4/5, TMPRSS2-ETV4/5, SLC5A3-ERG, SLC5A3-ETV1, SLC5A3-ETV5 or KLK2-ETV4, or those listed in FIGS. 19, 60 and in FIG. 1 for prostate cancer. A composition comprising the isolated exosome is also provided. Accordingly, in some embodiments, the composition comprises a population of exosomes comprising one or more prostate cancer specific biomarkers such as ACSL3-ETV1, C15ORF21-ETV1, FLJ35294-ETV1, HERV-ETV1, TMPRSS2-ERG, TMPRSS2-ETV1/4/5, TMPRSS2-ETV4/5, SLC5A3-ERG, SLC5A3-ETV1, SLC5A3-ETV5 or KLK2-ETV4, or those listed in FIGS. 19, 60 and in FIG. 1 for prostate cancer. The composition can comprise a substantially enriched population of exosomes, wherein the population of exosomes is substantially homogeneous for prostate cancer specific exosomes or exosomes comprising one or more prostate cancer specific biomarkers, such as ACSL3-ETV1, C15ORF21-ETV1, FLJ35294-ETV1, HERV-ETV1, TMPRSS2-ERG, TMPRSS2-ETV1/4/5, TMPRSS2-ETV4/5, SLC5A3-ERG, SLC5A3-ETV1, SLC5A3-ETV5 or KLK2-ETV4, or those listed in FIGS. 19, 60 and in FIG. 1 for prostate cancer.

One or more prostate cancer specific biomarkers, such as ACSL3-ETV1, C15ORF21-ETV1, FLJ35294-ETV1, HERV-ETV1, TMPRSS2-ERG, TMPRSS2-ETV1/4/5, TMPRSS2-ETV4/5, SLC5A3-ERG, SLC5A3-ETV1, SLC5A3-ETV5 or KLK2-ETV4, or those listed in FIGS. 19, 60 and in FIG. 1 for prostate cancer can also be detected by one or more systems disclosed herein, for characterizing a prostate cancer. For example, a detection system can comprise one or more probes to detect one or more prostate cancer specific biomarkers, such as ACSL3-ETV1, C15ORF21-ETV1, FLJ35294-ETV1, HERV-ETV1, TMPRSS2-ERG, TMPRSS2-ETV1/4/5, TMPRSS2-ETV4/5, SLC5A3-ERG, SLC5A3-ETV1, SLC5A3-ETV5 or KLK2-ETV4, or those listed in FIGS. 19, 60 and in FIG. 1 for prostate cancer, of one or more exosomes of a biological sample.

Melanoma

Melanoma specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 20, and can be used to create a melanoma specific exosome bio-signature. For example, the bio-signature can comprise one or more overexpressed miRs, such as, but not limited to, miR-19a, miR-144, miR-200c, miR-211, miR-324-5p, miR-331, or miR-374, or any combination thereof. The bio-signature can also comprise one or more underexpressed miRs such as, but not limited to, miR-9, miR-15a, miR-17-3p, miR-23b, miR-27a, miR-28, miR-29b, miR-30b, miR-31, miR-34b, miR-34c, miR-95, miR-96, miR-100, miR-104, miR-105, miR-106a, miR-107, miR-122a, miR-124a, miR-125b, miR-127, miR-128a, miR-128b, miR-129, miR-135a, miR-135b, miR-137, miR-138, miR-139, miR-140, miR-141, miR-149, miR-154, miR-154#3, miR-181a, miR-182, miR-183, miR-184, miR-185, miR-189, miR-190, miR-199, miR-199b, miR-200a, miR-200b, miR-204, miR-213, miR-215, miR-216, miR-219, miR-222, miR-224, miR-299, miR-302a, miR-302b, miR-302c, miR-302d, miR-323, miR-325, let-7a, let-7b, let-7d, let-7e, or let-7g, or any combination thereof.

The one or more mRNAs that may be analyzed can include, but are not limited to, MUM-1, beta-catenin, or Nop/5/Sik, or any combination thereof and can be used as specific biomarkers from exosomes for melanoma.

A biomarker mutation for melanoma that can be assessed in an exosome includes, but is not limited to, a mutation of CDK4 or any combination of mutations specific for melanoma. The protein, ligand, or peptide that can be assessed in an exosome can include, but is not limited to, DUSP-1, Alix, hsp70, Gib2, Gia, moesin, GAPDH, malate dehydrogenase, p120 catenin, PGRL, syntaxin-binding protein 1 & 2, septin-2, or WD-repeat containing protein 1, or any combination thereof. The snoRNA that can be used as an exosomal biomarker for melanoma include, but are not limited to, H/ACA (U107f), SNORA11D, or any combination thereof. Furthermore, an exosome isolated or assayed can be melanoma cell specific, or derived from melanoma cells.

Also provided herein is an isolated exosome comprising one or more melanoma specific biomarkers, such as listed in FIG. 20 and in FIG. 1 for melanoma. A composition comprising the isolated exosome is also provided. Accordingly, in some embodiments, the composition comprises a population of exosomes comprising one or more melanoma specific biomarkers, such as listed in FIG. 20 and in FIG. 1 for melanoma. The composition can comprise a substantially enriched population of exosomes, wherein the population of exosomes is substantially homogeneous for melanoma specific exosomes or exosomes comprising one or more melanoma specific biomarkers, such as listed in FIG. 20 and in FIG. 1 for melanoma.

One or more melanoma specific biomarkers, such as listed in FIG. 20 and in FIG. 1 for melanoma can also be detected by one or more systems disclosed herein, for characterizing a melanoma. For example, a detection system can comprise one or more probes to detect one or more cancer specific biomarkers, such as listed in FIG. 20 and in FIG. 1 for melanoma, of one or more exosomes of a biological sample.

Pancreatic Cancer

Pancreatic cancer specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 21, and can be used to create a pancreatic cancer specific exosome bio-signature. For example, the bio-signature can comprise one or more overexpressed miRs, such as, but not limited to, miR-221, miR-181a, miR-155, miR-210, miR-213, miR-181b, miR-222, miR-181b-2, miR-21, miR-181b-1, miR-220, miR-181d, miR-223, miR-100-1/2, miR-125a, miR-143, miR-10a, miR-146, miR-99, miR-100, miR-199a-1, miR-10b, miR-199a-2, miR-221, miR-181a, miR-155, miR-210, miR-213, miR-181b, miR-222, miR-181b-2, miR-21, miR-181b-1, miR-181c, miR-220, miR-181d, miR-223, miR-100-1/2, miR-125a, miR-143, miR-10a, miR-146, miR-99, miR-100, miR-199a-1, miR-10b, miR-199a-2, miR-107, miR-103, miR-103-2, miR-125b-1, miR-205, miR-23a, miR-221, miR-424, miR-301, miR-100, miR-376a, miR-125b-1, miR-21, miR-16-1, miR-181a, miR-181c, miR-92, miR-15, miR-155, let-7f-1, miR-212, miR-107, miR-024-1/2, miR-18a, miR-31, miR-93, miR-224, or let-7d, or any combination thereof.

The bio-signature can also comprise one or more underexpressed miRs such as, but not limited to, miR-148a, miR-148b, miR-375, miR-345, miR-142, miR-133a, miR-216, miR-217 or miR-139, or any combination thereof. The one or more mRNAs that may be analyzed can include, but are not limited to, PSCA, Mesothelin, or Osteopontin, or any combination thereof and can be used as specific biomarkers from exosomes for pancreatic cancer.

A biomarker mutation for pancreatic cancer that can be assessed in an exosome includes, but is not limited to, a mutation of KRAS, CTNNLB1, AKT, NCOA3, or B-RAF, or any combination of mutations specific for pancreatic cancer. The biomarker can also be BRCA2, PALB2, or p16. Furthermore, an exosome isolated or assayed can be pancreatic cancer cell specific, or derived from pancreatic cancer cells.

Also provided herein is an isolated exosome comprising one or more pancreatic cancer specific biomarkers, such as listed in FIG. 21. A composition comprising the isolated exosome is also provided. Accordingly, in some embodiments, the composition comprises a population of exosomes comprising one or more pancreatic cancer specific biomarkers, such as listed in FIG. 21. The composition can comprise a substantially enriched population of exosomes, wherein the population of exosomes is substantially homogeneous for pancreatic cancer specific exosomes or exosomes comprising one or more pancreatic cancer specific biomarkers, such as listed in FIG. 21.

One or more pancreatic cancer specific biomarkers, such as listed in FIG. 21, can also be detected by one or more systems disclosed herein, for characterizing a pancreatic cancer. For example, a detection system can comprise one or more probes to detect one or more pancreatic cancer specific biomarkers, such as listed in FIG. 21, of one or more exosomes of a biological sample.

Brain Cancer

Brain cancer (including, but not limited to, gliomas, glioblastomas, meinigiomas, acoustic neuroma/schwannomas, medulloblastoma) specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 22, and can be used to create a brain cancer specific exosome bio-signature. For example, the bio-signature can comprise one or more overexpressed miRs, such as, but not limited to miR-21, miR-10b, miR-130a, miR-221, miR-125b-1, miR-125b-2, miR-9-2, miR-21, miR-25, or miR-123, or any combination thereof.

The bio-signature can also comprise one or more underexpressed miRs such as, but not limited to, miR-128a, miR-181c, miR-181a, or miR-181b, or any combination thereof. The one or more mRNAs that may be analyzed include, but are not limited to, MGMT, which can be used as specific biomarker from exosomes for brain cancer. The protein, ligand, or peptide that can be assessed in an exosome can include, but is not limited to, EGFR.

Also provided herein is an isolated exosome comprising one or more brain cancer specific biomarkers, such as GOPC-ROS1, or those listed in FIG. 22 and in FIG. 1 for brain cancer. A composition comprising the isolated exosome is also provided. Accordingly, in some embodiments, the composition comprises a population of exosomes comprising one or more brain cancer specific biomarkers, such as GOPC-ROS1, or those listed in FIG. 22 and in FIG. 1 for brain cancer. The composition can comprise a substantially enriched population of exosomes, wherein the population of exosomes is substantially homogeneous for brain cancer specific exosomes or exosomes comprising one or more brain cancer specific biomarkers, such as GOPC-ROS1, or those listed in FIG. 22. and in FIG. 1 for brain cancer.

One or more brain cancer specific biomarkers, such as listed in FIG. 22 and in FIG. 1 for brain cancer, can also be detected by one or more systems disclosed herein, for characterizing a brain cancer. For example, a detection system can comprise one or more probes to detect one or more brain cancer specific biomarkers, such as GOPC-ROS1, or those listed in FIG. 22 and in FIG. 1 for brain cancer, of one or more exosomes of a biological sample.

Psoriasis

Psoriasis specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 23, and can be used to create a psoriasis specific exosome bio-signature. For example, the bio-signature can comprise one or more overexpressed miRs, such as, but not limited to, miR-146b, miR-20a, miR-146a, miR-31, miR-200a, miR-17-5p, miR-30e-5p, miR-141, miR-203, miR-142-3p, miR-21, or miR-106a, or any combination thereof. The bio-signature can also comprise one or more underexpressed miRs such a, but not limited to, miR-125b, miR-99b, miR-122a, miR-197, miR-100, miR-381, miR-518b, miR-524, let-7e, miR-30c, miR-365, miR-133b, miR-10a, miR-133a, miR-22, miR-326, or miR-215, or any combination thereof.

The one or more mRNAs that may be analyzed can include, but are not limited to, IL-20, VEGFR-1, VEGFR-2, VEGFR-3, or EGR1, or any combination thereof and can be used as specific biomarkers from exosomes for psoriasis. A biomarker mutation for psoriasis that can be assessed in an exosome includes, but is not limited to, a mutation of MGST2, or any combination of mutations specific for psoriasis.

Also provided herein is an isolated exosome comprising one or more psoriasis specific biomarkers, such as listed in FIG. 23 and in FIG. 1 for psoriasis. A composition comprising the isolated exosome is also provided. Accordingly, in some embodiments, the composition comprises a population of exosomes comprising one or more psoriasis specific biomarkers, such as listed in FIG. 23 and in FIG. 1 for psoriasis. The composition can comprise a substantially enriched population of exosomes, wherein the population of exosomes is substantially homogeneous for psoriasis specific exosomes or exosomes comprising one or more psoriasis specific biomarkers, such as listed in FIG. 23 and in FIG. 1 for psoriasis.

One or more psoriasis specific biomarkers, such as listed in FIG. 23 and in FIG. 1 for psoriasis, can also be detected by one or more systems disclosed herein, for characterizing psoriasis. For example, a detection system can comprise one or more probes to detect one or more psoriasis specific biomarkers, such as listed in FIG. 23 and in FIG. 1 for psoriasis, of one or more exosomes of a biological sample.

Cardiovascular Disease (CVD)

CVD specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 24, and can be used to create a CVD specific exosome bio-signature. For example, the bio-signature can comprise one or more overexpressed miRs, such as, but not limited to, miR-195, miR-208, miR-214, let-7b, let-7c, let-7e, miR-15b, miR-23a, miR-24, miR-27a, miR-27b, miR-93, miR-99b, miR-100, miR-103, miR-125b, miR-140, miR-145, miR-181a, miR-191, miR-195, miR-199a, miR-320, miR-342, miR-451, or miR-499, or any combination thereof.

The bio-signature can also comprise one or more underexpressed miRs such as, but not limited to, miR-1, miR-10a, miR-17-5p, miR-19a, miR-19b, miR-20a, miR-20b, miR-26b, miR-28, miR-30e-5p, miR-101, miR-106a, miR-126, miR-222, miR-374, miR-422b, or miR-423, or any combination thereof. The mRNAs that may be analyzed can include, but are not limited to, MRP14, CD69, or any combination thereof and can be used as specific biomarkers from exosomes for CVD.

A biomarker mutation for CVD that can be assessed in an exosome includes, but is not limited to, a mutation of MYH7, SCN5A, or CHRM2, or any combination of mutations specific for CVD.

The protein, ligand, or peptide that can be assessed in an exosome can include, but is not limited to, CK-MB, cTnI (cardiac troponin), CRP, BPN, IL-6, MCSF, CD40, CD40L, or any combination thereof. Furthermore, an exosome isolated or assayed can be a CVD cell specific, or derived from cardiac cells.

Also provided herein is an isolated exosome comprising one or more CVD specific biomarkers, such as listed in FIG. 24 and in FIG. 1 for CVD. A composition comprising the isolated exosome is also provided. Accordingly, in some embodiments, the composition comprises a population of exosomes comprising one or more CVD specific biomarkers, such as listed in FIG. 24 and in FIG. 1 for CVD. The composition can comprise a substantially enriched population of exosomes, wherein the population of exosomes is substantially homogeneous for CVD specific exosomes or exosomes comprising one or more CVD specific biomarkers, such as listed in FIG. 24 and in FIG. 1 for CVD.

One or more CVD specific biomarkers, such as listed in FIG. 24 and in FIG. 1 for CVD, can also be detected by one or more system's disclosed herein, for characterizing a CVD. For example, a detection system can comprise one or more probes to detect one or more CVD specific biomarkers, such as listed in FIG. 24 and in FIG. 1 for CVD, of one or more exosomes of a biological sample.

Blood Cancers

Hematological malignancies specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 25, and can be used to create a hematological malignancies specific exosome bio-signature. For example, the one or more mRNAs that may be analyzed can include, but are not limited to, HOX11, TAL1, LY1, LMO1, or LMO2, or any combination thereof and can be used as specific biomarkers from exosomes for hematological malignancies.

A biomarker mutation for a blood cancer that can be assessed in an exosome includes, but is not limited to, a mutation of c-kit, PDGFR, or ABL, or any combination of mutations specific for hematological malignancies.

Also provided herein is an isolated exosome comprising one or more blood cancer specific biomarkers, such as listed in FIG. 25 and in FIG. 1 for blood cancer. A composition comprising the isolated exosome is also provided. Accordingly, in some embodiments, the composition comprises a population of exosomes comprising one or more blood cancer specific biomarkers, such as listed in FIG. 25 and in FIG. 1 for blood cancer. The composition can comprise a substantially enriched population of exosomes, wherein the population of exosomes is substantially homogeneous for blood cancer specific exosomes or exosomes comprising one or more blood cancer specific biomarkers, such as listed in FIG. 25 and in FIG. 1 for blood cancer.

One or more blood cancer specific biomarkers, such as listed in FIG. 25 and in FIG. 1 for blood cancer, can also be detected by one or more systems disclosed herein, for characterizing a blood cancer. For example, a detection system can comprise one or more probes to detect one or more blood cancer specific biomarkers, such as listed in FIG. 25 and in FIG. 1 for blood cancer, of one or more exosomes of a biological sample.

The one or more blood cancer specific biomarkers can also be a gene fusion selected from the group consisting of: TTL-ETV6, CDK6-MLL, CDK6-TLX3, ETV6-FLT3, ETV6-RUNX1, ETV6-TTL, MLL-AFF1, MLL-AFF3, MLL-AFF4, MLL-GAS7, TCBA1-ETV6, TCF3-PBX1 or TCF3-TFPT, for acute lymphocytic leukemia (ALL); BCL11B-TLX3, IL2-TNFRFS17, NUP214-ABL1, NUP98-CCDC28A, TAL1-STIL, or ETV6-ABL2, for T-cell acute lymphocytic leukemia (T-ALL); ATIC-ALK, KIAA1618-ALK, MSN-ALK, MYH9-ALK, NPM1-ALK, TGF-ALK or TPM3-ALK, for anaplastic large cell lymphoma (ALCL); BCR-ABL1, BCR-JAK2, ETV6-EVI1, ETV6-MN1 or ETV6-TCBA1, for chronic myelogenous leukemia (CML); CBFB-MYH11, CHIC2-ETV6, ETV6-ABL1, ETV6-ABL2, ETV6-ARNT, ETV6-CDX2, ETV6-HLXB9, ETV6-PER1, MEF2D-DAZAP1, AML-AFF1, MLL-ARHGAP26, MLL-ARHGEF12, MLL-CASC5, MLL-CBL, MLL-CREBBP, MLL-DAB21P, MLL-ELL, MLL-EP300, MLL-EPS15, MLL-FNBP1, MLL-FOXO3A, MLL-GMPS, MLL-GPHN, MLL-MLLT1, MLL-MLLT11, MLL-MLLT3, MLL-MLLT6, MLL-MYO1F, MLL-PICALM, MLL-SEPT2, MLL-SEPT6, MLL-SORBS2, MYST3-SORBS2, MYST-CREBBP, NPM1-MLF1, NUP98-HOXA13, PRDM16-EVI1, RABEP1-PDGFRB, RUNX1-EVI1, RUNX1-MDS1, RUNX1-RPL22, RUNX1-RUNX1T1, RUNX1-SH3D19, RUNX1-USP42, RUNX1-YTHDF2, RUNX1-ZNF687, or TAF15-ZNF-384, for AML; CCND1-FSTL3, for chronic lymphocytic leukemia (CLL); and FLIP1-PDGFRA, FLT3-ETV6, KIAA1509-PDGFRA, PDE4DIP-PDGFRB, NIN-PDGFRB, TP53BP1-PDGFRB, or TPM3-PDGFRB, for hyper eosinophilia/chronic eosinophilia.

The one or more biomarkers for CLL can also include one or more of the following upregulated or overexpressed miRNAs, such as miR-23b, miR-24-1, miR-146, miR-155, miR-195, miR-221, miR-331, miR-29a, miR-195, miR-34a, or miR-29c; one or more of the following downregulated or underexpressed miRs, such as miR-15a, miR-16-1, miR-29 or miR-223, or any combination thereof.

The one or more biomarkers for ALL can also include one or more of the following upregulated or overexpressed miRNAs, such as miR-128b, miR-204, miR-218, miR-331, miR-181b-1, miR-17-92; or any combination thereof.

B-Cell Chronic Lymphocytic Leukemia (B-CLL)

B-CLL specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 26, and can be used to create a B-CLL specific exosome bio-signature. For example, the bio-signature can comprise one or more overexpressed miRs, such as, but not limited to, miR-183-prec, miR-190, miR-24-1-prec, miR-33, miR-19a, miR-140, miR-123, miR-10b, miR-15b-prec, miR-92-1, miR-188, miR-154, miR-217, miR-101, miR-141-prec, miR-153-prec, miR-196-2, miR-134, miR-141, miR-132, miR-192, or miR-181b-prec, or any combination thereof.

The bio-signature can also comprise one or more underexpressed miRs such as, but not limited to, miR-213, miR-220, or any combination thereof. The one or more mRNAs that may be analyzed can include, but are not limited to, ZAP70, AdipoR1, or any combination thereof and can be used as specific biomarkers from exosomes for B-CLL. A biomarker mutation for B-CLL that can be assessed in an exosome includes, but is not limited to, a mutation of IGHV, P53, ATM, or any combination of mutations specific for B-CLL.

Also provided herein is an isolated exosome comprising one or more B-CLL specific biomarkers, such as BCL3-MYC, MYC-BTG1, BCL7A-MYC, BRWD3-ARHGAP20 or BTG1-MYC, or those listed in FIG. 26. A composition comprising the isolated exosome is also provided. Accordingly, in some embodiments, the composition comprises a population of exosomes comprising one or more B-CLL specific biomarkers, such as BCL3-MYC, MYC-BTG1, BCL7A-MYC, BRWD3-ARHGAP20 or BTG1-MYC, or those listed in FIG. 26. The composition can comprise a substantially enriched population of exosomes, wherein the population of exosomes is substantially homogeneous for B-CLL specific exosomes or exosomes comprising one or more B-CLL specific biomarkers, such as BCL3-MYC, MYC-BTG1, BCL7A-MYC, BRWD3-ARHGAP20 or BTG1-MYC, or those listed in FIG. 26.

One or more B-CLL specific biomarkers, such as BCL3-MYC, MYC-BTG1, BCL7A-MYC, BRWD3-ARHGAP20 or BTG1-MYC, or those listed in FIG. 26, can also be detected by one or more systems disclosed herein, for characterizing a B-CLL. For example, a detection system can comprise one or more probes to detect one or more B-CLL specific biomarkers, such as BCL3-MYC, MYC-BTG1, BCL7A-MYC, BRWD3-ARHGAP20 or BTG1-MYC, or those listed in FIG. 26, of one or more exosomes of a biological sample.

B-Cell Lymphoma

B-cell lymphome specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 27, and can be used to create a B-cell lymphoma specific exosome bio-signature. For example, the bio-signature can comprise one or more overexpressed miRs, such as, but not limited to, miR-17-92 polycistron, miR-155, miR-210, or miR-21, miR-19a, miR-92, miR-142 miR-155, miR-221 miR-17-92, miR-21, miR-191, miR-205, or any combination thereof. Furthermore the snoRNA that can be used as an exosomal biomarker for B-cell lymphoma can include, but is not limited to, U50.

Also provided herein is an isolated exosome comprising one or more B-cell lymphoma specific biomarkers, such as listed in FIG. 27. A composition comprising the isolated exosome is also provided. Accordingly, in some embodiments, the composition comprises a population of exosomes comprising one or more B-cell lymphoma specific biomarkers, such as listed in FIG. 27. The composition can comprise a substantially enriched population of exosomes, wherein the population of exosomes is substantially homogeneous for B-cell lymphoma specific exosomes or exosomes comprising one or more B-cell lymphoma specific biomarkers, such as listed in FIG. 27.

One or more B-cell lymphoma specific biomarkers, such as listed in FIG. 27, can also be detected by one or more systems disclosed herein, for characterizing a B-cell lymphoma. For example, a detection system can comprise one or more probes to detect one or more B-cell lymphoma specific biomarkers, such as listed in FIG. 27, of one or more exosomes of a biological sample.

Diffuse Large B-Cell Lymphoma (DLBCL)

DLBCL specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 28, and can be used to create a DLBCL specific exosome bio-signature. For example, the bio-signature can comprise one or more overexpressed miRs, such as, but not limited to, miR-17-92, miR-155, miR-210, or miR-21, or any combination thereof. The one or more mRNAs that may be analyzed can include, but are not limited to, A-myb, LMO2, JNK3, CD10, bcl-6, Cyclin D2, IRF4, Flip, or CD44, or any combination thereof and can be used as specific biomarkers from exosomes for DLBCL.

Also provided herein is an isolated exosome comprising one or more DLBCL specific biomarkers, such as CITTA-BCL6, CLTC-ALK, IL21R-BCL6, PIM1-BCL6, TFCR-BCL6, IKZF1-BCL6 or SEC31A-ALK, or those listed in FIG. 28. A composition comprising the isolated exosome is also provided. Accordingly, in some embodiments, the composition comprises a population of exosomes comprising one or more DLBCL specific biomarkers, such as CITTA-BCL6, CLTC-ALK, IL21R-BCL6, PIM1-BCL6, TFCR-BCL6, IKZF1-BCL6 or SEC31A-ALK, or those listed in FIG. 28. The composition can comprise a substantially enriched population of exosomes, wherein the population of exosomes is substantially homogeneous for DLBCL specific exosomes or exosomes comprising one or more DLBCL specific biomarkers, such as CITTA-BCL6, CLTC-ALK, IL21R-BCL6, PIM1-BCL6, TFCR-BCL6, IKZF1-BCL6 or SEC31A-ALK, or those listed in FIG. 28.

One or more DLBCL specific biomarkers, such as CITTA-BCL6, CLTC-ALK, IL21R-BCL6, PIM1-BCL6, TFCR-BCL6, IKZF1-BCL6 or SEC31A-ALK, or those listed in FIG. 28, can also be detected by one or more systems disclosed herein, for characterizing a DLBCL. For example, a detection system can comprise one or more probes to detect one or more DLBCL specific biomarkers, such as CITTA-BCL6, CLTC-ALK, IL21R-BCL6, PIM1-BCL6, TFCR-BCL6, IKZF1-BCL6 or SEC31A-ALK, or those listed in FIG. 28, of one or more exosomes of a biological sample.

Burkitt's Lymphoma

Burkitt's lymphoma specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 29, and can be used to create a Burkitt's lymphoma specific exosome bio-signature. For example, the bio-signature can also comprise one or more underexpressed miRs such as, but not limited to, pri-miR-155, or any combination thereof. The one or more mRNAs that may be analyzed can include, but are not limited to, MYC, TERT, NS, NP, MAZ, RCF3, BYSL, IDE3, CDC7, TCL1A, AUTS2, MYBL1, BMP7, ITPR3, CDC2, BACK2, TTK, MME, ALOX5, or TOP1, or any combination thereof and can be used as specific biomarkers from exosomes for Burkitt's lymphoma. The protein, ligand, or peptide that can be assessed in an exosome can include, but is not limited to, BCL6, KI-67, or any combination thereof.

Also provided herein is an isolated exosome comprising one or more Burkitt's lymphoma specific biomarkers, such as IGH-MYC, LCP1-BCL6, or those listed in FIG. 29. A composition comprising the isolated exosome is also provided. Accordingly, in some embodiments, the composition comprises a population of exosomes comprising one or more Burkitt's lymphoma specific biomarkers, such as IGH-MYC, LCP1-BCL6, or those listed in FIG. 29. The composition can comprise a substantially enriched population of exosomes, wherein the population of exosomes is substantially homogeneous for Burkitt's lymphoma specific exosomes or exosomes comprising one or more Burkitt's lymphoma specific biomarkers, such as IGH-MYC, LCP1-BCL6, or those listed in FIG. 29.

One or more Burkitt's lymphoma specific biomarkers, such as IGH-MYC, LCP1-BCL6, or those listed in FIG. 29, can also be detected by one or more systems disclosed herein, for characterizing a Burkitt's lymphoma. For example, a detection system can comprise one or more probes to detect one or more Burkitt's lymphoma specific biomarkers, such as IGH-MYC, LCP1-BCL6, or those listed in FIG. 29, of one or more exosomes of a biological sample.

Hepatocellular Carcinoma

Hepatocellular carcinoma specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 30 and can be used to create a hepatocellular carcinoma specific exosome bio-signature. For example, the bio-signature can comprise one or more overexpressed miRs, such as, but not limited to, miR-221. The bio-signature can also comprise one or more underexpressed miRs such as, but not limited to, let-7a-1, let-7a-2, let-7a-3, let-7b, let-7c, let-7d, let-7e, let-7f-2, let-fg, miR-122a, miR-124a-2, miR-130a, miR-132, miR-136, miR-141, miR-142, miR-143, miR-145, miR-146, miR-150, miR-155(BIC), miR-181a-1, miR-181a-2, miR-181c, miR-195, miR-199a-1-5p, miR-199a-2-5p, miR-199b, miR-200b, miR-214, miR-223, or pre-miR-594, or any combination thereof. The one or more mRNAs that may be analyzed can include, but are not limited to, FAT10.

The one or more biomarkers of a bio-signature can also be used to characterize hepatitis C virus-associated hepatocellular carcinoma. The one or more biomarkers can be a miRNA, such as an overexpressed or underexpressed miRNA. For example, the upregulated or overexpressed miRNA can be miR-122, miR-100, or miR-10a and the downregulated miRNA can be miR-198 or miR-145.

Also provided herein is an isolated exosome comprising one or more hepatocellular carcinoma specific biomarkers, such as listed in FIG. 30 and in FIG. 1 for hepatocellular carcinoma. A composition comprising the isolated exosome is also provided. Accordingly, in some embodiments, the composition comprises a population of exosomes comprising one or more hepatocellular carcinoma specific biomarkers, such as listed in FIG. 30 and in FIG. 1 for hepatocellular carcinoma. The composition can comprise a substantially enriched population of exosomes, wherein the population of exosomes is substantially homogeneous for hepatocellular carcinoma specific exosomes or exosomes comprising one or more hepatocellular carcinoma specific biomarkers, such as listed in FIG. 30 and in FIG. 1 for hepatocellular carcinoma.

One or more hepatocellular carcinoma specific biomarkers, such as listed in FIG. 30 and in FIG. 1 for hepatocellular carcinoma, can also be detected by one or more systems disclosed herein, for characterizing a hepatocellular carcinoma. For example, a detection system can comprise one or more probes to detect one or more hepatocellular carcinoma specific biomarkers, such as listed in FIG. 30 and in FIG. 1 for hepatocellular carcinoma, of one or more exosomes of a biological sample.

Cervical Cancer

Cervical cancer specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 31, and can be used to create a cervical cancer specific exosome bio-signature. For example, the one or more mRNAs that may be analyzed can include, but are not limited to, HPV E6, HPV E7, or p53, or any combination thereof and can be used as specific biomarkers from exosomes for cervical cancer.

Also provided herein is an isolated exosome comprising one or more cervical cancer specific biomarkers, such as listed in FIG. 31 and in FIG. 1 for cervical cancer. A composition comprising the isolated exosome is also provided. Accordingly, in some embodiments, the composition comprises a population of exosomes comprising one or more cervical cancer specific biomarkers, such as listed in FIG. 31 and in FIG. 1 for cervical cancer. The composition can comprise a substantially enriched population of exosomes, wherein the population of exosomes is substantially homogeneous for cervical cancer specific exosomes or exosomes comprising one or more cervical cancer specific biomarkers, such as listed in FIG. 31 and in FIG. 1 for cervical cancer.

One or more cervical cancer specific biomarkers, such as listed in FIG. 31 and in FIG. 1 for cervical cancer, can also be detected by one or more systems disclosed herein, for characterizing a cervical cancer. For example, a detection system can comprise one or more probes to detect one or more cervical cancer specific biomarkers, such as listed in FIG. 31 and in FIG. 1 for cervical cancer, of one or more exosomes of a biological sample.

Endometrial Cancer

Endometrial cancer specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 32 and can be used to create a endometrial cancer specific exosome bio-signature. For example, the bio-signature can comprise one or more overexpressed miRs, such as, but not limited to, miR-185, miR-106a, miR-181a, miR-210, miR-423, miR-103, miR-107, or let-7c, or any combination thereof. The bio-signature can also comprise one or more underexpressed miRs such as, but not limited to, miR-71, miR-221, miR-193, miR-152, or miR-30c, or any combination thereof.

A biomarker mutation for endometrial cancer that can be assessed in an exosome includes, but is not limited to, a mutation of PTEN, K-RAS, B-catenin, p53, Her2/neu, or any combination of mutations specific for endometrial cancer. The protein, ligand, or peptide that can be assessed in an exosome can include, but is not limited to, NLRP7, AlphaV Beta6 integrin, or any combination thereof.

Also provided herein is an isolated exosome comprising one or more endometrial cancer specific biomarkers, such as listed in FIG. 32 and in FIG. 1 for endometrial cancer. A composition comprising the isolated exosome is also provided. Accordingly, in some embodiments, the composition comprises a population of exosomes comprising one or more endometrial cancer specific biomarkers, such as listed in FIG. 32 and in FIG. 1 for endometrial cancer. The composition can comprise a substantially enriched population of exosomes, wherein the population of exosomes is substantially homogeneous for endometrial cancer specific exosomes or exosomes comprising one or more endometrial cancer specific biomarkers, such as listed in FIG. 32 and in FIG. 1 for endometrial cancer.

One or more endometrial cancer specific biomarkers, such as listed in FIG. 32 and in FIG. 1 for endometrial cancer, can also be detected by one or more systems disclosed herein, for characterizing a endometrial cancer. For example, a detection system can comprise one or more probes to detect one or more endometrial cancer specific biomarkers, such as listed in FIG. 32 and in FIG. 1 for endometrial cancer, of one or more exosomes of a biological sample.

Head and Neck Cancer

Head and neck cancer specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 33, and can be used to create a head and neck cancer specific exosome bio-signature. For example, the bio-signature can comprise one or more overexpressed miRs, such as, but not limited to, miR-21, let-7, miR-18, miR-29c, miR-142-3p, miR-155, miR-146b, miR-205, or miR-21, or any combination thereof. The bio-signature can also comprise one or more underexpressed miRs such as, but not limited to, miR-494. The one or more mRNAs that may be analyzed include, but are not limited to, HPV E6, HPV E7, p53, IL-8, SAT, H3FA3, or EGFR, or any combination thereof and can be used as specific biomarkers from exosomes for head and neck cancer.

A biomarker mutation for head and neck cancer that can be assessed in an exosome includes, but is not limited to, a mutation of GSTM1, GSTT1, GSTP1, OGG1, XRCC1, XPD, RAD51, EGFR, p53, or any combination of mutations specific for head and neck cancer. The protein, ligand, or peptide that can be assessed in an exosome can include, but is not limited to, EGFR, EphB4, or EphB2, or any combination thereof.

Also provided herein is an isolated exosome comprising one or more head and neck cancer specific biomarkers, such as CHCHD7-PLAG1, CTNNB1-PLAG1, FHIT-HMGA2, HMGA2-NFIB, LIFR-PLAG1, or TCEA1-PLAG1, or those listed in FIG. 33 and in FIG. 1 for head and neck cancer. A composition comprising the isolated exosome is also provided. Accordingly, in some embodiments, the composition comprises a population of exosomes comprising one or more head and neck cancer specific biomarkers, such as CHCHD7-PLAG1, CTNNB1-PLAG1, FHIT-HMGA2, HMGA2-NFIB, LIFR-PLAG1, or TCEA1-PLAG1, or those listed in FIG. 33 and in FIG. 1 for head and neck cancer. The composition can comprise a substantially enriched population of exosomes, wherein the population of exosomes is substantially homogeneous for head and neck cancer specific exosomes or exosomes comprising one or more head and neck cancer specific biomarkers, such as CHCHD7-PLAG1, CTNNB1-PLAG1, FHIT-HMGA2, HMGA2-NFIB, LIFR-PLAG1, or TCEA1-PLAG1, or those listed in FIG. 33 and in FIG. 1 for head and neck cancer.

One or more head and neck cancer specific biomarkers, such as listed in FIG. 33 and in FIG. 1 for head and neck cancer, can also be detected by one or more systems disclosed herein, for characterizing a head and neck cancer. For example, a detection system can comprise one or more probes to detect one or more head and neck cancer specific biomarkers, such as CHCHD7-PLAG1, CTNNB1-PLAG1, FHIT-HMGA2, HMGA2-NFIB, LIFR-PLAG1, or TCEA1-PLAG1, or those listed in FIG. 33 and in FIG. 1 for head and neck cancer, of one or more exosomes of a biological sample.

Inflammatory Bowel Disease (IBD)

IBD specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 34, and can be used to create a IBD specific exosome bio-signature. The one or more mRNAs that may be analyzed can include, but are not limited to, Trypsinogen IV, SERT, or any combination thereof and can be used as specific biomarkers from exosomes for IBD.

A biomarker mutation for IBD that can be assessed in an exosome can include, but is not limited to, a mutation of CARD15 or any combination of mutations specific for IBD. The protein, ligand, or peptide that can be assessed in an exosome can include, but is not limited to, Il-16, Il-1beta, Il-12, TNF-alpha, interferon gamma, Il-6, Rantes, MCP-1, Resistin, or 5-HT, or any combination thereof.

Also provided herein is an isolated exosome comprising one or more IBD specific biomarkers, such as listed in FIG. 34 and in FIG. 1 for IBD. A composition comprising the isolated exosome is also provided. Accordingly, in some embodiments, the composition comprises a population of exosomes comprising one or more IBD specific biomarkers, such as listed in FIG. 34 and in FIG. 1 for IBD. The composition can comprise a substantially enriched population of exosomes, wherein the population of exosomes is substantially homogeneous for IBD specific exosomes or exosomes comprising one or more IBD specific biomarkers, such as listed in FIG. 34 and in FIG. 1 for IBD.

One or more IBD specific biomarkers, such as listed in FIG. 34 and in FIG. 1 for IBD, can also be detected by one or more systems disclosed herein, for characterizing a IBD. For example, a detection system can comprise one or more probes to detect one or more IBD specific biomarkers, such as listed in FIG. 34 and in FIG. 1 for IBD, of one or more exosomes of a biological sample.

Diabetes

Diabetes specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 35, and can be used to create a diabetes specific exosome bio-signature. For example, the one or more mRNAs that may be analyzed can include, but are not limited to, Il-8, CTSS, ITGB2, HLA-DRA, CD53, PLAG27, or MMP9, or any combination thereof and can be used as specific biomarkers from exosomes for diabetes. The protein, ligand, or peptide that can be assessed in an exosome can include, but is not limited to, RBP4.

Also provided herein is an isolated exosome comprising one or more diabetes specific biomarkers, such as listed in FIG. 35 and in FIG. 1 for diabetes. A composition comprising the isolated exosome is also provided. Accordingly, in some embodiments, the composition comprises a population of exosomes comprising one or more diabetes specific biomarkers, such as listed in FIG. 35 and in FIG. 1 for diabetes. The composition can comprise a substantially enriched population of exosomes, wherein the population of exosomes is substantially homogeneous for diabetes specific exosomes or exosomes comprising one or more diabetes specific biomarkers, such as listed in FIG. 35 and in FIG. 1 for diabetes.

One or more diabetes specific biomarkers, such as listed in FIG. 35 and in FIG. 1 for diabetes, can also be detected by one or more systems disclosed herein, for characterizing a diabetes. For example, a detection system can comprise one or more probes to detect one or more diabetes specific biomarkers, such as listed in FIG. 35 and in FIG. 1 for diabetes, of one or more exosomes of a biological sample.

Barrett's Esophagus

Barrett's Esophagus specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 36, and can be used to create a Barrett's Esophagus specific exosome bio-signature. For example, the bio-signature can comprise one or more overexpressed miRs, such as, but not limited to, miR-21, miR-143, miR-145, miR-194, or miR-215, or any combination thereof. The one or more mRNAs that may be analyzed include, but are not limited to, S100A2, S100A4, or any combination thereof and can be used as specific biomarkers from exosomes for Barrett's Esophagus.

A biomarker mutation for Barrett's Esophagus that can be assessed in an exosome includes, but is not limited to, a mutation of p53 or any combination of mutations specific for Barrett's Esophagus. The protein, ligand, or peptide that can be assessed in an exosome can include, but is not limited to, p53, MUC1, MUC2, or any combination thereof.

Also provided herein is an isolated exosome comprising one or more Barrett's Esophagus specific biomarkers, such as listed in FIG. 36 and in FIG. 1 for Barrett's Esophagus. A composition comprising the isolated exosome is also provided. Accordingly, in some embodiments, the composition comprises a population of exosomes comprising one or more Barrett's Esophagus specific biomarkers, such as listed in FIG. 36 and in FIG. 1 for Barrett's Esophagus. The composition can comprise a substantially enriched population of exosomes, wherein the population of exosomes is substantially homogeneous for Barrett's Esophagus specific exosomes or exosomes comprising one or more Barrett's Esophagus specific biomarkers, such as listed in FIG. 36 and in FIG. 1 for Barrett's Esophagus.

One or more Barrett's Esophagus specific biomarkers, such as listed in FIG. 36 and in FIG. 1 for Barrett's Esophagus, can also be detected by one or more systems disclosed herein, for characterizing a Barrett's Esophagus. For example, a detection system can comprise one or more probes to detect one or more Barrett's Esophagus specific biomarkers, such as listed in FIG. 36 and in FIG. 1 for Barrett's Esophagus, of one or more exosomes of a biological sample.

Fibromyalgia

Fibromyalgia specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 37, and can be used to create a fibromyalgia specific exosome bio-signature. The one or more mRNAs that may be analyzed can include, but are not limited to, NR2D which can be used as a specific biomarker from exosomes for fibromyalgia.

Also provided herein is an isolated exosome comprising one or more fibromyalgia specific biomarkers, such as listed in FIG. 37 and in FIG. 1 for fibromyalgia. A composition comprising the isolated exosome is also provided. Accordingly, in some embodiments, the composition comprises a population of exosomes comprising one or more fibromyalgia specific biomarkers, such as listed in FIG. 37 and in FIG. 1 for fibromyalgia. The composition can comprise a substantially enriched population of exosomes, wherein the population of exosomes is substantially homogeneous for fibromyalgia specific exosomes or exosomes comprising one or more fibromyalgia specific biomarkers, such as listed in FIG. 37 and in FIG. 1 for fibromyalgia.

One or more fibromyalgia specific biomarkers, such as listed in FIG. 37 and in FIG. 1 for fibromyalgia, can also be detected by one or more systems disclosed herein, for characterizing a fibromyalgia. For example, a detection system can comprise one or more probes to detect one or more fibromyalgia specific biomarkers, such as listed in FIG. 37 and in FIG. 1 for fibromyalgia, of one or more exosomes of a biological sample.

Stroke

Stroke specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 38, and can be used to create a stroke specific exosome bio-signature. For example, the one or more mRNAs that may be analyzed can include, but are not limited to, MMP9, S100-P, S100A12, SI00A9, coag factor V, ArginaseI, CA-IV, monocarboxylic acid transporter, ets-2, EIF2alpha, cytoskeleton associated protein 4, N-formylpeptide receptor, Ribonuclease2, N-acetylneuraminate pyruvate lyase, BCL-6, or Glycogen phosphorylase, or any combination thereof and can be used as specific biomarkers from exosomes for stroke.

Also provided herein is an isolated exosome comprising one or more stroke specific biomarkers, such as listed in FIG. 38 and in FIG. 1 for stroke. A composition comprising the isolated exosome is also provided. Accordingly, in some embodiments, the composition comprises a population of exosomes comprising one or more stroke specific biomarkers, such as listed in FIG. 38 and in FIG. 1 for stroke. The composition can comprise a substantially enriched population of exosomes, wherein the population of exosomes is substantially homogeneous for stroke specific exosomes or exosomes comprising one or more stroke specific biomarkers, such as listed in FIG. 38 and in FIG. 1 for stroke.

One or more stroke specific biomarkers, such as listed in FIG. 38 and in FIG. 1 for stroke, can also be detected by one or more systems disclosed herein, for characterizing a stroke. For example, a detection system can comprise one or more probes to detect one or more stroke specific biomarkers, such as listed in FIG. 38 and in FIG. 1 for stroke, of one or more exosomes of a biological sample.

Multiple Sclerosis (MS)

MS specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 39, and can be used to create a MS specific exosome bio-signature. For example, the one or more mRNAs that may be analyzed can include, but are not limited to, IL-6, IL-17, PAR-3, IL-17, T1/ST2, JunD, 5-LO, LTA4H, MBP, PLP, or alpha-beta crystallin, or any combination thereof and can be used as specific biomarkers from exosomes for MS.

Also provided herein is an isolated exosome comprising one or more MS specific biomarkers, such as listed in FIG. 39 and in FIG. 1 for MS. A composition comprising the isolated exosome is also provided. Accordingly, in some embodiments, the composition comprises a population of exosomes comprising one or more MS specific biomarkers, such as listed in FIG. 39 and in FIG. 1 for MS. The composition can comprise a substantially enriched population of exosomes, wherein the population of exosomes is substantially homogeneous for MS specific exosomes or exosomes comprising one or more MS specific biomarkers, such as listed in FIG. 39 and in FIG. 1 for MS.

One or more MS specific biomarkers, such as listed in FIG. 39 and in FIG. 1 for MS, can also be detected by one or more systems disclosed herein, for characterizing a MS. For example, a detection system can comprise one or more probes to detect one or more MS specific biomarkers, such as listed in FIG. 39 and in FIG. 1 for MS, of one or more exosomes of a biological sample.

Parkinson's Disease

Parkinson's disease specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 40, and can be used to create a Parkinson's disease specific exosome bio-signature. For example, the bio-signature can include, but is not limited to, one or more underexpressed miRs such as miR-133b. The one or more mRNAs that may be analyzed can include, but are not limited to Nurr1, BDNF, TrkB, gstm1, or 5100 beta, or any combination thereof and can be used as specific biomarkers from exosomes for Parkinson's disease.

A biomarker mutation for Parkinson's disease that can be assessed in an exosome includes, but is not limited to, a mutation of FGF20, alpha-synuclein, FGF20, NDUFV2, FGF2, CALB1, B2M, or any combination of mutations specific for Parkinson's disease. The protein, ligand, or peptide that can be assessed in an exosome can include, but is not limited to, apo-H, Ceruloplasmin, BDNF, IL-8, Beta2-microglobulin, apoAII, tau, ABeta1-42, DJ-1, or any combination thereof.

Also provided herein is an isolated exosome comprising one or more Parkinson's disease specific biomarkers, such as listed in FIG. 40 and in FIG. 1 for Parkinson's disease A composition comprising the isolated exosome is also provided. Accordingly, in some embodiments, the composition comprises a population of exosomes comprising one or more Parkinson's disease specific biomarkers, such as listed in FIG. 40 and in FIG. 1 for Parkinson's disease. The composition can comprise a substantially enriched population of exosomes, wherein the population of exosomes is substantially homogeneous for Parkinson's disease specific exosomes or exosomes comprising one or more Parkinson's disease specific biomarkers, such as listed in FIG. 40 and in FIG. 1 for Parkinson's disease.

One or more Parkinson's disease specific biomarkers, such as listed in FIG. 40 and in FIG. 1 for Parkinson's disease, can also be detected by one or more systems disclosed herein, for characterizing a Parkinson's disease. For example, a detection system can comprise one or more probes to detect one or more Parkinson's disease specific biomarkers, such as listed in FIG. 40 and in FIG. 1 for Parkinson's disease, of one or more exosomes of a biological sample.

Rheumatic Disease

Rheumatic disease specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 41, and can be used to create a rheumatic disease specific exosome bio-signature. For example, the bio-signature can also comprise one or more underexpressed miRs such as, but not limited to, miR-146a, miR-155, miR-132, miR-16, or miR-181, or any combination thereof. The one or more mRNAs that may be analyzed can include, but are not limited to, HOXD10, HOXD11, HOXD13, CCL8, LIM homeobox2, or CENP-E, or any combination thereof and can be used as specific biomarkers from exosomes for rheumatic disease. The protein, ligand, or peptide that can be assessed in an exosome can include, but is not limited to, TNFα.

Also provided herein is an isolated exosome comprising one or more rheumatic disease specific biomarkers, such as listed in FIG. 41 and in FIG. 1 for rheumatic disease. A composition comprising the isolated exosome is also provided. Accordingly, in some embodiments, the composition comprises a population of exosomes comprising one or more rheumatic disease specific biomarkers, such as listed in FIG. 41 and in FIG. 1 for rheumatic disease. The composition can comprise a substantially enriched population of exosomes, wherein the population of exosomes is substantially homogeneous for rheumatic disease specific exosomes or exosomes comprising one or more rheumatic disease specific biomarkers, such as listed in FIG. 41 and in FIG. 1 for rheumatic disease.

One or more rheumatic disease specific biomarkers, such as listed in FIG. 41 and in FIG. 1 for rheumatic disease, can also be detected by one or more systems disclosed herein, for characterizing a rheumatic disease. For example, a detection system can comprise one or more probes to detect one or more rheumatic disease specific biomarkers, such as listed in FIG. 41 and in FIG. 1 for rheumatic disease, of one or more exosomes of a biological sample.

Alzheimer's Disease

Alzheimer's disease specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 42, and can be used to create a Alzheimers disease specific exosome bio-signature. For example, the bio-signature can also comprise one or more underexpressed miRs such as miR-107, miR-29a, miR-29b-1, or miR-9, or any combination thereof. The bio-signature can also comprise one or more overexpressed miRs such as miR-128 or any combination thereof.

The one or more mRNAs that may be analyzed can include, but are not limited to, HIF-1α, BACE1, Reelin, CHRNA7, or 3Rtau/4Rtau, or any combination thereof and can be used as specific biomarkers from exosomes for Alzheimer's disease.

A biomarker mutation for Alzheimer's disease that can be assessed in an exosome includes, but is not limited to, a mutation of APP, presenilin1, presenilin2, APOE4, or any combination of mutations specific for Alzheimer's disease. The protein, ligand, or peptide that can be assessed in an exosome can include, but is not limited to, BACE1, Reelin, Cystatin C, Truncated Cystatin C, Amyloid Beta, C3a, t-Tau, Complement factor H, or alpha-2-macroglobulin, or any combination thereof.

Also provided herein is an isolated exosome comprising one or more Alzheimer's disease specific biomarkers, such as listed in FIG. 42 and in FIG. 1 for Alzheimer's disease. A composition comprising the isolated exosome is also provided. Accordingly, in some embodiments, the composition comprises a population of exosomes comprising one or more Alzheimer's disease specific biomarkers, such as listed in FIG. 42 and in FIG. 1 for Alzheimer's disease. The composition can comprise a substantially enriched population of exosomes, wherein the population of exosomes is substantially homogeneous for Alzheimer's disease specific exosomes or exosomes comprising one or more Alzheimer's disease specific biomarkers, such as listed in FIG. 42 and in FIG. 1 for Alzheimer's disease.

One or more Alzheimer's disease specific biomarkers, such as listed in FIG. 42 and in FIG. 1 for Alzheimer's disease, can also be detected by one or more systems disclosed herein, for characterizing a Alzheimer's disease. For example, a detection system can comprise one or more probes to detect one or more Alzheimer's disease specific biomarkers, such as listed in FIG. 42 and in FIG. 1 for Alzheimer's disease, of one or more exosomes of a biological sample.

Prion Disease

Prion specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 43, and can be used to create a prion specific exosome bio-signature. For example, the one or more mRNAs that may be analyzed can include, but are not limited to, Amyloid B4, App, IL-1R1, or SOD1, or any combination thereof and can be used as specific biomarkers from exosomes for a prion. The protein, ligand, or peptide that can be assessed in an exosome can include, but is not limited to, PrP(c), 14-3-3, NSE, S-100, Tau, AQP-4, or any combination thereof.

Also provided herein is an isolated exosome comprising one or more prion disease specific biomarkers, such as listed in FIG. 43 and in FIG. 1 for prion disease. A composition comprising the isolated exosome is also provided. Accordingly, in some embodiments, the composition comprises a population of exosomes comprising one or more prion disease specific biomarkers, such as listed in FIG. 43 and in FIG. 1 for prion disease. The composition can comprise a substantially enriched population of exosomes, wherein the population of exosomes is substantially homogeneous for prion disease specific exosomes or exosomes comprising one or more prion disease specific biomarkers, such as listed in FIG. 43 and in FIG. 1 for prion disease.

One or more prion disease specific biomarkers, such as listed in FIG. 43 and in FIG. 1 for prion disease, can also be detected by one or more systems disclosed herein, for characterizing a prion disease. For example, a detection system can comprise one or more probes to detect one or more prion disease specific biomarkers, such as listed in FIG. 43 and in FIG. 1 for prion disease, of one or more exosomes of a biological sample.

Sepsis

Sepsis specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 44, and can be used to create a sepsis specific exosome bio-signature. For example, the one or more mRNAs that may be analyzed can include, but are not limited to, 15-Hydroxy-PG dehydrogenase (up), LAIR1 (up), NFKB1A (up), TLR2, PGLYPR1, TLR4, MD2, TLR5, IFNAR2, IRAK2, IRAK3, IRAK4, PI3K, PI3KCB, MAP2K6, MAPK14, NFKB1A, NFKB1, IL1R1, MAP2K1IP1, MKNK1, FAS, CASP4, GADD45B, SOCS3, TNFSF10, TNFSF13B, OSM, HGF, or IL18R1, or any combination thereof and can be used as specific biomarkers from exosomes for sepsis.

Also provided herein is an isolated exosome comprising one or more sepsis specific biomarkers, such as listed in FIG. 44. A composition comprising the isolated exosome is also provided. Accordingly, in some embodiments, the composition comprises a population of exosomes comprising one or more sepsis specific biomarkers, such as listed in FIG. 44. The composition can comprise a substantially enriched population of exosomes, wherein the population of exosomes is substantially homogeneous for sepsis specific exosomes or exosomes comprising one or more sepsis specific biomarkers, such as listed in FIG. 44.

One or more sepsis specific biomarkers, such as listed in FIG. 44, can also be detected by one or more systems disclosed herein, for characterizing a sepsis. For example, a detection system can comprise one or more probes to detect one or more sepsis specific biomarkers, such as listed in FIG. 44, of one or more exosomes of a biological sample.

Chronic Neuropathic Pain

Chronic neuropathic pain (CNP) specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 45, and can be used to create a CNP specific exosome bio-signature. For example, the one or more mRNAs that may be analyzed can include, but are not limited to, ICAM-1 (rodent), CGRP (rodent), TIMP-1 (rodent), CLR-1 (rodent), HSP-27 (rodent), FABP (rodent), or apolipoprotein D (rodent), or any combination thereof and can be used as specific biomarkers from exosomes for CNP. The protein, ligand, or peptide that can be assessed in an exosome can include, but is not limited to, chemokines, chemokine receptors (CCR2/4), or any combination thereof.

Also provided herein is an isolated exosome comprising one or more chronic neuropathic pain specific biomarkers, such as listed in FIG. 45 and in FIG. 1 for chronic neuropathic pain. A composition comprising the isolated exosome is also provided. Accordingly, in some embodiments, the composition comprises a population of exosomes comprising one or more chronic neuropathic pain specific biomarkers, such as listed in FIG. 45 and in FIG. 1 for chronic neuropathic pain. The composition can comprise a substantially enriched population of exosomes, wherein the population of exosomes is substantially homogeneous for chronic neuropathic pain specific exosomes or exosomes comprising one or more chronic neuropathic pain specific biomarkers, such as listed in FIG. 45 and in FIG. 1 for chronic neuropathic pain.

One or more chronic neuropathic pain specific biomarkers, such as listed in FIG. 45 and in FIG. 1 for chronic neuropathic pain, can also be detected by one or more systems disclosed herein, for characterizing a chronic neuropathic pain. For example, a detection system can comprise one or more probes to detect one or more chronic neuropathic pain specific biomarkers, such as listed in FIG. 45 and in FIG. 1 for chronic neuropathic pain, of one or more exosomes of a biological sample.

Peripheral Neuropathic Pain

Peripheral neuropathic pain (PNP) specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 46, and can be used to create a PNP specific exosome bio-signature. For example, the protein, ligand, or peptide that can be assessed in an exosome can include, but is not limited to, OX42, ED9, or any combination thereof.

Also provided herein is an isolated exosome comprising one or more peripheral neuropathic pain specific biomarkers, such as listed in FIG. 46 and in FIG. 1 for peripheral neuropathic pain. A composition comprising the isolated exosome is also provided. Accordingly, in some embodiments, the composition comprises a population of exosomes comprising one or more peripheral neuropathic pain specific biomarkers, such as listed in FIG. 46 and in FIG. 1 for peripheral neuropathic pain. The composition can comprise a substantially enriched population of exosomes, wherein the population of exosomes is substantially homogeneous for peripheral neuropathic pain specific exosomes or exosomes comprising one or more peripheral neuropathic pain specific biomarkers, such as listed in FIG. 46 and in FIG. 1 for peripheral neuropathic pain.

One or more peripheral neuropathic pain specific biomarkers, such as listed in FIG. 46 and in FIG. 1 for peripheral neuropathic pain, can also be detected by one or more systems disclosed herein, for characterizing a peripheral neuropathic pain. For example, a detection system can comprise one or more probes to detect one or more peripheral neuropathic pain specific biomarkers, such as listed in FIG. 46 and in FIG. 1 for peripheral neuropathic pain, of one or more exosomes of a biological sample.

Schizophrenia

Schizophrenia specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 47, and can be used to create a schizophrenia specific exosome bio-signature. For example, the bio-signature can comprise one or more overexpressed miRs, such as, but not limited to, miR-181b. The bio-signature can also comprise one or more underexpressed miRs such as, but not limited to, miR-7, miR-24, miR-26b, miR-29b, miR-30b, miR-30e, miR-92, or miR-195, or any combination thereof.

The one or more mRNAs that may be analyzed can include, but are not limited to, IFITM3, SERPINA3, GLS, or ALDH7A1BASP1, or any combination thereof and can be used as specific biomarkers from exosomes for schizophrenia. A biomarker mutation for schizophrenia that can be assessed in an exosome includes, but is not limited to, a mutation of to DISC1, dysbindin, neuregulin-1, seratonin 2a receptor, NURR1, or any combination of mutations specific for schizophrenia.

The protein, ligand, or peptide that can be assessed in an exosome can include, but is not limited to, ATP5B, ATP5H, ATP6V1B, DNM1, NDUFV2, NSF, PDHB, or any combination thereof.

Also provided herein is an isolated exosome comprising one or more schizophrenia specific biomarkers, such as listed in FIG. 47 and in FIG. 1 for schizophrenia. A composition comprising the isolated exosome is also provided. Accordingly, in some embodiments, the composition comprises a population of exosomes comprising one or more schizophrenia specific biomarkers, such as listed in FIG. 47 and in FIG. 1 for schizophrenia. The composition can comprise a substantially enriched population of exosomes, wherein the population of exosomes is substantially homogeneous for schizophrenia specific exosomes or exosomes comprising one or more schizophrenia specific biomarkers, such as listed in FIG. 47 and in FIG. 1 for schizophrenia.

One or more schizophrenia specific biomarkers, such as listed in FIG. 47 and in FIG. 1 for schizophrenia, can also be detected by one or more systems disclosed herein, for characterizing a schizophrenia. For example, a detection system can comprise one or more probes to detect one or more schizophrenia specific biomarkers, such as listed in FIG. 47 and in FIG. 1 for schizophrenia, of one or more exosomes of a biological sample.

Bipolar Disease

Bipolar disease specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 48, and can be used to create a bipolar disease specific exosome bio-signature. For example, the one or more mRNAs that may be analyzed can include, but are not limited to, FGF2, ALDH7A1, AGXT2L1, AQP4, or PCNT2, or any combination thereof and can be used as specific biomarkers from exosomes for bipolar disease. A biomarker mutation for bipolar disease that can be assessed in an exosome includes, but is not limited to, a mutation of Dysbindin, DAOA/G30, DISC1, neuregulin-1, or any combination of mutations specific for bipolar disease.

Also provided herein is an isolated exosome comprising one or more bipolar disease specific biomarkers, such as listed in FIG. 48. A composition comprising the isolated exosome is also provided. Accordingly, in some embodiments, the composition comprises a population of exosomes comprising one or more bipolar disease specific biomarkers, such as listed in FIG. 48. The composition can comprise a substantially enriched population of exosomes, wherein the population of exosomes is substantially homogeneous for bipolar disease specific exosomes or exosomes comprising one or more bipolar disease specific biomarkers, such as listed in FIG. 48.

One or more bipolar disease specific biomarkers, such as listed in FIG. 48, can also be detected by one or more systems disclosed herein, for characterizing a bipolar disease. For example, a detection system can comprise one or more probes to detect one or more bipolar disease specific biomarkers, such as listed in FIG. 48, of one or more exosomes of a biological sample.

Depression

Depression specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 49, and can be used to create a depression specific exosome bio-signature. For example, the one or more mRNAs that may be analyzed can include, but are not limited to, FGFR1, FGFR2, FGFR3, or AQP4, or any combination thereof can also be used as specific biomarkers from exosomes for depression.

Also provided herein is an isolated exosome comprising one or more depression specific biomarkers, such as listed in FIG. 49. A composition comprising the isolated exosome is also provided. Accordingly, in some embodiments, the composition comprises a population of exosomes comprising one or more depression specific biomarkers, such as listed in FIG. 49. The composition can comprise a substantially enriched population of exosomes, wherein the population of exosomes is substantially homogeneous for depression specific exosomes or exosomes comprising one or more depression specific biomarkers, such as listed in FIG. 49.

One or more depression specific biomarkers, such as listed in FIG. 49, can also be detected by one or more systems disclosed herein, for characterizing a depression. For example, a detection system can comprise one or more probes to detect one or more depression specific biomarkers, such as listed in FIG. 49, of one or more exosomes of a biological sample.

Gastrointestinal Stromal Tumor (GIST)

GIST specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 50, and can be used to create a GIST specific exosome bio-signature. For example, the one or more mRNAs that may be analyzed can include, but are not limited to, DOG-1, PKC-theta, KIT, GPR20, PRKCQ, KCNK3, KCNH2, SCG2, TNFRSF6B, or CD34, or any combination thereof and can be used as specific biomarkers from exosomes for GIST.

A biomarker mutation for GIST that can be assessed in an exosome includes, but is not limited to, a mutation of PKC-theta or any combination of mutations specific for GIST. The protein, ligand, or peptide that can be assessed in an exosome can include, but is not limited to, PDGFRA, c-kit, or any combination thereof.

Also provided herein is an isolated exosome comprising one or more GIST specific biomarkers, such as listed in FIG. 50 and in FIG. 1 for GIST. A composition comprising the isolated exosome is also provided. Accordingly, in some embodiments, the composition comprises a population of exosomes comprising one or more GIST specific biomarkers, such as listed in FIG. 50 and in FIG. 1 for GIST. The composition can comprise a substantially enriched population of exosomes, wherein the population of exosomes is substantially homogeneous for GIST specific exosomes or exosomes comprising one or more GIST specific biomarkers, such as listed in FIG. 50 and in FIG. 1 for GIST.

One or more GIST specific biomarkers, such as listed in FIG. 50 and in FIG. 1 for GIST, can also be detected by one or more systems disclosed herein, for characterizing a GIST. For example, a detection system can comprise one or more probes to detect one or more GIST specific biomarkers, such as listed in FIG. 50 and in FIG. 1 for GIST, of one or more exosomes of a biological sample.

Renal Cell Carcinoma

Renal cell carcinoma specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 51, and can be used to create a renal cell carcinoma specific exosome bio-signature. For example, the bio-signature can also comprise one or more underexpressed miRs such as, but not limited to, miR-141, miR-200c, or any combination thereof. The one or more upregulated or overexpressed miRNA can be miR-28, miR-185, miR-27, miR-let-7f-2, or any combination thereof.

The one or more mRNAs that may be analyzed can include, but are not limited to, laminin receptor 1, betaig-h3, Galectin-1, a-2 Macroglobulin, Adipophilin, Angiopoietin 2, Caldesmon 1, Class II MHC-associated invariant chain (CD74), Collagen IV-al, Complement component, Complement component 3, Cytochrome P450, subfamily IIJ polypeptide 2, Delta sleep-inducing peptide, Fc g receptor 111a (CD16), HLA-B, HLA-DRa, HLA-DRb, HLA-SB, IFN-induced transmembrane protein 3, IFN-induced transmembrane protein 1, or Lysyl Oxidase, or any combination thereof and can be used as specific biomarkers from exosomes for renal cell carcinoma.

A biomarker mutation for renal cell carcinoma that can be assessed in an exosome includes, but is not limited to, a mutation of VHL or any combination of mutations specific renal cell carcinoma.

The protein, ligand, or peptide that can be assessed in an exosome can include, but is not limited to, IF1 alpha, VEGF, PDGFRA, or any combination thereof.

Also provided herein is an isolated exosome comprising one or more RCC specific biomarkers, such as ALPHA-TFEB, NONO-TFE3, PRCC-TFE3, SFPQ-TFE3, CLTC-TFE3, or MALAT1-TFEB, or those listed in FIG. 51 and in FIG. 1 for RCC. A composition comprising the isolated exosome is also provided. Accordingly, in some embodiments, the composition comprises a population of exosomes comprising one or more RCC specific biomarkers, such as ALPHA-TFEB, NONO-TFE3, PRCC-TFE3, SFPQ-TFE3, CLTC-TFE3, or MALAT1-TFE, or those listed in FIG. 51 and in FIG. 1 for RCC. The composition can comprise a substantially enriched population of exosomes, wherein the population of exosomes is substantially homogeneous for RCC specific exosomes or exosomes comprising one or more RCC specific biomarkers, such as ALPHA-TFEB, NONO-TFE3, PRCC-TFE3, SFPQ-TFE3, CLTC-TFE3, or MALAT1-TFE, or those listed in FIG. 51 and in FIG. 1 for RCC.

One or more RCC specific biomarkers, such as ALPHA-TFEB, NONO-TFE3, PRCC-TFE3, SFPQ-TFE3, CLTC-TFE3, or MALAT1-TFE, or those listed in FIG. 51 and in FIG. 1 for RCC, can also be detected by one or more systems disclosed herein, for characterizing a RCC. For example, a detection system can comprise one or more probes to detect one or more RCC specific biomarkers, such as ALPHA-TFEB, NONO-TFE3, PRCC-TFE3, SFPQ-TFE3, CLTC-TFE3, or MALAT1-TFE, or those listed in FIG. 51 and in FIG. 1 for RCC, of one or more exosomes of a biological sample.

Cirrhosis

Cirrhosis specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 52, and can be used to create a cirrhosis specific exosome bio-signature. The one or more mRNAs that may be analyzed include, but are not limited to, NLT, which can be used as a specific biomarker from exosomes for cirrhosis.

The protein, ligand, or peptide that can be assessed in an exosome can include, but is not limited to, NLT, HBsAG, AST, YKL-40, Hyaluronic acid, TIMP-1, alpha 2 macroglobulin, a-1-antitrypsin PlZ allele, haptoglobin, or acid phosphatase ACP AC, or any combination thereof.

Also provided herein is an isolated exosome comprising one or more cirrhosis specific biomarkers, such as those listed in FIG. 52 and in FIG. 1 for cirrhosis. A composition comprising the isolated exosome is also provided. Accordingly, in some embodiments, the composition comprises a population of exosomes comprising one or more cirrhosis specific biomarkers, such as those listed in FIG. 52 and in FIG. 1 for cirrhosis. The composition can comprise a substantially enriched population of exosomes, wherein the population of exosomes is substantially homogeneous for cirrhosis specific exosomes or exosomes comprising one or more cirrhosis specific biomarkers, such as those listed in FIG. 52 and in FIG. 1 for cirrhosis.

One or more cirrhosis specific biomarkers, such as those listed in FIG. 52 and in FIG. 1 for cirrhosis, can also be detected by one or more systems disclosed herein, for characterizing cirrhosis. For example, a detection system can comprise one or more probes to detect one or more cirrhosis specific biomarkers, such as those listed in FIG. 52 and in FIG. 1 for cirrhosis, of one or more exosomes of a biological sample.

Esophageal Cancer

Esophageal cancer specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 53, and can be used to create a esophageal cancer specific exosome bio-signature. For example, the bio-signature can comprise one or more overexpressed miRs, such as, but not limited to, miR-192, miR-194, miR-21, miR-200c, miR-93, miR-342, miR-152, miR-93, miR-25, miR-424, or miR-151, or any combination thereof. The bio-signature can also comprise one or more underexpressed miRs such as, but not limited to, miR-27b, miR-205, miR-203, miR-342, let-7c, miR-125b, miR-100, miR-152, miR-192, miR-194, miR-27b, miR-205, miR-203, miR-200c, miR-99a, miR-29c, miR-140, miR-103, or miR-107, or any combination thereof. The one or more mRNAs that may be analyzed include, but are not limited to, MTHFR and can be used as specific biomarkers from exosomes for esophageal cancer.

Also provided herein is an isolated exosome comprising one or more esophageal cancer specific biomarkers, such as listed in FIG. 53 and in FIG. 1 for esophageal cancer. A composition comprising the isolated exosome is also provided. Accordingly, in some embodiments, the composition comprises a population of exosomes comprising one or more esophageal cancer specific biomarkers, such as listed in FIG. 53 and in FIG. 1 for esophageal cancer. The composition can comprise a substantially enriched population of exosomes, wherein the population of exosomes is substantially homogeneous for esophageal cancer specific exosomes or exosomes comprising one or more esophageal cancer specific biomarkers, such as listed in FIG. 53 and in FIG. 1 for esophageal cancer.

One or more esophageal cancer specific biomarkers, such as listed in FIG. 53 and in FIG. 1 for esophageal cancer, can also be detected by one or more systems disclosed herein, for characterizing a esophageal cancer. For example, a detection system can comprise one or more probes to detect one or more esophageal cancer specific biomarkers, such as listed in FIG. 53 and in FIG. 1 for esophageal cancer, of one or more exosomes of a biological sample.

Gastric Cancer

Gastric cancer specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 54, and can be used to create a gastric cancer specific exosome bio-signature. For example, the bio-signature can comprise one or more overexpressed miRs, such as, but not limited to, miR-106a, miR-21, miR-191, miR-223, miR-24-1, miR-24-2, miR-107, miR-92-2, miR-214, miR-25, or miR-221, or any combination thereof. The bio-signature can also comprise one or more underexpressed miRs such as, but not limited to, let-7a.

The one or more mRNAs that may be analyzed include, but are not limited to, RRM2, EphA4, or survivin, or any combination thereof and can be used as specific biomarkers from exosomes for gastric cancer. A biomarker mutation for gastric cancer that can be assessed in an exosome includes, but is not limited to, a mutation of APC or any combination of mutations specific for gastric cancer. The protein, ligand, or peptide that can be assessed in an exosome can include, but is not limited to EphA4.

Also provided herein is an isolated exosome comprising one or more gastric cancer specific biomarkers, such as listed in FIG. 54. A composition comprising the isolated exosome is also provided. Accordingly, in some embodiments, the composition comprises a population of exosomes comprising one or more gastric cancer specific biomarkers, such as listed in FIG. 54. The composition can comprise a substantially enriched population of exosomes, wherein the population of exosomes is substantially homogeneous for gastric cancer specific exosomes or exosomes comprising one or more gastric cancer specific biomarkers, such as listed in FIG. 54.

One or more gastric cancer specific biomarkers, such as listed in FIG. 54, can also be detected by one or more systems disclosed herein, for characterizing a gastric cancer. For example, a detection system can comprise one or more probes to detect one or more gastric cancer specific biomarkers, such as listed in FIG. 54, of one or more exosomes of a biological sample.

Autism

Autism specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 55, and can be used to create an autism specific exosome bio-signature. For example, the bio-signature can comprise one or more overexpressed miRs, such as, but not limited to, miR-484, miR-21, miR-212, miR-23a, miR-598, miR-95, miR-129, miR-431, miR-7, miR-15a, miR-27a, miR-15b, miR-148b, miR-132, or miR-128, or any combination thereof. The bio-signature can also comprise one or more underexpressed miRs such as, but not limited to, miR-93, miR-106a, miR-539, miR-652, miR-550, miR-432, miR-193b, miR-181d, miR-146b, miR-140, miR-381, miR-320a, or miR-106b, or any combination thereof. The protein, ligand, or peptide that can be assessed in an exosome can include, but is not limited to, GM1, GD1a, GD1b, or GT1b, or any combination thereof.

Also provided herein is an isolated exosome comprising one or more autism specific biomarkers, such as listed in FIG. 55 and in FIG. 1 for autism. A composition comprising the isolated exosome is also provided. Accordingly, in some embodiments, the composition comprises a population of exosomes comprising one or more autism specific biomarkers, such as listed in FIG. 55 and in FIG. 1 for autism. The composition can comprise a substantially enriched population of exosomes, wherein the population of exosomes is substantially homogeneous for autism specific exosomes or exosomes comprising one or more autism specific biomarkers, such as listed in FIG. 55 and in FIG. 1 for autism.

One or more autism specific biomarkers, such as listed in FIG. 55 and in FIG. 1 for autism, can also be detected by one or more systems disclosed herein, for characterizing a autism. For example, a detection system can comprise one or more probes to detect one or more autism specific biomarkers, such as listed in FIG. 55 and in FIG. 1 for autism, of one or more exosomes of a biological sample.

Organ Rejection

Organ rejection specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 56, and can be used to create an organ rejection specific exosome bio-signature. For example, the bio-signature can comprise one or more overexpressed miRs, such as, but not limited to, miR-658, miR-125a, miR-320, miR-381, miR-628, miR-602, miR-629, or miR-125a, or any combination thereof. The bio-signature can also comprise one or more underexpressed miRs such as, but not limited to, miR-324-3p, miR-611, miR-654, miR-330_MM1, miR-524, miR-17-3p_MM1, miR-483, miR-663, miR-516-5p, miR-326, miR-197_MM2, or miR-346, or any combination thereof. The protein, ligand, or peptide that can be assessed in an exosome can include, but is not limited to, matix metalloprotein-9, proteinase 3, or HNP, or any combinations thereof. The biomarker can be a member of the matrix metalloproteinases.

Also provided herein is an isolated exosome comprising one or more organ rejection specific biomarkers, such as listed in FIG. 56. A composition comprising the isolated exosome is also provided. Accordingly, in some embodiments, the composition comprises a population of exosomes comprising one or more organ rejection specific biomarkers, such as listed in FIG. 56. The composition can comprise a substantially enriched population of exosomes, wherein the population of exosomes is substantially homogeneous for organ rejection specific exosomes or exosomes comprising one or more organ rejection specific biomarkers, such as listed in FIG. 56.

One or more organ rejection specific biomarkers, such as listed in FIG. 56, can also be detected by one or more systems disclosed herein, for characterizing a organ rejection. For example, a detection system can comprise one or more probes to detect one or more organ rejection specific biomarkers, such as listed in FIG. 56, of one or more exosomes of a biological sample.

Methicillin-Resistant *Staphylococcus aureus*

Methicillin-resistant *Staphylococcus aureus* specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 57, and can be used to create a methicillin-resistant *Staphylococcus aureus* specific exosome bio-signature.

The one or more mRNAs that may be analyzed include, but are not limited to, TSST-1 which can be used as a specific biomarker from exosomes for methicillin-resistant *Staphylococcus aureus*. A biomarker mutation for methicillin-resistant *Staphylococcus aureus* that can be assessed in an exosome includes, but is not limited to, a mutation of mecA, Protein A SNPs, or any combination of mutations specific for methicillin-resistant *Staphylococcus aureus*. The protein, ligand, or peptide that can be assessed in an exosome can include, but is not limited to, ETA, ETB, TSST-1, or leukocidins, or any combination thereof.

Also provided herein is an isolated exosome comprising one or more methicillin-resistant *Staphylococcus aureus* specific biomarkers, such as listed in FIG. 57. A composition comprising the isolated exosome is also provided. Accordingly, in some embodiments, the composition comprises a population of exosomes comprising one or more methicillin-resistant *Staphylococcus aureus* specific biomarkers, such as listed in FIG. 57. The composition can comprise a substantially enriched population of exosomes, wherein the population of exosomes is substantially homogeneous for methicillin-resistant *Staphylococcus aureus* specific exosomes or exosomes comprising one or more methicillin-resistant *Staphylococcus aureus* specific biomarkers, such as listed in FIG. 57.

One or more methicillin-resistant *Staphylococcus aureus* specific biomarkers, such as listed in FIG. 57, can also be detected by one or more systems disclosed herein, for characterizing a methicillin-resistant *Staphylococcus aureus*. For example, a detection system can comprise one or more probes to detect one or more methicillin-resistant *Staphylococcus aureus* specific biomarkers, such as listed in FIG. 57, of one or more exosomes of a biological sample.

Vulnerable Plaque

Vulnerable plaque specific biomarkers from exosomes can include one or more (for example, 2, 3, 4, 5, 6, 7, 8, or more) overexpressed miRs, underexpressed miRs, mRNAs, genetic mutations, proteins, ligands, peptides, snoRNA, or any combination thereof, such as listed in FIG. 58, and can be used to create a vulnerable plaque specific exosome bio-signature. The protein, ligand, or peptide that can be assessed in an exosome can include, but is not limited to, IL-6, MMP-9, PAPP-A, D-dimer, fibrinogen, Lp-PLA2, SCD40L, Il-18, oxLDL, GPx-1, MCP-1, P1GF, or CRP, or any combination thereof.

Also provided herein is an isolated exosome comprising one or more vulnerable plaque specific biomarkers, such as listed in FIG. 58 and in FIG. 1 for vulnerable plaque. A composition comprising the isolated exosome is also provided. Accordingly, in some embodiments, the composition comprises a population of exosomes comprising one or more vulnerable plaque specific biomarkers, such as listed in FIG. 58 and in FIG. 1 for vulnerable plaque. The composition can comprise a substantially enriched population of exosomes, wherein the population of exosomes is substantially homogeneous for vulnerable plaque specific exosomes or exosomes comprising one or more vulnerable plaque specific biomarkers, such as listed in FIG. 58 and in FIG. 1 for vulnerable plaque.

One or more vulnerable plaque specific biomarkers, such as listed in FIG. 58 and in FIG. 1 for vulnerable plaque, can also be detected by one or more systems disclosed herein, for characterizing a vulnerable plaque. For example, a detection system can comprise one or more probes to detect one or more vulnerable plaque specific biomarkers, such as listed in FIG. 58 and in FIG. 1 for vulnerable plaque, of one or more exosomes of a biological sample.

Autoimmune Disease

Also provided herein is an isolated exosome comprising one or more autoimmune disease specific biomarkers, such as listed in FIG. 1 for autoimmune disease. A composition comprising the isolated exosome is also provided. Accordingly, in some embodiments, the composition comprises a population of exosomes comprising one or more autoimmune disease specific biomarkers, such as listed in FIG. 1 for autoimmune disease. The composition can comprise a substantially enriched population of exosomes, wherein the population of exosomes is substantially homogeneous for autoimmune disease specific exosomes or exosomes comprising one or more autoimmune disease specific biomarkers, such as listed in FIG. 1 for autoimmune disease.

One or more autoimmune disease specific biomarkers, such as listed in FIG. 1 for autoimmune disease, can also be detected by one or more systems disclosed herein, for characterizing a autoimmune disease. For example, a detection system can comprise one or more probes to detect one or more autoimmune disease specific biomarkers, such as listed in FIG. 1 for autoimmune disease, of one or more exosomes of a biological sample.

Tuberculosis (TB)

Also provided herein is an isolated exosome comprising one or more TB disease specific biomarkers, such as listed in FIG. 1 for TB disease. A composition comprising the isolated exosome is also provided. Accordingly, in some embodiments, the composition comprises a population of exosomes comprising one or more TB disease specific biomarkers, such as listed in FIG. 1 for TB disease. The composition can comprise a substantially enriched population of exosomes, wherein the population of exosomes is substantially homogeneous for TB disease specific exosomes or exosomes comprising one or more TB disease specific biomarkers, such as listed in FIG. 1 for TB disease.

One or more TB disease specific biomarkers, such as listed in FIG. 1 for TB disease, can also be detected by one or more systems disclosed herein, for characterizing a TB disease. For example, a detection system can comprise one or more probes to detect one or more TB disease specific biomarkers, such as listed in FIG. 1 for TB disease, of one or more exosomes of a biological sample.

HIV

Also provided herein is an isolated exosome comprising one or more HIV disease specific biomarkers, such as listed in FIG. 1 for HIV disease. A composition comprising the isolated exosome is also provided. Accordingly, in some embodiments, the composition comprises a population of exosomes comprising one or more HIV disease specific biomarkers, such as listed in FIG. 1 for HIV disease. The composition can comprise a substantially enriched population of exosomes, wherein the population of exosomes is substantially homogeneous for HIV disease specific exosomes or exosomes comprising one or more HIV disease specific biomarkers, such as listed in FIG. 1 for HIV disease.

One or more HIV disease specific biomarkers, such as listed in FIG. 1 for HIV disease, can also be detected by one or more systems disclosed herein, for characterizing a HIV disease. For example, a detection system can comprise one or more probes to detect one or more HIV disease specific biomarkers, such as listed in FIG. 1 for HIV disease, of one or more exosomes of a biological sample.

The one or more biomarker can also be a miRNA, such as an upregulated or overexpressed miRNA. The upregulated miRNA can be miR-29a, miR-29b, miR-149, miR-378 or miR-324-5p. One or more biomarkers can also be used to characterize HIV-1 latency, such as by assessing one or more miRNAs. The miRNA can be miR-28, miR-125b, miR-150, miR-223 and miR-382, and upregulated.

Asthma

Also provided herein is an isolated exosome comprising one or more asthma disease specific biomarkers, such as listed in FIG. 1 for asthma disease. A composition comprising the isolated exosome is also provided. Accordingly, in some embodiments, the composition comprises a population of exosomes comprising one or more asthma disease specific biomarkers, such as listed in FIG. 1 for asthma disease. The composition can comprise a substantially enriched population of exosomes, wherein the population of exosomes is substantially homogeneous for asthma disease specific exosomes or exosomes comprising one or more asthma disease specific biomarkers, such as listed in FIG. 1 for asthma disease.

One or more asthma disease specific biomarkers, such as listed in FIG. 1 for asthma disease, can also be detected by one or more systems disclosed herein, for characterizing a asthma disease. For example, a detection system can comprise one or more probes to detect one or more asthma disease specific biomarkers, such as listed in FIG. 1 for asthma disease, of one or more exosomes of a biological sample.

Lupus

Also provided herein is an isolated exosome comprising one or more lupus disease specific biomarkers, such as listed in FIG. 1 for lupus disease. A composition comprising the isolated exosome is also provided. Accordingly, in some embodiments, the composition comprises a population of exosomes comprising one or more lupus disease specific biomarkers, such as listed in FIG. 1 for lupus disease. The composition can comprise a substantially enriched population of exosomes, wherein the population of exosomes is substantially homogeneous for lupus disease specific exosomes or exosomes comprising one or more lupus disease specific biomarkers, such as listed in FIG. 1 for lupus disease.

One or more lupus disease specific biomarkers, such as listed in FIG. 1 for lupus disease, can also be detected by one or more systems disclosed herein, for characterizing a lupus disease. For example, a detection system can comprise one or more probes to detect one or more lupus disease specific biomarkers, such as listed in FIG. 1 for lupus disease, of one or more exosomes of a biological sample.

Influenza

Also provided herein is an isolated exosome comprising one or more influenza disease specific biomarkers, such as listed in FIG. 1 for influenza disease. A composition comprising the isolated exosome is also provided. Accordingly, in some embodiments, the composition comprises a population of exosomes comprising one or more influenza disease specific biomarkers, such as listed in FIG. 1 for influenza disease. The composition can comprise a substantially enriched population of exosomes, wherein the population of exosomes is substantially homogeneous for influenza disease specific exosomes or exosomes comprising one or more influenza disease specific biomarkers, such as listed in FIG. 1 for influenza disease.

One or more influenza disease specific biomarkers, such as listed in FIG. 1 for influenza disease, can also be detected by one or more systems disclosed herein, for characterizing a influenza disease. For example, a detection system can comprise one or more probes to detect one or more influenza disease specific biomarkers, such as listed in FIG. 1 for influenza disease, of one or more exosomes of a biological sample.

Thyroid Cancer

Also provided herein is an isolated exosome comprising one or more thyroid cancer specific biomarkers, such as AKAP-BRAF, CCDC6-RET, ERC1-RETM, GOLGA5-RET, HOOK3-RET, HRH4-RET, KTN1-RET, NCOA4-RET, PCM1-RET, PRKARA1A-RET, RFG-RET, RFG9-RET, Ria-RET, TGF-NTRK1, TPM3-NTRK1, TPM3-TPR, TPR-MET, TPR-NTRK1, TRIM24-RET, TRIM27-RET or TRIM33-RET, characteristic of papillary thyroid carcinoma; or PAX8-PPARy, characteristic of follicular thyroid cancer. A composition comprising the isolated exosome is also provided. Accordingly, in some embodiments, the composition comprises a population of exosomes comprising one or more thyroid cancer specific biomarkers, such as listed in FIG. 1 for thyroid cancer. The composition can comprise a substantially enriched population of exosomes, wherein the population of exosomes is substantially homogeneous for thyroid cancer specific exosomes or exosomes comprising one or more thyroid cancer specific biomarkers, such as listed in FIG. 1 for thyroid cancer.

One or more thyroid cancer specific biomarkers, such as listed in FIG. 1 for thyroid cancer, can also be detected by one or more systems disclosed herein, for characterizing a thyroid cancer. For example, a detection system can comprise one or more probes to detect one or more thyroid cancer specific biomarkers, such as listed in FIG. 1 for thyroid cancer, of one or more exosomes of a biological sample.

Gene Fusions

The one or more biomarkers assessed of an exosome can be a gene fusion, such as one or more listed in FIG. 59. A fusion gene is a hybrid gene created by the juxtaposition of two previously separate genes. This can occur by chromosomal translocation or inversion, deletion or via trans-splicing. The resulting fusion gene can cause abnormal temporal and spatial expression of genes, such as leading to abnormal expression of cell growth factors, angiogenesis factors, tumor promoters or other factors contributing to the neoplastic transformation of the cell and the creation of a tumor. Such fusion genes can be oncogenic due to the juxtaposition of: 1) a strong promoter region of one gene next to the coding region of a cell growth factor, tumor promoter or other gene promoting oncogenesis leading to elevated gene expression, or 2) due to the fusion of coding regions of two different genes, giving rise to a chimeric gene and thus a chimeric protein with abnormal activity.

An example of a fusion gene is BCR-ABL, a characteristic molecular aberration in ~90% of chronic myelogenous leukemia (CML) and in a subset of acute leukemias (Kurzrock et al., *Annals of Internal Medicine* 2003; 138(10): 819-830). The BCR-ABL results from a translocation between chromosomes 9 and 22. The translocation brings together the 5' region of the BCR gene and the 3' region of ABL1, generating a chimeric BCR-ABL1 gene, which encodes a protein with constitutively active tyrosine kinase activity (Mittleman et al., Nature *Reviews Cancer* 2007; 7(4):233-245). The aberrant tyrosine kinase activity leads to de-regulated cell signaling, cell growth and cell survival, apoptosis resistance and growth factor independence, all of which contribute to the pathophysiology of leukemia (Kurzrock et al., *Annals of Internal Medicine* 2003; 138(10):819-830).

Another fusion gene is IGH-MYC, a defining feature of ~80% of Burkitt's lymphoma (Ferry et al. *Oncologist* 2006; 11(4):375-83). The causal event for this is a translocation between chromosomes 8 and 14, bringing the c-Myc oncogene adjacent to the strong promoter of the immunoglobin heavy chain gene, causing c-myc overexpression (Mittleman et al., *Nature Reviews Cancer* 2007; 7(4):233-245). The c-myc rearrangement is a pivotal event in lymphomagenesis as it results in a perpetually proliferative state. It has wide ranging effects on progression through the cell cycle, cellular differentiation, apoptosis, and cell adhesion (Ferry et al. *Oncologist* 2006; 11(4):375-83).

A number of recurrent fusion genes have been catalogued in the Mittleman database (http://cgap.nci.nih.gov/Chromosomes/Mitelman) and can be assess in an exosome and used to characterize a phenotype. The gene fusion can be used to characterize a hematological malignancy or epithelial tumor. For example, TMPRSS2-ERG, TMPRSS2-ETV and SLC45A3-ELK4 fusions can be detected and used to characterize prostate cancer; and ETV6-NTRK3 and ODZ4-NRG1 for breast cancer.

Furthermore, assessing the presence or absence, or expression level of a fusion gene can be used to diagnosis a phenotype such as a cancer as well as a monitoring a therapeutic response to selecting a treatment. For example, the presence of the BCR-ABL fusion gene is a characteristic not only for the diagnosis of CML, but is also the target of the Novartis drug Imatinib mesylate (Gleevec), a receptor tyrosine kinase inhibitor, for the treatment of CML. Imatinib treatment has led to molecular responses (disappearance of BCR-ABL+ blood cells) and improved progression-free survival in BCR-ABL+CML patients (Kantarjian et al., *Clinical Cancer Research* 2007; 13(4):1089-1097).

Assessing an exosome for the presence, absence, or expression level of a gene fusion can be of a heterogeneous population of exosomes. Alternatively, the exosome can be derived from a specific cell type, such as cell-or-origin specific exosomes, as described above.

Breast Cancer

To characterize a breast cancer, an exosome can be assessed for one or more breast cancer specific fusions, including, but not limited to, ETV6-NTRK3. The exosome can be derived from breast cancer cells.

Lung Cancer

To characterize a lung cancer, an exosome can be assessed for one or more lung cancer specific fusions, including, but not limited to, RLF-MYCL1, TGF-ALK, or CD74-ROS1. The exosome can be derived from lung cancer cells.

Prostate Cancer

To characterize a prostate cancer, an exosome can be assessed for one or more prostate cancer specific fusions, including, but not limited to, ACSL3-ETV1, C15ORF21-ETV1, FLJ35294-ETV1, HERV-ETV1, TMPRSS2-ERG, TMPRSS2-ETV1/4/5, TMPRSS2-ETV4/5, SLC5A3-ERG, SLC5A3-ETV1, SLC5A3-ETV5 or KLK2-ETV4. The exosome can be derived from prostate cancer cells.

Brain Cancer

To characterize a brain cancer, an exosome can be assessed for one or more brain cancer specific fusions, including, but not limited to, GOPC-ROS1. The exosome can be derived from brain cancer cells.

Head and Neck Cancer

To characterize ahead and neck cancer, an exosome can be assessed for one or more head and neck cancer specific fusions, including, but not limited to, CHCHD7-PLAG1, CTNNB1-PLAG1, FHIT-HMGA2, HMGA2-NFIB, LIFR-PLAG1, or TCEA1-PLAG1. The exosome can be derived from head and neck cancer cells.

Renal Cell Carcinoma (RCC)

To characterize a RCC, an exosome can be assessed for one or more RCC specific fusions, including, but not limited to, ALPHA-TFEB, NONO-TFE3, PRCC-TFE3, SFPQ-TFE3, CLTC-TFE3, or MALAT1-TFEB. The exosome can be derived from RCC cells.

Thyroid Cancer

To characterize a thyroid cancer, an exosome can be assessed for one or more thyroid cancer specific fusions, including, but not limited to, AKAP9-BRAF, CCDC6-RET, ERC1-RETM, GOLGA5-RET, HOOK3-RET, HRH4-RET, KTN1-RET, NCOA4-RET, PCM1-RET, PRKARA1A-RET, RFG-RET, RFG9-RET, Ria-RET, TGF-NTRK1, TPM3-NTRK1, TPM3-TPR, TPR-MET, TPR-NTRK1, TRIM24-RET, TRIM27-RET or TRIM33-RET, characteristic of papillary thyroid carcinoma; or PAX8-PPARy, characteristic of follicular thyroid cancer. The exosome can be derived from thyroid cancer cells.

Blood Cancers

To characterize a blood cancer, an exosome can be assessed for one or more blood cancer specific fusions, including, but not limited to, TTL-ETV6, CDK6-MLL, CDK6-TLX3, ETV6-FLT3, ETV6-RUNX1, ETV6-TTL, MLL-AFF1, MLL-AFF3, MLL-AFF4, MLL-GAS7, TCBA1-ETV6, TCF3-PBX1 or TCF3-TFPT, characteristic of acute lymphocytic leukemia (ALL); BCL11B-TLX3, IL2-TNFRFS17, NUP214-ABL1, NUP98-CCDC28A, TALI-STIL, or ETV6-ABL2, characteristic of T-cell acute lymphocytic leukemia (T-ALL); ATIC-ALK, KIAA1618-ALK, MSN-ALK, MYH9-ALK, NPM1-ALK, TGF-ALK or TPM3-ALK, characteristic of anaplastic large cell lymphoma (ALCL); BCR-ABL1, BCR-JAK2, ETV6-EVI1, ETV6-MN1 or ETV6-TCBA1, characteristic of chronic myelogenous leukemia (CML); CBFB-MYH11, CHIC2-ETV6, ETV6-ABL1, ETV6-ABL2, ETV6-ARNT, ETV6-CDX2, ETV6-HLXB9, ETV6-PER1, MEF2D-DAZAP1, AML-AFF1, MLL-ARHGAP26, MLL-ARHGEF12, MLL-CASC5, MLL-CBL, MLL-CREBBP, MLL-DAB21P, MLL-ELL, MLL-EP300, MLL-EPS15, MLL-FNBP1, MLL-FOXO3A, MLL-GMPS, MLL-GPHN, MLL-MLLT1, MLL-MLLT11, MLL-MLLT3, MLL-MLLT6, MLL-MYO1F, MLL-PICALM, MLL-SEPT2, MLL-SEPT6, MLL-SORBS2, MYST3-SORBS2, MYST-CREBBP, NPM1-MLF1, NUP98-HOXA13, PRDM16-EVI1, RABEP1-PDGFRB, RUNX1-EVI1, RUNX1-MDS1, RUNX1-RPL22, RUNX1-RUNX1T1, RUNX1-SH3D19, RUNX1-USP42, RUNX1-YTHDF2, RUNX1-ZNF687, or TAF15-ZNF-384, characteristic of AML; CCND1-FSTL3, characteristic of chronic lymphocytic leukemia (CLL); BCL3-MYC, MYC-BTG1, BCL7A-MYC, BRWD3-ARHGAP20 or BTG1-MYC, characteristic of B-cell chronic lymphocytic leukemia (B-CLL); CITTA-BCL6, CLTC-ALK, IL21R-BCL6, PIM1-BCL6, TFCR-BCL6, IKZF1-BCL6 or SEC31A-ALK, characteristic of diffuse large B-cell lymphomas (DLBCL); FLIP1-PDGFRA, FLT3-ETV6, KIAA1509-PDGFRA, PDE4DIP-PDGFRB, NIN-PDGFRB, TP53BP1-PDGFRB, or TPM3-PDGFRB, characteristic of hyper eosinophilia/chronic eosinophilia; IGH-MYC or LCP1-BCL6, characteristic of Burkitt's lymphoma. The exosome can be derived from blood cancer cells.

Also provided herein is an isolated exosome comprising one or more gene fusions as disclosed herein, such as listed in FIG. 59. A composition comprising the isolated exosome is also provided. Accordingly, in some embodiments, the composition comprises a population of exosomes comprising one or more gene fusions, such as listed in FIG. 59. The composition can comprise a substantially enriched population of exosomes, wherein the population of exosomes is substantially homogeneous for exosomes comprising one or more gene fusions, such as listed in FIG. 59.

Also provided herein is a detection system for detecting one or more gene fusions, such as gene fusions listed in FIG. 59. For example, a detection system can comprise one or more probes to detect one or more gene fusions listed in FIG. 59. Detection of the one or more gene fusions can be used to characterize a cancer.

Gene-Associated mRNA Biomarkers

The one or more biomarkers assessed can also include one or more genes selected from the group consisting of PFKFB3, RHAMM (HMMR), cDNA FLJ42103, ASPM, CENPF, NCAPG, Androgen Receptor, EGFR, HSP90, SPARC, DNMT3B, GART, MGMT, SSTR3, and TOP2B. The microRNA that interacts with the one or more genes can also be a biomarker (see for example, FIG. 60). Furthermore, the one or more biomarkers can be used to characterize prostate cancer.

Also provided herein is an isolated exosome comprising one or more one or more biomarkers consisting of PFKFB3, RHAMM (HMMR), cDNA FLJ42103, ASPM, CENPF, NCAPG, Androgen Receptor, EGFR, HSP90, SPARC, DNMT3B, GART, MGMT, SSTR3, and TOP2B; or the microRNA that interacts with the one or more genes (see for example, FIG. 60). Also provided is a composition comprising the isolated exosome. Accordingly, in some embodiments, the composition comprises a population of exosomes comprising one or more biomarkers consisting of PFKFB3, RHAMM (HMMR), cDNA FLJ42103, ASPM, CENPF, NCAPG, Androgen Receptor, EGFR, HSP90, SPARC, DNMT3B, GART, MGMT, SSTR3, and TOP2B; or the microRNA that interacts with the one or more genes, such as listed in FIG. 60. The composition can comprise a substantially enriched population of exosomes, wherein the population of exosomes is substantially homogeneous for exosomes comprising one or more biomarkers consisting of PFKFB3, RHAMM (HMMR), cDNA FLJ42103, ASPM, CENPF, NCAPG, Androgen Receptor, EGFR, HSP90, SPARC, DNMT3B, GART, MGMT, SSTR3, and TOP2B; or the microRNA that interacts with the one or more genes, such as listed in FIG. 60.

One or more prostate cancer specific biomarkers, such as listed in FIG. 60 can also be detected by one or more systems disclosed herein. For example, a detection system can comprise one or more probes to detect one or more prostate cancer specific biomarkers, such as listed in FIG. 60, of one or more exosomes of a biological sample.

The miRNA that interacts with PFKFB3 can be miR-513a-3p, miR-128, miR-488, miR-539, miR-658, miR-524-5p, miR-1258, miR-150, miR-216b, miR-377, miR-135a, miR-26a, miR-548a-5p, miR-26b, miR-520d-5p, miR-224, miR-1297, miR-1197, miR-182, miR-452, miR-509-3-5p, miR-548m, miR-625, miR-509-5p, miR-1266, miR-135b, miR-190b, miR-496, miR-616, miR-621, miR-650, miR-105, miR-19a, miR-346, miR-620, miR-637, miR-651, miR- 1283, miR-590-3p, miR-942, miR-1185, miR-577, miR-602, miR-1305, miR-220c, miR-1270, miR-1282, miR-432, miR-491-5p, miR-548n, miR-765, miR-768-3p or miR-924, and can be used as a biomarker.

Also provided herein is an isolated exosome comprising one or more one or more miRNA that interacts with PFKFB3. Also provided is a composition comprising the isolated exosome. Accordingly, in some embodiments, the composition comprises a population of exosomes comprising one or more biomarkers consisting of miRNA that interacts with PFKFB3. The composition can comprise a substantially enriched population of exosomes, wherein the population of exosomes is substantially homogeneous for exosomes comprising one or more miRNA that interacts with PFKFB3. Furthermore, the one or more miRNA that interacts with PFKFB3 can also be detected by one or more systems disclosed herein. For example, a detection system can comprise one or more probes to detect one or more one or more miRNA that interacts with PFKFB3 of one or more exosomes of a biological sample.

The miRNA that interacts with RHAMM can be miR-936, miR-656, miR-105, miR-361-5p, miR-194, miR-374a, miR-590-3p, miR-186, miR-769-5p, miR-892a, miR-380, miR-875-3p, miR-208a, miR-208b, miR-586, miR-125a-3p, miR-630, miR-374b, miR-411, miR-629, miR-1286, miR-1185, miR-16, miR-200b, miR-671-5p, miR-95, miR-421, miR-496, miR-633, miR-1243, miR-127-5p, miR-143, miR-15b, miR-200c, miR-24 or miR-34c-3p.

Also provided herein is an isolated exosome comprising one or more one or more miRNA that interacts with RHAMM. Also provided is a composition comprising the isolated exosome. Accordingly, in some embodiments, the composition comprises a population of exosomes comprising one or more biomarkers consisting of miRNA that interacts with RHAMM. The composition can comprise a substantially enriched population of exosomes, wherein the population of exosomes is substantially homogeneous for exosomes comprising one or more miRNA that interacts with RHAMM. Furthermore, the one or more miRNA that interacts with RHAMM can also be detected by one or more systems disclosed herein. For example, a detection system can comprise one or more probes to detect one or more one or more miRNA that interacts with RHAMM of one or more exosomes of a biological sample.

The miRNA that interacts with CENPF can be miR-30c, miR-30b, miR-190, miR-508-3p, miR-384, miR-512-5p, miR-548p, miR-297, miR-520f, miR-376a, miR-1184, miR-577, miR-708, miR-205, miR-376b, miR-520g, miR-520h, miR-519d, miR-596, miR-768-3p, miR-340, miR-620, miR-539, miR-567, miR-671-5p, miR-1183, miR-129-3p, miR-636, miR-106a, miR-1301, miR-17, miR-20a, miR-570, miR-656, miR-1263, miR-1324, miR-142-5p, miR-28-5p, miR-302b, miR-452, miR-520d-3p, miR-548o, miR-892b, miR-302d, miR-875-3p, miR-106b, miR-1266, miR-1323, miR-20b, miR-221, miR-520e, miR-664, miR-920, miR-922, miR-93, miR-1228, miR-1271, miR-30e, miR-483-3p, miR-509-3-5p, miR-515-3p, miR-519e, miR-520b, miR-520c-3p or miR-582-3p.

Also provided herein is an isolated exosome comprising one or more one or more miRNA that interacts with CENPF. Also provided is a composition comprising the isolated exosome. Accordingly, in some embodiments, the composition comprises a population of exosomes comprising one or more biomarkers consisting of miRNA that interacts with CENPF. The composition can comprise a substantially enriched population of exosomes, wherein the population of exosomes is substantially homogeneous for exosomes comprising one or more miRNA that interacts with CENPF. Furthermore, the one or more miRNA that interacts with CENPF can also be detected by one or more systems disclosed herein. For example, a detection system can comprise one or more probes to detect one or more one or more miRNA that interacts with CENPF of one or more exosomes of a biological sample.

The miRNA that interacts with NCAPG can be miR-876-5p, miR-1260, miR-1246, miR-548c-3p, miR-1224-3p, miR-619, miR-605, miR-490-5p, miR-186, miR-448, miR-129-5p, miR-188-3p, miR-516b, miR-342-3p, miR-1270, miR-548k, miR-654-3p, miR-1290, miR-656, miR-34b, miR-520g, miR-1231, miR-1289, miR-1229, miR-23a, miR-23b, miR-616 or miR-620.

Also provided herein is an isolated exosome comprising one or more one or more miRNA that interacts with NCAPG. Also provided is a composition comprising the isolated exosome. Accordingly, in some embodiments, the composition comprises a population of exosomes comprising one or more biomarkers consisting of miRNA that interacts with NCAPG. The composition can comprise a substantially enriched population of exosomes, wherein the population of exosomes is substantially homogeneous for exosomes comprising one or more miRNA that interacts with NCAPG. Furthermore, the one or more miRNA that interacts with NCAPG can also be detected by one or more systems disclosed herein. For example, a detection system can comprise one or more probes to detect one or more one or more miRNA that interacts with NCAPG of one or more exosomes of a biological sample.

The miRNA that interacts with Androgen Receptor can be miR-124a, miR-130a, miR-130b, miR-143, miR-149, miR-194, miR-29b, miR-29c, miR-301, miR-30a-5p, miR-30d, miR-30e-5p, miR-337, miR-342, miR-368, miR-488, miR-493-5p, miR-506, miR-512-5p, miR-644, miR-768-5p or miR-801.

The miRNA that interacts with EGFR can be miR-105, miR-128a, miR-128b, miR-140, miR-141, miR-146a, miR-146b, miR-27a, miR-27b, miR-302a, miR-302d, miR-370, miR-548c, miR-574, miR-587 or miR-7.

Also provided herein is an isolated exosome comprising one or more one or more miRNA that interacts with AR. Also provided is a composition comprising the isolated exosome. Accordingly, in some embodiments, the composition comprises a population of exosomes comprising one or more biomarkers consisting of miRNA that interacts with AR. The composition can comprise a substantially enriched population of exosomes, wherein the population of exosomes is substantially homogeneous for exosomes comprising one or more miRNA that interacts with AR. Furthermore, the one or more miRNA that interacts with AR can also be detected by one or more systems disclosed herein. For example, a detection system can comprise one or more probes to detect one or more one or more miRNA that interacts with AR of one or more exosomes of a biological sample.

The miRNA that interacts with HSP90 can be miR-1, miR-513a-3p, miR-548d-3p, miR-642, miR-206, miR-450b-3p, miR-152, miR-148a, miR-148b, miR-188-3p, miR-23a, miR-23b, miR-578, miR-653, miR-1206, miR-192, miR-215, miR-181b, miR-181d, miR-223, miR-613, miR-769-3p, miR-99a, miR-100, miR-454, miR-548n, miR-640, miR-99b, miR-150, miR-181a, miR-181c, miR-522, miR-624, miR-130a, miR-130b, miR-146, miR-148a, miR-148b, miR-152, miR-181a, miR-181b, miR-181c, miR-204, miR-206, miR-211, miR-212, miR-215, miR-223, miR-23a, miR-23b, miR-301, miR-31, miR-325, miR-363, miR-566, miR-9 or miR-99b.

Also provided herein is an isolated exosome comprising one or more one or more miRNA that interacts with HSP90.

Also provided is a composition comprising the isolated exosome. Accordingly, in some embodiments, the composition comprises a population of exosomes comprising one or more biomarkers consisting of miRNA that interacts with HSP90. The composition can comprise a substantially enriched population of exosomes, wherein the population of exosomes is substantially homogeneous for exosomes comprising one or more miRNA that interacts with HSP90. Furthermore, the one or more miRNA that interacts with HSP90 can also be detected by one or more systems disclosed herein. For example, a detection system can comprise one or more probes to detect one or more one or more miRNA that interacts with HSP90 of one or more exosomes of a biological sample.

The miRNA that interacts with SPARC can be miR-768-5p, miR-203, miR-196a, miR-569, miR-187, miR-641, miR-1275, miR-432, miR-622, miR-296-3p, miR-646, miR-196b, miR-499-5p, miR-590-5p, miR-495, miR-625, miR-1244, miR-512-5p, miR-1206, miR-1303, miR-186, miR-302d, miR-494, miR-562, miR-573, miR-10a, miR-203, miR-204, miR-211, miR-29, miR-29b, miR-29c, miR-339, miR-433, miR-452, miR-515-5p, miR-517a, miR-517b, miR-517c, miR-592 or miR-96.

Also provided herein is an isolated exosome comprising one or more one or more miRNA that interacts with SPARC. Also provided is a composition comprising the isolated exosome. Accordingly, in some embodiments, the composition comprises a population of exosomes comprising one or more biomarkers consisting of miRNA that interacts with SPARC. The composition can comprise a substantially enriched population of exosomes, wherein the population of exosomes is substantially homogeneous for exosomes comprising one or more miRNA that interacts with SPARC. Furthermore, the one or more miRNA that interacts with SPARC can also be detected by one or more systems disclosed herein. For example, a detection system can comprise one or more probes to detect one or more one or more miRNA that interacts with SPARC of one or more exosomes of a biological sample.

The miRNA that interacts with DNMT3B can be miR-618, miR-1253, miR-765, miR-561, miR-330-5p, miR-326, miR-188, miR-203, miR-221, miR-222, miR-26a, miR-26b, miR-29a, miR-29b, miR-29c, miR-370, miR-379, miR-429, miR-519e, miR-598, miR-618 or miR-635.

Also provided herein is an isolated exosome comprising one or more one or more miRNA that interacts with DNMT3B. Also provided is a composition comprising the isolated exosome. Accordingly, in some embodiments, the composition comprises a population of exosomes comprising one or more biomarkers consisting of miRNA that interacts with DNMT3B. The composition can comprise a substantially enriched population of exosomes, wherein the population of exosomes is substantially homogeneous for exosomes comprising one or more miRNA that interacts with DNMT3B. Furthermore, the one or more miRNA that interacts with DNMT3B can also be detected by one or more systems disclosed herein. For example, a detection system can comprise one or more probes to detect one or more one or more miRNA that interacts with DNMT3B of one or more exosomes of a biological sample.

The miRNA that interacts with GART can be miR-101, miR-141, miR-144, miR-182, miR-189, miR-199a, miR-199b, miR-200a, miR-200b, miR-202, miR-203, miR-223, miR-329, miR-383, miR-429, miR-433, miR-485-5p, miR-493-5p, miR-499, miR-519a, miR-519b, miR-519c, miR-569, miR-591, miR-607, miR-627, miR-635, miR-636 or miR-659.

Also provided herein is an isolated exosome comprising one or more one or more miRNA that interacts with GART. Also provided is a composition comprising the isolated exosome. Accordingly, in some embodiments, the composition comprises a population of exosomes comprising one or more biomarkers consisting of miRNA that interacts with GART. The composition can comprise a substantially enriched population of exosomes, wherein the population of exosomes is substantially homogeneous for exosomes comprising one or more miRNA that interacts with GART. Furthermore, the one or more miRNA that interacts with GART can also be detected by one or more systems disclosed herein. For example, a detection system can comprise one or more probes to detect one or more one or more miRNA that interacts with GART of one or more exosomes of a biological sample.

The miRNA that interacts with MGMT can be miR-122a, miR-142-3p, miR-17-3p, miR-181a, miR-181b, miR-181c, miR-181d, miR-199b, miR-200a, miR-217, miR-302b, miR-32, miR-324-3p, miR-34a, miR-371, miR-425-5p, miR-496, miR-514, miR-515-3p, miR-516-3p, miR-574, miR-597, miR-603, miR-653, miR-655, miR-92, miR-92b or miR-99a.

Also provided herein is an isolated exosome comprising one or more one or more miRNA that interacts with MGMT. Also provided is a composition comprising the isolated exosome. Accordingly, in some embodiments, the composition comprises a population of exosomes comprising one or more biomarkers consisting of miRNA that interacts with MGMT. The composition can comprise a substantially enriched population of exosomes, wherein the population of exosomes is substantially homogeneous for exosomes comprising one or more miRNA that interacts with MGMT. Furthermore, the one or more miRNA that interacts with MGMT can also be detected by one or more systems disclosed herein. For example, a detection system can comprise one or more probes to detect one or more one or more miRNA that interacts with MGMT of one or more exosomes of a biological sample.

The miRNA that interacts with SSTR3 can be miR-125a, miR-125b, miR-133a, miR-133b, miR-136, miR-150, miR-21, miR-380-5p, miR-504, miR-550, miR-671, miR-766 or miR-767-3p.

Also provided herein is an isolated exosome comprising one or more one or more miRNA that interacts with SSTR3. Also provided is a composition comprising the isolated exosome. Accordingly, in some embodiments, the composition comprises a population of exosomes comprising one or more biomarkers consisting of miRNA that interacts with SSTR3. The composition can comprise a substantially enriched population of exosomes, wherein the population of exosomes is substantially homogeneous for exosomes comprising one or more miRNA that interacts with SSTR3. Furthermore, the one or more miRNA that interacts with SSTR3 can also be detected by one or more systems disclosed herein. For example, a detection system can comprise one or more probes to detect one or more one or more miRNA that interacts with SSTR3 of one or more exosomes of a biological sample.

The miRNA that interacts with TOP2B can be miR-548f, miR-548a-3p, miR-548g, miR-513a-3p, miR-548c-3p, miR-101, miR-653, miR-548d-3p, miR-575, miR-297, miR-576-3p, miR-548b-3p, miR-624, miR-548n, miR-758, miR-1253, miR-1324, miR-23b, miR-320a, miR-320b, miR-1183, miR-1244, miR-23a, miR-451, miR-568, miR-1276, miR-548e, miR-590-3p, miR-1, miR-101, miR-126, miR-129, miR-136, miR-140, miR-141, miR-144, miR-147, miR-149, miR-18, miR-181b, miR-181c, miR-182, miR-184, miR-186, miR-189, miR-191, miR-19a, miR-19b, miR-200a, miR-206, miR-210, miR-218, miR-223, miR-23a, miR-23b, miR-24, miR-27a, miR-302, miR-30a, miR-31, miR-320, miR-323, miR-362, miR-374, miR-383, miR-409-3p, miR-451, miR-489, miR-493-3p, miR-514, miR-542-3p, miR-544, miR- 548a, miR-548b, miR-548c, miR-548d, miR-559, miR-568, miR-575, miR-579, miR-585, miR-591, miR-598, miR-613, miR-649, miR-651, miR-758, miR-768-3p or miR-9.

Also provided herein is an isolated exosome comprising one or more one or more miRNA that interacts with TOP2B. Also provided is a composition comprising the isolated exosome. Accordingly, in some embodiments, the composition comprises a population of exosomes comprising one or more biomarkers consisting of miRNA that interacts with TOP2B. The composition can comprise a substantially enriched population of exosomes, wherein the population of exosomes is substantially homogeneous for exosomes comprising one or more miRNA that interacts with TOP2B. Furthermore, the one or more miRNA that interacts with TOP2B can also be detected by one or more systems disclosed herein. For example, a detection system can comprise one or more probes to detect one or more one or more miRNA that interacts with TOP2B of one or more exosomes of a biological sample.

Bio-Signatures: Biomarker Detection

Bio-signatures can be detected qualitatively or quantitatively. Exosome levels may be characterized as described above. Analysis of exosomes can comprise detecting the level of exosomes in combination with determining the biomarkers of the exosomes. Determining the level or amount of exosome can be performed in conjunction with determining the biomarkers of the exosome. Alternatively, determining the amount of exosome may be performed prior to or subsequent to determining the biomarkers of the exosomes. Methods for analyzing biomarkers of tissues or cells can be used to analyze the biomarkers associated with or contained in exosomes.

For example, biomarkers can be detected by microarray analysis, PCR (including PCR-based methods such as RT-PCR, qPCR and the like), hybridization with allele-specific probes, enzymatic mutation detection, ligation chain reaction (LCR), oligonucleotide ligation assay (OLA), flow-cytometric heteroduplex analysis, chemical cleavage of mismatches, mass spectrometry, nucleic acid sequencing, single strand conformation polymorphism (SSCP), denaturing gradient gel electrophoresis (DGGE), temperature gradient gel electrophoresis (TGGE), restriction fragment polymorphisms, serial analysis of gene expression (SAGE), or any combinations thereof. The biomarker, such as a nucleic acid, can be amplified prior to detection. Biomarkers can also be detected by immunoblot, immunoprecipitation, ELISA, RIA, flow cytometry, or electron microscopy.

One method of detecting biomarkers can include purifying or isolating a heterogeneous exosome population from a biological sample, as described above, and performing a sandwich assay. An exosome in the population can be captured with a primary antibody, such as an antibody bound to a substrate, for example an array, well, or particle. The captured or bound exosome can be detected with a detection antibody. For example, the detection antibody can be for an antigen of the exosome. The detection antibody can be directly labeled and detected. Alternatively, an enzyme linked secondary antibody can react with the detection antibody. A detection reagent or detection substrate is added and the reaction can be detected, such as described in PCT Publication No. WO2009092386. The primary antibody can be an anti-Rab 5b antibody and the detection antibody anti-CD63 or anti-caveolin-1. Alternatively, the capture antibody can be an antibody to CD9, PSCA, TNFR, CD63, B7H3, MFG-E8, EpCam, Rab, CD81, STEAP, PCSA, PSMA, or 5T4. The detection antibody can be an antibody to CD63, CD9, CD81, B7H3, or EpCam.

In some embodiments, the capture agent binds or targets EpCam, and the one or more biomarkers detected on the exosome is CD9, CD63, or both CD9 and CD63. In other embodiments, the capture agent targets PCSA, and the one or more biomarkers detected on the captured exosome is B7H3, PSMA, or both B7H3 and PSMA. In yet other embodiments, the capture agent targets CD63 and the one or more biomarkers detected on the exosome is CD81, CD83, CD9, CD63, or any combination thereof. The different capture agent and biomarker combinations can be used to characterize a phenotype, such as prostate cancer or colon cancer. For example, capturing one or more exosomes can be performed with a capture agent targeting EpCam and detection of CD9 and CD63; a capture agent targeting PCSA and detection of B7H3 and PSMA; or a capture agent of CD63 and detection of CD81; can be used to characterize prostate cancer. A capture agent targeting CD63 and detection of CD63, or a capture agent targeting CD9 and detecting CD63, can be used to characterize colon cancer.

Other methods can include the use of a planar substrate such as an array (i.e., biochip or microarray), with immobilized molecules as capture agents, which can facilitate the detection of a particular bio-signature of exosomes. The arrays can be provided as part of a kit for assaying exosomes. Molecules that identify the biomarkers described above and shown in FIG. 3-60, as well as antigens in FIG. 1 can be included in a custom array for detection and diagnosis of diseases including presymtomatic diseases. Arrays comprising biomolecules that specifically identify selected biomarkers can be used to develop a database of information using data provided in the present specification. Additional biomolecules that identify bio-signatures which lead to improved cross-validated error rates in multivariate prediction models (e.g., logistic regression, discriminant analysis, or regression tree models) can be included in a custom array.

Customized array(s) provide an opportunity to study the biology of a disease, condition or syndrome and profile exosomes that are shed in defined physiological states. Standard p values of significance (0.05) can be chosen to exclude or include additional specific biomolecules on the microarray that identify particular biomarkers.

A planar array can generally contain addressable locations (e.g., pads, addresses, or micro-locations) of biomolecules in an array format. The size of the array will depend on the composition and end use of the array. Arrays containing from about 2 different molecules to many thousands can be made. Generally, the array can comprise from two to as many as 100,000 or more molecules, depending on the end use of the array and the method of manufacture. A microarray can generally comprise at least one biomolecule that identifies or captures a biomarker present in a bio-signature of specific cell-of-origin exosomes. In some embodiments, the compositions of the invention may not be in an array format; that is, for some embodiments, compositions comprising a single biomolecule may be made as well. In addition, in some arrays, multiple substrates may be used, either of different or identical compositions. Thus, for example, large planar arrays may comprise a plurality of smaller substrates.

An array of the present invention encompasses any means for detecting a biomarker. For example, microarrays can be biochips that provide high-density immobilized arrays of recognition molecules (e.g., antibodies), where biomarker binding is monitored indirectly (e.g., via fluorescence). In addition, an array can be of a format that involves the capture of proteins by biochemical or intermolecular interaction, coupled with direct detection by mass spectrometry (MS).

Arrays and microarrays that can be used to detect the biomarkers of a bio-signature of exosomes can be made according to the methods described in U.S. Pat. Nos. 6,329,209; 6,365,418; 6,406,921; 6,475,808; and 6,475,809, and U.S. patent application Ser. No. 10/884,269, each of which is herein incorporated by reference in its entirety. New arrays, to detect specific selections of sets of biomarkers described herein can also be made using the methods described in these patents. Furthermore, commercially available microarrays, such as for protein or nucleic acid detection can also be used, such as from Affymetrix (Santa Clara, Calif.), Illumina (San Diego, Calif.), Agilent (Santa Clara, Calif.), Exiqon (Denmark), or Invitrogen (Carlsbad, Calif.).

In many embodiments, immobilized molecules, or molecules to be immobilized, are proteins or peptides. One or more types of proteins may be immobilized on a surface. In certain embodiments, the proteins are immobilized using methods and materials that minimize the denaturing of the proteins, that minimize alterations in the activity of the proteins, or that minimize interactions between the protein and the surface on which they are immobilized.

Surfaces useful may be of any desired shape (form) and size. Non-limiting examples of surfaces include chips, continuous surfaces, curved surfaces, flexible surfaces, films, plates, sheets, tubes, or the like. Surfaces can have areas ranging from approximately a square micron to approximately 500 $cm^2$. The area, length, and width of surfaces according to the present invention may be varied according to the requirements of the assay to be performed. Considerations may include, for example, ease of handling, limitations of the material(s) of which the surface is formed, requirements of detection systems, requirements of deposition systems (e.g., arrayers), or the like.

In certain embodiments, it is desirable to employ a physical means for separating groups or arrays of binding islands or immobilized biomolecules: such physical separation facilitates exposure of different groups or arrays to different solutions of interest. Therefore, in certain embodiments, arrays are situated within microwell plates having any number of wells. In such embodiments, the bottoms of the wells may serve as surfaces for the formation of arrays, or arrays may be formed on other surfaces and then placed into wells. In certain embodiments, such as where a surface without wells is used, binding islands may be formed or molecules may be immobilized on a surface and a gasket having holes spatially arranged so that they correspond to the islands or biomolecules may be placed on the surface. Such a gasket is preferably liquid tight. A gasket may be placed on a surface at any time during the process of making the array and may be removed if separation of groups or arrays is no longer necessary.

The immobilized molecules can bind to exosomes present in a biological sample overlying the immobilized molecules. Alternatively, the immobilized molecules modify or are modified by molecules present in exosomes overlying the immobilized molecules.

Modifications or binding of molecules in solution or immobilized on an array may be detected using detection techniques known in the art. Examples of such techniques include immunological techniques such as competitive binding assays and sandwich assays; fluorescence detection using instruments such as confocal scanners, confocal microscopes, or CCD-based systems and techniques such as fluorescence, fluorescence polarization (FP), fluorescence resonant energy transfer (FRET), total internal reflection fluorescence (TIRF), fluorescence correlation spectroscopy (FCS); colorimetric/spectrometric techniques; surface plasmon resonance, by which changes in mass of materials adsorbed at surfaces may be measured; techniques using radioisotopes, including conventional radioisotope binding and scintillation proximity assays (SPA); mass spectroscopy, such as matrix-assisted laser desorption/ionization mass spectroscopy (MALDI) and MALDI-time of flight (TOF) mass spectroscopy; ellipsometry, which is an optical method of measuring thickness of protein films; quartz crystal microbalance (QCM), a very sensitive method for measuring mass of materials adsorbing to surfaces; scanning probe microscopies, such as AFM and SEM; and techniques such as electrochemical, impedance, acoustic, microwave, and IR/Raman detection. See, e.g., Mere L, et al., "*Miniaturized FRET assays and microfluidics: key components for ultra-high-throughput screening,*" *Drug Discovery Today* 4(8):363-369 (1999), and references cited therein; Lakowicz J R, *Principles of Fluorescence Spectroscopy, 2nd Edition*, Plenum Press (1999), or Jain K K: *Integrative Omics, Pharmacoproteomics, and Human Body Fluids. In: Thongboonkerd V, ed., ed. Proteomics of Human Body Fluids: Principles, Methods and Applications. Volume* 1: Totowa, N.J.: Humana Press, 2007, each of which is herein incorporated by reference in its entirety.

Microarray technology can be combined with mass spectroscopy (MS) analysis and other tools. Electrospray interface to a mass spectrometer can be integrated with a capillary in microfluidics devices. For example, one commercially available system contains eTag reporters that are fluorescent labels with unique and well-defined electrophoretic mobilities; each label is coupled to biological or chemical probes via cleavable linkages. The distinct mobility address of each eTag reporter allows mixtures of these tags to be rapidly deconvoluted and quantitated by capillary electrophoresis. This system allows concurrent gene expression, protein expression, and protein function analyses from the same sample Jain K K: *Integrative Omics, Pharmacoproteomics, and Human Body Fluids. In: Thongboonkerd V, ed., ed. Proteomics of Human Body Fluids Principles, Methods and Applications. Volume* 1: Totowa, N.J.: Humana Press, 2007, which is herein incorporated by reference in its entirety.

These biochips can include components for microfluidic or nanofluidic assays. Microfluidic devices can be used for isolating exosomes, such as described herein, in combination with analyzing the exosomes, such as determining bio-signatures. Such systems miniaturize and compartmentalize processes that allow for capturing of exosomes, detection of exosomal biomarkers, and other processes. The microfluidic devices can utilize detection reagents in at least one aspect of the system, and such detection reagents may be used to detect one or more biomarkers of exosomes. For example, the device can detect biomarkers on the isolated exosomes or bound exosomes. One or more biomarkers of a sample of isolated exosomes can be detected through the use of a microfluidic device. For example, various probes, antibodies, proteins, or other binding agents can be used to detect a biomarker. The detection agents may be immobilized in different compartments of the microfluidic device or be entered into a hybridization or detection reaction through various channels of the device.

An exosome in a microfluidic device may be lysed and the contents, such as proteins or nucleic acids, such as DNA or RNA (such as miRNA, mRNA) can be detected within a microfluidic device. The nucleic acid may be amplified prior to detection, or directly detected, within the microfluidic device. Thus microfluidic systems can also be used for multiplexing detection of various biomarkers.

Novel nanofabrication techniques are opening up the possibilities for biosensing applications that rely on fabrication of high-density, precision arrays, e.g., nucleotide-based chips and protein arrays otherwise know as heterogeneous nanoarrays. Nanofluidics allows a further reduction in the quantity of fluid analyte in a microchip to nanoliter levels, and the chips used here are referred to as nanochips. (See, e.g., Unger M et al., *Biotechniques* 1999; 27(5):1008-14, Kartalov E P et al., *Biotechniques* 2006; 40(1):85-90, each of which are herein incorporated by reference in their entireties.) Commercially available nanochips currently provide simple one step assays such as total cholesterol, total protein or glucose assays that can be run by combining sample and reagents, mixing and monitoring of the reaction. Gel-free analytical approaches based on liquid chromatography (LC) and nanoLC separations (Cutillas et al. *Proteomics,* 2005; 5:101-112 and Cutillas et al., *Mol Cell Proteomics* 2005; 4:1038-1051, each of which is herein incorporated by reference in its entirety) can be used in combination with the nanochips.

Arrays suitable for identifying a disease, condition or a syndrome or physiological status may be included in kits. Such kits may also include, as non-limiting examples, reagents useful for preparing molecules for immobilization onto binding islands or areas of an array, reagents useful for detecting binding of exosomes or exosomal components to immobilized molecules, and instructions for use.

Further provided herein is a rapid detection device that facilitates the detection of a particular bio-signature of exosomes in a biological sample. The device can integrate biological sample preparation with polymerase chain reaction (PCR) on a chip. The device can facilitate the detection of a particular bio-signature of exosomes in a biological sample, and an example is provided as described in Pipper et al., *Angewandte Chemie,* 47(21), p. 3900-3904 (2008), which is herein incorporated by reference in its entirety. The bio-signatures of the exosomes can be incorporated using micro-/nano-electrochemical system (MEMS/NEMS) sensors and oral fluid for diagnostic applications as described in Li et al., *Adv Dent Res* 18(1): 3-5 (2005), which is herein incorporated by reference in its entirety.

Figure 64A:
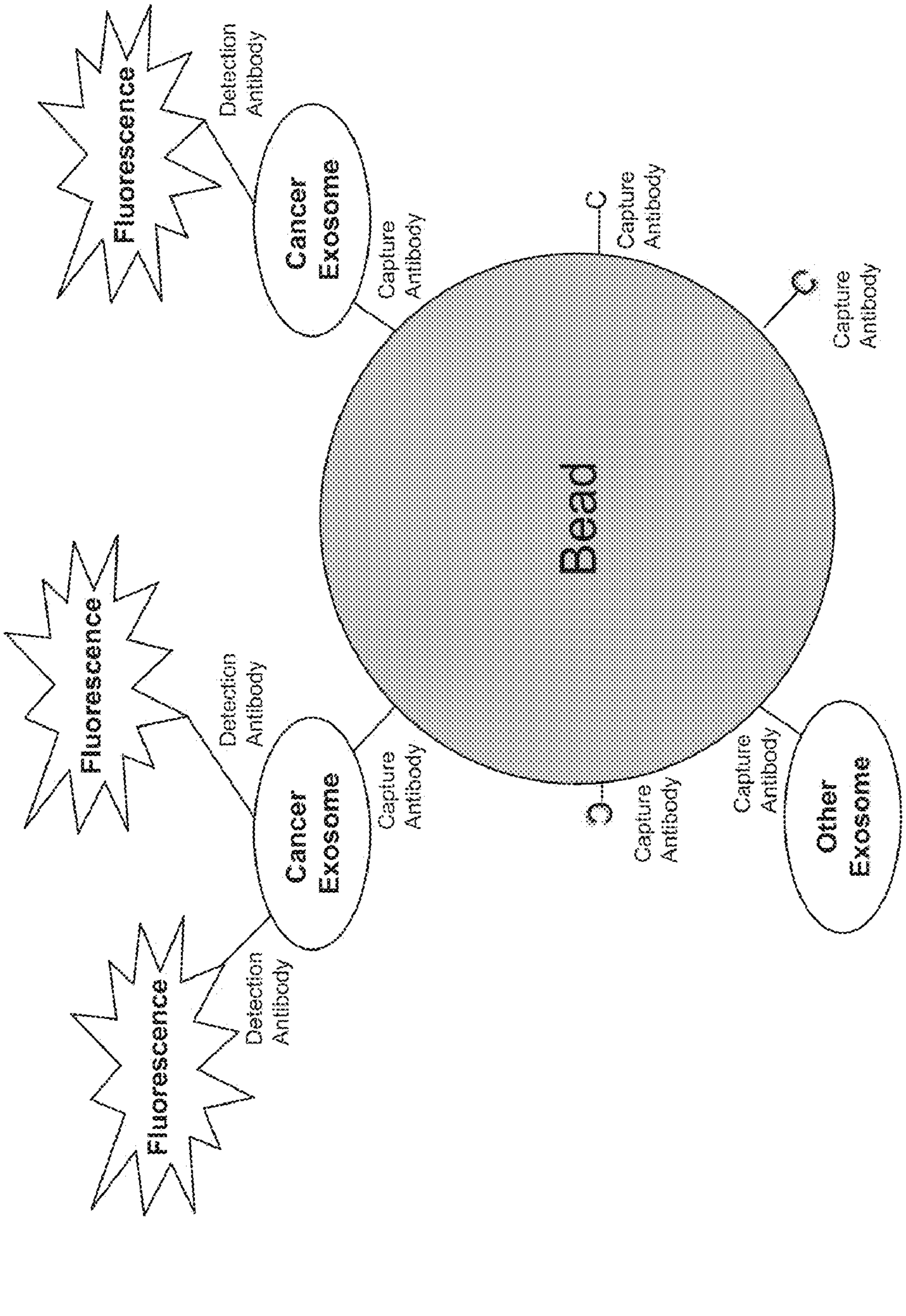
FIG. 64 illustrates a particle based method of isolating exosomes. (A) is a schematic of a bead coated with a capture antibody, which captures exosomes expressing that protein. In this schematic, the capture antibody is for an exosomal protein that is not specific for exosomes derived from cancer cells ("cancer exosome"). The detection antibody binds to the captured exosome and fluoresces a signal. The detection antibody in this example detects an antigen that is associated with cancer exosomes. (B) is an example of a screening scheme that can be performed by multiplexing using the beads as shown in (A).

As an alternative to planar arrays, assays using particles, such as bead based assays as described herein, can be used in combination with flow cytometry. Multiparametric assays or other high throughput detection assays using bead coatings with cognate ligands and reporter molecules with specific activities consistent with high sensitivity automation can be used. In bead based assay systems, the binding agents, such as an antibody for exosomes, can be immobilized on addressable microspheres. Each binding agent for each individual binding assay is coupled to a distinct type of microsphere (i.e., microbead) and the assay reaction takes place on the surface of the microspheres, such as depicted in FIG. 64A. A binding agent for an exosome, such as a capture antibody is coupled to a bead. Dyed microspheres with discrete fluorescence intensities are loaded separately with their appropriate binding agent or capture probes. The different bead sets carrying different binding agents can be pooled as necessary to generate custom bead arrays. Bead arrays are then incubated with the sample in a single reaction vessel to perform the assay. Examples of microfluidic devices that may be used, or adapted for use with exosomes, include but are not limited to those described herein.

Product formation of the biomarker with their immobilized capture molecules or binding agents can be detected with a fluorescence based reporter system (see for example, FIG. 64A). The biomarker can either be labeled directly by a fluorophore or detected by a second fluorescently labeled capture biomolecule. The signal intensities derived from captured biomarkers are measured in a flow cytometer. The flow cytometer first identifies each microsphere by its individual color code. For example, distinct beads can be dyed with discrete fluorescence intensities such that each bead with a different intensity has a different binding agent. The beads can be labeled or dyed with at least 2 different labels or dyes. In some embodiments, the beads are labeled with at least 3, 4, 5, 6, 7, 8, 9, or 10 different labels. The beads with more than one label or dye can also have various ratios and combinations of the labels or dyes. The beads can be labeled or dyed externally or may have intrinsic fluorescence or signaling labels.

Figure 64B:
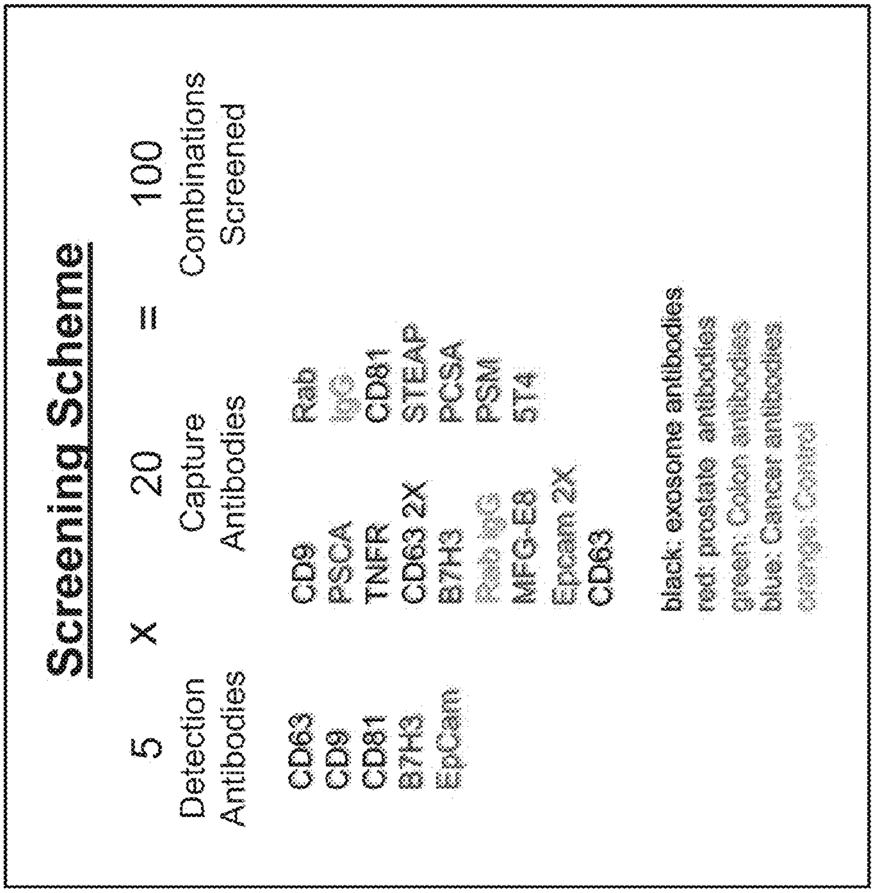
Figure 65A:
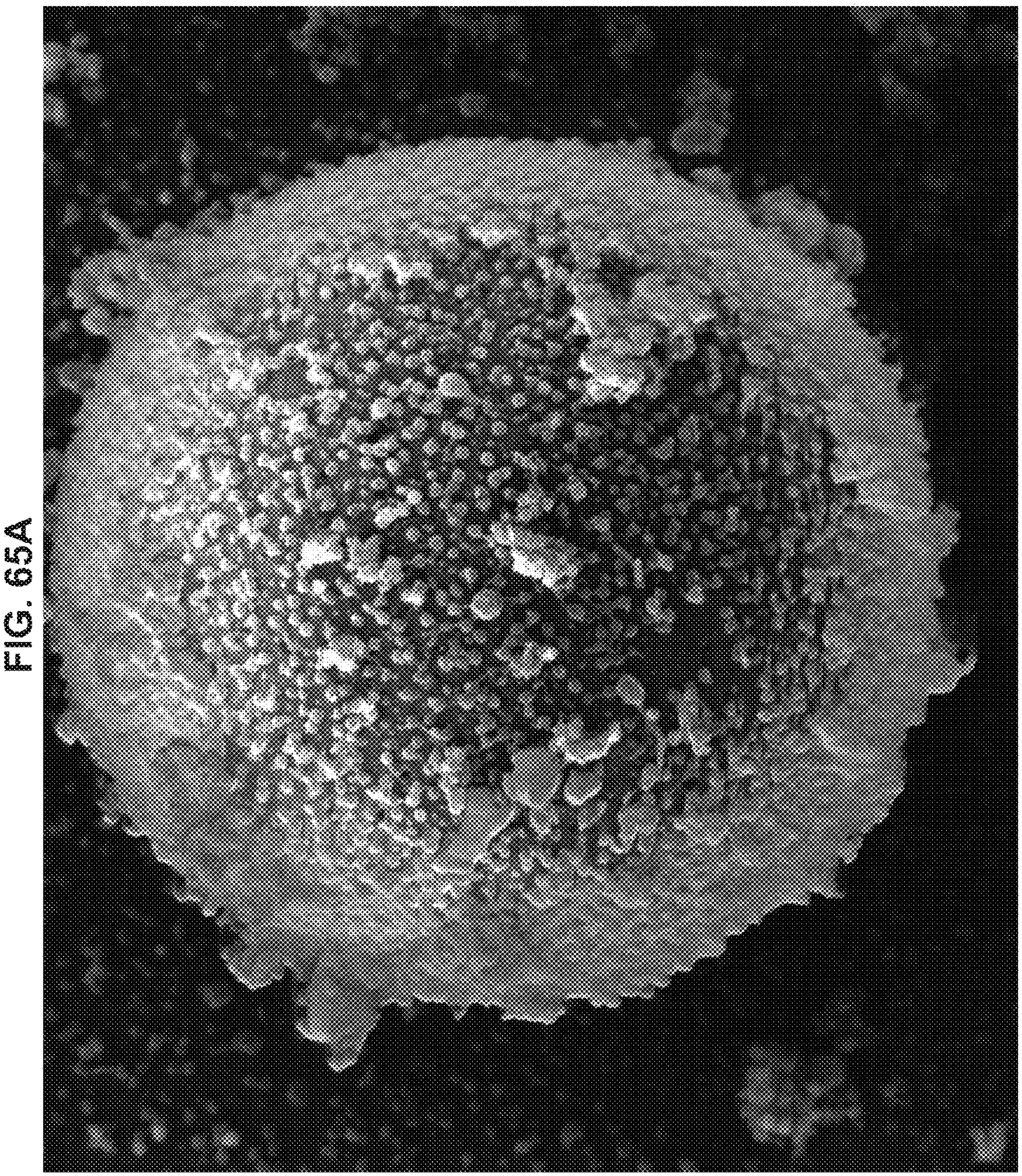
FIG. 65 depicts scanning electron micrographs (SEMs) of EpCam conjugated beads that have been incubated with VCaP exosomes. (A) A glass slide was coated with poly-L-lysine and incubated with the bead solution. After attachment, the beads were (i) fixed sequentially with glutaraldehyde and osmium tetroxide, 30 min per fix step with a few washes in between; (ii) gradually dehydrated in acetone, 20% increments, about 5-7 min per step; (iii) critical-point dried; and (iv) sputter-coated with gold. (B) Left: depicts a higher magnification of exosomes on an EpCam coated bead as in (A). Right: depicts exosomes isolated by ultracentrifugation and adhered to a poly-L-lysine coated glass slide and fixed and stained as in (A).
Figure 65B:
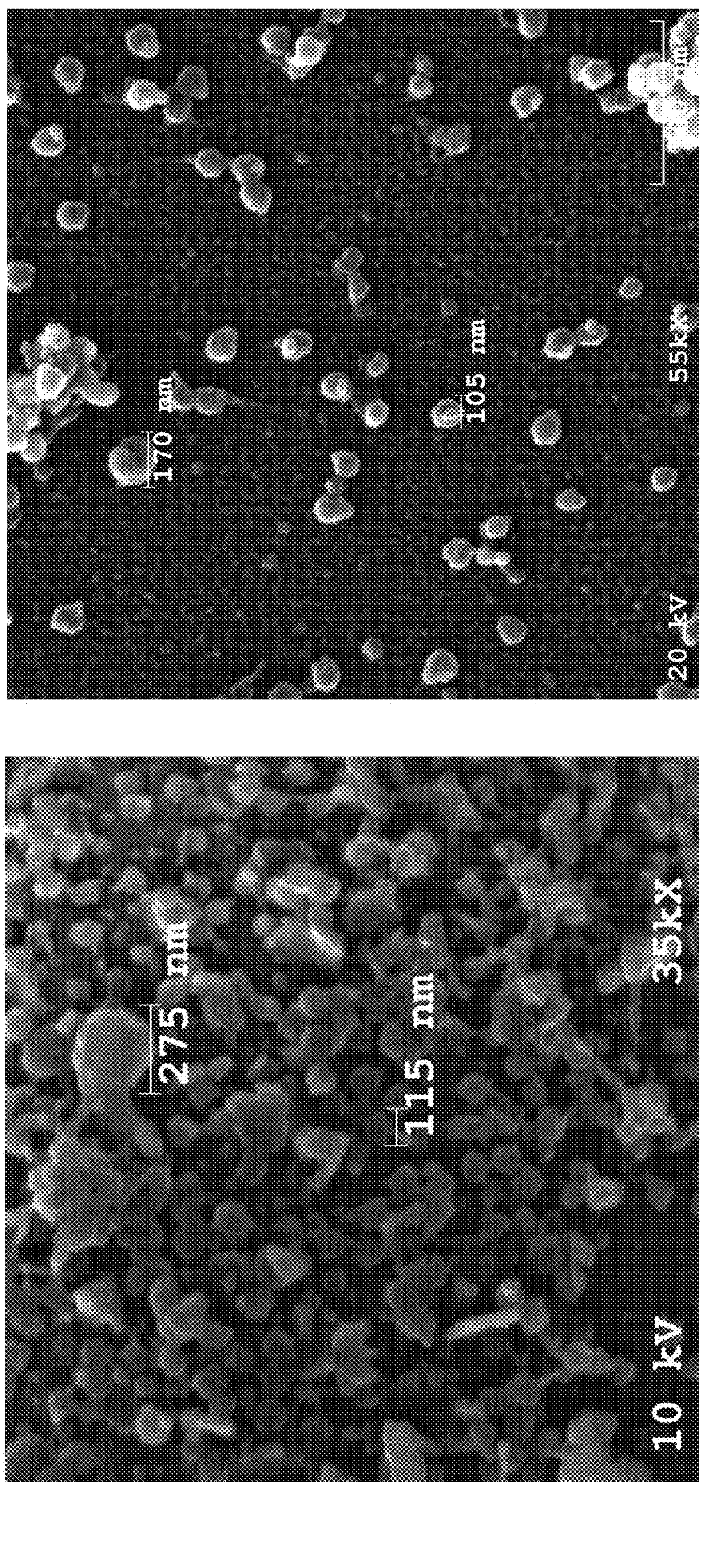
Figure 66:
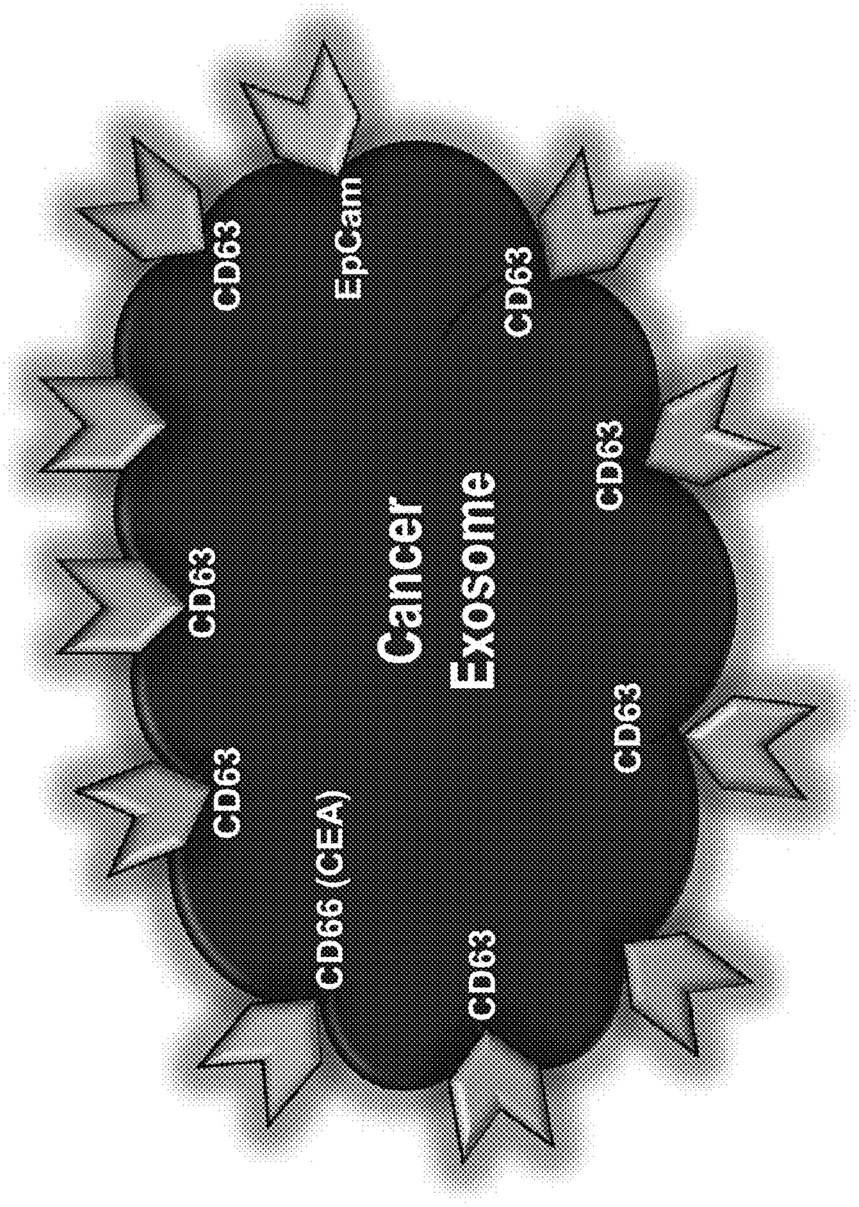
FIG. 66 is a schematic of an exosome protein expression patterns. Different proteins are typically not distributed evenly or uniformly on exosome shell. Exosome-specific proteins are typically more common, while cancer-specific proteins are less common. Exosome capture can be more easily accomplished using a more common, less cancer-specific protein, and cancer-specific proteins used in the detection phase.
Figure 67A:
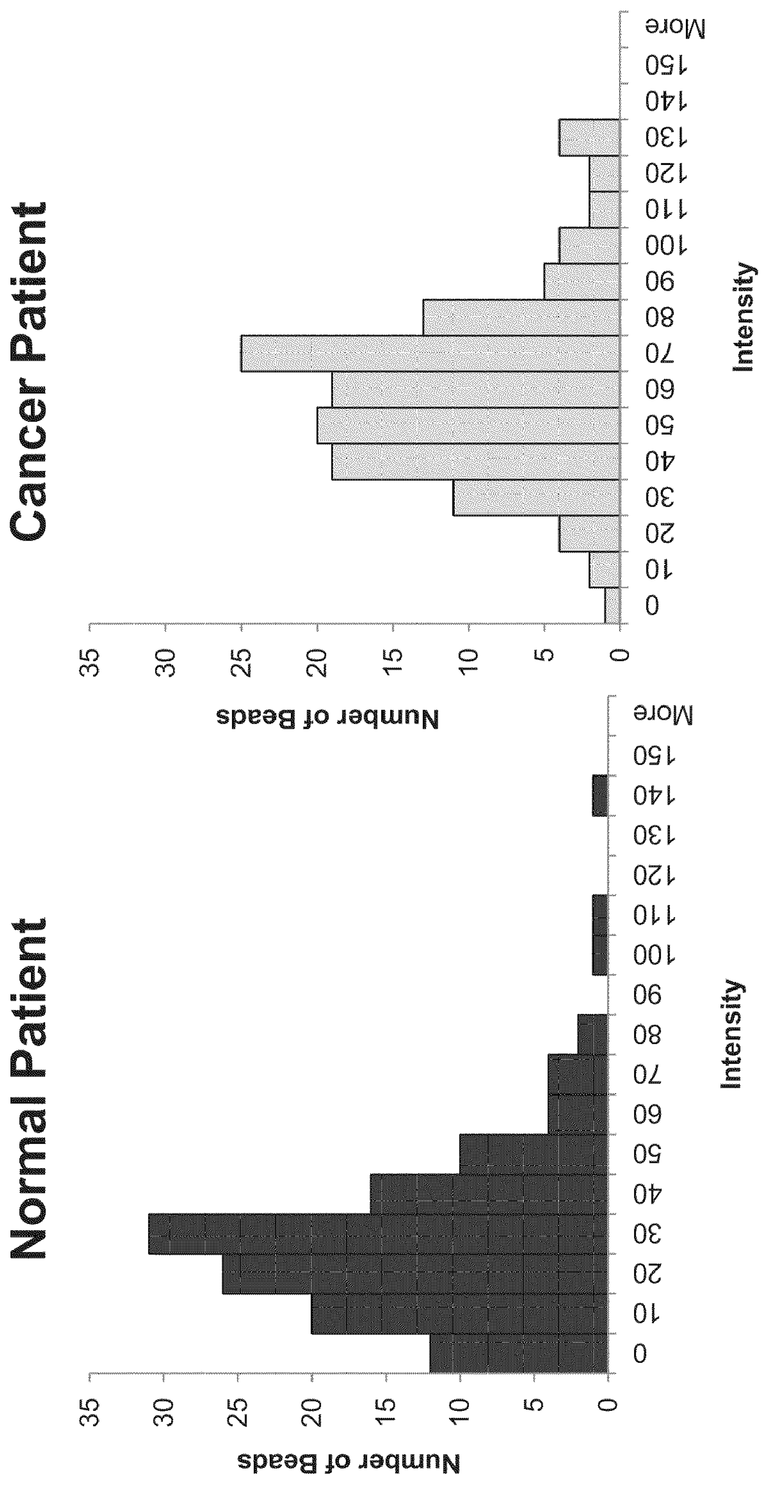
FIG. 67 illustrates the method of depicting the results using the bead based method of detecting exosomes from a subject. (A) For an individual patient, a graph of the bead enumeration and signal intensity using a screening scheme as depicted in FIG. 64B, where ~100 capture beads are used for each capture/detection combination assay per patient. For a given patient, the output shows number of beads detected vs. intensity of signal. The number of beads captured at a given intensity is an indication of how frequently an exosome expresses the detection protein at that intensity. The more intense the signal for a given bead, the greater the expression of the detection protein. (B) is a normalized graph obtained by combining normal patients into one curve and cancer patients into another, and using bio-statistical analysis to differentiate the curves. Data from each individual is normalized to account for variation in the number of beads read by the detection machine, added together, and then normalized again to account for the different number of samples in each population.
Figure 67B:
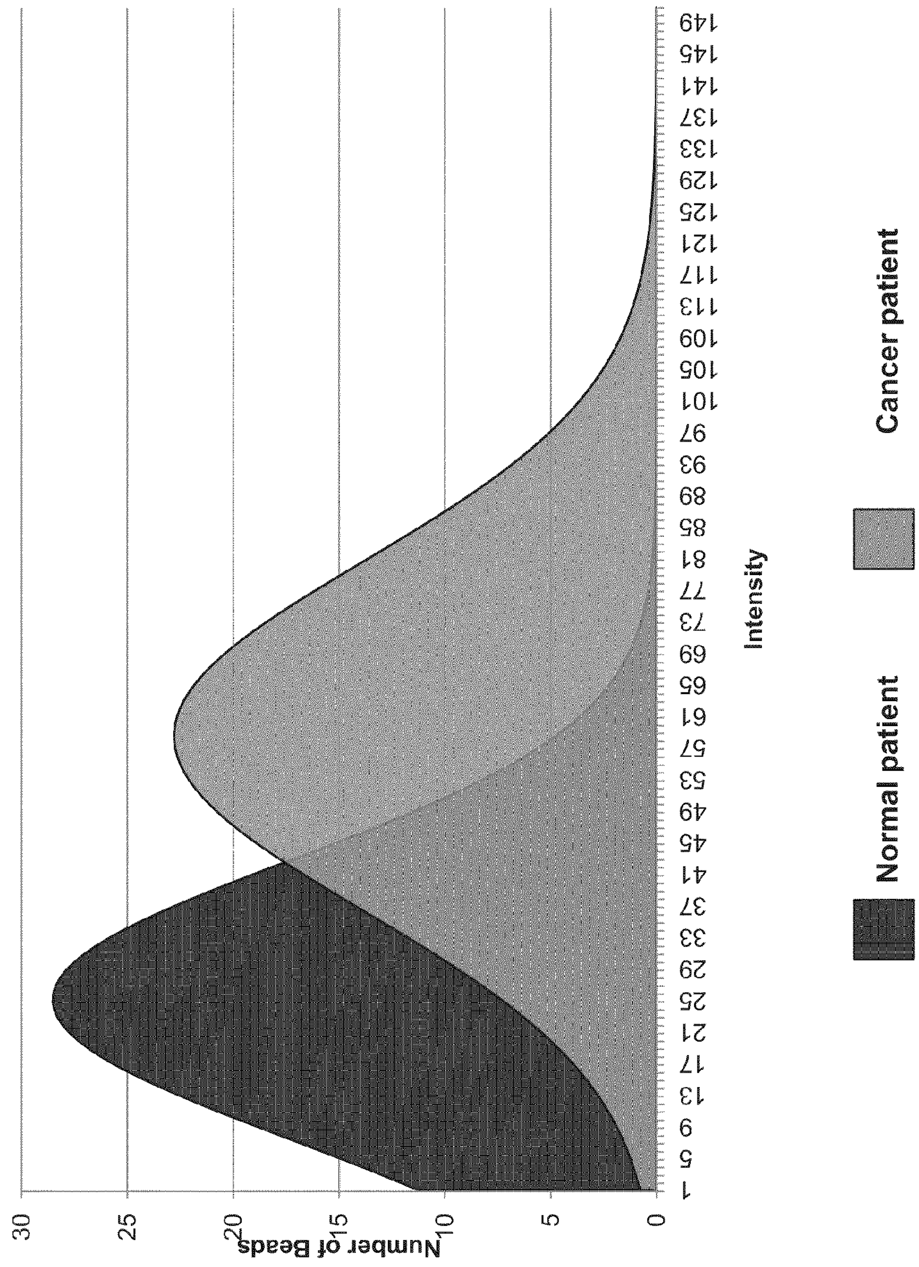
Figure 68A:
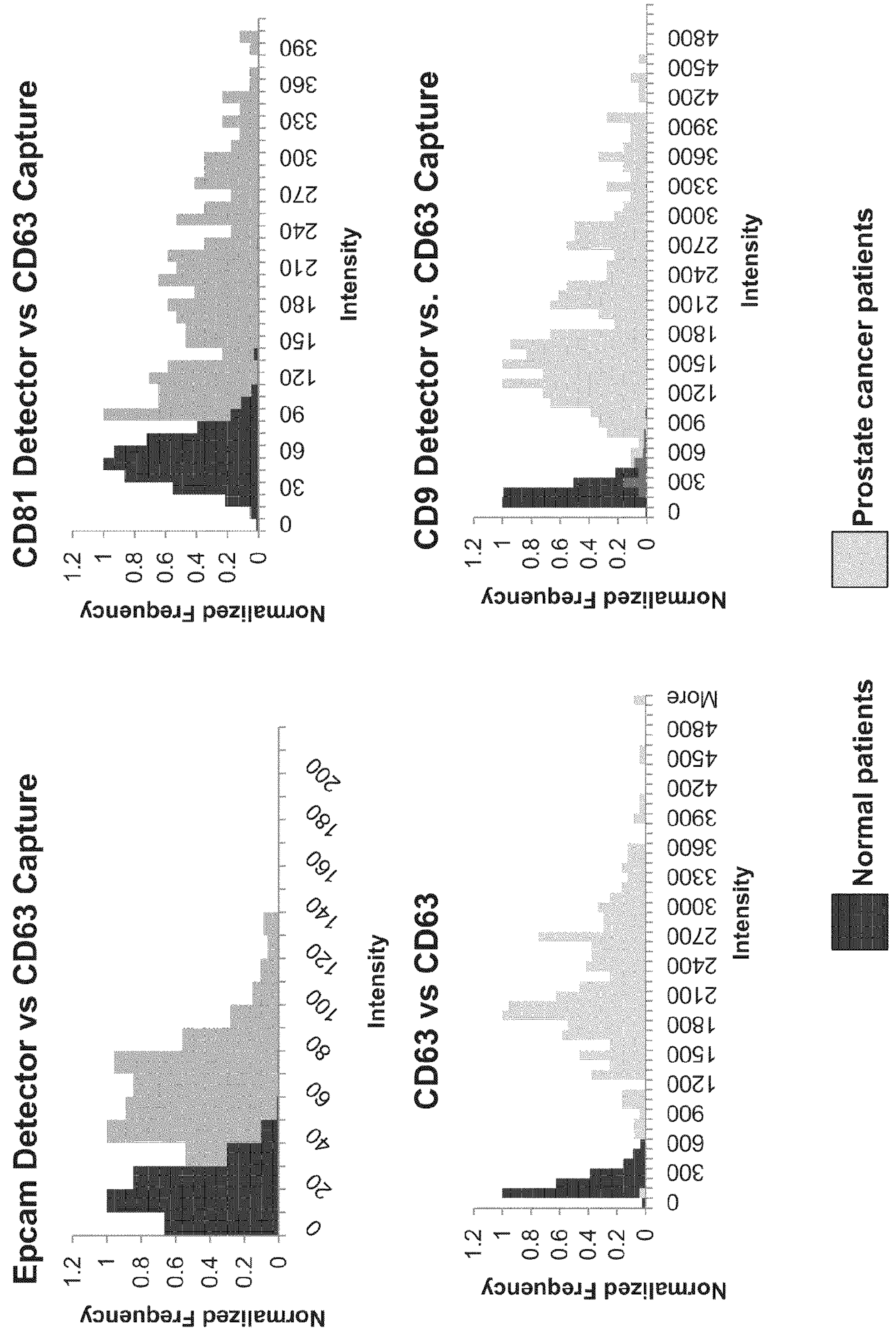
FIG. 68 illustrates prostate cancer bio-signatures. (A) is a histogram of intensity values collected from a multiplexing experiment using the Luminex platform, where beads were functionalized with CD63 antibody, incubated with exosomes purified from patient plasma, and then labeled with a phycoerythrin (PE) conjugated EpCam antibody. The darker shaded bars (blue) represent the population from 12 normal subjects and the lighter shaded bars (green) are from 7 stage 3 prostate cancer patients. (B) is a normalized graph for each of the histograms shown in (A), as described in FIG. 67. The distributions are of a Gaussian fit to intensity values from the Luminex results of (A) for both prostate patient samples and normal samples. (C) is an example of one of the prostate bio-signatures shown in (B), the CD63 versus CD63 bio-signature (upper graph) where CD63 is used as the detector and capture antibody. The lower three panels show the results of flow cytometry on three prostate cancer cell lines (VCaP, LNcap, and 22RV1). Points above the horizontal line indicate beads that captured exosomes with CD63 that contain B7H3. Beads to the right of the vertical line indicate beads that have captured exosomes with CD63 that have PSMA. Those beads that are above and to the right of the lines have all three antigens. CD63 is a surface protein that is associated with exosomes, PSMA is surface protein that is associated with prostate cells, and B7H3 is a surface protein that is associated with aggressive cancers (specifically prostate, ovarian, and non-small-cell lung). The combination of all three antigens together identifies exosomes that are from cancer prostate cells. The majority of CD63 expressing prostate cancer exosomes also have prostate-specific membrane antigen, PSMA, and B7H3 (implicated in regulation of tumor cell migration and invasion and an indicator of aggressive cancer as well as clinical outcome). (D) is a prostate cancer exosome topography. The upper panels show the results of capturing and labeling with CD63, CD9, and CD81 in various combinations. Almost all points are in the upper right quadrant indicating that these three markers are highly coupled. If an exosome has one of them, it typically has all three. The lower row depicts the results of capturing cell line exosomes with B7H3 and labeling with CD63 and PSMA. Both VCaP and 22RV1 show that most exosomes captured with B7H3 also have CD63, and that there are two populations, those with PSMA and those without. The presence of B7H3 may be an indication of how aggressive the cancer is, as LNcap does not have a high amount of B7H3 containing exosomes (not many spots with CD63). LnCap is an earlier stage prostate cancer analogue cell line.
Figure 68B:
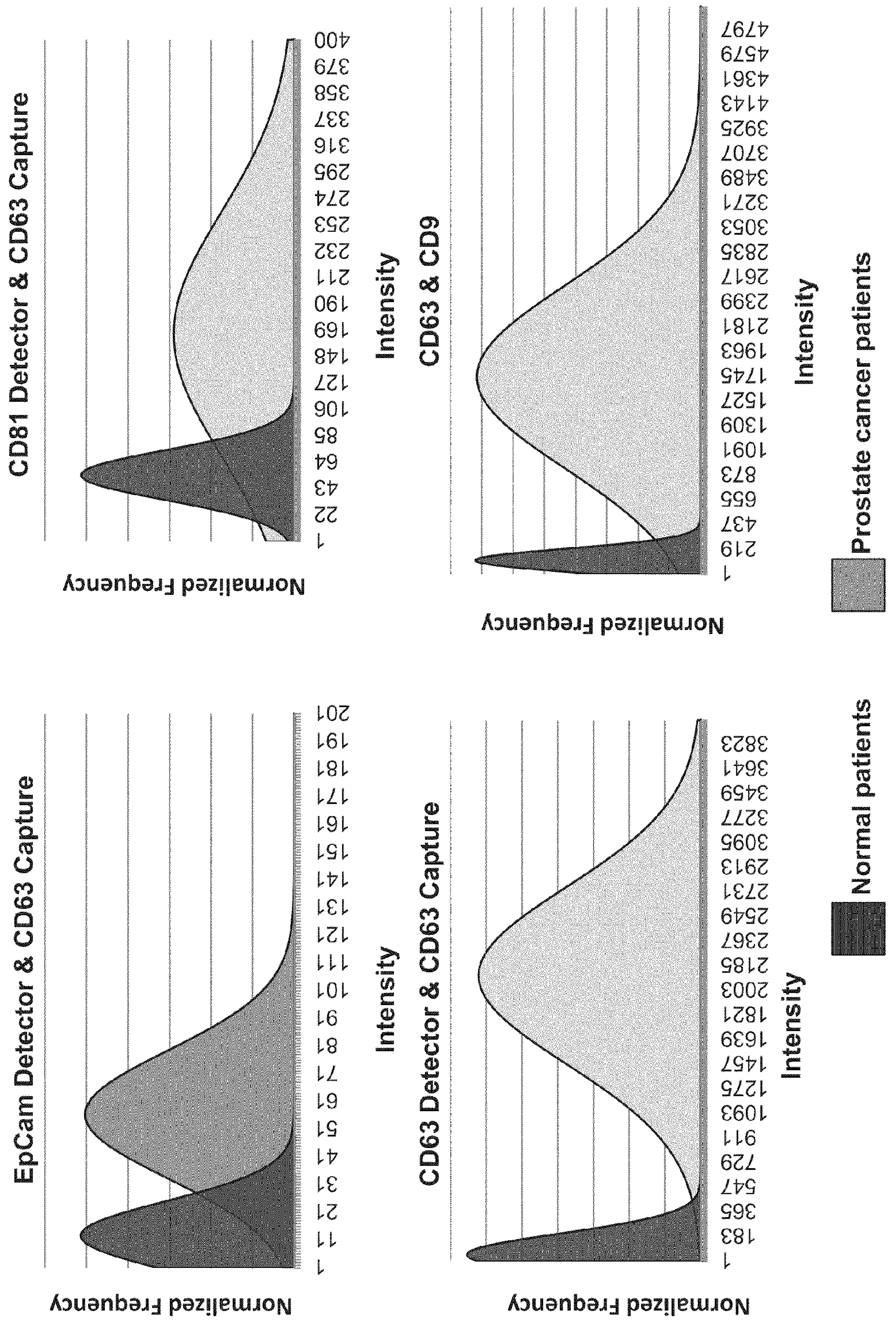
Figure 68C:
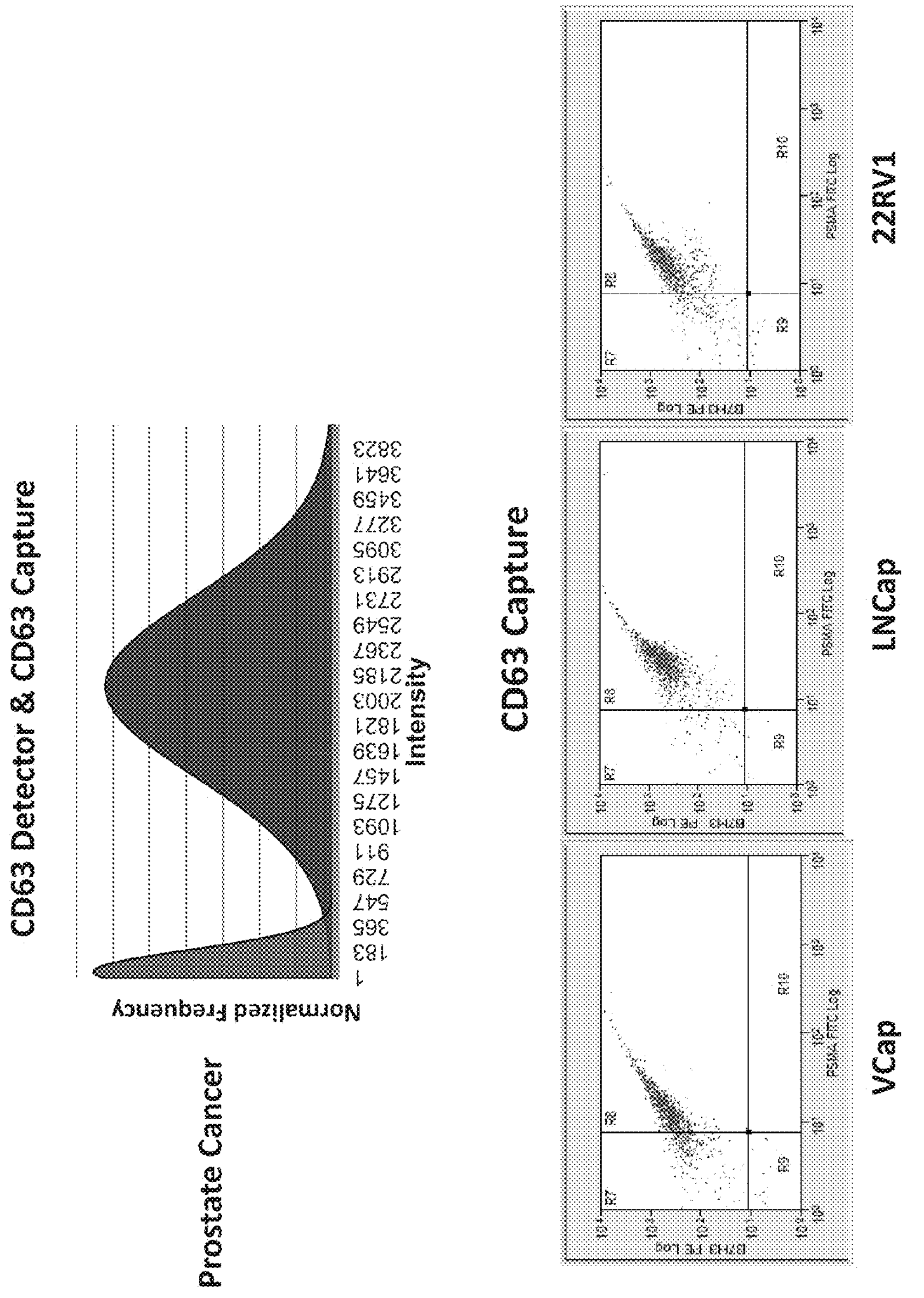
Figure 68D:
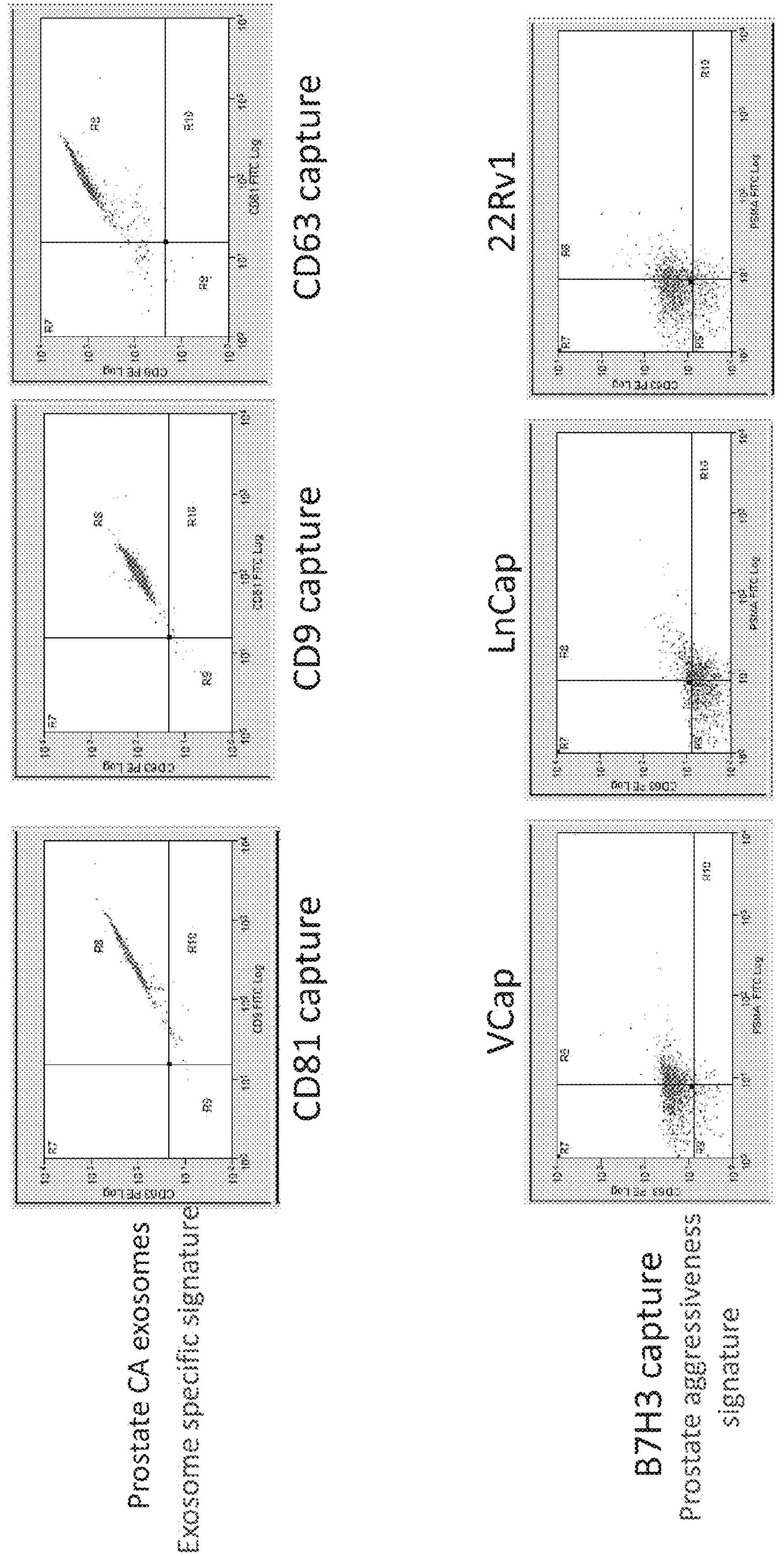

The amount of captured biomarkers on each individual bead can be measured by the second color fluorescence specific for the bound target. This allows multiplexed quantitation of multiple targets from a single sample within the same experiment. Sensitivity, reliability and accuracy are compared, or can be improved to standard microtiter ELISA procedures. An advantage of bead-based systems is the individual coupling of the capture biomolecule, or binding agent for an exosome, to distinct microspheres, which provides multiplexing. For example, as depicted in FIG. 64B, a combination of 5 different biomarkers to be detected (detected by antibodies to antigens such as CD63, CD9, CD81, B7H3, and EpCam) and 20 biomarkers for which to capture the exosome (using capture antibodies, such as antibodies to CD9, PSCA, TNFR, CD63, B7H3, MFG-E8, EpCam, Rab, CD81, STEAP, PCSA, PSMA, and 5T4) can result in 100 combinations to be detected. Thus, captured exosomes can be detected using detection agents, such as antibodies. The detection agents can be labeled directly or indirectly, such as described above.

Multiplexing of at least 2, 3, 4, 5, 6, 7, 8, 9, 10, 11, 12, 13, 14, 15, 16, 17, 18, 19, 20, 25, 50, 75 or 100 different biomarkers may be performed. For example, an assay of a heterogeneous population of exosomes can be performed with a plurality of particles that are differentially labeled. There can be at least 2, 3, 4, 5, 6, 7, 8, 9, 10, 11, 12, 13, 14, 15, 16, 17, 18, 19, 20, 25, 50, 75 or 100 differentially labeled particles. The particles may be externally labeled, such as with a tag, or they may be intrinsically labeled. Each differentially labeled particle can be coupled to a capture agent, such as a binding agent, for an exosome, resulting in capture of an exosome. Biomarkers of the captured exosomes can then be detected by a plurality of binding agents. The binding agent can be directly labeled and thus, detected. Alternatively, the binding agent is labeled by a secondary agent. For example, the binding agent may be an antibody for a biomarker on the exosome. The binding agent is linked to biotin. A secondary agent comprises streptavidin linked to a reporter and can be added to detect the biomarker. In some embodiments, the captured exosomes are assayed for at least 2, 3, 4, 5, 6, 7, 8, 9, 10, 11, 12, 13, 14, 15, 16, 17, 18, 19, 20, 25, 50, 75 or 100 different biomarkers. For example, as depicted in FIG. 70, multiple detectors, i.e. detection of multiple biomarkers of a captured exosome, can increase the signal obtained, permitted increased sensitivity, specificity or both, and the use of smaller amounts of samples.

ELISA based methods, so sandwich assay can also be used to detect biomarkers on an exosome. A binding agent or capture agent can be bound to a well, for example an antibody to an exosomal antigen. Biomarkers on the captured exosome can be detected based on the methods described herein.

Peptide or protein biomarkers can be analyzed by mass spectrometry or flow cytometry. Proteomic analysis of exosomes may also be carried out on exosomes by immunocytochemical staining, Western blotting, electrophoresis, chromatography or x-ray crystallography in accordance with procedures well known in the art. In other embodiments, the protein bio-signatures of exosomes may be analyzed using 2 D differential gel electrophoresis as described in, Chromy et al. *J Proteome Res,* 2004; 3:1120-1127, which is herein incorporated by reference in its entirety, or with liquid chromatography mass spectrometry as described in Zhang et al. *Mol Cell Proteomics,* 2005; 4:144-155, which is herein incorporated by reference in its entirety. Exosomes may be subjected to activity-based protein profiling described for example, in Berger et al., *Am J Pharmacogenomics,* 2004; 4:371-381, which is in incorporated by reference in its entirety. In other embodiments, exosomes may be profiled using nanospray liquid chromatography-tandem mass spectrometry as described in Pisitkun et al., *Proc Natl Acad Sci USA,* 2004; 101:13368-13373, which is herein incorporated by reference in its entirety. In another embodiment, the exosomes may be profiled using tandem mass spectrometry (MS) such as liquid chromatography/MS/MS (LC-MS/MS) using for example a LTQ and LTQ-FT ion trap mass spectrometer. Protein identification can be determined and relative quantitation can be assessed by comparing spectral counts as described in Smalley et al., *J Proteome Res,* 2008; 7:2088-2096, which is herein incorporated by reference in its entirety.

Protein expression of exosomes can also be identified, such as following the isolation of cell-of-origin specific exosomes, such exosomes can be resuspended in buffer, centrifuged at 100×g for example, for 3 minutes using a cytocentrifuge on adhesive slides in preparation for immunocytochemical staining. The cytospins can be air-dried overnight and stored at—80° C. until staining. Slides can then be fixed and blocked with serum-free blocking reagent. The slides can then be incubated with a specific antibody to detect the expression of a protein of interest. In some embodiments, the exosomes are not purified, isolated or concentrated prior to protein expression analysis.

Exosomes, such as isolated cell-of-origin specific exosomes can be characterized by analysis of metabolite markers or metabolites, which can also form a bio-signature for exosomes. Various metabolite-oriented approaches have been described such as metabolite target analyses, metabolite profiling, or metabolic fingerprinting, see for example, Denkert et al., *Molecular Cancer* 2008; 7: 4598-4617, Ellis et al., *Analyst* 2006; 8: 875-885, Kuhn et al., *Clinical Cancer Research* 2007; 24: 7401-7406, Fiehn O., *Comp Funct Genomics* 2001; 2:155-168, Fancy et al., *Rapid Commun Mass Spectrom* 20(15): 2271-80 (2006), Lindon et al., *Pharm Res,* 23(6): 1075-88 (2006), Holmes et al., *Anal Chem.* 2007 Apr. 1; 79(7):2629-40. Epub 2007 Feb. 27. *Erratum in: Anal Chem.* 2008 Aug. 1; 80(15):6142-3, Stanley et al., *Anal Biochem.* 2005 Aug. 15; 343(2):195-202., *Lehtimäki et al., J Biol. Chem.* 2003 Nov. 14; 278(46):45915-23, each of which is herein incorporated by reference in its entirety.

Peptides from exosomes can be analyzed by systems described in Jain K K: *Integrative Omics, Pharmacoproteomics, and Human Body Fluids. In: Thongboonkerd V. ed., ed. Proteomics of Human Body Fluids: Principles, Methods and Applications. Volume* 1: Totowa, N.J.: Humana Press, c2007, 2007, which is herein incorporated by reference in its entirety. This system can generate sensitive molecular fingerprints of proteins present in a body fluid as well as in exosomes. Commercial applications which include the use of chromatography/mass spectroscopy and reference libraries of all stable metabolites in the human body, for example Paradigm Genetic's Human Metabolome Project, may be used to determine the metabolite bio-signature of exosomes, such as isolated cell-of-origin specific exosomes. Other methods for analyzing a metabolic profile can include methods and devices described in U.S. Pat. No. 6,683,455 (Metabometrix), U.S. Patent Application Publication Nos. 20070003965 and 20070004044 (Biocrates Life Science), each of which is herein incorporated by reference in its entirety. Other proteomic profiling techniques are described in Kennedy, *Toxicol Lett* 120:379-384 (2001), Berven et al., *Curr Pharm Biotechnol* 7(3): 147-58 (2006), Conrads et al., *Expert Rev Proteomics* 2(5): 693-703, Decramer et al., *World J Urol* 25(5): 457-65 (2007), Decramer et al., *Mol Cell Proteomics* 7(10): 1850-62 (2008), Decramer et al., *Contrib Nephrol,* 160: 127-41 (2008), Diamandis, *J Proteome Res* 5(9): 2079-82 (2006), Immler et al., *Proteomics* 6(10): 2947-58 (2006), Khan et al., *J Proteome Res* 5(10): 2824-38 (2006), Kumar et al., *Biomarkers* 11(5): 385-405 (2006), Noble et al., *Breast Cancer Res Treat* 104(2): 191-6 (2007), Omenn, *Dis Markers* 20(3): 131-4 (2004), Powell et al., *Expert Rev Proteomics* 3(1): 63-74 (2006), Rai et al., *Arch Pathol Lab Med,* 126(12): 1518-26 (2002), Ramstrom et al., *Proteomics,* 3(2): 184-90 (2003), Tammen et al., *Breast Cancer Res Treat,* 79(1): 83-93 (2003), Theodorescu et al., *Lancet Oncol,* 7(3): 230-40 (2006), or Zurbig et al., *Electrophoresis,* 27(11): 2111-25 (2006).

For analysis of mRNAs, miRNAs or other small RNAs, the total RNA can be first isolated from exosomes using any other known methods for isolating nucleic acids such as methods described in U.S. Patent Application Publication No. 2008132694, which is herein incorporated by reference in its entirety. These include, but are not limited to, kits for performing membrane based RNA purification, which are commercially available. Generally, kits are available for the small-scale (30 mg or less) preparation of RNA from cells and tissues, for the medium scale (250 mg tissue) preparation of RNA from cells and tissues, and for the large scale (1 g maximum) preparation of RNA from cells and tissues. Other commercially available kits for effective isolation of small RNA-containing total RNA are available.

Alternatively, RNA can be isolated using the method described in U.S. Pat. No. 7,267,950, which is herein incorporated by reference in its entirety. U.S. Pat. No. 7,267,950 describes a method of extracting RNA from biological systems (cells, cell fragments, organelles, tissues, organs, or organisms) in which a solution containing RNA is contacted with a substrate to which RNA can bind and RNA is withdrawn from the substrate by applying negative pressure. Alternatively, RNA may be isolated using the method described in U.S. Patent Application No. 20050059024, which is herein incorporated by reference in its entirety, which describes the isolation of small RNA molecules. Other methods are described in U.S. Patent Application No. 20050208510, 20050277121, 20070238118, each of which is incorporated by reference in its entirety.

In one embodiment, mRNA expression analysis can be carried out on mRNAs from exosomes isolated from a sample. In some embodiments, the exosomes are cell-of-origin specific exosomes. Expression patterns generated from these exosomes can be indicative of a given disease state, disease stage, therapy related signature, or physiological condition. Once the total RNA has been isolated, cDNA can be synthesized and either qRT-PCR assays (e.g. Applied Biosystem's Taqman® assays) for specific mRNA targets can be performed according to manufacturer's protocol, or an expression microarray can be performed to look at highly multiplexed sets of expression markers in one experiment. Methods for establishing gene expression profiles include determining the amount of RNA that is produced by a gene that can code for a protein or peptide. This is accomplished by quantitative reverse transcriptase PCR (qRT-PCR), competitive RT-PCR, real time RT-PCR, differential display RT-PCR, Northern Blot analysis or other related tests. While it is possible to conduct these techniques using individual PCR reactions, it is also possible to amplify complementary DNA (cDNA) or complementary RNA (cRNA) produced from mRNA and analyze it via microarray.

The level of a miRNA product in a sample can be measured using any technique that is suitable for detecting mRNA expression levels in a biological sample, including but not limited to Northern blot analysis, RT-PCR, qRT-PCR, in situ hybridization or microarray analysis. For example, using gene specific primers and target cDNA, qRT-PCR enables sensitive and quantitative miRNA measurements of either a small number of target miRNAs (via singleplex and multiplex analysis) or the platform can be adopted to conduct high throughput measurements using 96-well or 384-well plate formats. See for example, Ross J S et al, *Oncologist.* 2008 May; 13(5):477-93, which is herein incorporated by reference in its entirety. A number of different array configurations and methods for microarray production are known to those of skill in the art and are described in U.S. patents such as: U.S. Pat. Nos. 5,445,934; 5,532,128; 5,556,752; 5,242,974; 5,384,261; 5,405,783; 5,412,087; 5,424,186; 5,429,807; 5,436,327; 5,472,672; 5,527,681; 5,529,756; 5,545,531; 5,554,501; 5,561,071; 5,571,639; 5,593,839; 5,599,695; 5,624,711; 5,658,734; or 5,700,637; each of which is herein incorporated by reference in its entirety. Other methods of profiling miRNAs are described in Taylor et al., *Gynecol Oncol.* 2008 July; 110(1):13-21, Gilad et al, *PLoS ONE.* 2008 Sep. 5; 3(9): e3148, Lee et al., *Annu Rev Pathol.* 2008 Sep. 25 and Mitchell et al, *Proc Natl Acad Sci USA.* 2008 Jul. 29; 105(30):10513-8, Shen R et al, *BMC Genomics.* 2004 Dec. 14; 5(1):94, Mina L et al, *Breast Cancer Res Treat.* 2007 June; 103(2):197-208, Zhang L et al, *Proc Natl Acad Sci USA.* 2008 May 13; 105 (19):7004-9, Ross J S et al, *Oncologist.* 2008 May; 13(5):477-93, Schetter A J et al, *JAMA.* 2008 Jan. 30; 299(4):425-36, Staudt L M, *N Engl J Med* 2003; 348:1777-85, Mulligan G et al, *Blood.* 2007 Apr. 15; 109(8):3177-88. Epub 2006 Dec. 21, McLendon R et al, *Nature.* 2008 Oct. 23; 455(7216):1061-8, and U.S. Pat. Nos. 5,538,848, 5,723,591, 5,876,930, 6,030,787, 6,258,569, and 5,804,375, each of which is herein incorporated by reference.

Microarray technology allows for the measurement of the steady-state mRNA or miRNA levels of thousands of transcripts or miRNAs simultaneously thereby presenting a powerful tool for identifying effects such as the onset, arrest, or modulation of uncontrolled cell proliferation. Two microarray technologies, such as cDNA arrays and oligonucleotide arrays can be used. The product of these analyses are typically measurements of the intensity of the signal received from a labeled probe used to detect a cDNA sequence from the sample that hybridizes to a nucleic acid sequence at a known location on the microarray. Typically, the intensity of the signal is proportional to the quantity of cDNA, and thus mRNA or miRNA, expressed in the sample cells. A large number of such techniques are available and useful. Methods for determining gene expression can be found in U.S. Pat. No. 6,271,002 to Linsley, et al.; U.S. Pat. No. 6,218,122 to Friend, et al.; U.S. Pat. No. 6,218,114 to Peck et al.; or U.S. Pat. No. 6,004,755 to Wang, et al., each of which is herein incorporated by reference in its entirety.

Analysis of the expression levels is conducted by comparing such intensities. This can be performed by generating a ratio matrix of the expression intensities of genes in a test sample versus those in a control sample. The control sample may be used as a reference, and different references to account for age, ethnicity and sex may be used. Different references can be used for different conditions or diseases, as well as different stages of diseases or conditions, as well as for determining therapeutic efficacy.

For instance, the gene expression intensities of mRNA or miRNAs isolated from exosomes derived from a diseased tissue can be compared with the expression intensities generated from exosomes isolated from normal tissue of the same type (e.g., diseased breast tissue sample versus. normal breast tissue sample). A ratio of these expression intensities indicates the fold-change in gene expression between the test and control samples. Alternatively, if exosomes are not normally present in from normal tissues (e.g. breast) then absolute quantitation methods, as is known in the art, can be used to define the number of miRNA molecules present without the requirement of miRNA or mRNA isolated from exosomes derived from normal tissue.

Gene expression profiles can also be displayed in a number of ways. The most common method is to arrange raw fluorescence intensities or ratio matrix into a graphical dendogram where columns indicate test samples and rows indicate genes. The data is arranged so genes that have similar expression profiles are proximal to each other. The expression ratio for each gene is visualized as a color. For example, a ratio less than one (indicating down-regulation) may appear in the blue portion of the spectrum while a ratio greater than one (indicating up-regulation) may appear as a color in the red portion of the spectrum. Commercially available computer software programs are available to display such data.

mRNAs or miRNAs that are considered differentially expressed can be either over expressed or under expressed in patients with a disease relative to disease free individuals. Over and under expression are relative terms meaning that a detectable difference (beyond the contribution of noise in the system used to measure it) is found in the amount of expression of the mRNAs or miRNAs relative to some baseline. In this case, the baseline is the measured mRNA/miRNA expression of a non-diseased individual. The mRNA/miRNA of interest in the diseased cells can then be either over or under expressed relative to the baseline level using the same measurement method. Diseased, in this context, refers to an alteration of the state of a body that interrupts or disturbs, or has the potential to disturb, proper performance of bodily functions as occurs with the uncontrolled proliferation of cells. Someone is diagnosed with a disease when some aspect of that person's genotype or phenotype is consistent with the presence of the disease. However, the act of conducting a diagnosis or prognosis includes the determination of disease/status issues such as determining the likelihood of relapse or metastasis and therapy monitoring. In therapy monitoring, clinical judgments are made regarding the effect of a given course of therapy by comparing the expression of genes over time to determine whether the mRNA/miRNA expression profiles have changed or are changing to patterns more consistent with normal tissue.

Levels of over and under expression are distinguished based on fold changes of the intensity measurements of hybridized microarray probes. A 2× difference is preferred for making such distinctions or a p-value less than 0.05. That is, before an mRNA/miRNA is said to be differentially expressed in diseased/relapsing versus normal/non-relapsing cells, the diseased cell is found to yield at least 2 times more, or 2 times less intensity than the normal cells. The greater the fold difference, the more preferred is use of the gene as a diagnostic or prognostic tool. mRNA/miRNAs selected for the expression profiles of the instant invention have expression levels that result in the generation of a signal that is distinguishable from those of the normal or non-modulated genes by an amount that exceeds background using clinical laboratory instrumentation.

Statistical values can be used to confidently distinguish modulated from non-modulated mRNA/miRNA and noise. Statistical tests find the mRNA/miRNA most significantly different between diverse groups of samples. The Student's t-test is an example of a robust statistical test that can be used to find significant differences between two groups. The lower the p-value, the more compelling the evidence that the gene is showing a difference between the different groups. Nevertheless, since microarrays measure more than one mRNA/miRNA at a time, tens of thousands of statistical tests may be performed at one time. Because of this, one is unlikely to see small p-values just by chance and adjustments for this using a Sidak correction as well as a randomization/permutation experiment can be made. A p-value less than 0.05 by the t-test is evidence that the gene is significantly different. More compelling evidence is a p-value less then 0.05 after the Sidak correction is factored in. For a large number of samples in each group, a p-value less than 0.05 after the randomization/permutation test is the most compelling evidence of a significant difference.

In one embodiment, a method of generating a posterior probability score to enable diagnostic, prognostic, therapy-related, or physiological state specific bio-signature scores can be arrived at by obtaining mRNA or miRNA (biomarker) expression data from a statistically significant number of patient exosomes, such as cell-of-origin specific exosomes; applying linear discrimination analysis to the data to obtain selected biomarkers; and applying weighted expression levels to the selected biomarkers with discriminate function factor to obtain a prediction model that can be applied as a posterior probability score. Other analytical tools can also be used to answer the same question such as, logistic regression and neural network approaches.

For instance, the following can be used for linear discriminant analysis:

where, $I(p_s i_d)$=The log base 2 intensity of the probe set enclosed in parenthesis. d(cp)=The discriminant function for the disease positive class $d(C_N)$=The discriminant function for the disease negative class $P(_{CP})$=The posterior p-value for the disease positive class $P(_{CN})$=The posterior p-value for the disease negative class Numerous other well-known methods of pattern recognition are available. The following references provide some examples: Weighted Voting: Golub et al. (1999); Support Vector Machines: Su et al. (2001); and Ramaswamy et al. (2001); K-nearest Neighbors: Ramaswamy (2001); and Correlation Coefficients: van't Veer et al. (2002), all of which are herein incorporated by reference in their entireties.

Bio-signature portfolios, further described below, can be established such that the combination of biomarkers in the portfolio exhibit improved sensitivity and specificity relative to individual biomarkers or randomly selected combinations of biomarkers. In one embodiment, the sensitivity of the bio-signature portfolio can be reflected in the fold differences, for example, exhibited by a transcript's expression in the diseased state relative to the normal state. Specificity can be reflected in statistical measurements of the correlation of the signaling of transcript expression with the condition of interest. For example, standard deviation can be a used as such a measurement. In considering a group of biomarkers for inclusion in a bio-signature portfolio, a small standard deviation in expression measurements correlates with greater specificity. Other measurements of variation such as correlation coefficients can also be used in this capacity.

Another parameter that can be used to select mRNA/miRNA that generate a signal that is greater than that of the non-modulated mRNA/miRNA or noise is the use of a measurement of absolute signal difference. The signal generated by the modulated mRNA/miRNA expression is at least 20% different than those of the normal or non-modulated gene (on an absolute basis). It is even more preferred that such mRNA/miRNA produce expression patterns that are at least 30% different than those of normal or non-modulated mRNA/miRNA.

MiRNA can also be detected and measured by amplification from a biological sample and measured using methods described in U.S. Pat. No. 7,250,496, U.S. Application Publication Nos. 20070292878, 20070042380 or 20050222399 and references cited therein, each of which is herein incorporated by reference in its entirety.

Peptide nucleic acids (PNAs) which are a new class of synthetic nucleic acid analogs in which the phosphate-sugar polynucleotide backbone is replaced by a flexible pseudo-peptide polymer may be utilized in analysis of bio-signatures of exosomes. PNAs are capable of hybridizing with high affinity and specificity to complementary RNA and DNA sequences and are highly resistant to degradation by nucleases and proteinases. Peptide nucleic acids (PNAs) are an attractive new class of probes with applications in cytogenetics for the rapid in situ identification of human chromosomes and the detection of copy number variation (CNV). Multicolor peptide nucleic acid-fluorescence in situ hybridization (PNA-FISH) protocols have been described for the identification of several human CNV-related disorders and infectious diseases. PNAs can also be utilized as molecular diagnostic tools to non-invasively measure oncogene mRNAs with tumor targeted radionuclide-PNA-peptide chimeras. Methods of using PNAs are described further in Pellestor F et al., *Curr Pharm Des.* 2008; 14(24):2439-44, Tian X et al, *Ann N Y Acad. Sci.* 2005 November, 1059:106-44, Paulasova P and Pellestor F, *Annales de Génétique,* 47 (2004) 349-358, Stender H. *Expert Rev Mol. Diagn.* 2003 September; 3(5): 649-55. *Review*, Vigneault et al., *Nature Methods,* 5(9), 777±779 (2008), each reference is herein incorporated by reference in its entirety. These methods can be used to screen the genetic materials isolated from exosomes. When applying these techniques to cell-of-origin specific exosomes they can be used to identify a given molecular signal that directly pertains to the cell of origin.

In addition, mutational analysis may be carried out for mRNAs and DNA that are identified from the exosomes. For mutational analysis of targets or biomarkers that are of RNA origin, the RNA (mRNA, miRNA or other) can be reverse transcribed into cDNA and subsequently sequenced or assayed for known SNPs (by Taqman SNP assays, for example), or single nucleotide mutations, as well as using sequencing to look for insertions or deletions to determine mutations present in the cell-of-origin. Muliplexed ligation dependent probe amplification (MLPA) could alternatively be used for the purpose of identifying CNV in small and specific areas of interest. For example, once the total RNA has been obtained from isolated colon cancer-specific exosomes, cDNA can be synthesized and primers specific for exons 2 and 3 of the KRAS gene can be used to amplify these two exons containing codons 12, 13 and 61 of the KRAS gene. The same primers used for PCR amplification can be used for Big Dye Terminator sequence analysis on the ABI 3730 to identify mutations in exons 2 and 3 of KRAS. Mutations in these codons are known to confer resistance to drugs such as Cetuximab and Panitumimab. Methods of conducting mutational analysis are described in Maheswaran S et al., Jul. 2, 2008 (10.1056/NEJMoa0800668) and Orita, M et al, *PNAS* 1989, (86): 2766-70, each of which is herein incorporated by reference in its entirety. Other methods of conducting mutational analysis can include miRNA sequencing. Applications for identifying and profiling miRNAs can be done by cloning techniques and the use of capillary DNA sequencing or "next-generation" sequencing technologies. The new sequencing technologies currently available allow the identification of low-abundance miRNAs or those exhibiting modest expression differences between samples, which may not be detected by hybridization-based methods. Such new sequencing technologies include the massively parallel signature sequencing (MPSS) methodology described in Nakano et al. 2006, *Nucleic Acids Res.* 2006; 34:D731D735. doi: 10.1093/nar/gkj077, the Roche/454 platform described in Margulies et al. 2005, *Nature.* 2005; 437:376-380 or the Illumina sequencing platform described in Berezikov et al. *Nat. Genet.* 2006b; 38:1375-1377, each of which is incorporated by reference in its entirety.

Additional methods to determine bio-signatures include assaying biomarkers by allele-specific PCR which include specific primers to amplify and discriminate between two alleles of a gene simultaneously, single-strand conformation polymorphism (SSCP) which involves the electrophoretic separation of single-stranded nucleic acids based on subtle differences in sequence and DNA and RNA aptamers. DNA and RNA aptamers are short oligonucleotide sequences that can be selected from random pools based on their ability to bind a particular molecule with high affinity. Methods of using aptamers are described in Ulrich H et al, *Comb Chem High Throughput Screen.* 2006 September; 9(8):619-32, Ferreira C S et al, *Anal Bioanal Chem.* 2008 February; 390(4): 1039-50, Ferreira C S et al, *Tumour Biol.* 2006; 27(6):289-301, each of which is herein incorporated by reference in its entirety.

Exosome biomarkers can also be detected using fluorescence in situ hybridization (FISH). Methods of using FISH to detect and localize specific DNA sequences, localize specific mRNAs within tissue samples or identify chromosomal abnormalities are described in Shaffer D R et al, *Clin Cancer Res.* 2007 Apr. 1; 13(7):2023-9, Cappuzo F et al, *Journal of Thoracic Oncology, Volume* 2, Number 5, May 2007, Moroni M et al., *Lancet Oncol.* 2005 May; 6(5):279-86, each of which is herein incorporated by reference in its entirety.

Bio-Signature: Binding Agents

Bio-signatures of exosomes can comprise binding agents for exosomes. The binding agent can be DNA, RNA, aptamers, monoclonal antibodies, polyclonal antibodies, Fabs, Fab', single chain antibodies, synthetic antibodies, aptamers (DNA/RNA), peptoids, zDNA, peptide nucleic acids (PNAs), locked nucleic acids (LNAs), lectins, synthetic or naturally occurring chemical compounds (including but not limited to drugs, labeling reagents).

Binding agents can used to isolate exosomes by binding to exosomal components, as described above. The binding agents can be used to detect the exosomes, such as for detecting cell-of-origin specific exosomes. A binding agent or multiple binding agents can themselves form a binding agent profile that provides a bio-signature for an exosome. One or more binding agents can be selected from FIG. 2. For example, if an exosome population is detected or isolated using two, three or four binding agents in a differential detection or isolation of an exosome from a heterogeneous population of exosomes, the particular binding agent profile for the exosome population provides a bio-signature for the particular exosome population.

As an illustrative example, an exosome for analysis for lung cancer can be detected with one or more binding agents including, but not limited to, SCLC specific aptamer HCA 12, SCLC specific aptamer HCC03, SCLC specific aptamer HCH07, SCLC specific aptamer HCH01, A-p50 aptamer (NF-KB), Cetuximab, Panitumumab, Bevacizumab, L19 Ab, F16 Ab, anti-CD45 (anti-ICAM-1, aka UV3), or L2G7 Ab (anti-HGF), or any combination thereof.

An exosome for analysis for colon cancer can be detected with one or more binding agents including, but not limited to, angiopoietin 2 specific aptamer, beta-catenin aptamer, TCF1 aptamer, anti-Derlin1 ab, anti-RAGE, mAbgb3.1, Galectin-3, Cetuximab, Panitumumab, Matuzumab, Bevacizumab, or Mac-2, or any combination thereof.

An exosome for analysis for adenoma versus colorectal cancer (CRC) can be detected with one or more binding agents including, but not limited to, Complement C3, histidine-rich glycoprotein, kininogen-1, or Galectin-3, or any combination thereof.

An exosome for analysis for adenoma with low grade hyperplasia versus adenoma with high grade hyperplasia can be detected with a binding agent such as, but not limited to, Galectin-3 or any combination of binding agents specific for this comparison.

An exosome for analysis for CRC versus normal state can be detected with one or more binding agents including, but not limited to, anti-ODC mAb, anti-CEA mAb, or Mac-2, or any combination thereof.

An exosome for analysis for prostate cancer can be detected with one or more binding agents including, but not limited to, PSA, PSMA, TMPRSS2, mAB 5D4, XPSM-A9, XPSM-A10, Galectin-3, E-selectin, Galectin-1, or E4 (IgG2a kappa), or any combination thereof.

An exosome for analysis for melanoma can be detected with one or more binding agents including, but not limited to, Tremelimumab (anti-CTLA4), Ipilimumumab (anti-CTLA4), CTLA-4 aptamers, STAT-3 peptide aptamers, Galectin-1, Galectin-3, or PNA, or any combination thereof.

An exosome for analysis for pancreatic cancer can be detected with one or more binding agents including, but not limited to, H38-15 (anti-HGF) aptamer, H38-21 (anti-HGF) aptamer, Matuzumab, Cetuximanb, or Bevacizumab, or any combination thereof.

An exosome for analysis for brain cancer can be detected with one or more binding agents including, but not limited to, aptamer III.1 (pigpen) and/or TTA1 (Tenascin-C) aptamer, or any combination thereof.

An exosome for analysis for psoriasis can be detected with one or more binding agents including, but not limited to, E-selectin, ICAM-1, VLA-4, VCAM-1, alphaEbeta7, or any combination thereof.

An exosome for analysis for cardiovascular disease (CVD) can be detected with one or more binding agents including, but not limited to, RB007 (factor IXA aptamer), ARC1779 (anti VWF) aptamer, or LOX1, or any combination thereof.

An exosome for analysis for hematological malignancies can be detected with one or more binding agents including, but not limited to, anti-CD20 and/or anti-CD52, or any combination thereof.

An exosome for analysis for B-cell chronic lymphocytic leukemias can be detected with one or more binding agents including, but not limited to, Rituximab, Alemtuzumab, Apt48 (BCL6), R0-60, or D-R15-8, or any combination thereof.

An exosome for analysis for B-cell lymphoma can be detected with one or more binding agents including, but not limited to, Ibritumomab, Tositumomab, Anti-CD20 Antibodies, Alemtuzumab, Galiximab, Anti-CD40 Antibodies, Epratuzumab, Lumiliximab, Hu1D10, Galectin-3, or Apt48, or any combination thereof.

An exosome for analysis for Burkitt's lymphoma can be detected with one or more binding agents including, but not limited to, TD05 aptamer, IgM mAB (38-13), or any combination thereof.

An exosome for analysis for cervical cancer can be detected with one or more binding agents including, but not limited to, Galectin-9 and/or HPVE7 aptamer, or any combination thereof.

An exosome for analysis for endometrial cancer can be detected with one or more binding agents including, but not limited to, Galectin-1 or any combinations of binding agents specific for endometrial cancer.

An exosome for analysis for head and neck cancer can be detected with one or more binding agents including, but not limited to, (111)In-cMAb U36, anti-LOXL4, U36, BIWA-1, BIWA-2, BIWA-4, or BIWA-8, or any combination thereof.

An exosome for analysis for IBD can be detected with one or more binding agents including, but not limited to, ACCA (anti-glycan Ab), ALCA (anti-glycan Ab), or AMCA (anti-glycan Ab), or any combination thereof.

An exosome for analysis for diabetes can be detected with one or more binding agents including, but not limited to, RBP4 aptamer or any combination of binding agents specific for diabetes.

An exosome for analysis for fibromyalgia can be detected with one or more binding agents including, but not limited to, L-selectin or any combination of binding agents specific for fibromyalgia.

An exosome for analysis for multiple sclerosis (MS) can be detected with one or more binding agents including, but not limited to, Natalizumab (Tysabri) or any combination of binding agents specific for MS.

In addition, An exosome for analysis for rheumatic disease can be detected with one or more binding agents including, but not limited to, Rituximab (anti-CD20 Ab) and/or Keliximab (anti-CD4 Ab), or any combination of binding agents specific for rheumatic disease.

An exosome for analysis for Alzheimer disease can be detected with one or more binding agents including, but not limited to, TH14-BACE1 aptapers, S10-BACE1 aptapers, anti-Abeta, Bapineuzumab (AAB-001)-Elan, LY2062430 (anti-amyloid beta Ab)-Eli Lilly, or BACE1-Anti sense, or any combination thereof.

An exosome for analysis for Prion specific diseases can be detected with one or more binding agents including, but not limited to, rhuPrP(c) aptamer, DP7 aptamer, Thioaptamer 97, SAF-93 aptamer, 15B3 (anti-PrPSc Ab), monoclonal anti PrPSc antibody P1:1, 1.5D7, 1.6F4 Abs, mab 14D3, mab 4F2, mab 8G8, or mab 12F10, or any combination thereof.

An exosome for analysis for sepsis can be detected with one or more binding agents including, but not limited to, HA-1A mAb, E-5 mAb, TNF-alpha MAb, Afelimomab, or E-selectin, or any combination thereof.

An exosome for analysis for schizophrenia can be detected with one or more binding agents including, but not limited to, L-selectin and/or N-CAM, or any combination of binding agents specific for schizophrenia.

An exosome for analysis for depression can be detected with one or more binding agents including, but not limited to, GPIb or any combination of binding agents specific for depression.

An exosome for analysis for GIST can be detected with one or more binding agents including, but not limited to, ANTI-DOG1 Ab or any combination of binding agents specific for GIST.

An exosome for analysis for esophageal cancer can be detected with one or more binding agents including, but not limited to, CaSR binding agent or any combination of binding agents specific for esophageal cancer.

An exosome for analysis for gastric cancer can be detected with one or more binding agents including, but not limited to, Calpain nCL-2 binding agent and/or drebrin binding agent, or any combination of binding agents specific for gastric cancer.

An exosome for analysis for COPD can be detected with one or more binding agents including, but not limited to, CXCR3 binding agent, CCR5 binding agent, or CXCR6 binding agent, or any combination of binding agents specific for COPD.

An exosome for analysis for asthma can be detected with one or more binding agents including, but not limited to, VIP binding agent, PACAP binding agent, CGRP binding agent, NT3 binding agent, YKL-40 binding agent, S-nitrosothiols, SCCA2 binding agent, PAI binding agent, amphiregulin binding agent, or Periostin binding agent, or any combination of binding agents specific for asthma.

An exosome for analysis for vulnerable plaque can be detected with one or more binding agents including, but not limited to, Gd-DTPA-g-mimRGD (Alpha v Beta 3 integrin binding peptide), or MMP-9 binding agent, or any combination of binding agents specific for vulnerable plaque.

An exosome for analysis for ovarian cancer can be detected with one or more binding agents including, but not limited to, (90)Y-muHMFG1 binding agent and/or OC125 (anti-CA125 antibody), or any combination of binding agents specific for ovarian cancer.

The binding agent can be for a general exosome marker, or "housekeeping protein" or antigen, such as CD9, CD63, or CD81. For example, the binding agent can be an antibody for CD9, CD63, or CD81. The binding agent can also be for other exosomal proteins, such as for prostate specific exosomes, or cancer specific exosomes, such as PCSA, PSMA, EpCam, B7H3, or STEAP. For example, the binding agent can be an antibody for PCSA, PSMA, EpCam, B7H3, or STEAP.

Furthermore, additional cellular binding partners or binding agents may be identified by any conventional methods known in the art, or as described herein, and may additionally be used as a diagnostic, prognostic or therapy-related marker.

Bio-Signatures: Prostate Cancer, Colon Cancer and Ovarian Cancer

Prostate Cancer

An exosome bio-signature can be used to characterize prostate cancer. As described above, a bio-signature for prostate cancer can comprise a binding agent associated with prostate cancer (for example, as shown in FIG. 2), and one or more additional biomarkers, such as shown in FIG. 19. For example, a bio-signature for prostate cancer can comprise a binding agent to PSA, PSMA, TMPRSS2, mAB 5D4, XPSM-A9, XPSM-A10, Galectin-3, E-selectin, Galectin-1, E4 (IgG2a kappa), or any combination thereof, with one or more additional biomarkers, such as one or more miRNA, one or more DNA, one or more additional peptide, protein, or antigen associated with prostate cancer, such as, but not limited to, those shown in FIG. 19.

A bio-signature for prostate cancer can comprise an antigen associated with prostate cancer (for example, as shown in FIG. 1), and one or more additional biomarkers, such as shown in FIG. 19. A bio-signature for prostate cancer can comprise one or more antigens associated with prostate cancer, such as, but not limited to, KIA1, intact fibronectin, PSA, TMPRSS2, FASLG, TNFSF10, PSMA, NGEP, IL-7RI, CSCR4, CysLT1R, TRPM8, Kv1.3, TRPV6, TRPM8, PSGR, MISIIR, or any combination thereof. The bio-signature for prostate cancer can comprise one or more of the aforementioned antigens and one or more additional biomarkers, such as, but not limited to miRNA, mRNA, DNA, or any combination thereof.

A bio-signature for prostate cancer can also comprise one or more antigens associated with prostate cancer, such as, but not limited to, KIA1, intact fibronectin, PSA, TMPRSS2, FASLG, TNFSF10, PSMA, NGEP, IL-7RI, CSCR4, CysLT1R, TRPM8, Kv1.3, TRPV6, TRPM8, PSGR, MISIIR, or any combination thereof, and one or more miRNA biomarkers, such as, but not limited to, miR-202, miR-210, miR-296, miR-320, miR-370, miR-373, miR-498, miR-503, miR-184, miR-198, miR-302c, miR-345, miR-491, miR-513, miR-32, miR-182, miR-31, miR-26a-1/2, miR-200c, miR-375, miR-196a-1/2, miR-370, miR-425, miR-425, miR-194-1/2, miR-181a-1/2, miR-34b, let-71, miR-188, miR-25, miR-106b, miR-449, miR-99b, miR-93, miR-92-1/2, miR-125a, miR-141, let-7a, let-7b, let-7c, let-7d, let-7g, miR-16, miR-23a, miR-23b, miR-26a, miR-92, miR-99a, miR-103, miR-125a, miR-125b, miR-143, miR-145, miR-195, miR-199, miR-221, miR-222, miR-497, let-7f, miR-19b, miR-22, miR-26b, miR-27a, miR-27b, miR-29a, miR-29b, miR-30__5p, miR-30c, miR-100, miR-141, miR-148a, miR-205, miR-520h, miR-494, miR-490, miR-133a-1, miR-1-2, miR-218-2, miR-220, miR-128a, miR-221, miR-499, miR-329, miR-340, miR-345, miR-410, miR-126, miR-205, miR-7-1/2, miR-145, miR-34a, miR-487, or let-7b, or any combination thereof.

Furthermore, the miRNA for a prostate cancer bio-signature can be a miRNA that interacts with PFKFB3, RHAMM (HMMR), cDNA FLJ42103, ASPM, CENPF, NCAPG, Androgen Receptor, EGFR, HSP90, SPARC, DNMT3B, GART, MGMT, SSTR3, TOP2B, or any combination thereof, such as those described herein and depicted in FIG. 60. The miRNA can also be miR-9, miR-629, miR-141, miR-671-3p, miR-491, miR-182, miR-125a-3p, miR-324-5p, miR-148B, miR-222, or any combination thereof.

The bio-signature for prostate cancer can comprise one or more antigens associated with prostate cancer, such as, but not limited to, KIA1, intact fibronectin, PSA, TMPRSS2, FASLG, TNFSF10, PSMA, NGEP, IL-7RI, CSCR4, CysLT1R, TRPM8, Kv1.3, TRPV6, TRPM8, PSGR, MISIIR, or any combination thereof, and one or more additional biomarkers such as, but not limited to, the aforementioned miRNAs, mRNAs (such as, but not limited to, AR or PCA3), snoRNA (such as, but not limited to, U50) or any combination thereof.

The bio-signature can also comprise one or more gene fusions, such as ACSL3-ETV1, C15ORF21-ETV1, FLJ35294-ETV1, HERV-ETV1, TMPRSS2-ERG, TMPRSS2-ETV1/4/5, TMPRSS2-ETV4/5, SLC5A3-ERG, SLC5A3-ETV1, SLC5A3-ETV5 or KLK2-ETV4.

An exosome can be isolated and assayed for one or more miRNA and one or more antigens associated with prostate cancer to provide a diagnostic, prognostic or theranostic profile, such as the stage of the cancer, the efficacy of the cancer, or other characteristics of the cancer. Alternatively, the exosome can be directly assayed from a sample, such that the exosomes are not purified or concentrated prior to assaying for one or more miRNA or antigens associated with prostate cancer.

As depicted in FIG. 68, a prostate cancer bio-signature can comprise assaying EpCam, CD63, CD81, CD9, or any combination thereof, of an exosome. The prostate cancer bio-signature can comprise detection of EpCam, CD9, CD63, CD81, PCSA or any combination thereof. For example, the prostate cancer bio-signature can comprise EpCam, CD9, CD63 and CD81 or PCSA, CD9, CD63 and CD81 (see for example, FIG. 70A). The prostate cancer bio-signature can also comprise PCSA, PSMA, B7H3, or any combination thereof (see for example, FIG. 70B).

Furthermore, assessing a plurality of biomarkers can provide increased sensitivity, specificity, or signal intensity, as compared to assessing less than a plurality of biomarkers. For example, assessing PSMA and B7H3 can provide increased sensitivity in detection as compared to assessing PSMA or B7H3 alone. Assessing CD9 and CD63 can provide increased sensitivity in detection as compared to assessing CD or CD63 alone.

Prostate cancer can also be characterized based on meeting at least 1, 2, 3, 4, 5, 6, 7, 8, 9, or 10 criteria. For example, a number of different criteria can be used: 1) if the amount of exosomes in a sample from a subject is higher than a reference value; 2) if the amount of prostate cell derived exosomes is higher than a reference value; and 3) if the amount of exosomes with one or more cancer specific biomarkers is higher than a reference value, the subject is diagnosed with prostate cancer. The method can further include a quality control measure, such that the subject is diagnosed with prostate cancer if the determination of the other criteria The prostate cancer can be characterizing using one or more processes disclosed herein with at least 60, 61, 62, 63, 64, 65, 66, 67, 68, 69, or 70% sensitivity. The prostate cancer can be characterized with at least 80, 81, 82, 83, 84, 85, 86, or 87% sensitivity. For example, the prostate cancer can be characterized with at least 87.1, 87.2, 87.3, 87.4, 87.5, 87.6, 87.7, 87.8, 87.9, 88.0, or 89% sensitivity, such as with at least 90% sensitivity, such as at least 91, 92, 93, 94, 95, 96, 97, 98, 99 or 100% sensitivity.

The prostate cancer of a subject can also be characterized with at least 70, 71, 72, 73, 74, 75, 76, 77, 78, 79, 80, 81, 82, 83, 84, 85, 86, 87, 88, 89, 90, 91, 92, 93, 94, 95, 96, or 97% specificity, such as with at least 97.1, 97.2, 97.3, 97.4, 97.5, 97.6, 97.7, 97.8, 97.8, 97.9, 98.0, 98.1, 98.2, 98.3, 98.4, 98.5, 98.6, 98.7, 98.8, 98.9, 99.0, 99.1, 99.2, 99.3, 99.4, 99.5, 99.6, 99.7, 99.8, 99.9 or 100% specificity.

The prostate cancer can also be characterized with at least 70% sensitivity and at least 80, 90, 95, 99, or 100% specificity; at least 80% sensitivity and at least 80, 85, 90, 95, 99, or 100% specificity; at least 85% sensitivity and at least 80, 85, 90, 95, 99, or 100% specificity; at least 86% sensitivity and at least 80, 85, 90, 95, 99, or 100% specificity; at least 87% sensitivity and at least 80, 85, 90, 95, 99, or 100% specificity; at least 88% sensitivity and at least 80, 85, 90, 95, 99, or 100% specificity; at least 89% sensitivity and at least 80, 85, 90, 95, 99, or 100% specificity; at least 90% sensitivity and at least 80, 85, 90, 95, 99, or 100% specificity; at least 95% sensitivity and at least 80, 85, 90, 95, 99, or 100% specificity; at least 99% sensitivity and at least 80, 85, 90, 95, 99, or 100% specificity; or at least 100% sensitivity and at least 80, 85, 90, 95, 99, or 100% specificity.

Furthermore, the confidence level for determining the specificity, sensitivity, or both, may be with at least 90, 91, 92, 93, 94, 95, 96, 97, 98, or 99% confidence.

Colon Cancer

A colon cancer bio-signature can comprise any one or more antigens for colon cancer as listed in FIG. 1, any one or more binding agents associated with isolating an exosome for characterizing colon cancer (for example, as shown in FIG. 2), any one or more additional biomarkers, such as shown in FIG. 6.

The bio-signature can comprise one or more miRNA selected from the group consisting of miR-24-1, miR-29b-2, miR-20a, miR-10a, miR-32, miR-203, miR-106a, miR-17-5p, miR-30c, miR-223, miR-126, miR-128b, miR-21, miR-24-2, miR-99b, miR-155, miR-213, miR-150, miR-107, miR-191, miR-221, miR-20a, miR-510, miR-92, miR-513, miR-19a, miR-21, miR-20, miR-183, miR-96, miR-135b, miR-31, miR-21, miR-92, miR-222, miR-181b, miR-210, miR-20a, miR-106a, miR-93, miR-335, miR-338, miR-133b, miR-346, miR-106b, miR-153a, miR-219, miR-34a, miR-99b, miR-185, miR-223, miR-211, miR-135a, miR-127, miR-203, miR-212, miR-95, or miR-17-5p, or any combination thereof. The bio-signature can also comprise one or more underexpressed miRs such as miR-143, miR-145, miR-143, miR-126, miR-34b, miR-34c, let-7, miR-9-3, miR-34a, miR-145, miR-455, miR-484, miR-101, miR-145, miR-133b, miR-129, miR-124a, miR-30-3p, miR-328, miR-106a, miR-17-5p, miR-342, miR-192, miR-1, miR-34b, miR-215, miR-192, miR-301, miR-324-5p, miR-30a-3p, miR-34c, miR-331, and miR-148b.

The bio-signature can comprise assessing one or more genes, such as EFNB1, ERCC1, HER2, VEGF, and EGFR. A biomarker mutation for colon cancer that can be assessed in an exosome can also include one or more mutations of EGFR, KRAS, VEGFA, B-Raf, APC, or p53. The bio-signature can also comprise one or more proteins, ligands, or peptides that can be assessed of an exosome such as AFRs, Rabs, ADAM10, CD44, NG2, ephrin-B1, MIF, b-catenin, Junction, plakoglobin, glalectin-4, RACK1, tetrspanin-8, FasL, TRAIL, A33, CEA, EGFR, dipeptidase 1, hsc-70, tetraspanins, ESCRT, TS, PTEN, or TOPO1

An exosome can be isolated and assayed for to provide a diagnostic, prognostic or theranostic profile, such as the stage of the cancer, the efficacy of the cancer, or other characteristics of the cancer. Alternatively, the exosome can be directly assayed from a sample, such that the exosomes are not purified or concentrated prior to assaying for a bio-signature associated with colon cancer.

Figure 69A:
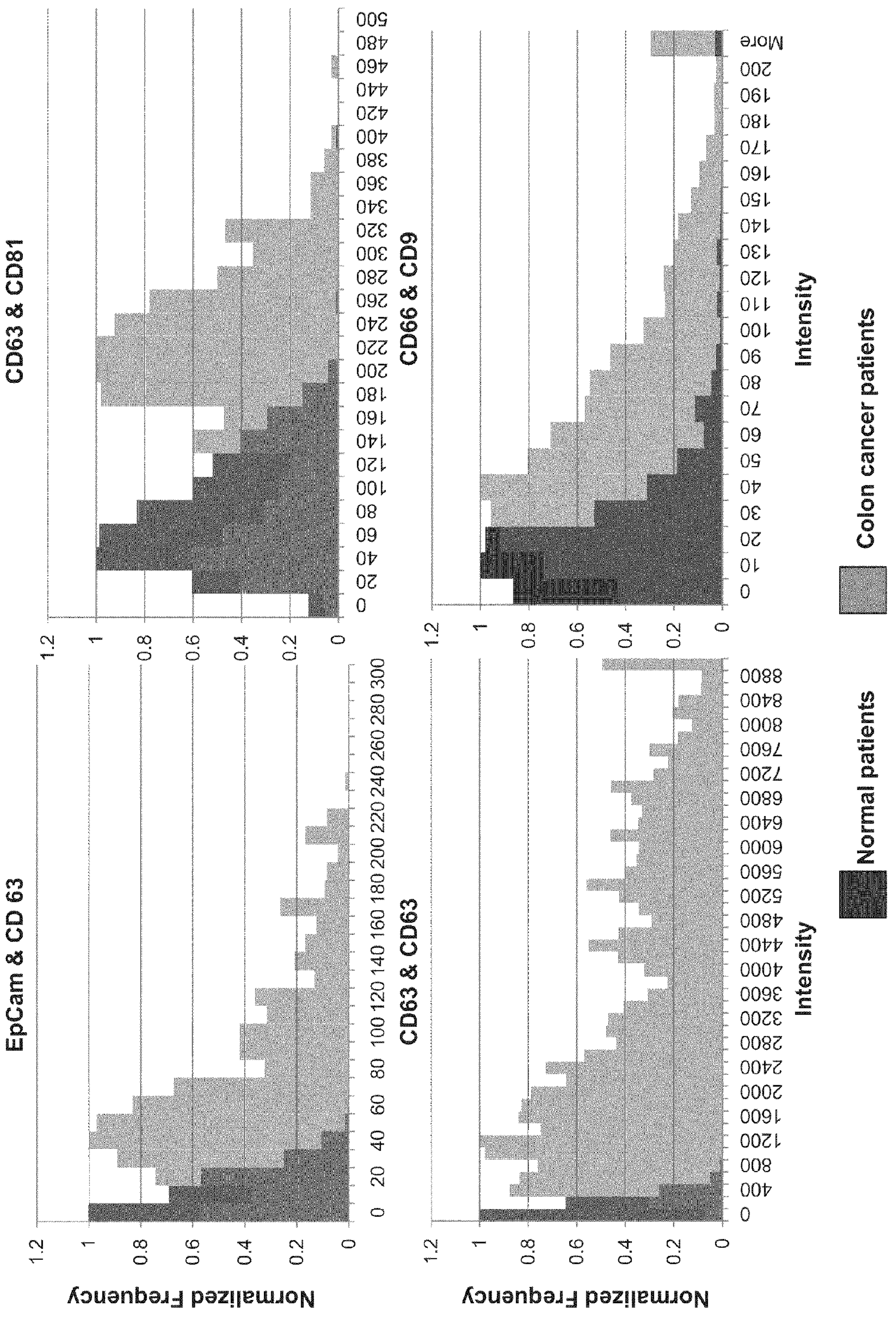
FIG. 69: illustrates colon cancer bio-signatures. (A) shows histograms of intensity values collected from various multiplexing experiments using the Luminex platform, where beads were functionalized with a capture antibody, incubated with exosomes purified form patient plasma, and then labeled with a detector antibody. The darker shaded bars (blue) represent the population from normals and the lighter shaded bars (green) are from colon cancer patients. (B) shows a normalized graph for each of the histograms shown in (A). (C) shows a histogram of intensity values collected from a Luminex experiment where beads where functionalized with CD66 antibody (the capture antibody), incubated with exosomes purified from patient plasma, and then labeled with a PE conjugated EpCam antibody (the detector antibody). The red population is from 6 normals and the green is from 21 colon cancer patients. Data from each individual was normalized to account for variation in the number of beads read by the Luminex machine, added together, and then normalized again to account for the different number of samples in each population.
Figure 69B:
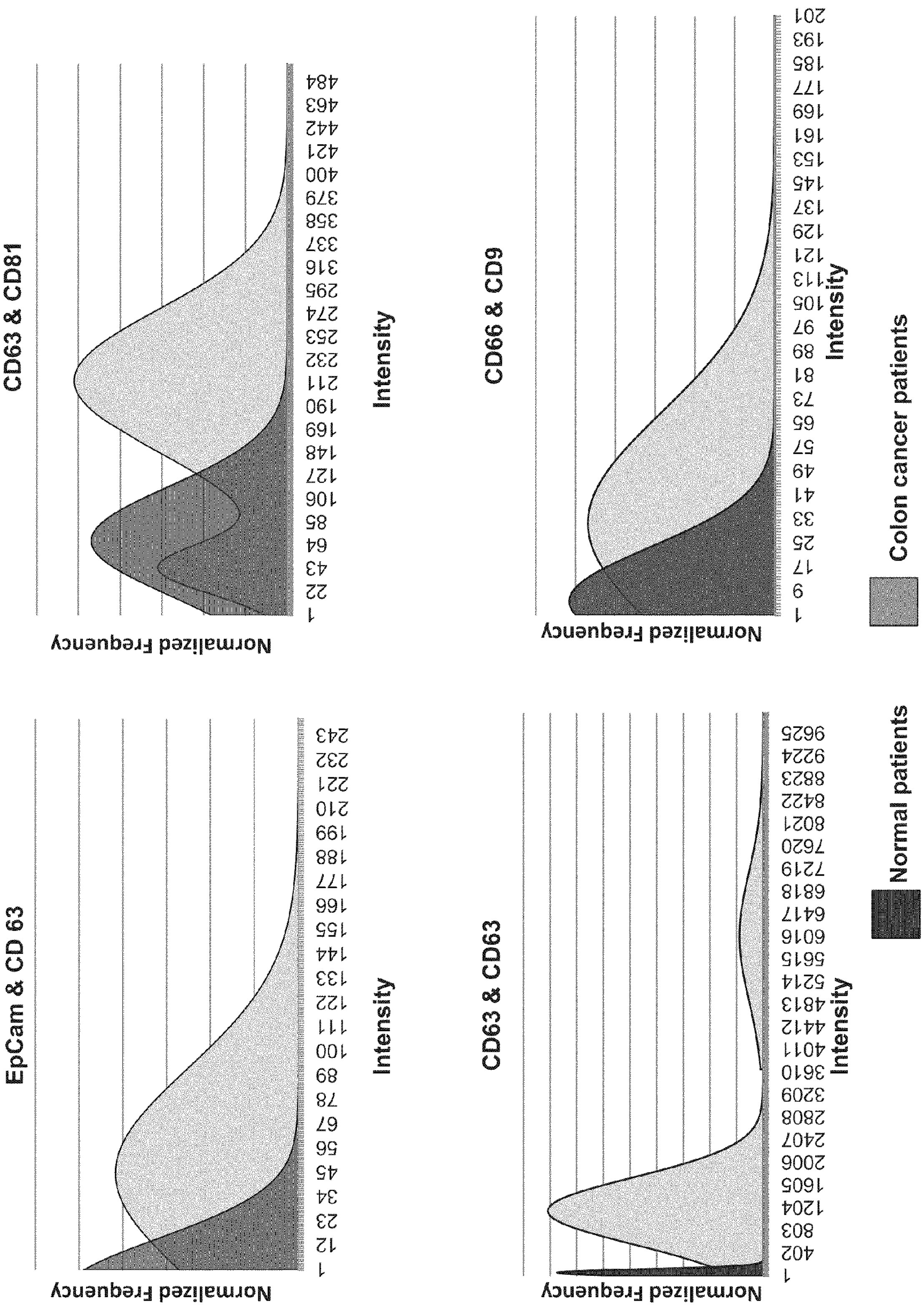
Figure 69C:
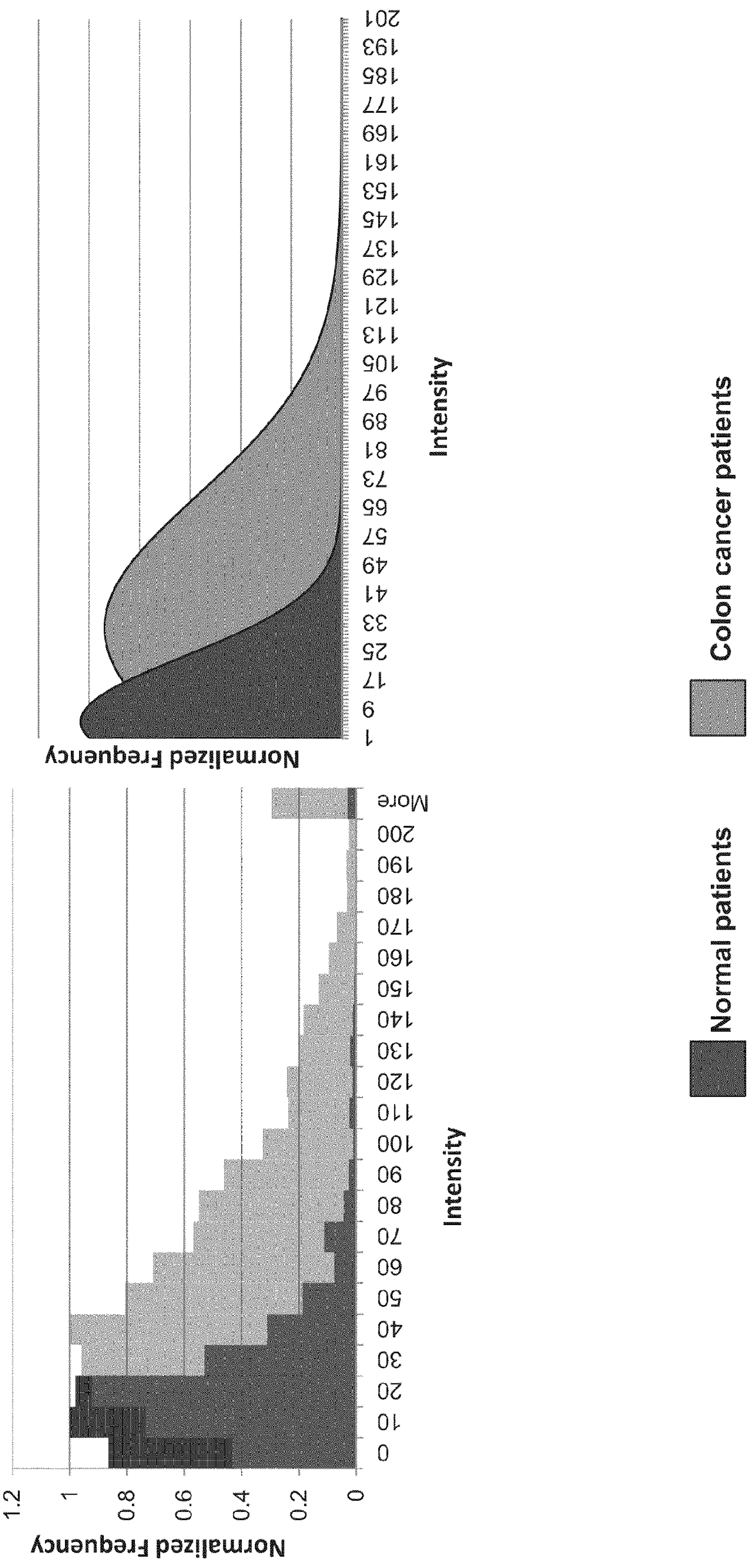

As depicted in FIG. 69, a colon cancer signature can comprise detection of EpCam, CD63, CD81, CD9, CD66, or any combination thereof, of an exosome. Furthermore, a colon cancer-bio-signature for various stages of cancer can comprise CD63, CD9, EpCam, or any combination thereof (see for example, FIGS. 71 and 72). For example, the bio-signature can comprise CD9 and EpCam.

The colon cancer can be characterizing using one or more processes disclosed herein with at least 60, 61, 62, 63, 64, 65, 66, 67, 68, 69, or 70% sensitivity. The colon cancer can be characterized with at least 80, 81, 82, 83, 84, 85, 86, or 87% sensitivity. For example, the colon cancer can be characterized with at least 87.1, 87.2, 87.3, 87.4, 87.5, 87.6, 87.7, 87.8, 87.9, 88.0, or 89% sensitivity, such as with at least 90% sensitivity, such as at least 91, 92, 93, 94, 95, 96, 97, 98, 99 or 100% sensitivity.

The colon cancer of a subject can also be characterized with at least 70, 71, 72, 73, 74, 75, 76, 77, 78, 79, 80, 81, 82, 83, 84, 85, 86, 87, 88, 89, 90, 91, 92, 93, 94, 95, 96, or 97% specificity, such as with at least 97.1, 97.2, 97.3, 97.4, 97.5, 97.6, 97.7, 97.8, 97.8, 97.9, 98.0, 98.1, 98.2, 98.3, 98.4, 98.5, 98.6, 98.7, 98.8, 98.9, 99.0, 99.1, 99.2, 99.3, 99.4, 99.5, 99.6, 99.7, 99.8, 99.9 or 100% specificity.

The colon cancer can also be characterized with at least 70% sensitivity and at least 80, 90, 95, 99, or 100%) specificity; at least 80% sensitivity and at least 80, 85, 90, 95, 99, or 100% specificity; at least 85% sensitivity and at least 80, 85, 90, 95, 99, or 100% specificity; at least 86% sensitivity and at least 80, 85, 90, 95, 99, or 100% specificity; at least 87% sensitivity and at least 80, 85, 90, 95, 99, or 100% specificity; at least 88% sensitivity and at least 80, 85, 90, 95, 99, or 100% specificity; at least 89% sensitivity and at least 80, 85, 90, 95, 99, or 100% specificity; at least 90% sensitivity and at least 80, 85, 90, 95, 99, or 100% specificity; at least 95% sensitivity and at least 80, 85, 90, 95, 99, or 100% specificity; at least 99% sensitivity and at least 80, 85, 90, 95, 99, or 100% specificity; or at least 100% sensitivity and at least 80, 85, 90, 95, 99, or 100% specificity.

Furthermore, the confidence level for determining the specificity, sensitivity, or both, may be with at least 90, 91, 92, 93, 94, 95, 96, 97, 98, or 99% confidence.

Ovarian Cancer

A bio-signature for characterizing ovarian cancer can comprise an antigen associated with ovarian cancer (for example, as shown in FIG. 1), and one or more additional biomarkers, such as shown in FIG. 4. In one embodiment, a bio-signature for ovarian cancer can comprise one or more antigens associated with ovarian cancer, such as, but not limited to, CD24, CA125, VEGF1, VEGFR2, HER2, MISIIR, or any combination thereof. The bio-signature for ovarian cancer can comprise one or more of the aforementioned antigens and one or more additional biomarker, such as, but not limited to miRNA, mRNA, DNA, or any combination thereof. The bio-signature for ovarian cancer can comprise one or more antigens associated with ovarian cancer, such as, but not limited to, CD24, CA125, VEGF1, VEGFR2, HER2, MISIIR; or any combination thereof, with one or more miRNA biomarkers, such as, but not limited to, miR-200a, miR-141, miR-200c, miR-200b, miR-21, miR-141, miR-200a, miR-200b, miR-200c, miR-203, miR-205, miR-214, miR-215, miR-199a, miR-140, miR-145, miR-125b-1, or any combination thereof.

A bio-signature for ovarian cancer can comprise one or more antigens associated with ovarian cancer, such as, but not limited to, CD24, CA125, VEGF1, VEGFR2, HER2, MISIIR, or any combination thereof, with one or more miRNA biomarkers (such as the aforementioned miRNA), mRNAs (such as, but not limited to, ERCC1, ER, TOPO1, TOP2A, AR, PTEN, HER2/neu, EGFR), mutations (including, but not limited to, those relating to KRAS and/or B-Raf) or any combination thereof.

An exosome can be isolated and assayed for one or more miRNA and one or more antigens associated with ovarian cancer to provide a diagnostic, prognostic or theranostic profile. Alternatively, the exosome can be directly assayed from a sample, such that the exosomes are not purified or concentrated prior to assaying for one or more miRNA or antigens associated with ovarian cancer.

Bio-Signatures: Assessing Organ Transplant Rejection and Autoimmune Conditions

An exosome can also be used for determining phenotypes such as organ distress and/or organ transplant rejection. As used herein organ transplant includes partial organ or tissue transplant. The presence, absence or levels of one or more biomarkers present in exosomes is assessed to monitor organ rejection or success. The level, or amount, of exosomes in the sample can also be used to assess organ rejection or success. The assessment can be determined with at least 80, 81, 82, 83, 84, 85, 86, 87, 88, 89, 90, 91, 92, 93, 94, 95, 96, 97, 98, or 99% specificity, sensitivity, or both. For example, the assessment can be determined with at least 97.5, 97.6, 97.7, 97.8, 97.8, 97.9, 98.0, 98.1, 98.2, 98.3, 98.4, 98.5, 98.6, 98.7, 98.8, 98.9, 99.0, 99.1, 998.2, 99.3, 99.4, 99.5, 99.6, 99.7, 99.8, 99.9% sensitivity, specificity, or both The exosome can be purified or concentrated prior to analysis. Alternatively, the level, or amount, of exosomes can be directly assayed from a sample, without prior purification or concentration. The exosome quantitated can be a cell-of-origin specific exosome. For example, a cell or tissue-specific exosome can be isolated using one or more binding agents specific for a particular organ. The cell-of-origin specific exosome can be assessed for one or more molecular features, such as one or more biomarkers associated with organ distress or organ transplant rejection. The presence, absence or levels of one or more biomarkers present in an isolated cell-of-origin specific exosome can be assessed to monitor organ rejection or success.

One or more exosomes can be analyzed for the assessment, detection or diagnosis of the rejection of a tissue or organ transplant by a subject. The tissue or organ transplant rejection can be hyperacute, acute, or chronic rejection. The exosome can also be analyzed for the assessment, detection or diagnosis of graft versus host disease in a subject. The subject can be the recipient of an autogenic, allogenic or xenogenic tissue or organ transplant.

The exosome can also be analyzed to detect the rejection of a tissue or organ transplant. The exosome may be produced by the tissue or organ transplant. Such tissues or organs include, but are not limited to, a heart, lung, pancreas, kidney, eye, cornea, muscle, bone marrow, skin, cartilage, bone, appendages, hair, face, tendon, stomach, intestine, vein, artery, differentiated cells, partially differentiated cells or stem cells.

The exosome can comprise at least one biomarker which is used to assess, diagnose or determine the probability or occurrence of rejection of a tissue or organ transplant by a subject. A biomarker can also be used to assess, diagnose or detect graft versus host disease in a subject. The biomarker can be a protein, a polysaccharide, a fatty acid or a nucleic acid (such as DNA or RNA). The biomarker can be associated with the rejection of a specific tissue or organ or systemic organ failure. More than one biomarker can be analyzed, for example, one or more proteins marker can be analyzed in combination with one or more nucleic acid markers. The biomarker may be an intracellular or extracellular marker.

The exosome can also be analyzed for at least one marker for the assessment, detection or diagnosis of cell apoptosis or necrosis associated with, or the causation of, rejection of a tissue or organ transplant by a subject.

The presence of a biomarker can be indicative of the rejection of a tissue or an organ by a subject, wherein the biomarker includes, but is not limited to, CD40, CD40 ligand, N-acetylmuramoyl-L-alanine amidase precursor, adiponectin, AMBP protein precursor, C4b-binding protein a-chain precursor, ceruloplasmin precursor, complement C3 precursor, complement component C9 precursor, complement factor D precursor, alpha 1-B-glycoprotein, beta2-glycoprotein I precursor, heparin cofactor II precursor, Immunoglobulin mu chain C region protein, Leucine-rich alpha2-glycoprotein precursor, pigment epithelium-derived factor precursor, plasma retinol-binding protein precursor, translation initiation factor 3 subunit 10, ribosomal protein L7, beta-transducin, 1-TRAF, or lysyl-tRNA synthetase.

Rejection of a kidney by a subject can also be detected by analyzing exosomes for the presence of beta-transducin. Rejection of transplanted tissue can also be detected by isolating a cell-of-origin specific exosome from CD40-expressing cells and detecting for the increase of Bcl-2 or TNFalpha.

Rejection of a liver transplant by a subject can be detected by analyzing the exosomes for the presence of an F1 antigen marker. The F1 antigen is, without being bound to theory, specific to liver to and can be used to detect an increase in liver cell-of-origin specific exosomes. This increase can be used as an early indication of organ distress/rejection.

Bronchiolitis obliterans due to bone marrow and/or lung transplantation or other causes, or graft atherosclerosis/graft phlebosclerosis can also be diagnosed by the analysis of an exosome.

An exosome can also be analyzed for the detection, diagnosis or assessment of an autoimmune or other immunological reaction-related phenotypes in a subject. Examples of such a disorder include, but are not limited to, systemic lupus erythematosus (SLE), discoid lupus, lupus nephritis, sarcoidosis, inflammatory arthritis, including juvenile arthritis, rheumatoid arthritis, psoriatic arthritis, Reiter's syndrome, ankylosing spondylitis, and gouty arthritis, multiple sclerosis, hyper IgE syndrome, polyarteritis nodosa, primary biliary cirrhosis, inflammatory bowel disease, Crohn's disease, celiac's disease (gluten-sensitive enteropathy), autoimmune hepatitis, pernicious anemia, autoimmune hemolytic anemia, psoriasis, scleroderma, myasthenia gravis, autoimmune thrombocytopenic purpura, autoimmune thyroiditis, Grave's disease, Hasimoto's thyroiditis, immune complex disease, chronic fatigue immune dysfunction syndrome (CFIDS), polymyositis and dermatomyositis, cryoglobulinemia, thrombolysis, cardiomyopathy, pemphigus vulgaris, pulmonary interstitial fibrosis, asthma, Churg-Strauss syndrome (allergic granulomatosis), atopic dermatitis, allergic and irritant contact dermatitis, urtecaria, IgE-mediated allergy, atherosclerosis, vasculitis, idiopathic inflammatory myopathies, hemolytic disease, Alzheimer's disease, chronic inflammatory demyelinating polyneuropathy and AIDs.

One or more biomarkers from the exosome can be used to assess, diagnose or determine the probability of the occurrence of an autoimmune or other immunological reaction-related disorder in a subject. The biomarker can be a protein, a polysaccharide, a fatty acid or a nucleic acid (such as DNA or RNA). The biomarker can be associated with a specific autoimmune disorder, a systemic autoimmune disorder, or other immunological reaction-related disorder. More than one biomarker can be analyzed. For example one or more protein markers can be analyzed in combination with one or more nucleic acid markers. The biomarker can be an intracellular or extracellular marker. The biomarker can also be used to detect, diagnose or assess inflammation.

Analysis of an exosome from subjects can be used identify subjects with inflammation associated with asthma, sarcoidosis, emphysema, cystic fibrosis, idiopathic pulmonary fibrosis, chronic bronchitis, allergic rhinitis and allergic diseases of the lung such as hypersensitivity pneumonitis, eosinophilic pneumonia, as well as pulmonary fibrosis resulting from collagen, vascular, and autoimmune diseases such as rheumatoid arthritis.

Exosome Compositions

Also provided herein is an isolated exosome with a particular bio-signature. The isolated exosome can comprise one or more biomarkers or bio-signatures specific for specific cell type, or for characterizing a phenotype, such as described above. For example, the isolated exosome can comprise one or more biomarkers, such as CD63, EpCam, CD81, CD9, PCSA, PSMA, B7H3, TNFR, MFG-E8, Rab, STEAP, 5T4, or CD59. The isolated exosome can have the one or more biomarkers on its surface of within the exosome. The isolated exosome can also comprise one or more miRNAs, such as miR-9, miR-629, miR-141, miR-671-3p, miR-491, miR-182, miR-125a-3p, miR-324-5p, miR-148B, or miR-222. An isolated exosome can comprise a biomarker such as CD66, and further comprise one or more biomarkers selected from the group consisting of: EpCam, CD63, or CD9. An isolated exosome can also comprise a fusion gene or protein, such as TMRSSG2:ERG.

An isolated exosome can also comprise one or more biomarkers, wherein the expression level of the one or more biomarkers is higher, lower, or the same for an isolated exosome as compared to an isolated exosome derived from a normal cell (ie. a cell derived from a subject without a phenotype of interest). For example, an isolated exosome can comprise one or more biomarkers selected from the group consisting of: B7H3, PSCA, MFG-E8, Rab, STEAP, PSMA, PCSA, 5T4, miR-9, miR-629, miR-141, miR-671-3p, miR-491, miR-182, miR-125a-3p, miR-324-5p, miR-148b, and miR-222, wherein the expression level of the one or more biomarkers is higher for an isolated exosome as compared to an isolated exosome derived from a normal cell. The isolated exosome can comprise at least 2, 3, 4, 5, 6, 7, 8, 9, 10, 11, 13, 14, 15, 16, 17, 18, or 19 of the biomarkers selected from the group. The isolated exosome can further comprising one or more biomarkers selected from the group consisting of: EpCam, CD63, CD59, CD81, or CD9.

An isolated exosome can comprise the biomarkers PCSA, EpCam, CD63, and CD8; the biomarkers PCSA, EpCam, B7H3 and PSMA. An isolated exosome can comprise the biomarkers miR-9, miR-629, miR-141, miR-671-3p, miR-491, miR-182, miR-125a-3p, miR-324-5p, miR-148b, and miR-222.

A composition comprising an isolated exosome is also provided herein. The composition can comprise one or more isolated exosomes. For example, the composition can comprise a plurality of exosomes, or one or more populations of exosomes.

The composition can be substantially enriched for exosomes. For example, the composition can be substantially absent of cellular debris, cells, or non-exosomal proteins, peptides, or nucleic acids (such as biological molecules not contained within the exosomes). The cellular debris, cells, or non-exosomal proteins, peptides, or nucleic acids, can be present in a biological sample along with exosomes. A composition can be substantially absent of cellular debris, cells, or non-exosomal proteins, peptides, or nucleic acids (such as biological molecules not contained within the exosomes), can be obtained by any method disclosed herein, such as through the use of one or more binding agents or capture agents for one or more exosomes. The exosomes can comprise at least 30, 40, 50, 60, 70, 80, 90, 95 or 99% of the total composition, by weight or by mass. The exosomes of the composition can be a heterogeneous or homogeneous population of exosomes. For example, a homogeneous population of exosomes comprises exosomes that are homogeneous as to one or more properties or characteristics. For example, the one or more characteristics can be selected from a group consisting of: one or more of the same biomarkers, a substantially similar or identical bio-signature, derived from the same cell type, exosomes of a particular size, and a combination thereof.

Thus, in some embodiments, the composition comprises a substantially enriched population of exosomes. The composition can be enriched for a population of exosomes that are at least 30, 40, 50, 60, 70, 80, 90, 95 or 99% homogeneous as to one or more properties or characteristics. For example, the one or more characteristics can be selected from a group consisting of: one or more of the same biomarkers, a substantially similar or identical bio-signature, derived from the same cell type, exosomes of a particular size, and a combination thereof. For example, the population of exosomes can be homogeneous by all having a particular bio-signature, having the same biomarker, having the same biomarker combination, or derived from the same cell type. In some embodiments, the composition comprises a substantially homogeneous population of exosomes, such as a population with a specific bio-signature, derived from a specific cell, or both.

The population of exosome can comprise one or more of the same biomarkers. The biomarker can be any component present in an exosome or on the exosome, such as any nucleic acid (e.g. RNA or DNA), protein, peptide, polypeptide, antigen, lipid, carbohydrate, or proteoglycan. For example, each exosome in a population can comprise the same or identical one or more biomarkers. In some embodiments, each exosome in the population comprises the same 1, 2, 3, 4, 5, 6, 3, 4, 5, 6, 7, 8, 9, 10, 11, 12, 13, 14, 15, 16, 17, 18, 19, 20, 25, 50, 75 or 100 biomarkers. The one or more biomarkers can be selected from FIGS. 1, 3-60.

The exosome population comprising the same or identical biomarker can refer to each exosome in the population having the same presence or absence, expression level, mutational state, or modification of the biomarker. For example, an enriched population of exosome can comprise exosomes, wherein each exosome has the same biomarker present, the same biomarker absent, the same expression level of a biomarker, the same modification of a biomarker, or the same mutation of a biomarker. The same expression level of a biomarker can refer to a quantitative or qualitative measurement, such as the exosomes in the population underexpress, overexpress, or have the same expression level of a biomarker as compared to a reference level. Alternatively, the same expression level of a biomarker can be a numerical value representing the expression of a biomarker that is similar for each exosome in a population. For example the copy number of a miRNA, the amount of protein, or the level of mRNA of each exosome can be quantitatively similar for each exosome in a population, such that the numerical amount of each exosome is ±1, 2, 3, 4, 5, 6, 7, 8, 9, 10, 15, or 20% from the amount in each other exosome in the population, as such variations are appropriate.

In some embodiments, the composition comprises a substantially enriched population of exosomes, wherein the exosomes in the enriched population has a substantially similar or identical bio-signature. The bio-signature can comprise one or more exosomal characteristic such as the level or amount of exosomes, temporal evaluation of the variation in exosomal half-life, circulating exosomal half-life or exosomal metabolic half-life, or the activity of an exosome. The bio-signature can also comprise the presence or absence, expression level, mutational state, or modification of a biomarker, such as those described herein.

The bio-signature of each exosome in the population can be at least 30, 40, 50, 60, 70, 80, 90, 95, or 99% identical. In some embodiments, the bio-signature of each exosome is 100% identical. The bio-signature of each exosome in the enriched population can have the same 1, 2, 3, 4, 5, 6, 3, 4, 5, 6, 7, 8, 9, 10, 11, 12, 13, 14, 15, 16, 17, 18, 19, 20, 25, 50, 75 or 100 exosomal characteristics. For example, a bio-signature of an exosome in an enriched population can be the presence of a first biomarker, the presence of a second biomarker, and the underexpression of a third biomarker. Another exosome in the same population can be 100% identical, having the same first and second biomarkers present and underexpression of the third biomarker. Alternatively, an exosome in the same population can have the same first and second biomarkers, but not have underexpression of the third biomarker.

In some embodiments, the composition comprises a substantially enriched population of exosomes, wherein the exosomes are derived from the same cell type. For example, the exosomes can all be derived from cells of a specific tissue, cells from a specific tumor of interest or a diseased tissue of interest, circulating tumor cells, or cells of maternal or fetal origin. The exosomes can all be derived from tumor cells. The exosomes can all be derived from lung, pancreas, stomach, intestine, bladder, kidney, ovary, testis, skin, colorectal, breast, prostate, brain, esophagus, liver, placenta, or fetal cells.

The composition comprising a substantially enriched population of exosomes can also comprise exosomes are of a particular size. For example, the exosomes can all a diameter of greater than about 10, 20, or 30 nm. They can all have a diameter of about 30-1000 nm, about 30-800 nm, about 30-200 nm, or about 30-100 nm. In some embodiments, the exosomes can all have a diameter of less than about 10,000 nm, 1000 nm, 800 nm, 500 nm, 200 nm, 100 nm or 50 nm.

The population of exosomes homogeneous for one or more characteristics can comprises at least about 30, 40, 50, 60, 70, 80, 90, 95, or 99% of the total exosome population of the composition. In some embodiments, a composition comprising a substantially enriched population of exosomes comprises at least 2, 3, 4, 5, 10, 20, 25, 50, 100, 250, 500, or 1000 times the concentration of an exosome as compared to a concentration of the exosome in a biological sample from which the composition was derived. In yet other embodiments, the composition can further comprise a second enriched population of exosomes, wherein the population of exosomes is at least 30% homogeneous as to one or more characteristics, as described herein.

Multiplex analysis can be used to obtain a composition substantially enriched for more than one population of exosomes, such as at least 2, 3, 4, 5, 6, 7, 8, 9, 10 exosome populations. Each substantially enriched exosome population can comprise at least 5, 10, 15, 20, 25, 30, 35, 40, 45, 46, 47, 48, or 49% of the composition, by weight or by mass. In some embodiments, the substantially enriched exosome populations comprises at least about 30, 40, 50, 60, 70, 80, 90, 95, or 99% of the composition, by weight or by mass.

A substantially enriched population of exosomes can be obtained by using one or more methods, processes, or systems as disclosed herein. For example, isolation of a population of exosomes from a sample can be performed by using one or more binding agents for one or more biomarkers of an exosome, such as using two or more binding agents that target two or more biomarkers of an exosome. One or more capture agents can be used to obtain a substantially enriched population of exosomes. One or more detection agents can be used to identify a substantially enriched population of exosomes.

In one embodiment, a population of exosomes with a particular bio-signature is obtained by using one or more binding agents for the biomarkers of the bio-signature. The exosomes can be isolated resulting in a composition comprising a substantially enriched population of exosomes with the particular bio-signature. In another embodiment, a population of exosomes with a particular bio-signature of interest can be obtained by using one or more binding agents for biomarkers that are not a component of the bio-signature of interest. Thus, the binding agents can be used to remove the exosomes that do not have the bio-signature of interest and the resulting composition is substantially enriched for the population of exosomes with the particular bio-signature of interest. The resulting composition can be substantially absent of the exosomes comprising a biomarker for the binding agent.

Detection System and Kits

Also provided is a detection system configured to determine one or more bio-signatures for an exosome. The detection system can be used to detect a heterogeneous population of exosomes or one or more homogeneous population of exosomes. The detection system can be configured to detect a plurality of exosomes, wherein at least a subset of said plurality of exosomes comprises a different bio-signature from another subset of said plurality of exosomes. The detection system detect at least 2, 3, 4, 5, 6, 7, 8, 9, 10, 15, 20, 25, 30, 40, 50, 60, 70, 80, 90, or 100 different subsets of exosomes, wherein each subset of exosomes comprises a different bio-signature. For example, a detection system, such as using one or more methods, processes, and compositions disclosed herein, can be used to detect at least 2, 3, 4, 5, 6, 7, 8, 9, 10, 15, 20, 25, 30, 40, 50, 60, 70, 80, 90, or 100 different populations of exosomes.

The detection system can be configured to assess at least 2, 3, 4, 5, 6, 7, 8, 9, 10, 15, 20, 25, 30, 40, 50, 60, 70, 80, 90, 100, 1000, 2500, 5000, 7500, 10,000, 100,000, 150,000, 200,000, 250,000, 300,000, 350,000, 400,000, 450,000, 500,000, 750, 000, or 1,000,000 different biomarkers for one or more exosomes. In some embodiments, the one or more biomarkers are selected from FIG. 1, 3-60, or as disclosed herein. The detection system can be configured to assess a specific population of exosomes, such as exosomes from a specific cell-of-origin, or to assess a plurality of specific populations of exosomes, wherein each population of exosomes has a specific bio-signature.

The detection system can be a low density detection system or a high density detection system. For example, a low density detection system can detect up to 1, 2, 3, 4, 5, 6, 7, 8, 9, or 10 different exosome populations, whereas a high density detection system can detect at least about 15, 20, 25, 50, or 100 different exosome populations In another embodiment, a low density detection system can detect up to about 100, 200, 300, 400, or 500 different biomarkers, whereas a high density detection system can detect at least about 750, 1000, 2000, 3000, 4000, 5000, 6000, 7000, 8000, 9,000, 10,000, 15,000, 20,000, 25,000, 50,000, or 100,000 different biomarkers. In yet another embodiment, a low density detection system can detect up to about 100, 200, 300, 400, or 500 different bio-signatures or biomarker combinations, whereas a high density detection system can detect at least about 750, 1000, 2000, 3000, 4000, 5000, 6000, 7000, 8000, 9,000, 10,000, 15,000, 20,000, 25,000, 50,000, or 100,000 bio-signatures or biomarker combinations.

The detection system can comprise a probe that selectively hybridizes to an exosome. The detection system can comprise a plurality of probes to detect an exosome. In some embodiments, a plurality of probes is used to detect the amount of exosomes in a heterogeneous population of exosomes. In yet other embodiments, a plurality of probes is used to detect a homogeneous population of exosomes. A plurality of probes can be used to isolate or detect at least two different subsets of exosomes, wherein each subset of exosomes comprises a different bio-signature.

A detection system, such as using one or more methods, processes, and compositions disclosed herein, can comprise a plurality of probes configured to detect, or isolate, such as using one or more methods, processes, and compositions disclosed herein at least 2, 3, 4, 5, 6, 7, 8, 9, 10, 15, 20, 25, 30, 40, 50, 60, 70, 80, 90, or 100 different subsets of exosomes, wherein each subset of exosomes comprises a different bio-signature.

For example, a detection system can comprise a plurality of probes configured to detect at least 2, 3, 4, 5, 6, 7, 8, 9, 10, 15, 20, 25, 30, 40, 50, 60, 70, 80, 90, or 100 different populations of exosomes. The detection system can comprise a plurality of probes configured to selectively hybridize to at least 2, 3, 4, 5, 6, 7, 8, 9, 10, 15, 20, 25, 30, 40, 50, 60, 70, 80, 90, 100, 1000, 2500, 5000, 7500, 10,000, 100,000, 150,000, 200,000, 250,000, 300,000, 350,000, 400,000, 450,000, 500,000, 750, 000, or 1,000,000 different biomarkers for one or more exosomes. In some embodiments, the one or more biomarkers are selected from FIG. 1, 3-60, or as disclosed herein. The plurality of probes can be configured to assess a specific population of exosomes, such as exosomes from a specific cell-of-origin, or to assess a plurality of specific populations of exosomes, wherein each population of exosomes has a specific bio-signature.

The detection system can be a low density detection system or a high density detection system comprising probes to detect exosomes. For example, a low density detection system can comprise probes to detect up to 1, 2, 3, 4, 5, 6, 7, 8, 9, or 10 different exosome populations, whereas a high density detection system can comprise probes to detect at least about 15, 20, 25, 50, or 100 different exosome populations In another embodiment, a low density detection system can comprise probes to detect up to about 100, 200, 300, 400, or 500 different biomarkers, whereas a high density detection system can comprise probes to detect at least about 750, 1000, 2000, 3000, 4000, 5000, 6000, 7000, 8000, 9,000, 10,000, 15,000, 20,000, 25,000, 50,000, or 100,000 different biomarkers. In yet another embodiment, a low density detection system can comprise probes to detect up to about 100, 200, 300, 400, or 500 different bio-signatures or biomarker combinations, whereas a high density detection system can comprise probes to detect at least about 750, 1000, 2000, 3000, 4000, 5000, 6000, 7000, 8000, 9,000, 10,000, 15,000, 20,000, 25,000, 50,000, or 100,000 bio-signatures or biomarker combinations.

The probes can be specific for detecting a specific exosome population, for example an exosome with a particular bio-signature, and as described above. A plurality of probes for detecting prostate specific exosomes is also provided. A plurality of probes can comprise probes for detecting one or more of the following biomarkers: CD9, PSCA, TNFR, CD63, MFG-E8, EpCAM, Rab, CD81, STEAP, PCSA, 5T4, EpCAM, PSMA, CD59, CD66, CD24 and B7H3. A plurality of probes for detecting Bcl-XL, ERCC1, Keratin 15, CD81/TAPA-1, CD9, Epithelial Specific Antigen (ESA), and Mast Cell Chymase can also be provided. A plurality of probes for detecting one or more miRNAs of an exosome can comprise probes for detecting one or more of the following miRNAs: miR-9, miR-629, miR-141, miR-671-3p, miR-491, miR-182, miR-125a-3p, miR-324-5p, miR-148b, and miR-222, The probes may be attached to a solid substrate, such as an array or bead. Alternatively, the probes are not attached. The detection system may be an array based system, a sequencing system, a PCR-based system, or a bead-based system, such as described above. For example, the detection system can be a microfluidic device as described above.

The detection system may be part of a kit. Alternatively, the kit may comprise the one or more probe sets, or plurality of probes, as described herein. The kit may comprise probes for detecting an isolated exosome, a plurality of exosomes, such as exosomes in a heterogeneous population. The kit may comprise probes for detecting a homogeneous population of exosomes. For example, the kit may comprise probes for detecting a population of specific cell-of-origin exosomes, or exosomes with the same specific bio-signature.

Portfolios

Portfolios of multiplexed markers to guide clinical decisions and disease detection and management can be established such that the combination of bio-signatures in the portfolio exhibit improved sensitivity and specificity relative to individual bio-signatures or randomly selected combinations of bio-signatures. In the context of the instant invention, the sensitivity of the portfolio can be reflected in the fold differences exhibited by a bio-signature's expression in the diseased state relative to the normal state. Specificity can be reflected in statistical measurements of the correlation of the signaling of gene expression, for example, with the condition of interest (e.g. standard deviation can be a used as such a measurement). In considering a group of bio-signature for inclusion in a portfolio, a small standard deviation in measurements correlates with greater specificity. Other measurements of variation such as correlation coefficients can also be used in this capacity.

When combining biomarkers or bio-signatures in this invention In Vitro Diagnostic Multivariate Index Assays (IVDMIAs) guidelines and regulations may apply. IVDMIAs can apply to bio-signatures as defined as a set of 2 or more markers composed of any combination of genes, gene alterations, mutations, amplifications, deletions, polymorphisms or methylations, or proteins, peptides, polypeptides or RNA molecules, miRNAs, mRNAs, snoRNAs, hnRNAs or RNA that can be grouped so that information obtained about the set of bio-signatures in the group provides a sound basis for making a clinically relevant judgment such as a diagnosis, prognosis, or treatment choice. These sets of bio-signatures make up various portfolios of the invention. As with most diagnostic markers, it is often desirable to use the fewest number of markers sufficient to make a correct medical judgment. This prevents a delay in treatment pending further analysis as well inappropriate use of time and resources. Preferably, portfolios are established such that the combination of bio-signatures in the portfolio exhibit improved sensitivity and specificity relative to individual bio-signatures or randomly selected combinations of bio-signatures. In the context of the instant invention, the sensitivity of the portfolio can be reflected in the fold differences exhibited by a bio-signature's expression in the diseased state relative to the normal state. Specificity can be reflected in statistical measurements of the correlation of the signaling of gene expression, for example, with the condition of interest. In considering a group of markers in a bio-signature for inclusion in a portfolio, standard deviations, variances, co-variances, correlation coefficients, weighted averages, arithmetic sums, means, multiplicative values, weighted or balanced values or any mathematical manipulation of the values of 2 or more markers that can together be used to calculate a value or score that taken as a whole can be shown to produce greater sensitivity, specificity, negative predictive value, positive predictive value or accuracy can also be used in this capacity and are within the scope of this invention.

In another embodiment pattern recognition methods can be used. One example involves comparing biomarker expression profiles for various biomarkers (or bio-signature portfolios) to ascribe diagnoses. The expression profiles of each of the biomarker comprising the bio-signature portfolio are fixed in a medium such as a computer readable medium.

In one example, a table can be established into which the range of signals (e.g., intensity measurements) indicative of disease or physiological state is input. Actual patient data can then be compared to the values in the table to determine whether the patient samples are normal, benign, diseased, or represent a specific physiological state. In a more sophisticated embodiment, patterns of the expression signals (e.g., fluorescent intensity) are recorded digitally or graphically. In the example of RNA expression patterns from the biomarker portfolios used in conjunction with patient samples are then compared to the expression patterns. Pattern comparison software can then be used to determine whether the patient samples have a pattern indicative of the disease, a given prognosis, a pattern that indicates likeliness to respond to therapy, or a pattern that is indicative of a particular physiological state. The expression profiles of the samples are then compared to the portfolio of a control cell. If the sample expression patterns are consistent with the expression pattern(s) for disease, prognosis, or therapy-related response then (in the absence of countervailing medical considerations) the patient is diagnosed as meeting the conditions that relate to these various circumstances. If the sample expression patterns are consistent with the expression pattern derived from the normal/control exosome population then the patient is diagnosed negative for these conditions.

In another exemplary embodiment, a method for establishing biomarker expression portfolios is through the use of optimization algorithms such as the mean variance algorithm widely used in establishing stock portfolios. This method is described in detail in the U.S. Application Publication No. 20030194734, incorporated herein by reference. Alternatively, measured DNA alterations, changes in mRNA, protein, or metabolites to phenotypic readouts of efficacy and toxicity may be modeled and analyzed using algorithms, systems and methods described in U.S. Pat. Nos. 7,089,168, 7,415,359 and U.S. Application Publication Nos. 20080208784, 20040243354, or 20040088116, each of which is herein incorporated by reference in its entirety.

An exemplary process of bio-signature portfolio selection and characterization of an unknown is summarized as follows:

1. Choose baseline class.

2. Calculate mean, and standard deviation of each biomarker for baseline class samples.

3. Calculate (X*Standard Deviation+Mean) for each biomarker. This is the baseline reading from which all other samples will be compared. X is a stringency variable with higher values of X being more stringent than lower.

4. Calculate ratio between each Experimental sample versus baseline reading calculated in step 3.

5. Transform ratios such that ratios less than 1 are negative (eg. using Log base 10). (Under expressed biomarkers now correctly have negative values necessary for MV optimization).

6. These transformed ratios are used as inputs in place of the asset returns that are normally used in the software application.

7. The software will plot the efficient frontier and return an optimized portfolio at any point along the efficient frontier.

8. Choose a desired return or variance on the efficient frontier.

9. Calculate the Portfolio's Value for each sample by summing the multiples of each gene's intensity value by the weight generated by the portfolio selection algorithm.

10. Calculate a boundary value by adding the mean Bio-signature Portfolio Value for Baseline groups to the multiple of Y and the Standard Deviation of the Baseline's Bio-signature Portfolio Values. Values greater than this boundary value shall be classified as the Experimental Class.

11. Optionally one can reiterate this process until best prediction.

The process of selecting a bio-signature portfolio can also include the application of heuristic rules. Preferably, such rules are formulated based on biology and an understanding of the technology used to produce clinical results. More preferably, they are applied to output from the optimization method. For example, the mean variance method of bio-signature portfolio selection can be applied to microarray data for a number of biomarkers differentially expressed in subjects with a specific disease. Output from the method would be an optimized set of biomarkers that could include those that are expressed in exosomes as well as in diseased tissue. If samples used in the testing method are obtained from exosomes and certain biomarkers differentially expressed in instances of disease or physiological state could also be differentially expressed in exosomes, then a heuristic rule can be applied in which a bio-signature portfolio is selected from the efficient frontier excluding those that are differentially expressed in exosomes. Of course, the rule can be applied prior to the formation of the efficient frontier by, for example, applying the rule during data pre-selection.

Other statistical, mathematical and computational algorithms for the analysis of linear and non-linear feature subspaces, feature extraction and signal deconvolution in large scale datasets to identify exosome-derived multiplex analyte profiles for diagnosis, prognosis and therapy selection and/or characterization of define physiological states can be done using any combination of unsupervised analysis methods, including but not limited to: principal component analysis (PCA) and linear and non-linear independent component analysis (ICA); blind source separation, nongaussinity analysis, natural gradient maximum likelihood estimation; joint-approximate diagonalization; eigenmatrices; Gaussian radical basis function, kernel and polynominal kernel analysis sequential floating forward selection.

Computer Systems

Figure 62:
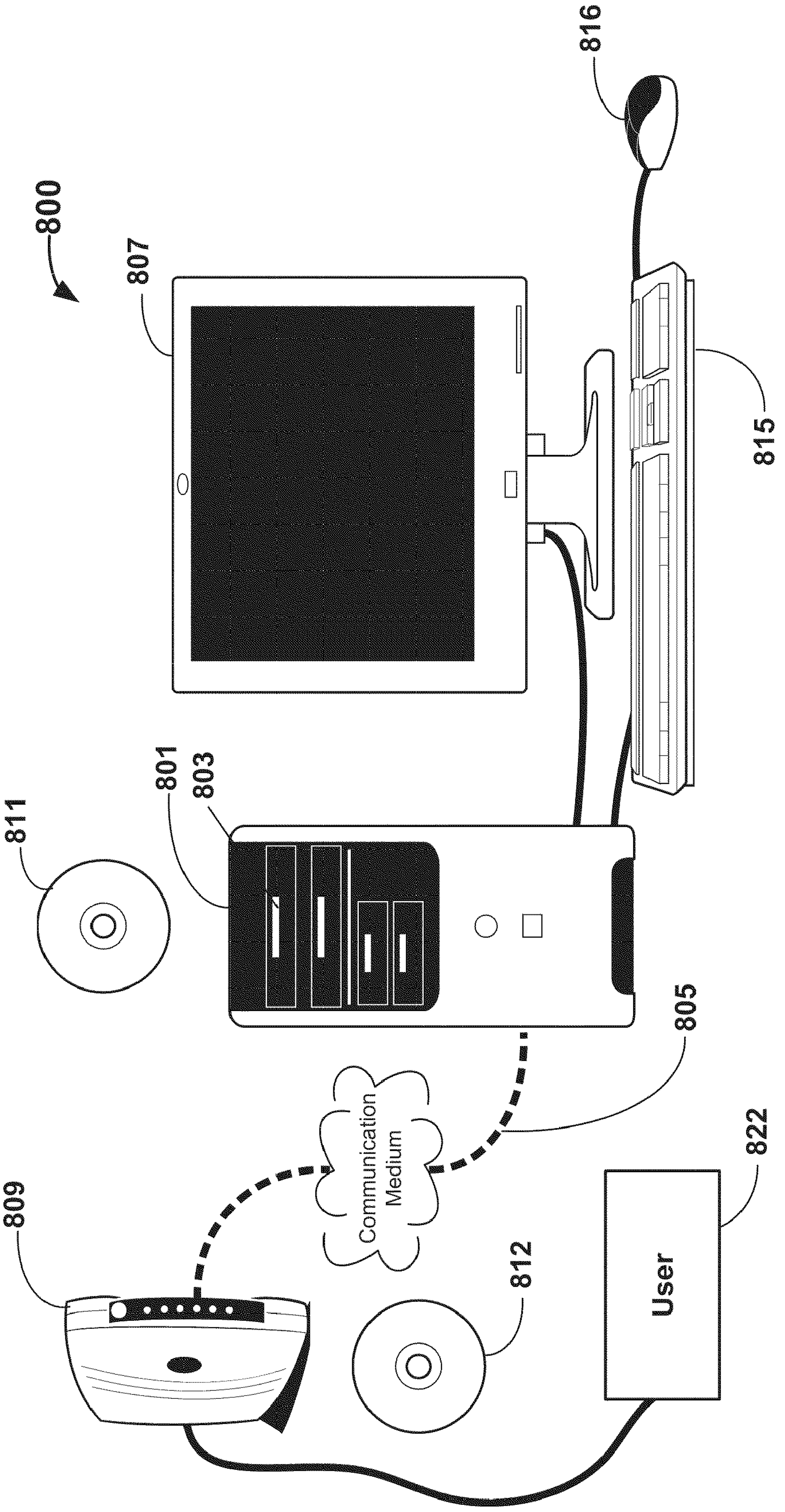
FIG. 62 illustrates a computer system that can be used in some exemplary embodiments of the invention.

An exosome can be assayed for molecular features, for example, by determining an amount, presence or absence of one or more biomarkers such as listed FIGS. 1, 3-60. The data generated can be used to produce a bio-signature, which can be stored and analyzed by a computer system, such as shown in FIG. 62. The assaying or correlating of the bio-signature with one or more phenotypes can also be performed by computer systems, such as by using computer executable logic.

A computer system, such as shown in FIG. 62, can be used to transmit data and results following analysis. Accordingly, FIG. 62 is a block diagram showing a representative example logic device through which results from exosome analysis can be reported or generated. FIG. 62 shows a computer system (or digital device) 800 to receive and store data generated from exosome analysis, analyze the data to generate one or more bio-signatures, and produce a report of the one or more bio-signatures. The computer system can also perform comparisons and analyses of bio-signatures generated, and transmit the results. Alternatively, the computer system can receive raw data of exosome analysis, such as through transmission of the data over a network, and perform the analysis.

The computer system 800 may be understood as a logical apparatus that can read instructions from media 811 and/or network port 805, which can optionally be connected to server 809 having fixed media 812. The system shown in FIG. 62 includes CPU 801, disk drives 803, optional input devices such as keyboard 815 and/or mouse 816 and optional monitor 807. Data communication can be achieved through the indicated communication medium to a server 809 at a local or a remote location. The communication medium can include any means of transmitting and/or receiving data. For example, the communication medium can be a network connection, a wireless connection or an Internet connection. Such a connection can provide for communication over the World Wide Web. It is envisioned that data relating to the present invention can be transmitted over such networks or connections for reception and/or review by a party 822. The receiving party 822 can be but is not limited to an individual, a health care provider or a health care manager. In one embodiment, a computer-readable medium includes a medium suitable for transmission of a result of an analysis of a biological sample, such as exosome bio-signatures. The medium can include a result regarding an exosome bio-signature of a subject, wherein such a result is derived using the methods described herein.

Ex vivo Harvesting of Exosomes

Exosomes for analysis and determination of a phenotype can also be from ex vivo harvesting. Cells can be cultured and that exosomes released from cells of interest in culture either result spontaneously or can be stimulated to release exosomes into the medium. (see for example, Zitvogel, et al./998. *Nat. Med.* 4: 594-600; Chaput, et al. 2004. *J. Immunol.* 172: 2137-214631: 2892-2900; Escudier, et al. 2005. *J. Transl. Med.* 3: 10; Morse, et al. 2005, *J. Transl. Med.* 3: 9; Peche, et al. 2006. *Am. J. Transplant.* 6: 1541-1550; Kim, et al. 2005. *J. Immunol.* 174: 6440-6448, all of which are herein incorporated by reference in their entireties). Cell lines or tissue samples can be grown to 80% confluence before being cultured in fresh DMEM for 72 h. Subsequent exosome production can be stimulated (see, for example, heat shock treatment of melanoma cells as described by Dressel, et al. 2003. *Cancer Res.* 63: 8212-8220, which is herein incorporated by reference in its entirety). The supernatant can then be harvested and exosomes prepared as described herein.

Exosomes produced ex vivo can, in one example, be cultured from a cell-of-origin or cell line of interest, exosomes can be isolated from the cell culture medium and subsequently labeled with a magnetic label, a fluorescent moiety, a radioisotope, an enzyme, a chemiluminescent probe, a metal particle, a non-metal colloidal particle, a polymeric dye particle, a pigment molecule, a pigment particle, an electrochemically active species, semiconductor nanocrystal or other nanoparticles including quantum dots or gold particles to be reintroduced in vivo as a label for imaging analysis. Ex vivo cultured exosomes can alternatively be used to identify novel bio-signatures by setting up culturing conditions for a given cell-of-origin with characteristics of interest, for example a culture of lung cancer cells or cell line with a known EGFR mutation that confers resistant to or susceptibility to gefitinib, then exposing the cell culture to gefitinib, isolating exosomes that arise from the culture and subsequently analyzing them on a discovery array to look for novel antigens or binding agents expressed on the outside of exosomes that could be used as a bio-signature to capture this species of exosome. Additionally, it would be possible to isolate any other biomarkers or bio-signatures found within these exosomes for discovery of novel signatures (including but not limited to nucleic acids, proteins, lipids, or combinations thereof) that may have clinical diagnostic, prognostic or therapy related implication.

Cells of interest can also be first isolated and cultured from tissues of interest. For example, human hair follicles in the growing phase, anagen, can be plucked individually from a patient's scalp using sterile equipment and plasticware, taking care not to damage the follicle. Each sample can be transferred to a Petri dish containing sterile PBS for tissue culture. Isolated human anagen hair follicles can be carefully transferred to an individual well of a 24-well plate containing 1 ml of William's E medium. Follicles can be maintained free-floating at 37° C. in an atmosphere of 5% $CO_2$ and 95% air in a humidified incubator. Medium can be changed every 3 days, taking care not to damage the follicles. Cells can then be collected and spun down from the media. Exosomes may then be isolated using antigens or cellular binding partners that are specific to such cell-of-origin specific exosomes using methods as previously described. Biomarkers and bio-signatures can then be isolated and characterized by methods known to those skilled in the art.

Cells of interest may also be cultured under microgravity or zero-gravity conditions or under a free-fall environment. For example, NASA's bioreactor technology will allow such cells to be grown at much faster rate and in much greater quantities. Exosomes may then be isolated using antigens or cellular binding partners that are specific to such cell-of-origin specific exosomes using methods as previously described.

Rotating wall vessels or RWVersus are a class of bioreactors developed by and for NASA that are designed to grow suspension cultures of cells in a quiescent environment that simulates microgravity can also be used. (see for example, U.S. Pat. Nos. 5,026,650; 5,153,131; 5,153,133; 5,437,998; 5,665,594; 5,702,941; 7,351,584, 5,523,228, 5,104,802, 6,117,674, Schwarz, R P, et al., *J. Tiss. Cult. Meth.* 14:51-58, 1992; Martin et al., *Trends in biotechnology* 2004; 22; 80-86, Li et al., *Biochemical Engineering Journal* 2004; 18; 97-104, Ashammakhi et al., *Journal Nanoscience Nanotechnology* 2006; 9-10: 2693-2711, Zhang et al., *International Journal of Medicine* 2007; 4: 623-638, Cowger, N L, et al., *Biotechnol. Bioeng* 64:14-26, 1999, Spaulding, G F, et al., *J. Cell. Biochem.* 51:249-251, 1993, Goodwin, T J, et al., *Proc. Soc. Exp. Biol. Med.* 202:181-192, 1993; Freed, L E et al., *In Vitro Cell. Dev. Biol.* 33:381-385, 1997, Clejan, S. et al, *Biotechnol. Bioeng.* 50:587-597, 1996). Khaoustov, V I, et al., *In Vitro Cell. Dev. Biol.* 35:501-509. 1999, each of which is herein incorporated by reference in its entirety).

Alternatively, cells of interest or cell-of-origin specific exosomes that have been isolated may be cultured in a stationary phase plug-flow bioreactor as generally described in U.S. Pat. No. 6,911,201, and U.S. Application Publication Nos. 20050181504, 20050180958, 20050176143 and 20050176137, each of which is herein incorporated by reference in its entirety. Alternatively, cells of interest or cell-origin specific exosomes may also be isolated and cultured as generally described in U.S. Pat. No. 5,486,359.

One embodiment can include the steps of providing a tissue specimen containing cells of interest or cell-origin specific exosomes, adding cells or exosomes from the tissue specimen to a medium which allows, when cultured, for the selective adherence of only the cells of interest or cell-origin specific exosomes to a substrate surface, culturing the specimen-medium mixture, and removing the non-adherent matter from the substrate surface is generally described in U.S. Pat. No. 5,486,359, which is herein incorporated by reference in its entirety.

Exosomes as Imaging Tools

In other embodiments, exosomes can be used as imaging tools. Labeled circulating tumor cells (CTCs) can be noninvasively visualized in vivo as they flow through the peripheral vasculature (He, W et al. (2007) *PNAS* 104(28)11760-11765). The method can involve i.v. injection of a tumor-specific fluorescent ligand followed by multiphoton fluorescence imaging of superficial blood vessels to quantitate the flowing CTCs. Studies in mice with metastatic tumors demonstrated that CTCs can be quantitated weeks before metastatic disease is detected by other means. Similar methods could be used and applied to circulating cell-of-origin specific exosomes as well. The decision to administer chemotherapy after tumor resection usually depends on an oncologist's assessment of the presence of microscopic metastatic disease. Although computed tomography, MRI, tissue/sentinel lymph node biopsy or serum cancer marker analysis can each detect some level of residual disease, the presence of circulating tumor derived exosomes can correlate most sensitively with cancer progression and metastasis. Noninvasive imaging of these exosomes in real time as they flow through the peripheral vasculature could improve detection sensitivity by enabling analysis of significantly larger blood volumes (potentially the entire blood volume of the patient). Exosomes isolated from bodily fluid, purified, labeled and then reintroduced into the system can be used for identification of early tumors not yet visible by traditional imaging methods (e.g. early breast tumors or early ovarian tumor cells). Labeled exosomes can also be used as a signal to identify tumors of metastatic potential.

In one embodiment, exosomes can be labeled by peptide/antigen targeting to label the exosomes either in vivo or in vitro and then reintroduce in the circulatory system for the purposes of diagnostic imaging. Suitable labels may include those that may be detected by intravital flow cytometry, X-radiography, NMR, PET/SPECT or MRI. For X-radiographic techniques, suitable labels include any radioisotope that emits detectable radiation but that is not overtly harmful to the patient, such as barium or cesium, for example. Suitable labels for NMR or MRI generally include those with a detectable characteristic spin, such as deuterium. Suitable imaging systems may be used to detect the labeled exosomes in the circulatory system.

The labeled exosomes can be administered by arterial or venous injection, and can be formulated as a sterile, pyrogen-free, parenterally acceptable aqueous solution. The preparation of such parenterally acceptable solutions, having due regard to pH, isotonicity, stability, and the like, is within the skill in the art. A preferred formulation for intravenous injection should contain, in addition to the labeled exosomes, an isotonic vehicle such as Sodium Chloride Injection, Ringer's Injection, Dextrose Injection, Dextrose and Sodium Chloride Injection, Lactated Ringer's Injection, or other vehicle. An effective amount of labeled exosomes can be an amount sufficient to yield an acceptable image using equipment which is available for clinical use. An effective amount of the labeled exosomes may be administered in more than one injection. Effective amounts of the labeled exosomes will vary according to factors such as the degree of susceptibility of the individual, the age, sex, and weight of the individual, idiosyncratic responses of the individual, the dosimetry. Effective amounts of the labeled exosomes will also vary according to instrument and film-related factors.

In a further embodiment, intravital flow cytometry can be used to noninvasively count labeled exosomes in vivo as they flow through the peripheral vasculature. The method can include i.v. injection of a tumor-specific fluorescent ligand followed by multiphoton fluorescence imaging of superficial blood vessels to quantitate the flowing exosomes. Intravital flow cytometry for detection of exosomes circumvents sampling limitations and renders quantitation of rare events statistically significant by enabling analysis of the majority of a patient's blood volume (≈5 liters).

Many human carcinomas overexpress a receptor for the vitamin folic acid (>90% of ovarian and endometrial cancers, 86% of kidney cancers, 78% of nonsmall cell lung cancers, etc). Alternatively, normal tissues either lack measurable folate receptors (FR) or express FR at a site that is inaccessible to parenterally administered drugs. Because FR-expressing cancer masses can be selectively labeled in vivo by injection of either radioactive or fluorescent folate conjugates that bind FR with nanomolar affinity it is possible for single exosomes to bind sufficient numbers of folate conjugates to allow their detection in vivo as they pass through a patient's peripheral vasculature. To increase signal-to-background ratios, a tumor-specific probe is used that rapidly clear circulation if left uncaptured by exosomes. For this purpose, folate-dye conjugates (e.g. folate-AlexaFluor 488) conjugates can be used because tumor-specific antibodies were found to promote phagocytic clearance of the exosomes to which they bound, thereby causing significant underestimation of exosomes counts. To further ensure that the cells labeled with folate-AlexaFluor 488 are indeed malignant, monoclonal anti-human antibodies can be used (e.g. CA125 for ovarian cancer) plus an appropriate secondary antibody conjugated to rhodamine-X.

In another embodiment, exosomes can be labeled in vivo by intravenously introducing a labeling agent that specifically targets the exosome for downstream imaging applications similar to those described above.

Reimbursement Codes

In one embodiment, the use of exosomes as diagnostic, therapy-related or prognostic markers in the identification of disease, disease stage, progression or therapy can be assigned specific U.S. Medicare reimbursement codes. In one embodiment, the isolation and the use of cell-of-origin specific exosomes are used. The reimbursement code may be a code developed under the National Council for Prescription Drug Programs Professional Pharmacy Services (NCPDP/PPS code). A reimbursement code can be a diagnosis code utilized or recognized by an insurance company, for example. The diagnostic code is assignable based upon a reimbursement requirement by a third party. Alternatively, the diagnostic code is assignable based upon a need to analyze the utilization of medical resources. A set of diagnosis codes can conform to and/or be compatible with, for example, ICD (International Classification of Diseases) codes, 9th Edition, Clinical Modification, (ICD-9-CM), Volumes 1, 2 and 3; ICD-10, which is maintained and distributed by the U.S. Health and Human Services department; HCPCS (Health Care Financing Administration Common Procedure Coding System); NDC (National Drug Codes); CPT-4 (Current Procedural Terminology); Fourth Edition CDPN (Code on Dental Procedures and Nomenclature); SNOMED-RT "Systematicized Nomenclature of Medicine, Reference Terminology" by the College of American Pathologists; UMLS (Unified Medical Language System), by the National Library of Medicine; LOINC Logical Observation Identifiers, Names, and Codes; Regenstrief Institute and the Logical Observation Identifiers Names and Codes (LOINC®) Committee; Clinical Terms also known as "Read Codes"; DIN Drug Identification Numbers; Reimbursement Classifications including DRGs (Diagnosis Related Groups); CDT Current Dental Terminology; NIC (Nursing intervention codes); or Commercial Vocabulary Services (such as HealthLanguage by HealthLanguage Inc.), each of which is incorporated by reference in its entirety.

In one embodiment, each of the isolation methods for exosomes described herein can be assigned a specific reimbursement code. For example, each of the isolation methods of cell-of-origin specific exosomes described herein can be assigned a specific reimbursement code. In another embodiment, the specific bio-signature(s) obtained from the analysis of exosomes can be assigned a specific reimbursement code. In yet another embodiment, the specific bio-signature(s) obtained from the analysis of cell-of-origin specific exosomes can be assigned a specific reimbursement code. Alternatively, kits for the detection of a particular bio-signature of exosomes in a biological sample can be assigned to a specific reimbursement code. Alternatively, kits for the detection of a particular bio-signature of specific cell-of-origin exosomes in a biological sample can be assigned to a specific reimbursement code.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Example 1

Purification of Exosomes from Prostate Cancer Cell Lines

Prostate cancer cell lines are cultured for 3-4 days in culture media containing 20% FBS (fetal bovine serum) and 1% P/S/G. The cells are then pre-spun for 10 minutes at 400×g at 4° C. The supernatant is kept and centrifuged for 20 minutes at 2000×g at 4. The supernatant containing exosomes can be concentrated using a Millipore Centricon Plus-70 (Cat # UFC710008 Fisher).

The Centricon is pre washed with 30 mls of PBS at 1000×g for 3 minutes at room temperature. Next, 15-70 mls of the pre-spun cell culture supernatant is poured into the Concentrate Cup and is centrifuged in a Swing Bucket Adapter (Fisher Cat #75-008-144) for 30 minutes at 1000×g at room temperature.

The flow through in the Collection Cup is poured off. The volume in the Concentrate Cup is brought back up to 60 mls with any additional supernatant. The Concentrate Cup is centrifuged for 30 minutes at 1000×g at room temperature until all of the cell supernatant is concentrated.

The Concentrate Cup is washed by adding 70 mls of PBS and centrifuged for 30-60 minutes at 1000×g until approximately 2 mls remains. The exosomes are removed from the filter by inverting the concentrate into the small sample cup and centrifuge for 1 minute at 4° C. The volume is brought up to 25 mls with PBS. The exosomes are now concentrated and are added to a 30% Sucrose Cushion.

To make a cushion, 4 mls of Tris/30% Sucrose/D2O solution (30 g protease-free sucrose, 2.4 g Tris base, 50 ml D2O, adjust pH to 7.4 with ION NCL drops, adjust volume to 100 mls with D2O, sterilize by passing thru a 0.22-um filter) is loaded to the bottom of a 30 ml V bottom thin walled Ultracentrifuge tube. The diluted 25 mls of concentrated exosomes is gently added above the sucrose cushion without disturbing the interface and is centrifuged for 75 minutes at 100,000×g at 4° C. The ~25 mls above the sucrose cushion is carefully removed with a 10 ml pipet and the ~3.5 mls of exosome is collected with a fine tip transfer pipet (SAMCO 233) and transferred to a fresh ultracentrifuge tube, where 30 mls PBS is added. The tube is centrifuged for 70 minutes at 100,000×g at 4° C. The supernatant is poured off carefully. The pellet is resuspended in 200 ul PBS and can be stored at 4° C. or used for assays. A BCA assay (1:2) can be used to determine protein content and Western blotting or electron micrography can be used to determine exosome purification.

Example 2

Purification of Exosomes from VCaP and 22Rv1

Exosomes from Vertebral-Cancer of the Prostate (VCaP) and 22Rv1, a human prostate carcinoma cell line, derived from a human prostatic carcinoma xenograft (CWR22R) were collected by ultracentrifugation by first diluting plasma with an equal volume of PBS (1 ml). The diluted fluid was transferred to a 15 ml falcon tube and centrifuged 30 minutes at 2000×g 4° C. The supernatant (~2 mls) was transferred to an ultracentrifuge tube 5.0 ml PA thinwall tube (Sorvall #03127) and centrifuged at 12,000×g, 4° C. for 45 minutes.

The supernatant (~2 mls) was transferred to a new 5.0 ml ultracentrifuge tubes and filled to maximum volume with addition of 2.5 mls PBS and centrifuged for 90 minutes at 110,000×g, 4° C. The supernatant was poured off without disturbing the pellet and the pellet resuspended with 1 ml PBS. The tube was filled to maximum volume with addition of 4.5 ml of PBS and centrifuged at 110,000×g, 4° C. for 70 minutes.

The supernatant was poured off without disturbing the pellet and an additional 1 ml of PBS was added to wash the pellet. The volume was increased to maximum volume with the addition of 4.5 mls of PBS and centrifuged at 110,000×g for 70 minutes at 4° C. The supernatant was removed with P-1000 pipette until ~100 µl of PBS was in the bottom of the tube. The ~90 µl remaining was removed with P-200 pipette and the pellet collected with the ~10 µl of PBS remaining by gently pipetting using a P-20 pipette into the microcentrifuge tube. The residual pellet was washed from the bottom of a dry tube with an additional 5 µl of fresh PBS and collected into microcentrifuge tube and suspended in phosphate buffered saline (PBS) to a concentration of 500 µg/ml.

Example 3

Plasma Collection and Exosome Purification

Blood is collected via standard veinpuncture in a 7 ml K2-EDTA tube. The sample is spun at 400 g for 10 minutes in a 4° C. centrifuge to separate plasma from blood cells (SORVALL Legend RT+ centrifuge). The supernatant (plasma) is transferred by careful pipetting to 15 ml Falcon centrifuge tubes. The plasma is spun at 2,000 g for 20 minutes and the supernatant is collected.

For storage, approximately 1 ml of the plasma (supernatant) is aliquoted to a cryovials, placed in dry ice to freeze them and stored in −80° C. Before exosome purification, if samples were stored at −80° C., samples are thawed in a cold water bath for 5 minutes. The samples are mixed end over end by hand to dissipate insoluble material.

In a first prespin, the plasma is diluted with an equal volume of PBS (example, approximately 2 ml of plasma is diluted with 2 ml of PBS). The diluted fluid is transferred to a 15 ml Falcon tube and centrifuged for 30 minutes at 2000×g at 4° C.

For a second prespin, the supernatant (approximately 4 mls) is carefully transferred to a 50 ml Falcon tube and centrifuged at 12,000×g at 4° C. for 45 minutes in a Sorval.

In the isolation step, the supernatant (approximately 2 mls) is carefully transferred to a 5.0 ml ultracentrifuge PA thinwall tube (Sorvall #03127) using a P1000 pipette and filled to maximum volume with an additional 0.5 mls of PBS. The tube is centrifuged for 90 minutes at 110,000×g at 4° C.

In the first wash, the supernatant is poured off without disturbing the pellet. The pellet is resuspended or washed with 1 ml PBS and the tube is filled to maximum volume with an additional 4.5 ml of PBS. The tube is centrifuged at 110,000×g at 4° C. for 70 minutes. A second wash is performed by repeating the same steps.

The exosomes are collected by removing the supernatant with P-1000 pipette until approximately 100 µl of PBS is in the bottom of the tube. Approximately 90 µl 1 of the PBS is removed and discarded with P-200 pipette. The pellet and remaining PBS is collected by gentle pipetting using a P-20 pipette. The residual pellet is washed from the bottom of the dry tube with an additional 5 µl of fresh PBS and collected into a microcentrifuge tube.

Example 4

Analysis of Exosomes Using Antibody-Coupled Microspheres and Directly Conjugated Antibodies This example demonstrates the use of particles coupled to an antibody, where the antibody captures the exosomes (see for example, FIG. 64A). An antibody, the detector antibody, is directly coupled to a label, and is used to detect a biomarker on the captured exosome.

First, an antibody-coupled microsphere set is selected (Luminex, Austin, Tex.). The microsphere set can comprise various antibodies, and thus allows multiplexing. The microspheres are resuspended by vortex and sonication for approximately 20 seconds. A Working Microsphere Mixture is prepared by diluting the coupled microsphere stocks to a final concentration of 100 microspheres of each set/µL in Startblock (Pierce (37538)). (Note: 50 µL of Working Microsphere Mixture is required for each well.) Either PBS-1% BSA or PBS-BN (PBS, 1% BSA, 0.05% Azide, pH 7.4) may be used as Assay Buffer.

A 1.2 µm Millipore filter plate is pre-wet with 100 µl/well of PBS-1% BSA (Sigma (P3688-10PAK+0.05% NaAzide (S8032))) and aspirated by vacuum manifold. An aliquot of 50 µl of the Working Microsphere Mixture is dispensed into the appropriate wells of the filter plate (Millipore Multiscreen HTS (MSBVN1250)). A 50 µl aliquot of standard or sample is dispensed into to the appropriate wells. The filter plate is covered and incubated for 60 minutes at room temperature on a plate shaker. The plate is covered with a sealer, placed on the orbital shaker and set to 900 for 15-30 seconds to re-suspend the beads. Following that the speed is set to 550 for the duration of the incubation.

The supernatant is aspirated by vacuum manifold (less than 5 inches Hg in all aspiration steps). Each well is washed twice with 100 µl of PBS-1% BSA (Sigma (P3688-10PAK+0.05% NaAzide (S8032))) and is aspirated by vacuum manifold. The microspheres are resuspended in 50 µL of PBS-1% BSA (Sigma (P3688-10PAK+0.05% NaAzide (S8032))). The PE conjugated detection antibody is diluted to 4 µg/mL (or appropriate concentration) in PBS-1% BSA (Sigma (P3688-10PAK+0.05% NaAzide (S8032))). (Note: 50 µL of diluted detection antibody is required for each reaction.) A 50 µl aliquot of the diluted detection antibody is added to each well. The filter plate is covered and incubated for 60 minutes at room temperature on a plate shaker. The filter plate is covered with a sealer, placed on the orbital shaker and set to 900 for 15-30 seconds to re-suspend the beads. Following that the speed is set to 550 for the duration of the incubation. The supernatant is aspirated by vacuum manifold. The wells are washed twice with 100 µl of PBS-1% BSA (Sigma (P3688-10PAK+0.05% NaAzide (S8032))) and aspirated by vacuum manifold. The microspheres are resuspended in 100 µl of PBS-1'% BSA (Sigma (P3688-10PAK+0.05% NaAzide (S8032))). The microspheres are analyzed on a Luminex analyzer according to the system manual.

Example 5

Analysis of Exosomes Using Antibody-Coupled Microspheres and Biotinylated Antibody This example demonstrates the use of particles coupled to an antibody, where the antibody captures the exosomes. An antibody, the detector antibody, is biotinylated. A label coupled to streptavidin is used to detect the biomarker.

First, the appropriate antibody-coupled microsphere set is selected (Luminex, Austin, Tex.). The microspheres are resuspended by vortex and sonication for approximately 20 seconds. A Working Microsphere Mixture is prepared by diluting the coupled microsphere stocks to a final concentration of 50 microspheres of each set/µL in Startblock (Pierce (37538)). (Note: 50 µl of Working Microsphere Mixture is required for each well.) Beads in Start Block should be blocked for 30 minutes and no more than 1 hour.

A 1.2 µm Millipore filter plate is pre-wet with 100 µl/well of PBS-1% BSA+Azide (PBS-BN)((Sigma (P3688-10PAK+0.05% NaAzide (S8032))) and is aspirated by vacuum manifold. A 50 µl aliquot of the Working Microsphere Mixture is dispensed into the appropriate wells of the filter plate (Millipore Multiscreen HTS (MSBVN1250)). A 50 µl aliquot of standard or sample is dispensed to the appropriate wells. The filter plate is covered with a seal and is incubated for 60 minutes at room temperature on a plate shaker. The covered filter plate is placed on the orbital shaker and set to 900 for 15-30 seconds to re-suspend the beads. Following that, the speed is set to 550 for the duration of the incubation.

The supernatant is aspirated by a vacuum manifold (less than 5 inches Hg in all aspiration steps). Aspiration can be done with the Pall vacuum manifold. The valve is place in the full off position when the plate is placed on the manifold. To aspirate slowly, the valve is opened to draw the fluid from the wells, which takes approximately 3 seconds for the 100 µl of sample and beads to be fully aspirated from the well. Once all of the sample is drained, the purge button on the manifold is pressed to release residual vacuum pressure from the plate.

Each well is washed twice with 100 µl of PBS-1% BSA+Azide (PBS-BN)(Sigma (P3688-10PAK+0.05% NaAzide (S8032))) and is aspirates by vacuum manifold. The microspheres are resuspended in 50 µl of PBS-1% BSA+Azide (PBS-BN)((Sigma (P3688-10PAK+0.05% NaAzide (S8032)))

The biotinylated detection antibody is diluted to 4 µg/mL in PBS-1% BSA+Azide (PBS-BN)((Sigma (P3688-10PAK+0.05% NaAzide (S8032))). (Note: 50 µl of diluted detection antibody is required for each reaction.) A 50 µl aliquot of the diluted detection antibody is added to each well.

The filter plate is covered with a sealer and is incubated for 60 minutes at room temperature on a plate shaker. The plate is placed on the orbital shaker and set to 900 for 15-30 seconds to re-suspend the beads. Following that, the speed is set to 550 for the duration of the incubation.

The supernatant is aspirated by vacuum manifold. Aspiration can be done with the Pall vacuum manifold. The valve is place in the full off position when the plate is placed on the manifold. To aspirate slowly, the valve is opened to draw the fluid from the wells, which takes approximately 3 seconds for the 100 ul of sample and beads to be fully aspirated from the well. Once all of the sample is drained, the purge button on the manifold is pressed to release residual vacuum pressure from the plate.

Each well is washed twice with 100 µl of PBS-1% BSA+Azide (PBS-BN)((Sigma (P3688-10PAK+0.05% NaAzide (S8032))) and is aspirated by vacuum manifold. The microspheres are resuspended in 50 µl of PBS-1% BSA (Sigma (P3688-10PAK+0.05% NaAzide (S8032))).

The streptavidin-R-phycoerythrin reporter (Molecular Probes 1 mg/ml) is diluted to 4 µg/mL in PBS-1% BSA+Azide (PBS-BN)((Note: 50 µl of diluted streptavidin-R-phycoerythrin is required for each reaction.) A 50 µl aliquot of the diluted streptavidin-R-phycoerythrin is added to each well.

The filter plate is covered with a sealer and is incubated for 60 minutes at room temperature on a plate shaker. The plate is placed on the orbital shaker and set to 900 for 15-30 seconds to re-suspend the beads. Following that, the speed is set to 550 for the duration of the incubation.

The supernatant is aspirated by vacuum manifold. Aspiration can be done with the Pall vacuum manifold. The valve is place in the full off position when the plate is placed on the manifold. To aspirate slowly, the valve is opened to draw the fluid from the wells, which takes approximately 3 seconds for the 100 ul of sample and beads to be fully aspirated from the well. Once all of the sample is drained, the purge button on the manifold is pressed to release residual vacuum pressure from the plate.

Each well is washed twice with 100 µl of PBS-1% BSA+Azide (PBS-BN)((Sigma (P3688-10PAK+0.05% NaAzide (S8032))) and is aspirated by vacuum manifold. The microspheres are resuspended in 100 µl of PBS-1% BSA+Azide (PBS-BN)((Sigma (P3688-10PAK+0.05% NaAzide (S8032))) and analyzed on the Luminex analyzer according to the system manual.

Example 6

Determining Bio-Signatures for Prostate Cancer Using Multiplexing

The exosomes samples obtained using methods as described in Example 1-3 are used in multiplexing assays as described in Examples 4 and 5. The detection antibodies used are CD63, CD9, CD81, B7H3 and EpCam. The capture antibodies used are CD9, PSCA, TNFR, CD63 2X, B7H3, MFG-E8, EpCam 2×, CD63, Rab, CD81, SETAP, PCSA, PSMA, 5T4, Rab IgG (control) and IgG (control), resulting in 100 combinations to be screened (FIG. 64B).

Figure 70A:
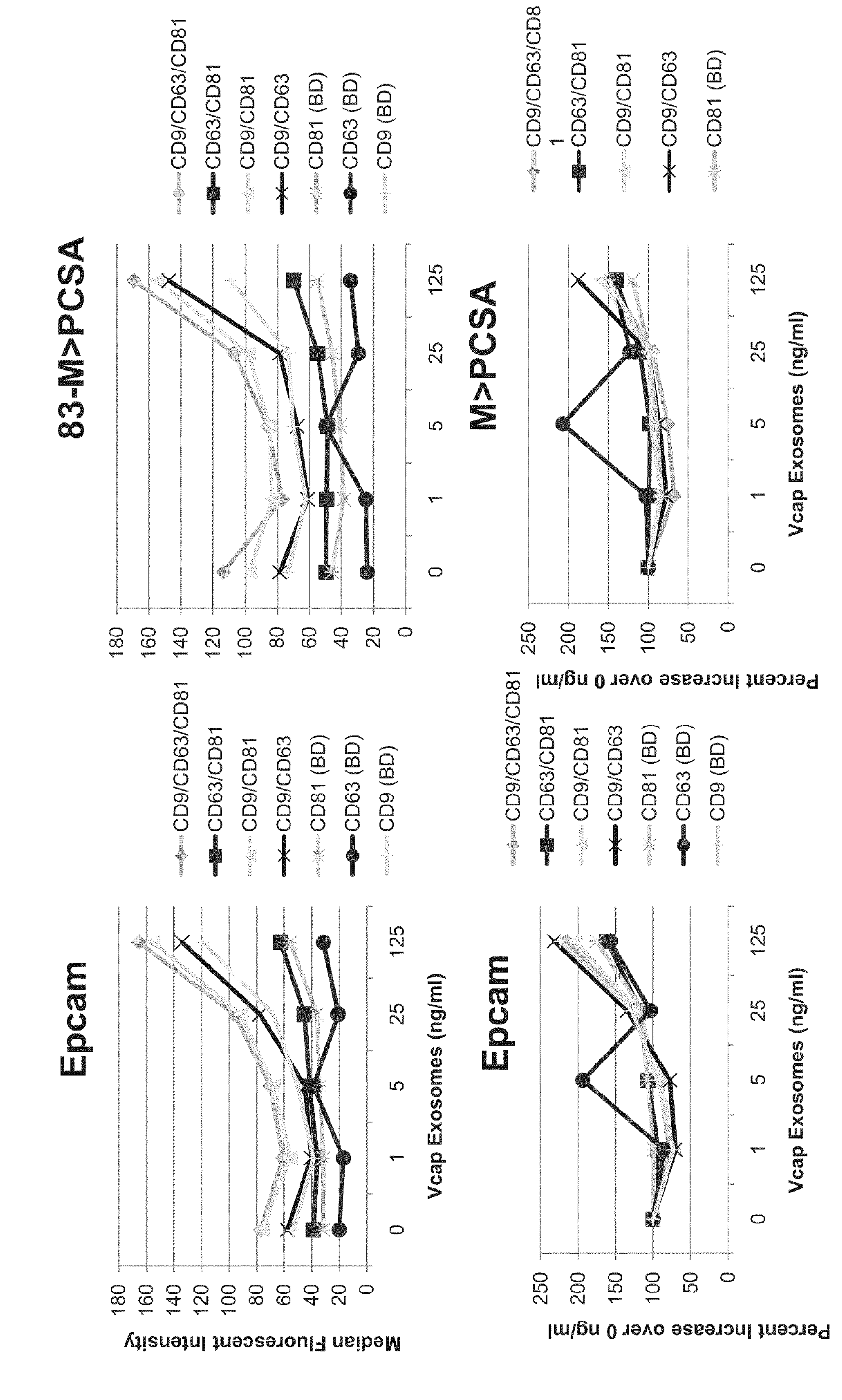
FIG. 70 illustrates multiple detectors can increase the signal of exosome detection. (A) Median intensity values are plotted as a function of purified exosome concentration from the VCaP cell line when labeled with a variety of prostate specific PE conjugated antibodies. Exosomes captured with EpCam (left graphs) or PCSA (right graphs) and the various proteins detected by the detector antibody are listed to the right of each graph. In both cases the combination of CD9 and CD63 gives the best increase in signal over background (bottom graphs depicting percent increase). The combination of CD9 and CD63 gave about 200% percent increase over background. (B) further illustrates prostate cancer/prostate exosome-specific marker multiplexing improves detection of prostate cancer cell derived exosomes. Median intensity values are plotted as a function of purified exosome concentration from the VCaP cell line when labeled with a variety of prostate specific PE conjugated antibodies. Exosomes captured with PCSA (left) and exosomes captured with EpCam (right) are depicted. In both cases the combination of B7H3 and PSMA gives the best increase in signal over background.
Figure 70B:
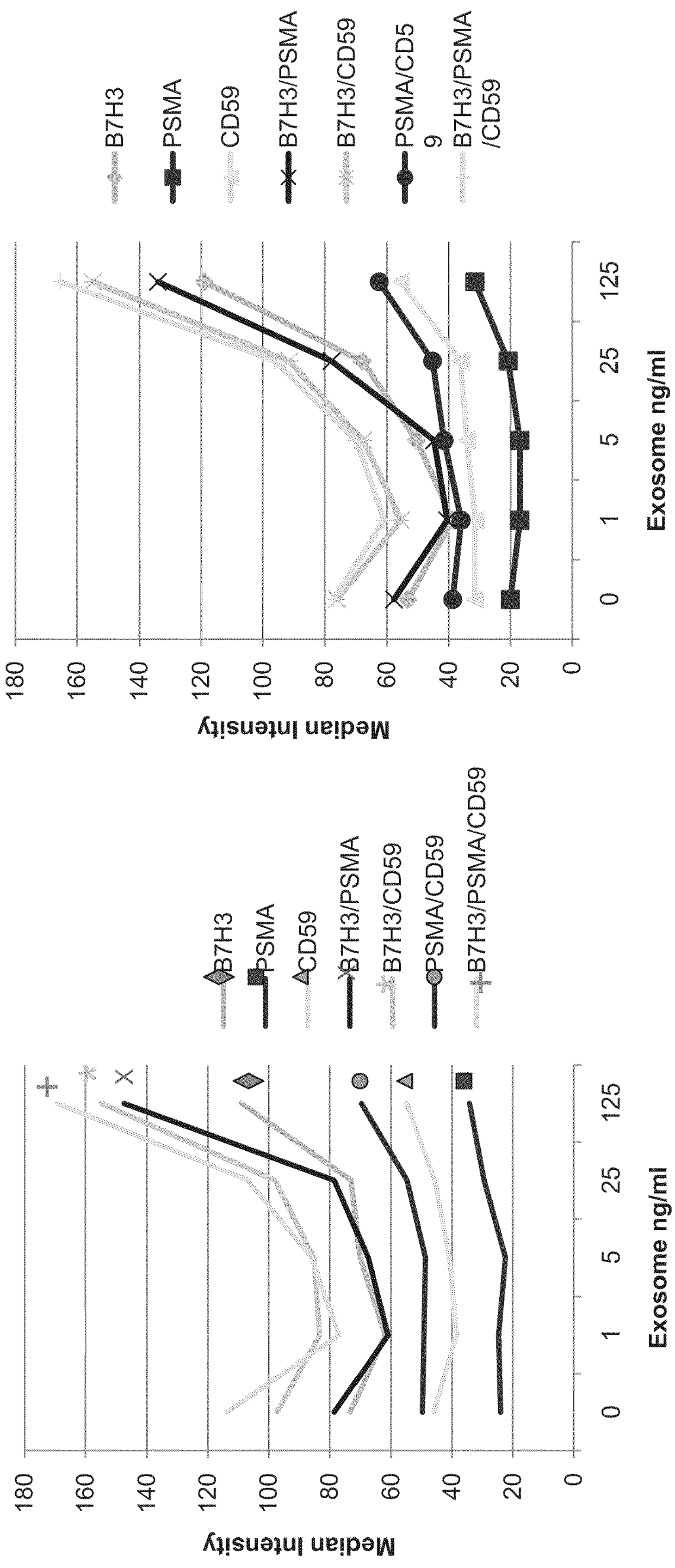
Figure 71A:
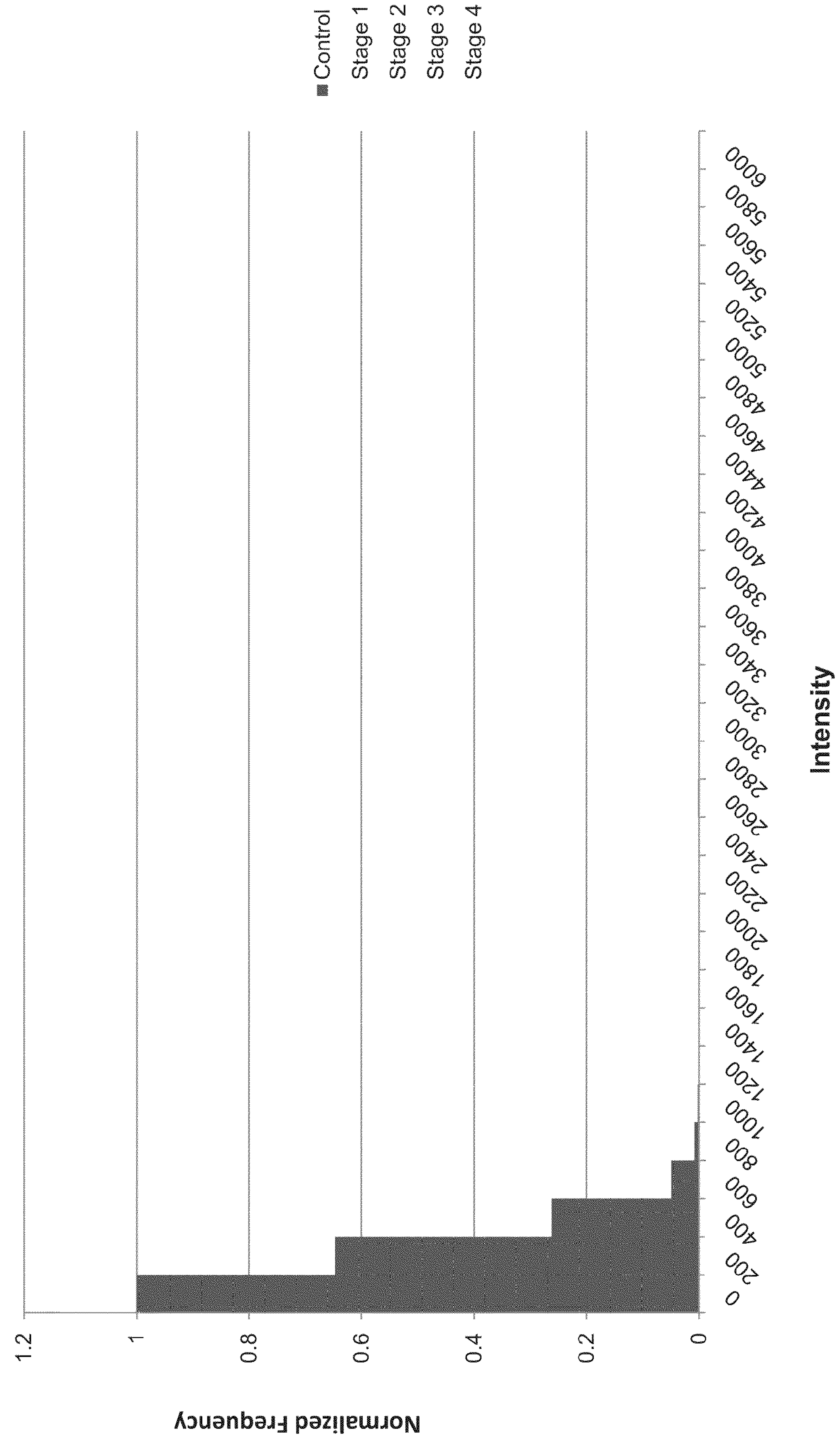
FIG. 71 illustrates a colon cancer bio-signature for colon cancer by stage, using CD63 detector and CD63 capture. The histograms of intensities from exosomes captured with CD63 coated beads and labeled with CD63 conjugated PE. There are 6 patients in the control group (A), 4 in stage I (B), 5 in stage II (C), 8 in stage III (D), and 4 stage IV (E). Data from each individual was normalized to account for variation in the number of beads read by the Luminex machine, added together, and then normalized again to account for the different number of samples in each population (F).
Figure 71B:
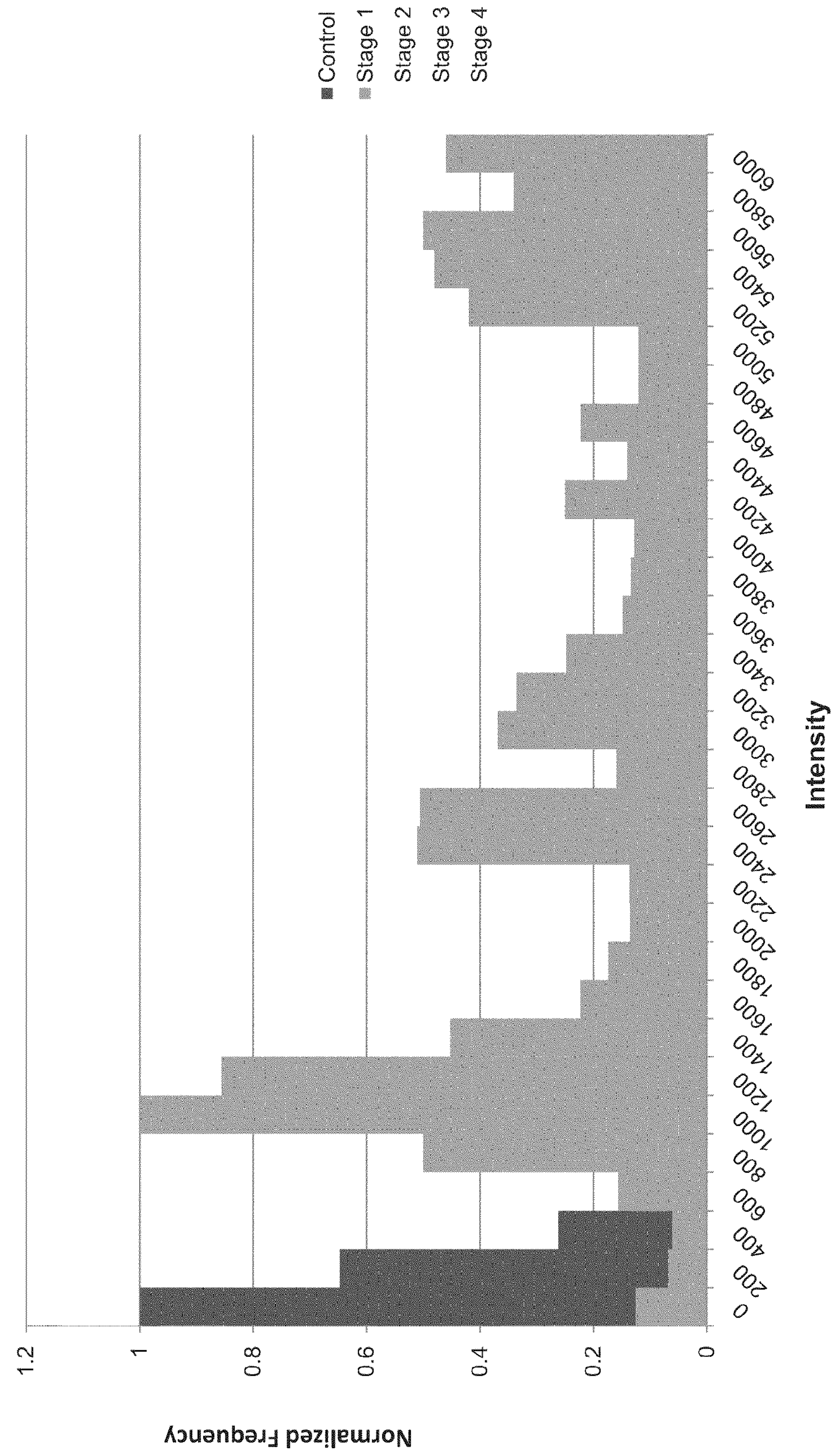
Figure 71C:
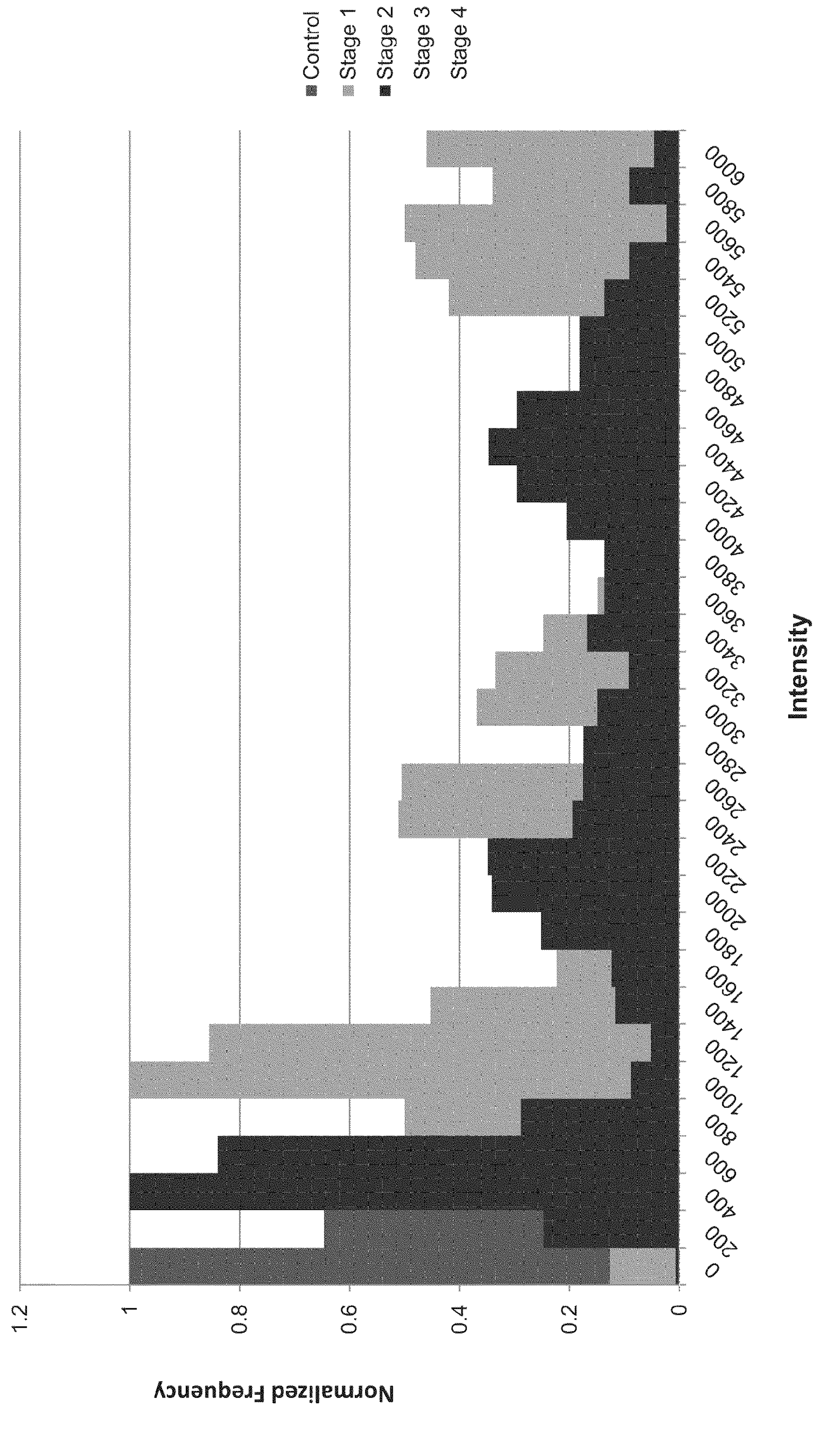
Figure 71D:
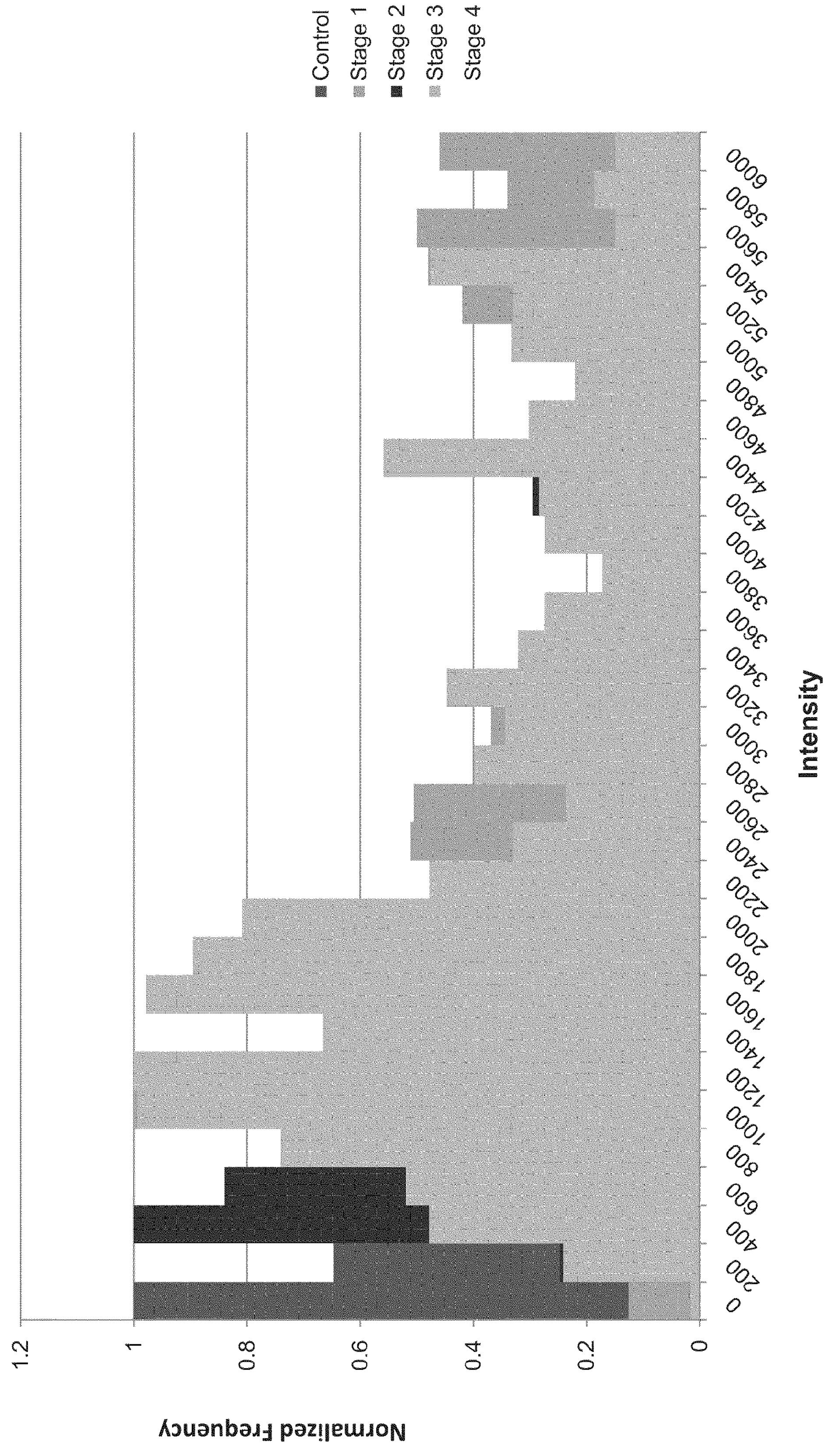
Figure 71E:
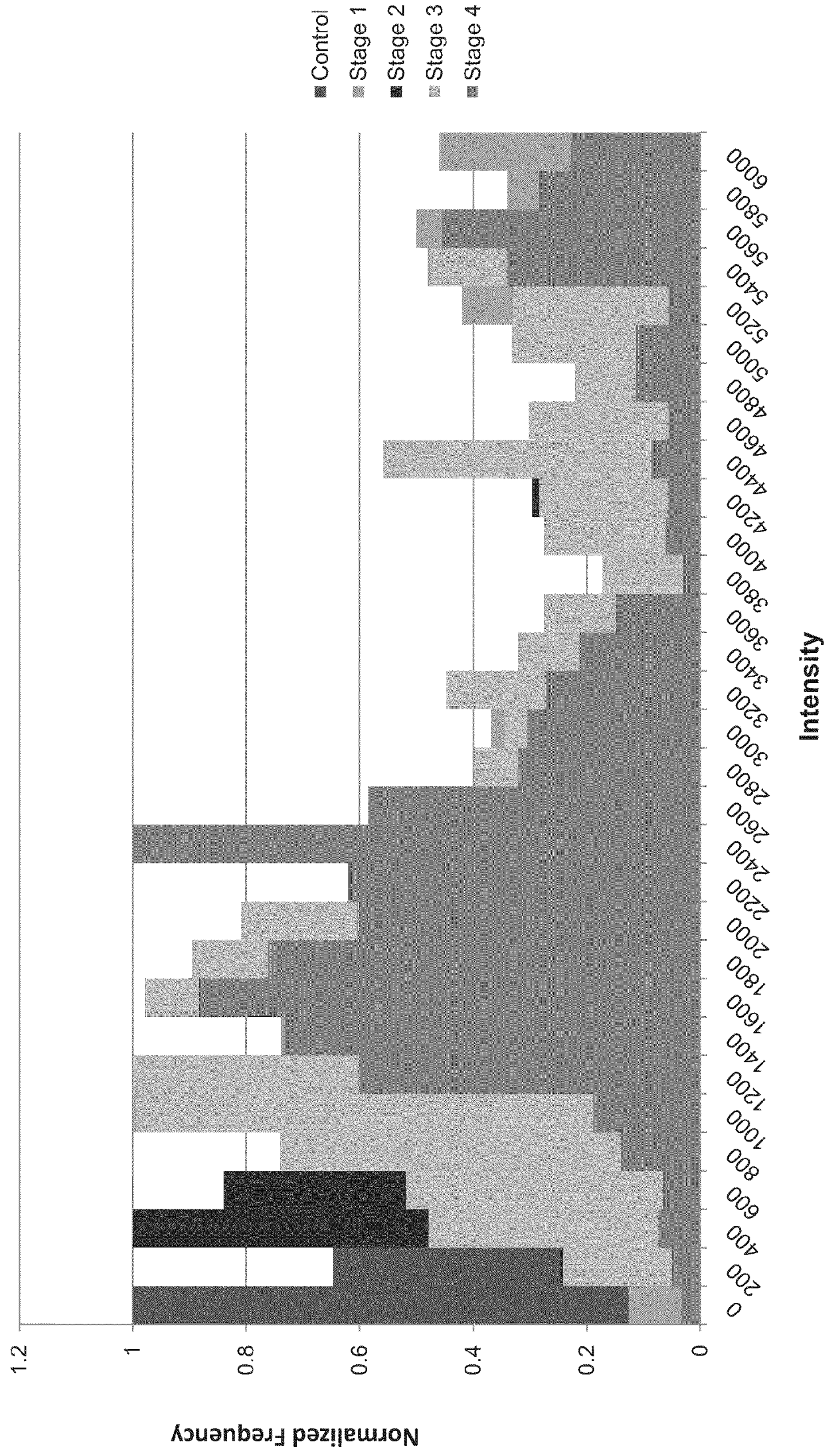
Figure 71F:
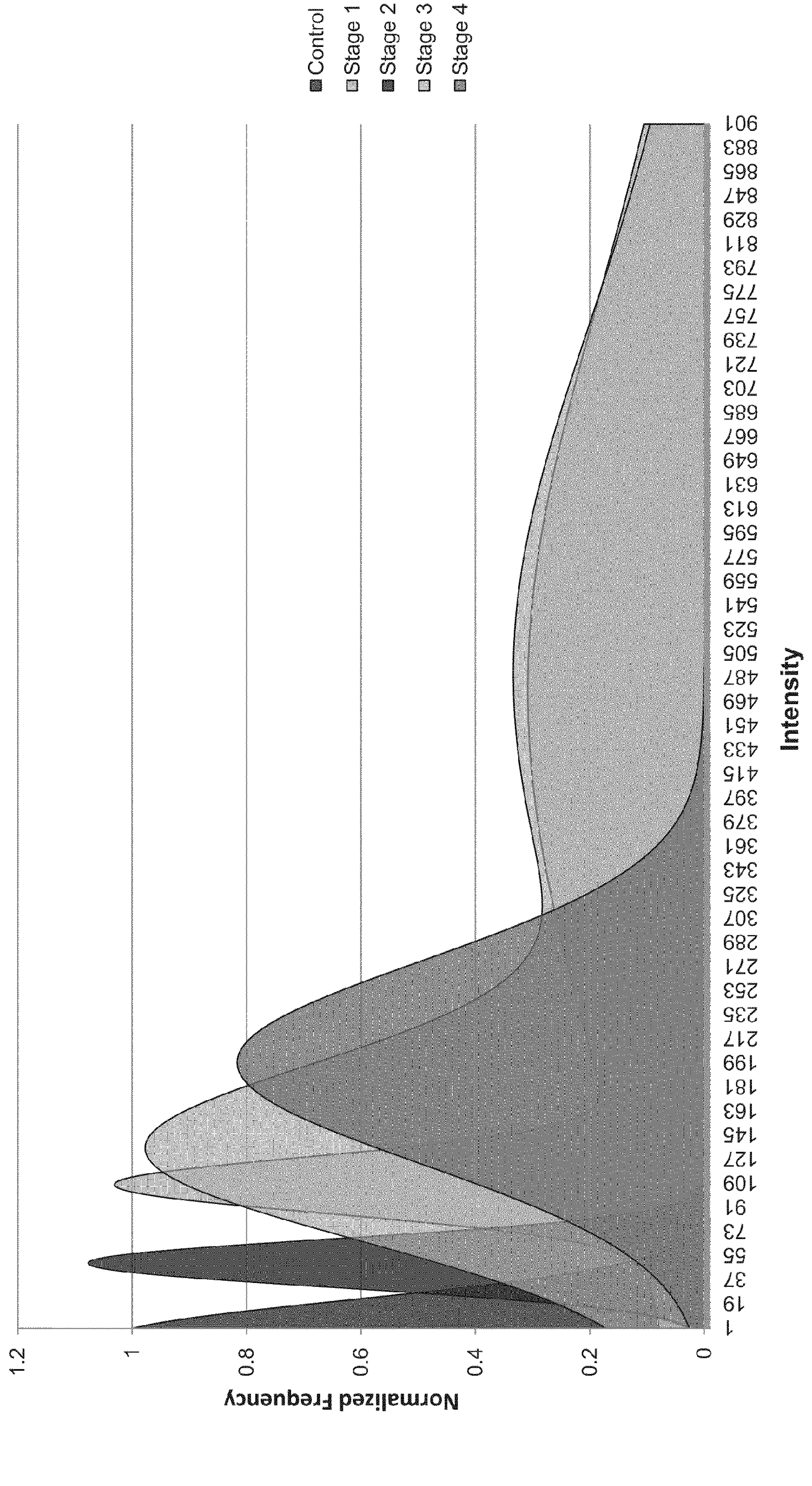
Figure 72A:
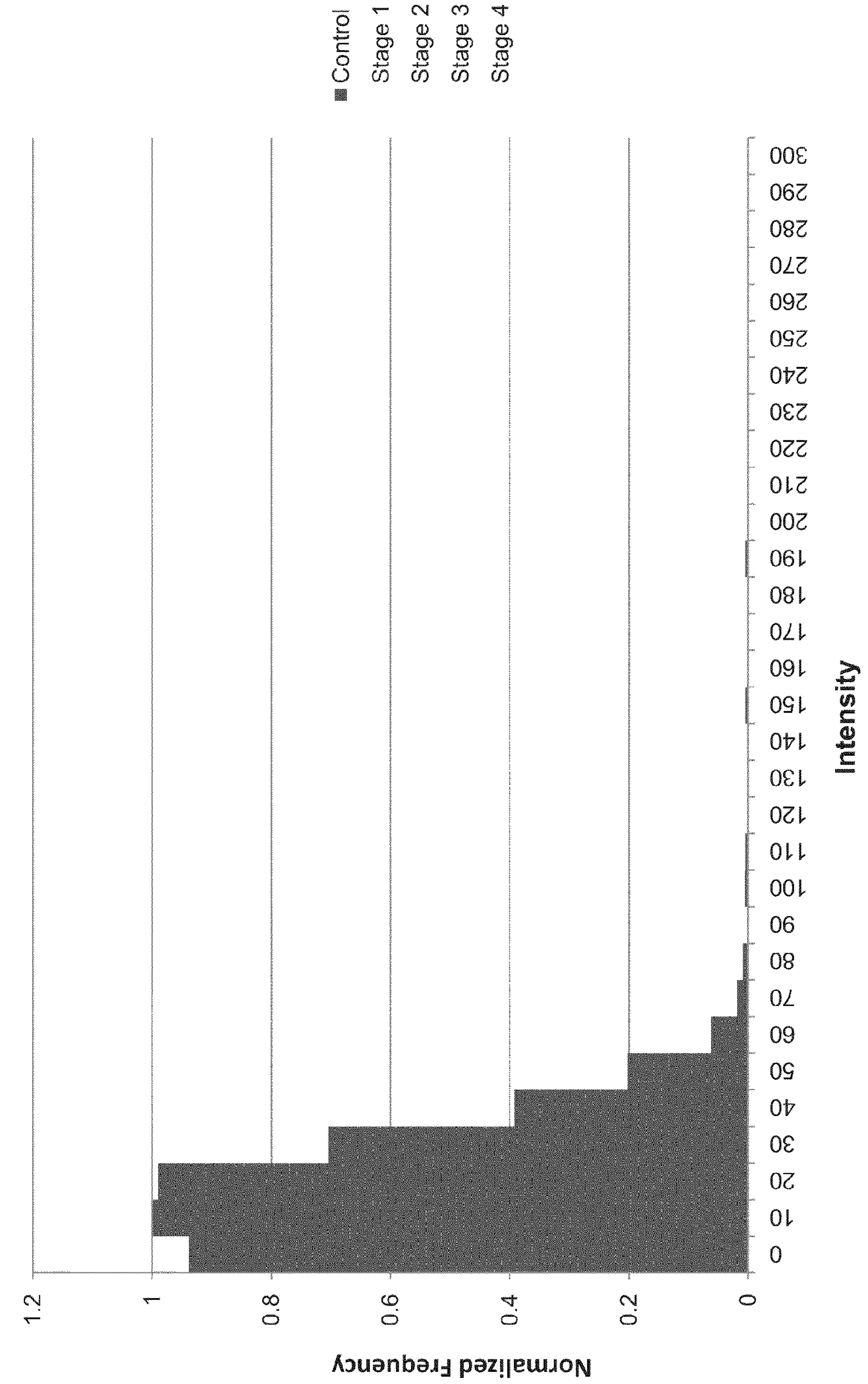
FIG. 72: illustrates colon cancer bio-signature for colon cancer by stage, using EpCam detector and CD9 capture. The histograms of intensities are from exosomes captured with CD9 coated beads and labeled with EpCam. There are patients in the (A) control group, (B) stage I, (C) stage II, (D) stage III, and (E) stage IV. Data from each individual was normalized to account for variation in the number of beads read by the Luminex machine, added together, and then normalized again to account for the different number of samples in each population (F).
Figure 72B:
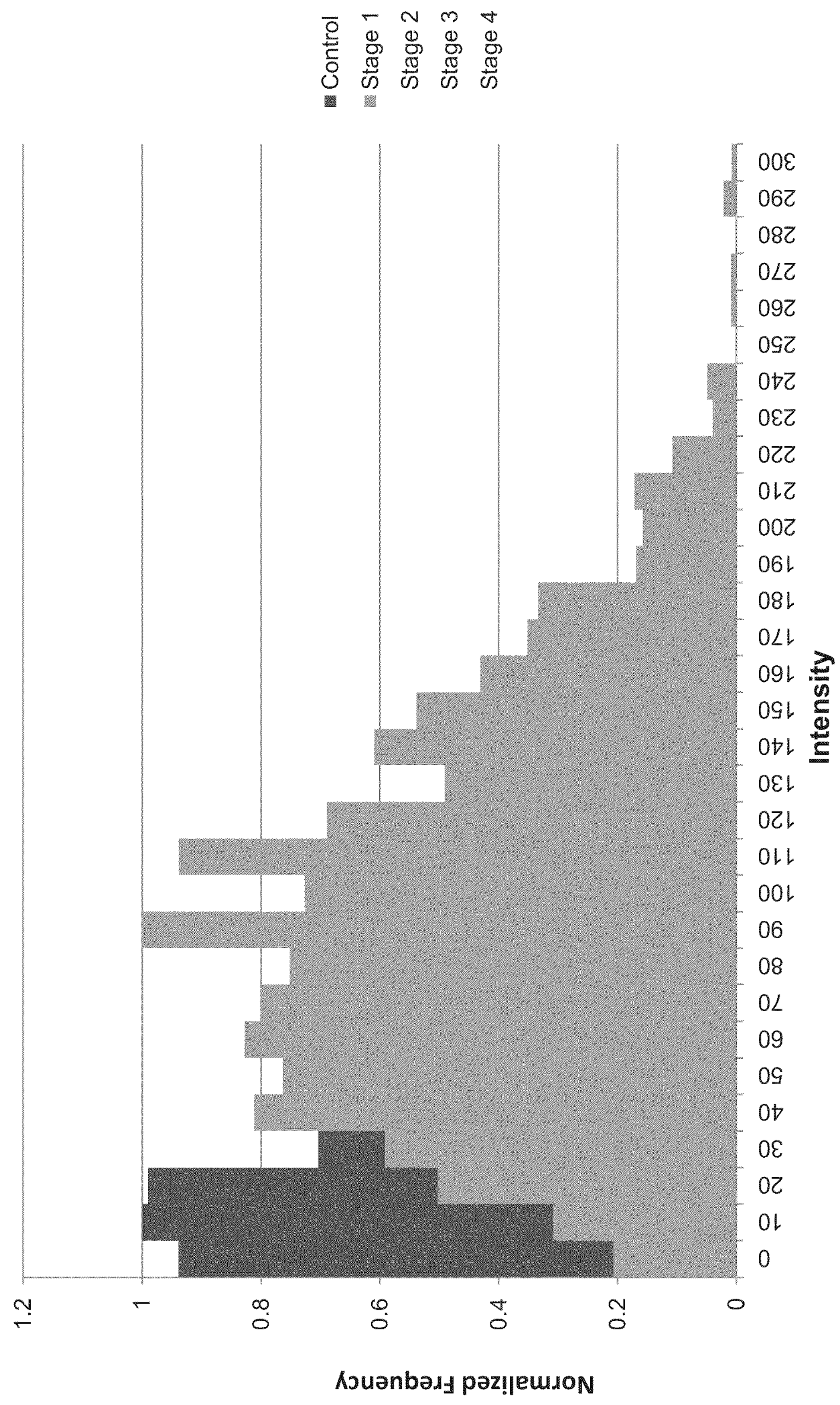
Figure 72C:
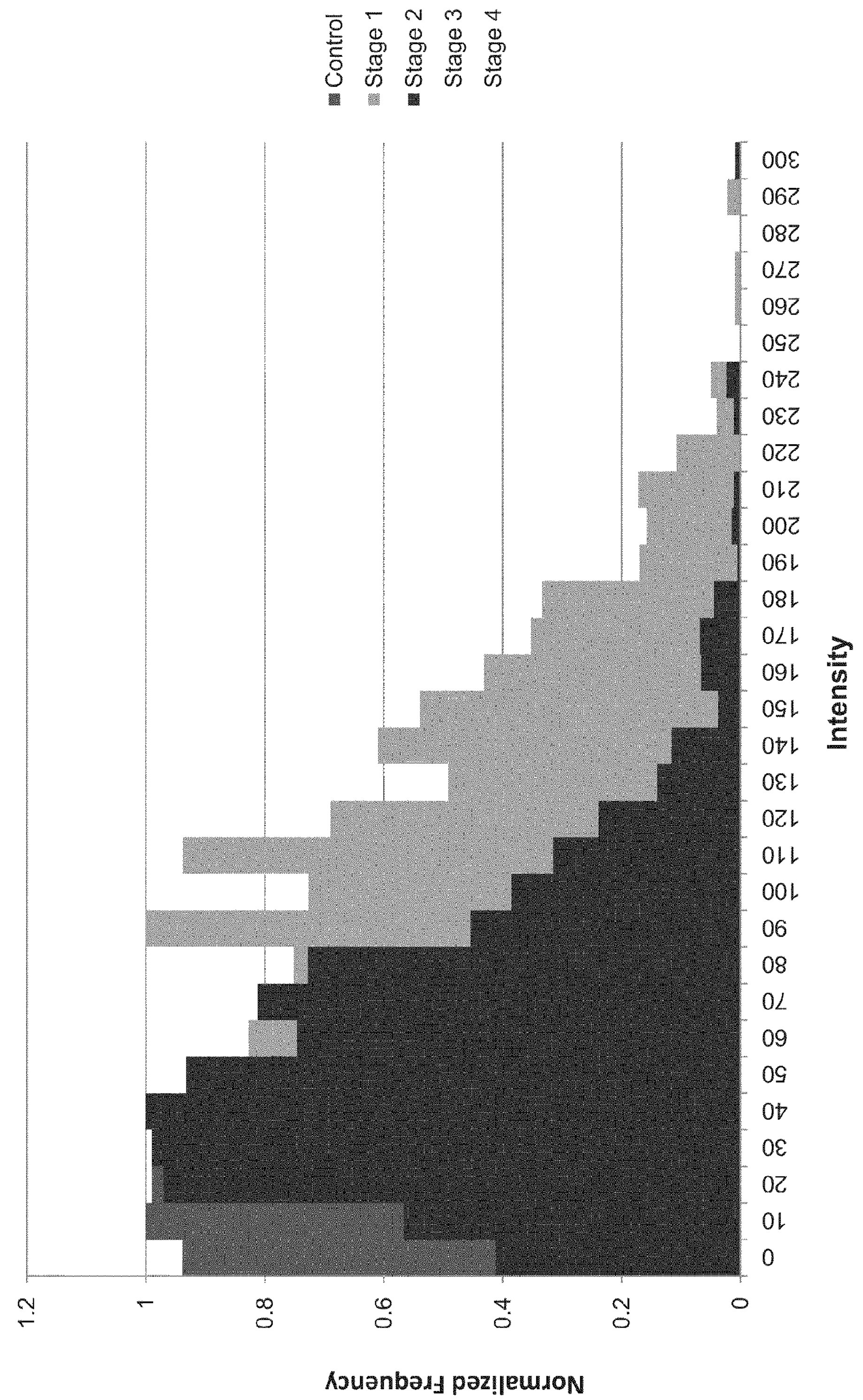
Figure 72D:
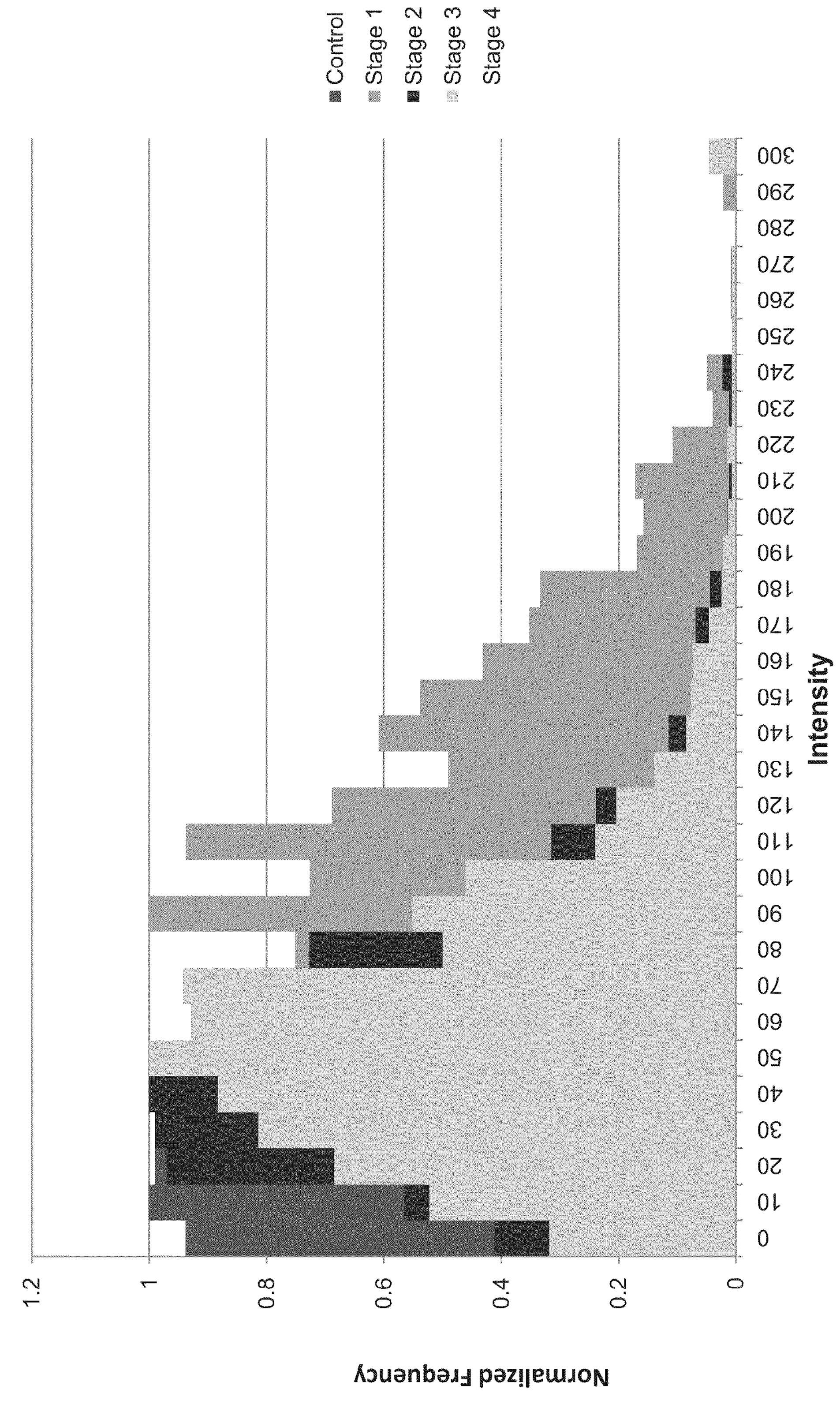
Figure 72E:
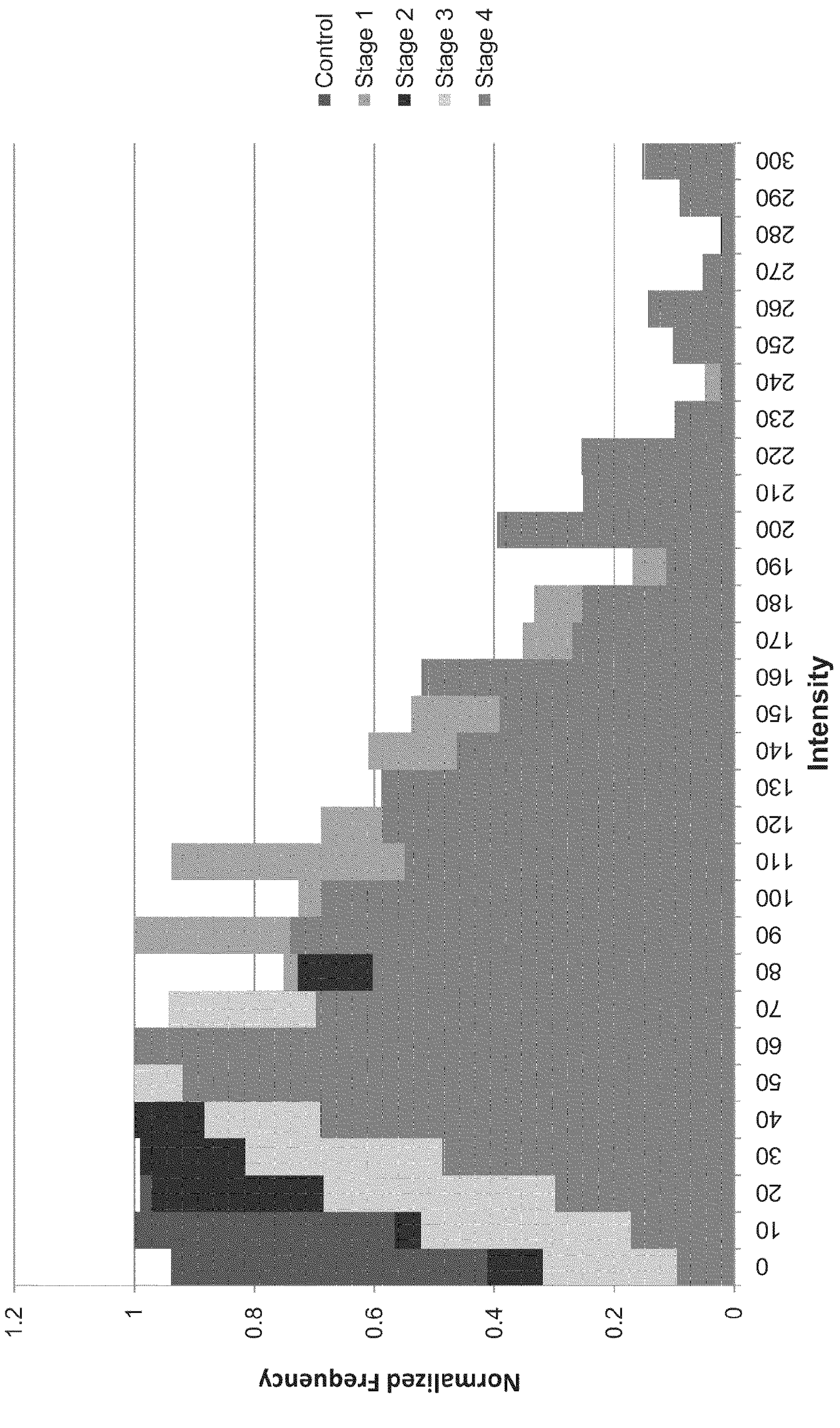
Figure 72F:
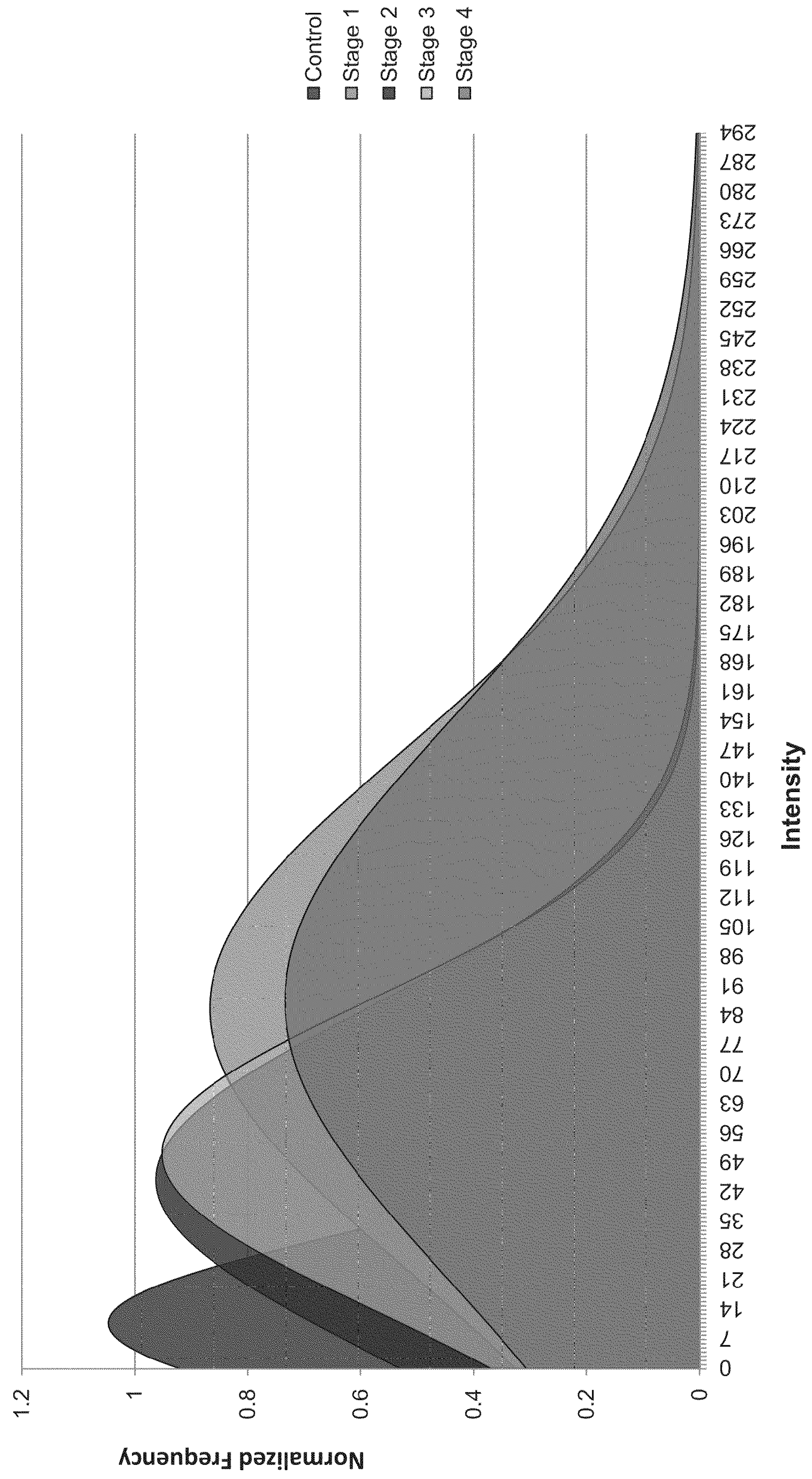

Ten prostate cancer patients and 12 normal control patients were screened. The results are depicted in FIG. 68 and FIG. 70A. FIG. 70B depicts the results of using PCSA capture antibodies (FIG. 70B, left graph) or EpCam capture antibodies (FIG. 70B, right graph), and detection using one or more detector antibodies. The sensitivity and specificity of the different combinations is depicted in FIG. 73.

Example 7

Determining Bio-Signatures for Colon Cancer Using Multiplexing

The exosomes samples obtained using methods as described in Example 3 is used in multiplexing assays as described in Examples 4 and 5. The detection antibodies used are CD63, CD9, CD81, B7H3 and EpCam. The capture antibodies used are CD9, PSCA, TNFR, CD63 2X, B7H3, MFG-E8, EpCam 2X, CD63, Rab, CD81, STEAP, PCSA, PSMA, 5T4, Rab IgG (control) and IgG (control), resulting in 100 combinations to be screened.

The results are depicted in FIGS. 69, 71, and 72. The sensitivity of the different combinations is depicted in FIG. 74.

Example 9

Capture of Exosomes Using Magnetic Beads

Exosomes isolated as described in Example 2 are used. Approximately 40 ul of the exosomes are incubated with approximately 5 ug (~50 µl) of EpCam antibody coated Dynal beads (Invitrogen, Carlsbad, Calif.) and 50 µl of Starting Block. The exosomes and beads are incubated with shaking for 2 hours at 45° C. in a shaking incubator. The tube containing the Dynal beads is placed on the magnetic separator for 1 minute and the supernatant removed. The beads are washed twice and the supernatant removed each time. Wash beads twice, discarding the supernatant each time.

Example 10

Detection of TMPRSS2:ERG in Exosomes

The RNA from the bead-bound exosomes of Example 9 was isolated using the Qiagen miRneasy™ kit, (Cat. No. 217061), according to the manufacturer's instructions.

The exosomes are homogenized in QIAzol™ Lysis Reagent (Cat. No. 79306). After addition of chloroform, the homogenate is separated into aqueous and organic phases by centrifugation. RNA partitions to the upper, aqueous phase, while DNA partitions to the interphase and proteins to the lower, organic phase or the interphase. The upper, aqueous phase is extracted, and ethanol is added to provide appropriate binding conditions for all RNA molecules from 18 nucleotides (nt) upwards. The sample is then applied to the RNeasy™ Mini spin column, where the total RNA binds to the membrane and phenol and other contaminants are efficiently washed away. High quality RNA is then eluted in RNase-free water.

RNA from the VCAP bead captured exosomes was measured with the Taqman TMPRSS:ERG fusion transcript assay (Kirsten D. Mertz et al. *Neoplasia.* 2007 March; 9(3): 200-206). RNA from the 22Rv1 bead captured exosomes was measured with the Taqman SPINK1 transcript assay (Scott A. Tomlin et al. *Cancer Cell* 2008 June 13(6):519-528). The GAPDH transcript (control transcript) was also measured for both sets of exosomal RNA.

Figure 75A:
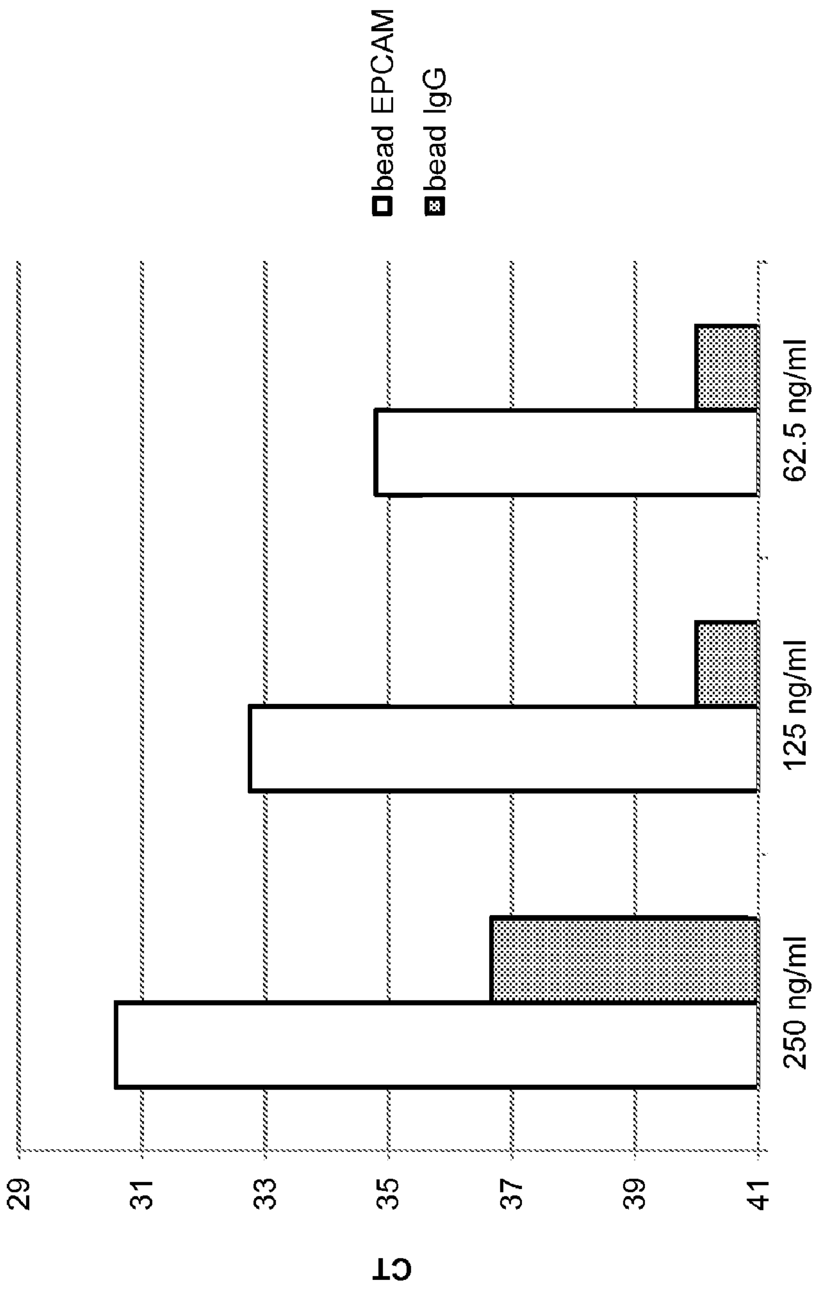
FIG. 75 illustrates the capture of prostate cancer cells-derived exosomes from plasma with EpCam by assessing TMPRSS2-ERG expression. (A) Graduated amounts of VCAP purified exosomes were spiked into normal plasma. Exosomes were isolated using Dynal beads with either EPCAM antibody or its isotype control. RNA from the exosomes was isolated and the expression of the TMPRSS2:ERG fusion transcript was measured using qRT-PCR. (B) VCaP purified exosomes were spiked into normal plasma and then incubated with Dynal magnetic beads coated with either the EpCam or isotype control antibody. RNA was isolated directly from the Dynal beads. Equal volumes of RNA from each sample were used for RT-PCR and subsequent Taqman assays. (C) Cycle threshold (CT) differences of the SPINK1 and GAPDH transcripts between 22RV1 exosomes captured with EpCam and IgG2 isotype negative control beads. Higher CT values indicate lower transcript expression.
Figure 75B:
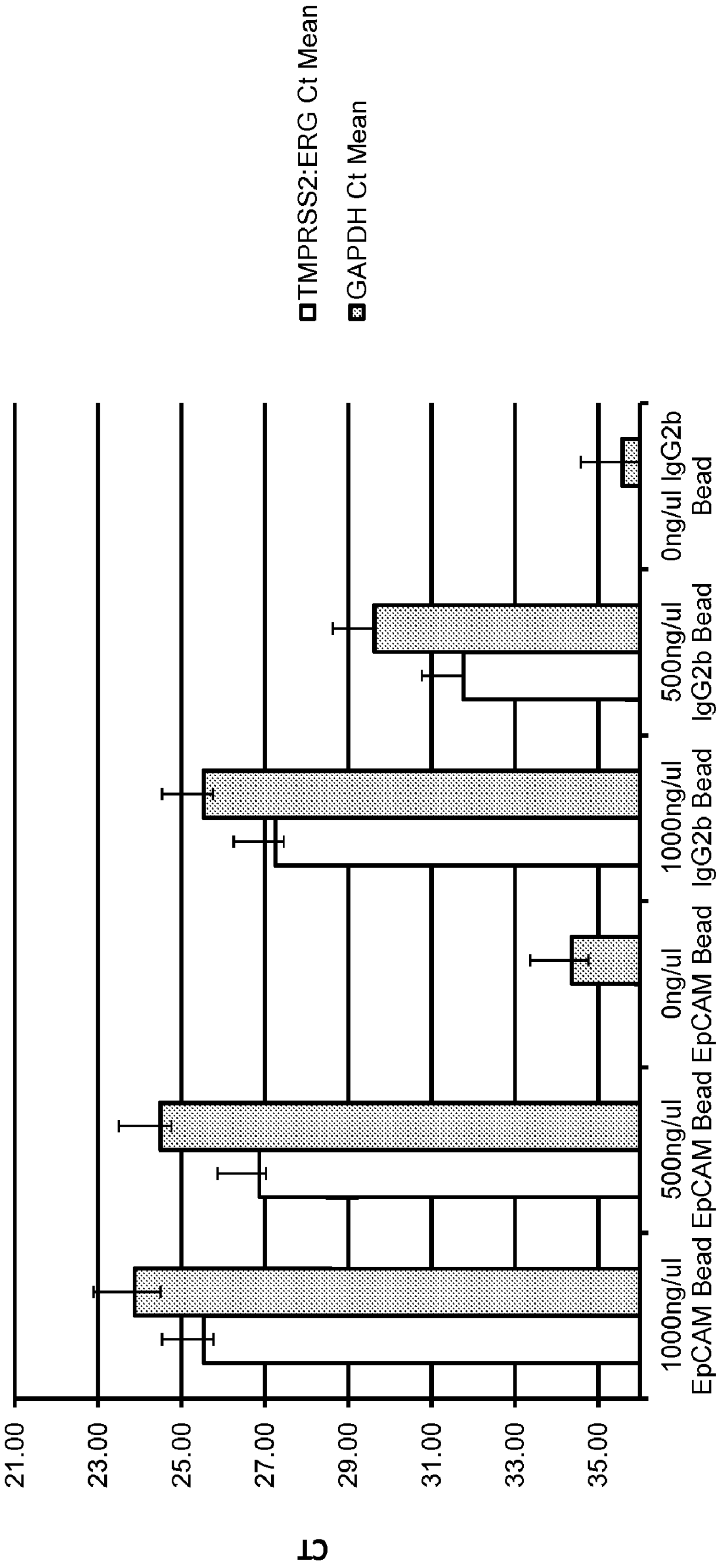
Figure 75C:
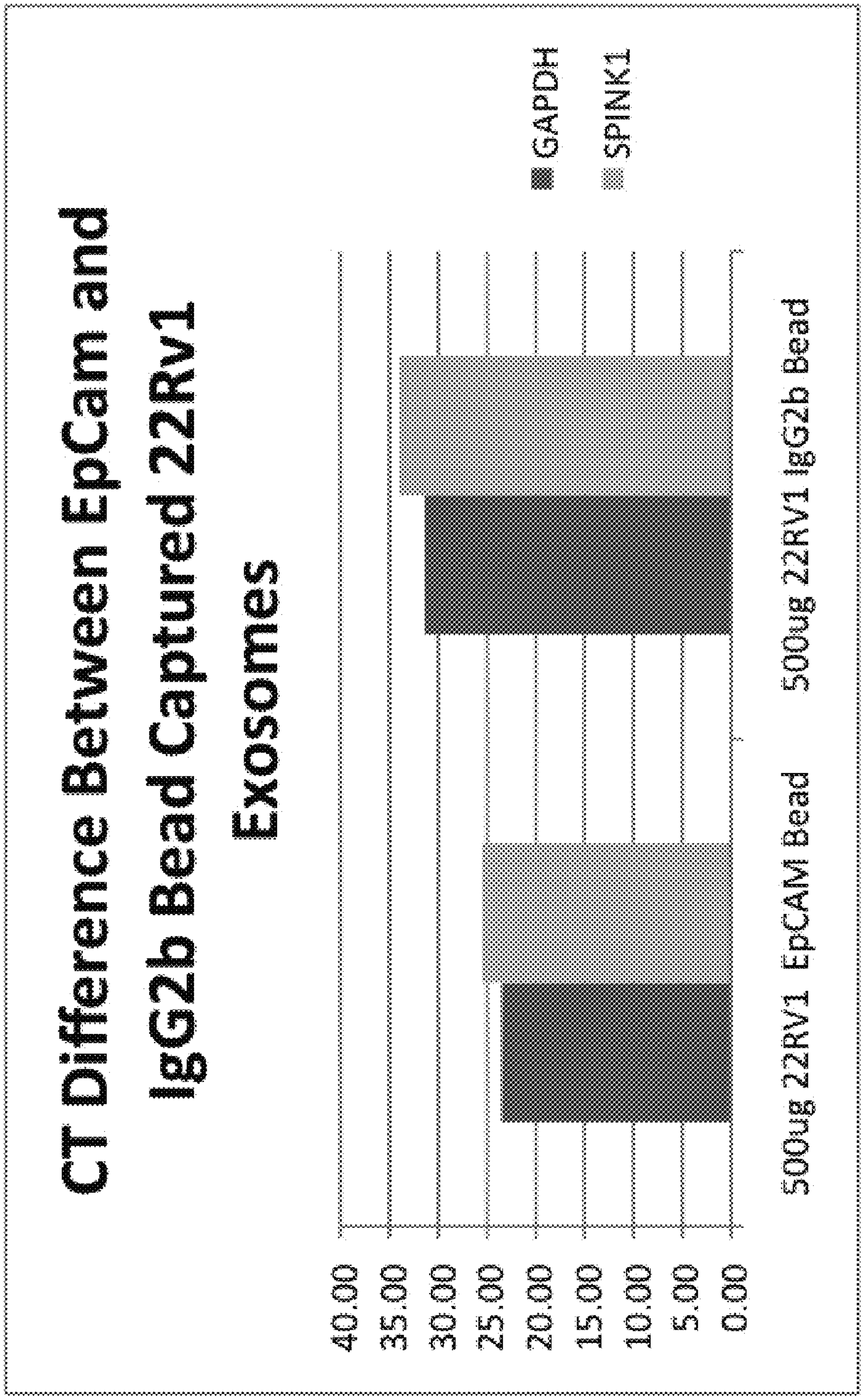

Higher CT values indicate lower transcript expression. One change in cycle threshold (CT) is equivalent to a 2 fold change, 3 CT difference to a 4 fold change, and so forth, which can be calculated with the following: $2^{\wedge CT1-CT2}$. This experiment shows a difference in CT of the expression of the fusion transcript TMPRSS:ERG and the equivalent captured with the IgG2 negative control bead (FIG. 75). The same comparison of the SPINK1 transcript in 22RV1 exosomes shows a CT difference of 6.14 for a fold change of 70.5 (FIG. 75C).

Example 11

MicroRNA Profiles in Exosomes

Exosomes were collected by ultracentrifugation from 22Rv1, LNCaP, Vcap and normal plasma (pooled from 16 donors) as described in Examples 1 and 2. RNA was extracted using the Exiqon miR isolation kit (Cat. No. 300110, 300111). Equals amounts of exosomes (30 µg) were used as determined by BCA assay.

Figure 76A:
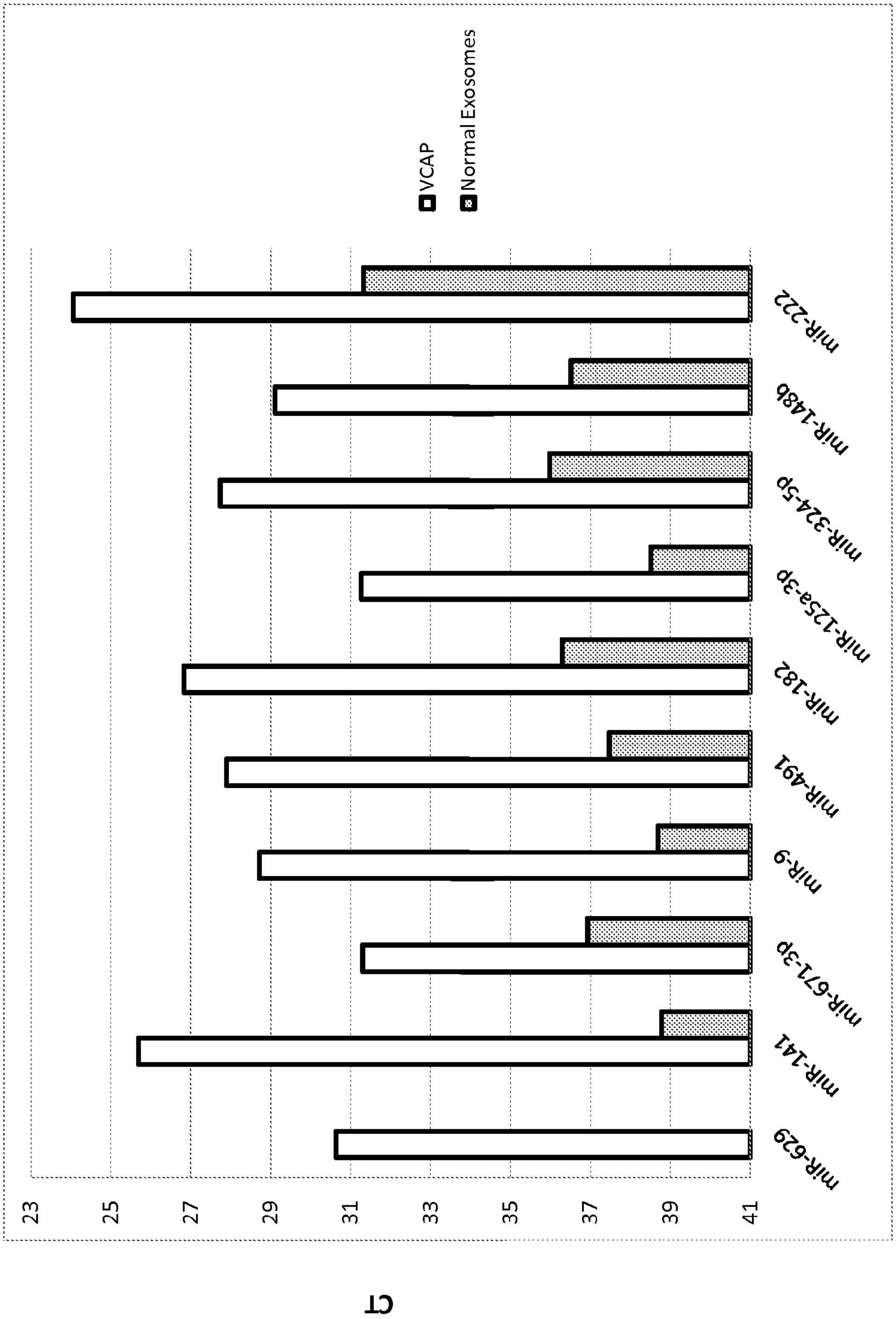
FIG. 76: illustrates the top ten differentially expressed microRNAs between VCaP prostate cancer cell derived exosomes and normal plasma exosomes. VCAP cell line exosomes and exosomes from normal plasma were isolated via ultracentrifugation followed by RNA isolation. MicroRNAs were profiled using qRT-PCR analysis. Prostate cancer cell line derived exosomes have higher levels (lower CT values) of the indicated microRNAs as depicted in the bar graph (A) and table (B).

Equal volumes (5 µl) were put into a reverse-transcription reaction for microRNA. The reverse-transcriptase reactions were diluted in 81 µl of nuclease-free water and then 9 µl of this solution was added to each individual miR assay. MiR-629 was found to only be expressed in PCa (prostate cancer) exosomes and was virtually undetectable in normal plasma exosomes. MiR-9 was found to be highly overexpressed (~704 fold increase over normal as measured by copy number) in all PCa cell lines, and has very low expression in normal plasma exosomes. The top ten differentially expressed miRNAs are depicted in FIG. 76.

Example 12

MicroRNA Profiles of Magnetic EpCam-Captured Exosomes

The bead-bound exosomes of Example 9 was placed in QIAzol™ Lysis Reagent (Cat. #79306). An aliquot of 125 fmol of *c. elegans* miR-39 was added. The RNA from the exosomes was isolated using the Qiagen miRneasy™ kit, (Cat. #217061), according to the manufacturer's instructions, and eluted in 30 ul RNAse free water.

10 μl of the purified RNA was placed into a pre-amplification reaction for miR-9, miR-141 and miR-629 using a Veriti 96-well thermocycler. A 1:5 dilution of the pre-amplification solution was used to set up a qRT-PCR reaction for miR9 (ABI 4373285), miR-141 (ABI 4373137) and miR-629 (ABI 4380969) as well as *c. elegans* miR-39 (ABI 4373455). The results were normalized to the *c. elegans* results for each sample.

Example 13

MicroRNA Profiles of CD9-Captured Exosomes

Figure 77:
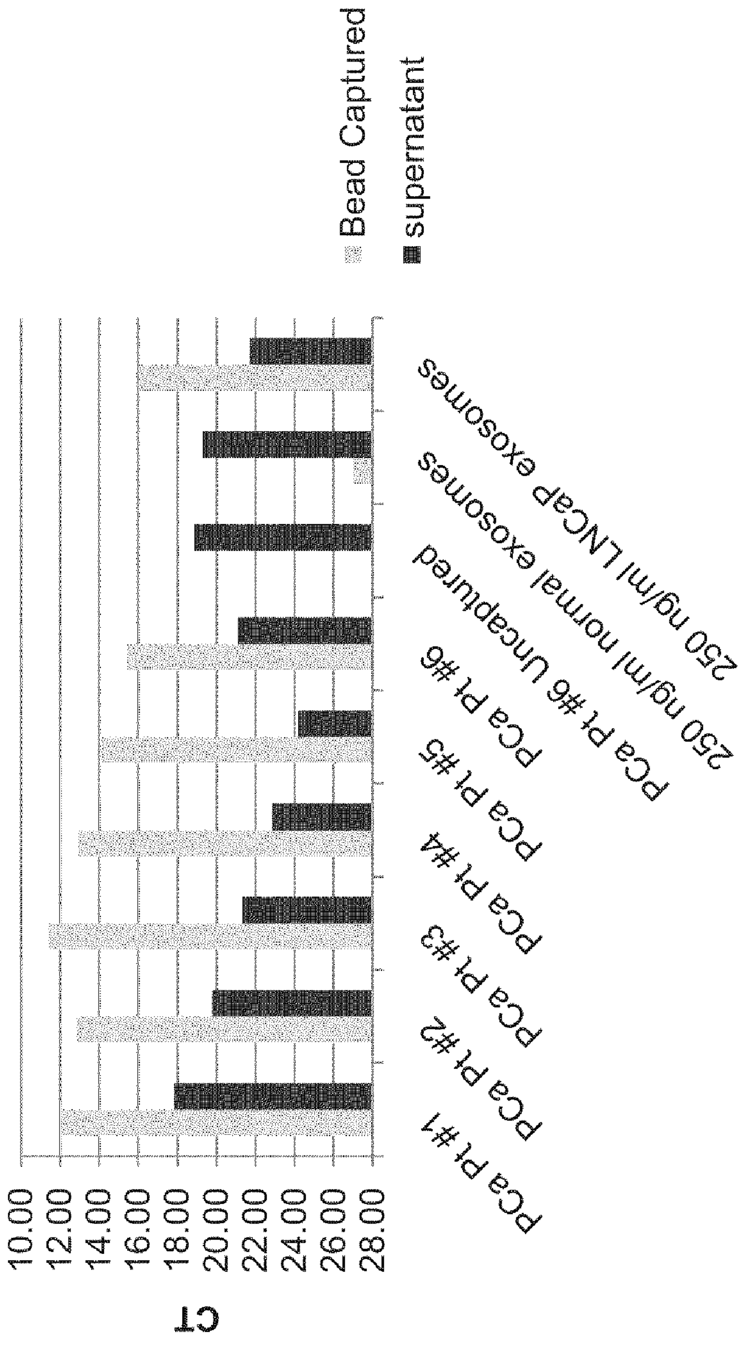
FIG. 77 depicts a bar graph of miR-21 expression with CD9 bead capture. 1 ml of plasma from prostate cancer patients, 250 ng/ml of LNCaP, or normal purified exosomes was incubated with CD9 coated Dynal beads. The RNA was isolated from the beads and the bead supernatant. One sample (#6) was also uncaptured for comparison. MiR-21 expression was measured with qRT-PCR and the mean CT values for each sample compared. CD9 capture improves the detection of miR-21 in prostate cancer samples.
Figure 78:
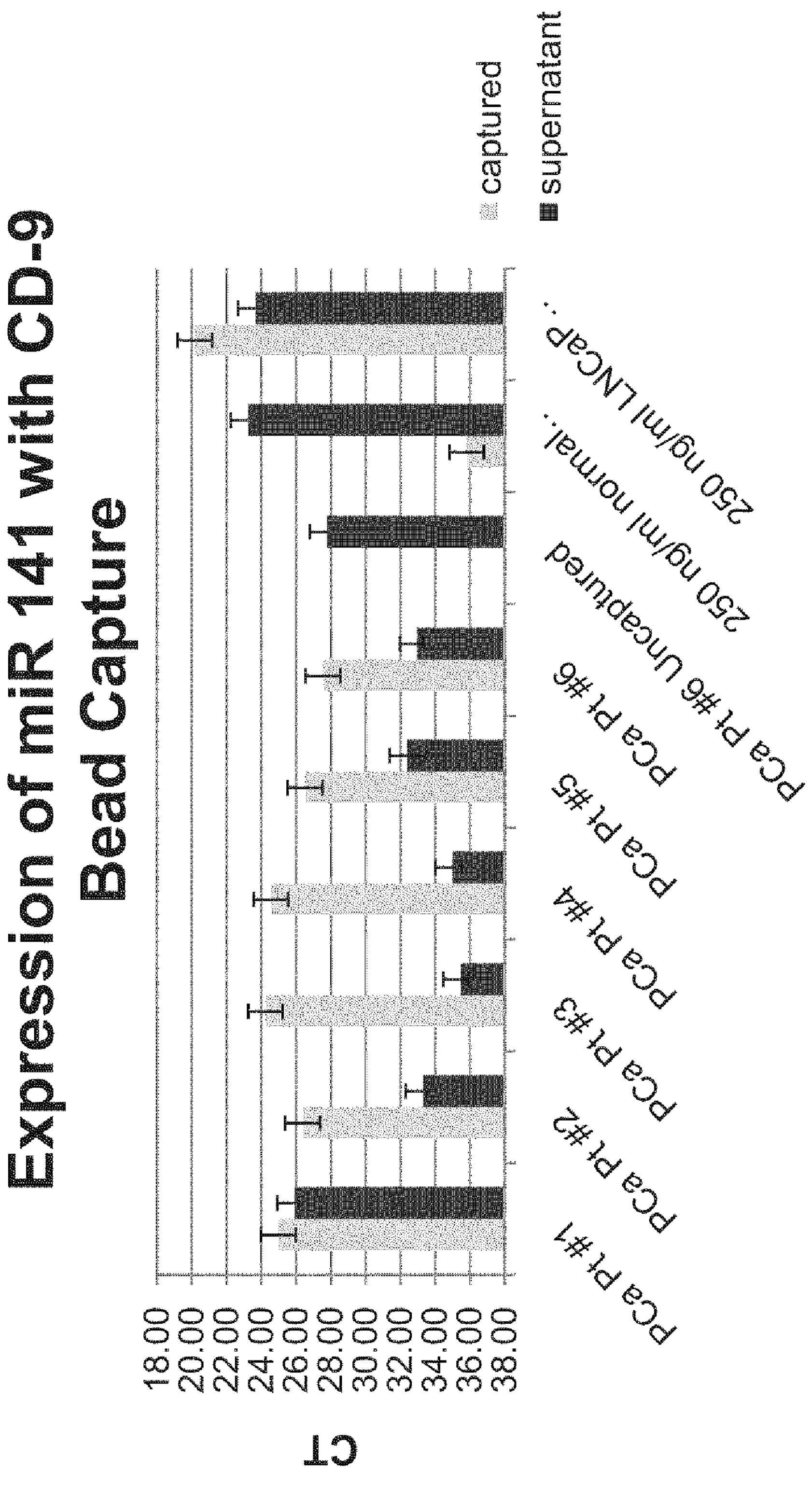
FIG. 78 depicts a bar graph of miR-141 expression with CD9 bead capture. The experiment was performed as in FIG. 77, with miR-141 expression measured with qRT-PCR instead of miR-21.

The CD9 coated Dynal beads (Invitrogen, Carlsbad, Calif.) were used instead of EpCam coated beads as in Example 12. Exosomes from prostate cancer patients, LNCaP, or normal purified exosomes were incubated with the CD9 coated beads and the RNA isolated as described in Example 12. The expression of miR-21 and miR-141 was detected by qRT-PCR and the results depicted in FIGS. 77 and 78.

Example 14

Reference Values for Prostate Cancer

Fourteen stage 3 prostate cancer subjects, eleven benign prostate hyperplasia (BPH) samples, and 15 normal samples were tested. Exosome samples were obtained using methods as described in Example 3 and used in multiplexing assays, such as described in Examples 4 and 5. The samples were analyzed to determine four criteria 1) if the sample has overexpressed exosomes, 2) if the sample has overexpressed prostate exosomes, 3) if the sample has overexpressed cancer exosomes, and 4) if the sample is reliable. If the sample met all four criteria, the categorization of the sample as positive for prostate cancer had varying sensitivities and specificities, depending on the different bio-signatures present for a sample as described below (Cancer-1, Cancer-2, and Cancer-3, FIG. 79). The four criteria were as follows:

Exosome Overexpression

The mean fluorescence intensities (MFIs) for a sample in three assays were averaged to determine a value for the sample. Each assay used a different capture antibody. The first used a CD9 capture antibody, the second a CD81 capture antibody, and the third a CD63 antibody. The same combination of detection antibodies was used for each assay, antibodies for CD9, CD81, and CD63. If the average value obtained for the three assays was greater than 3000, the sample was categorized as having overexpressed exosomes (FIG. 79, Exosome).

Prostate Exosome Overexpression

The MFIs for a sample in two assays were averaged to determine a value for the sample. Each assay used a different capture antibody. The first used a PCSA capture antibody and the second used a PSMA capture antibody. The same combination of detection antibodies was used for each assay, antibodies for CD9, CD81, and CD63. If the average value obtained for the two assays was greater than 100, the sample was categorized as having prostate exosomes overexpressed (FIG. 79, Prostate).

Cancer Exosome Overexpression

Three different cancer bio-signatures were used to determine if cancer exosomes were overexpressed in a sample. The first, Cancer-1, used an EpCam capture antibody and detection antibodies for CD81, CD9, and CD63. The second, Cancer-2, used a CD9 capture antibody with detection antibodies for EpCam and B7H3. If the MFI value of a sample for any two of the three cancer bio-signatures was above a reference value, the sample was categorized as having overexpressed cancer (see FIG. 79, Cancer-1, Cancer-2, Cancer-3).

Reliability of Sample

Two quality control measures, QC-1 and QC-2, were determined for each sample. If the sample met one of them; the sample was categorized as reliable.

For QC-1, the sum of all the MFIs of 7 assays was determined. Each of the 7 assays used detection antibodies for CD59 and PSMA. The capture antibody used for each assay was CD63, CD81, PCSA, PSMA, STEAP, B7H3, and EpCam. If the sum was greater than 4000, the sample was not reliable and not included.

For QC-2, the sum of all the MFIs of 5 assays was determined. Each of the 5 assays used detection antibodies for CD9, CD81 and CD63. The capture antibody used for each assay was PCSA, PSMA, STEAP, B7H3, and EpCam. If the sum was greater than 8000, the sample was not reliable and not included.

The sensitivity and specificity for samples with BPH and without BPH samples after a sample met the criteria as described herein, are shown in FIG. 79.

It will also be understood that the foregoing description is of exemplary embodiments of the invention and that the invention is not limited to the specific forms shown or described herein. Various modifications may be made in the design, arrangement, and type of elements disclosed herein, as well as the steps of utilizing the invention without departing from the scope of the invention as expressed in the appended claims.

What is claimed is:

1. A method of characterizing a cancer in a subject comprising:

(a) determining the presence or level of B7H3 protein and one or more tetraspanin protein biomarker from an exosome population isolated from a biological sample from said subject; and (b) comparing said presence or levels of said proteins from said isolated exosome population to a reference, wherein elevated presence or levels as compared to said reference indicates that said subject may be predisposed to or afflicted with cancer, thereby characterizing said cancer.

2. The method of claim 1, wherein the exosome population is isolated from a bodily fluid from said subject.

3. The method of claim 2, wherein said bodily fluid is peripheral blood, serum, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, female ejaculate, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, or umbilical cord blood.

4. The method of claim 1, wherein said exosome population comprises an exosome having a diameter of about 10 nm to about 800 nm.

5. The method of claim 1, wherein said exosome population comprises an exosome having a diameter of about 30 nm to about 200 nm.

6. The method of claim 1, wherein said exosome population is isolated from said biological sample with size exclusion chromatography, density gradient centrifugation, differential centrifugation, nanomembrane ultrafiltration, immunoabsorbent capture, affinity purification, affinity selection, microfluidic separation or a combination thereof.

7. The method of claim 1, wherein the cancer is a prostate, lung, colon, breast, bladder, endometrial, liver, pancreatic, ovarian, esophageal or kidney cancer.

8. The method of claim 1, wherein said one or more tetraspanin protein comprises CD9, CD63, CD81 or a combination thereof.

9. The method of claim 1, wherein the cancer is a prostate cancer.

10. The method of claim 1, wherein said one or more tetraspanin protein comprises CD9.

11. The method of claim 1, wherein said determining comprises measuring an expression level, presence, absence, mutation, truncation, insertion, modification, sequence variation or molecular association of said proteins from said isolated exosome population.

12. The method of claim 2, wherein said bodily fluid is blood, urine, serum or plasma.

13. The method of claim 1, wherein said characterizing comprises one or more of determining an amount of exosomes, a temporal evaluation of a variation in exosome half-life, a temporal evaluation of circulating exosome half-life, a temporal evaluation of exosome metabolic half-life, or determining exosome activity.

14. The method of claim 9, further comprising determining levels or presence of PCSA protein and/or PSMA protein from said isolated exosome population.

15. The method of claim 1, wherein said determining the presence or level of said B7H3 protein and said one or more tetraspanin protein comprises using one or more binding agent that binds to at least one of said proteins from said exosome population.

16. The method of claim 15, wherein said one or more binding agent is an antigen, DNA molecule, RNA molecule, antibody, antibody fragment, aptamer, peptoid, zDNA, peptide nucleic acid (PNA), locked nucleic acids (LNA), lectin, peptide, dendrimer or chemical compound.

17. The method of claim 1, wherein said characterizing comprises a diagnosis, prognosis, determination of drug efficacy, monitoring the status of said subject's response or resistance to a treatment or selection of a treatment for said cancer.

18. The method of claim 1, wherein said reference is derived from determining the presence or level of said B7H3 protein and one or more tetraspanin protein in said subject over a time course.

19. The method of claim 9, wherein said one or more tetraspanin protein biomarker comprises CD9, CD63 or CD81 protein or a combination thereof.

20. The method of claim 9, further comprising determining the presence or level of one or more prostate-specific biomarker from said exosome population.

21. The method of claim 20, wherein said one or more prostate-specific biomarker comprises PCSA.

22. The method of claim 20, wherein said one or more prostate-specific biomarker comprises PSMA.

23. The method of claim 20, wherein said one or more prostate-specific biomarker comprises miR-141.

24. The method of claim 20, wherein said one or more prostate-specific biomarker comprises TMPRSS2-ERG.

25. The method of claim 23 or 24, wherein said biomarker is assessed by quantitative PCR, nucleic acid sequencing, hybridization assay or a combination thereof.

26. The method of claim 1, further comprising determining a presence or level of at least one microRNA in said isolated exosome population.

27. A method of detecting prostate cancer in a patient comprising: detecting the levels of CD9 protein, PCSA protein, and B7H3 protein in isolated exosomes obtained from said patient, wherein elevated levels of CD9, PCSA, and B7H3 proteins in isolated exosomes obtained from said patient as compared to levels of CD9, PCSA, and B7H3 proteins in isolated exosomes obtained from a subject that does not have prostate cancer indicates said patient has prostate cancer.

28. The method of claim 26, wherein said exosomes are isolated from said patient with size exclusion chromatography, density gradient centrifugation, differential centrifugation, nanomembrane ultrafiltration, immunoabsorbent capture, affinity purification, affinity selection, microfluidic separation or a combination thereof.

29. The method of claim 28, wherein the affinity selection comprises contacting said exosomes with a binding agent that is specific for a protein biomarker selected from the group consisting of B7H3 protein, PCSA protein, CD9 protein, and a combination thereof.

30. The method of claim 29, further comprising determining a presence or level of at least one microRNA in said isolated exosomes.

31. A method of detecting one or more candidate biomarker in a biological sample, comprising isolating exosomes from said biological sample and detecting the levels of CD9 protein and B7H3 protein associated with said isolated exosomes.

32. The method of claim 31, wherein said exosomes are isolated from said sample with size exclusion chromatography, density gradient centrifugation, differential centrifugation, nanomembrane ultrafiltration, immunoabsorbent capture, affinity purification, affinity selection, microfluidic separation or a combination thereof.

33. The method of claim 32, wherein the affinity selection comprises contacting said exosomes with a binding agent that is specific for a protein biomarker selected from the group consisting of B7H3 protein, CD9 protein, and a combination thereof.

34. The method of claim 33, further comprising determining a presence or level of at least one microRNA in said isolated exosomes.

* * * * *

UNITED STATES PATENT AND TRADEMARK OFFICE

CERTIFICATE OF CORRECTION

PATENT NO. : 8,211,653 B2
APPLICATION NO. : 13/009285
DATED : July 3, 2012
INVENTOR(S) : Klass et al.

It is certified that error appears in the above-identified patent and that said Letters Patent is hereby corrected as shown below:

In the Claims

Column 138, line 27: “The method of claim 26, wherein said exosomes are” should read --The method of claim 27, wherein said exosomes are--.

Signed and Sealed this
Nineteenth Day of May, 2015

Michelle K. Lee
*Director of the United States Patent and Trademark Office*